United States Patent
Hucknall et al.

(10) Patent No.: US 11,752,213 B2
(45) Date of Patent: Sep. 12, 2023

(54) SURFACES HAVING REDUCED NON-SPECIFIC BINDING AND ANTIGENICITY

(71) Applicant: Duke University, Durham, NC (US)

(72) Inventors: Angus Hucknall, Durham, NC (US); Ashutosh Chilkoti, Durham, NC (US); Daniel Joh, Durham, NC (US); Nancy J. Ganson, Durham, NC (US); Yizhi Qi, Durham, NC (US); Michael S. Hershfield, Durham, NC (US)

(73) Assignee: Duke University, Durham, NC (US)

( * ) Notice: Subject to any disclaimer, the term of this patent is extended or adjusted under 35 U.S.C. 154(b) by 228 days.

(21) Appl. No.: 17/015,315

(22) Filed: Sep. 9, 2020

(65) Prior Publication Data

US 2021/0046188 A1 Feb. 18, 2021

Related U.S. Application Data

(63) Continuation-in-part of application No. 16/064,424, filed as application No. PCT/US2016/068141 on Dec. 21, 2016, now abandoned.

(60) Provisional application No. 62/899,353, filed on Sep. 12, 2019, provisional application No. 62/270,401, filed on Dec. 21, 2015, provisional application No. 62/310,534, filed on Mar. 18, 2016, provisional application No. 62/329,800, filed on Apr. 29, 2016, provisional application No. 62/407,403, filed on Oct. 12, 2016.

(51) Int. Cl.
| | | |
|---|---|---|
| A61K 47/58 | (2017.01) | |
| A61K 47/59 | (2017.01) | |
| C08L 71/08 | (2006.01) | |
| A61K 47/64 | (2017.01) | |

(52) U.S. Cl.
CPC .............. *A61K 47/58* (2017.08); *A61K 47/59* (2017.08); *A61K 47/641* (2017.08); *C08L 71/08* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 4,415,732 A | 11/1983 | Caruthers et al. |
| 4,458,066 A | 7/1984 | Caruthers et al. |
| 4,500,707 A | 2/1985 | Caruthers et al. |
| 4,554,101 A | 11/1985 | Hopp |
| 4,668,777 A | 5/1987 | Caruthers et al. |
| 4,973,679 A | 11/1990 | Caruthers et al. |
| 4,976,734 A | 12/1990 | Urry et al. |
| 5,153,319 A | 10/1992 | Caruthers et al. |
| 5,250,516 A | 10/1993 | Urry |
| 5,278,302 A | 1/1994 | Caruthers et al. |
| 5,336,256 A | 8/1994 | Urry |
| 5,453,496 A | 9/1995 | Caruthers et al. |
| 5,534,408 A | 7/1996 | Green et al. |
| 5,578,577 A | 11/1996 | Ching et al. |
| 5,580,859 A | 12/1996 | Feigner et al. |
| 5,602,244 A | 2/1997 | Caruthers et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Feigner et al. |
| 5,935,776 A | 8/1999 | Green et al. |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,207,749 B1 | 3/2001 | Mayes et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,245,515 B1 | 6/2001 | Vogelstein et al. |
| 6,296,831 B1 | 10/2001 | Weller et al. |
| 6,302,874 B1 | 10/2001 | Zhang et al. |
| 6,413,587 B1 | 7/2002 | Hawker et al. |
| 6,512,060 B1 | 1/2003 | Matyjaszewski et al. |
| 6,541,580 B1 | 4/2003 | Matyjaszewski et al. |
| 6,623,950 B1 | 9/2003 | Osten et al. |
| 6,649,138 B2 | 11/2003 | Adams et al. |
| 6,660,247 B1 | 12/2003 | Gutowska et al. |

(Continued)

FOREIGN PATENT DOCUMENTS

| | | |
|---|---|---|
| AU | 2007265628 B2 | 12/2012 |
| CA | 2327325 A1 | 11/1999 |

(Continued)

OTHER PUBLICATIONS

Hu et al., Biomaterials 47: 13-19 (Year: 2015).*

(Continued)

*Primary Examiner* — Phuong Huynh

(74) *Attorney, Agent, or Firm* — Michael Best & Friedrich LLP

(57) ABSTRACT

Disclosed herein are compositions and methods for reducing the antigenicity of molecules. The antigenicity of a molecule may be reduced or eliminated by conjugating at least one branched polymer to the molecule to form a molecule-polymer conjugate. The branched polymer may include a backbone and a plurality of side chains, each side chain covalently attached to the backbone.

40 Claims, 56 Drawing Sheets

Specification includes a Sequence Listing.

(56) References Cited

U.S. PATENT DOCUMENTS

| | | |
|---|---|---|
| 6,841,617 B2 | 1/2005 | Jeong et al. |
| 6,852,834 B2 | 2/2005 | Chilkoti |
| 6,869,588 B2 | 3/2005 | Weller et al. |
| 7,033,571 B2 | 4/2006 | Gutowska et al. |
| 7,087,244 B2 | 8/2006 | Jeong et al. |
| 7,300,922 B2 | 11/2007 | Sullenger et al. |
| 7,429,458 B2 | 9/2008 | Chilkoti |
| 7,531,524 B2 | 5/2009 | Rusconi |
| 7,664,545 B2 | 2/2010 | Westersten et al. |
| 7,674,882 B2 | 3/2010 | Kaplan et al. |
| 8,129,330 B2 | 3/2012 | Martinez et al. |
| 8,283,125 B2 | 10/2012 | Cebolla Ramirez et al. |
| 8,470,967 B2 | 6/2013 | Chilkoti et al. |
| 8,497,356 B2 | 7/2013 | Chilkoti et al. |
| 8,506,963 B2 | 8/2013 | Li et al. |
| 8,586,347 B2 | 11/2013 | Lochhead et al. |
| 8,841,414 B1 | 9/2014 | Raucher et al. |
| 8,912,310 B2 | 12/2014 | Chilkoti et al. |
| 8,937,153 B2 | 1/2015 | Abrahmsén et al. |
| 9,127,047 B2 | 9/2015 | Chilkoti |
| 9,132,178 B2 | 9/2015 | Philip |
| 9,138,743 B2 | 9/2015 | Yager et al. |
| 9,482,664 B2 | 11/2016 | Chilkoti et al. |
| 9,592,303 B2 | 3/2017 | Chilkoti et al. |
| 9,771,396 B2 | 9/2017 | Chilkoti et al. |
| 9,804,170 B2 | 10/2017 | Krishna et al. |
| 9,890,420 B2 | 2/2018 | Chilkoti et al. |
| 10,064,954 B2 | 9/2018 | Wu |
| 10,131,690 B2 | 11/2018 | Bonny et al. |
| 10,302,636 B2 | 5/2019 | Chilkoti et al. |
| 10,364,451 B2 | 7/2019 | Chilkoti et al. |
| 10,385,115 B2 | 8/2019 | Chilkoti et al. |
| 10,434,182 B2 | 10/2019 | Weng et al. |
| 2001/0034050 A1 | 10/2001 | Chilkoti |
| 2002/0052443 A1 | 5/2002 | Greenwald et al. |
| 2002/0146794 A1 | 10/2002 | Tomycz |
| 2003/0008308 A1 | 1/2003 | Enzelberger et al. |
| 2003/0138829 A1 | 1/2003 | Unger et al. |
| 2003/0175290 A1 | 9/2003 | Renner et al. |
| 2003/0185741 A1 | 10/2003 | Matyjaszewski et al. |
| 2003/0225251 A1 | 12/2003 | Sallberg et al. |
| 2003/0233675 A1 | 12/2003 | Cao et al. |
| 2004/0053976 A1 | 3/2004 | Martinez et al. |
| 2004/0101852 A1 | 5/2004 | Bennett et al. |
| 2004/0192072 A1 | 9/2004 | Snow et al. |
| 2005/0186214 A1 | 8/2005 | Liu et al. |
| 2005/0255554 A1 | 11/2005 | Chilkoti |
| 2005/0288229 A1 | 12/2005 | Sindrey et al. |
| 2006/0025524 A1 | 2/2006 | Schneider et al. |
| 2006/0034796 A1 | 2/2006 | Ashwell et al. |
| 2006/0051798 A1 | 3/2006 | Mirkin et al. |
| 2007/0087114 A1 | 4/2007 | Chilkoti et al. |
| 2007/0117173 A1 | 5/2007 | Levison et al. |
| 2008/0181861 A1 | 7/2008 | Jiang et al. |
| 2009/0098652 A1 | 4/2009 | Stupp et al. |
| 2009/0215194 A1 | 8/2009 | Magni et al. |
| 2009/0247424 A1* | 10/2009 | Chilkoti ............ G01N 33/54353 506/17 |
| 2010/0015070 A1 | 1/2010 | Bollschweiler et al. |
| 2010/0022455 A1 | 1/2010 | Chilkoti |
| 2010/0048473 A1 | 2/2010 | Chaikof et al. |
| 2010/0120018 A1 | 5/2010 | Quake et al. |
| 2010/0241054 A1 | 9/2010 | Dacey et al. |
| 2010/0311059 A1 | 12/2010 | Didion et al. |
| 2010/0311669 A1 | 12/2010 | Greene et al. |
| 2010/0325765 P1 | 12/2010 | Pait et al. |
| 2011/0082283 A1 | 4/2011 | Dagher et al. |
| 2011/0119778 A1 | 5/2011 | Liss |
| 2011/0165557 A1 | 7/2011 | Ah et al. |
| 2011/0207673 A1 | 8/2011 | Chilkoti et al. |
| 2011/0248698 A1 | 10/2011 | Kikuchi et al. |
| 2011/0294189 A1 | 12/2011 | Chilkoti et al. |
| 2011/0303303 A1 | 12/2011 | Proper et al. |
| 2011/0305718 A1 | 12/2011 | Mugica et al. |
| 2012/0172298 A1 | 7/2012 | Andersen et al. |
| 2012/0208742 A1 | 8/2012 | Primiano et al. |
| 2013/0039927 A1 | 2/2013 | Dewhurst et al. |
| 2013/0079277 A1 | 3/2013 | Chilkoti |
| 2013/0079280 A1 | 3/2013 | Baca et al. |
| 2013/0096058 A1 | 4/2013 | Baca et al. |
| 2013/0102993 A1 | 4/2013 | Kim et al. |
| 2013/0130384 A1 | 5/2013 | Okamoto et al. |
| 2013/0157889 A1 | 6/2013 | Chilkoti et al. |
| 2013/0165389 A1 | 6/2013 | Schellenberger et al. |
| 2013/0172274 A1 | 7/2013 | Chilkoti |
| 2013/0197359 A1 | 8/2013 | Park et al. |
| 2013/0315823 A1 | 11/2013 | Trieu |
| 2013/0330335 A1 | 12/2013 | Bremel et al. |
| 2014/0024600 A1 | 1/2014 | Chilkoti et al. |
| 2014/0163201 A1 | 6/2014 | Winter et al. |
| 2014/0275227 A1 | 9/2014 | Hoge et al. |
| 2014/0294932 A1 | 10/2014 | Kim et al. |
| 2015/0094270 A1 | 4/2015 | Harris et al. |
| 2015/0099707 A1 | 4/2015 | Pastan et al. |
| 2015/0112022 A1 | 4/2015 | Chilkoti et al. |
| 2016/0017278 A1 | 1/2016 | Montclare et al. |
| 2016/0114053 A1 | 4/2016 | Chilkoti |
| 2016/0120952 A1 | 5/2016 | Chilkoti |
| 2016/0200787 A1 | 7/2016 | Matern et al. |
| 2016/0209356 A1 | 7/2016 | Herget et al. |
| 2016/0220727 A1 | 8/2016 | Lu et al. |
| 2016/0250165 A1 | 9/2016 | Sullenger et al. |
| 2016/0271262 A1 | 9/2016 | Lopez et al. |
| 2016/0303091 A1 | 10/2016 | Wang |
| 2016/0348147 A1 | 12/2016 | Lopez et al. |
| 2016/0355802 A1 | 12/2016 | Isaacs et al. |
| 2017/0088670 A1 | 3/2017 | Rowan et al. |
| 2017/0102357 A1 | 4/2017 | Liang et al. |
| 2017/0166621 A1 | 6/2017 | Boettcher et al. |
| 2017/0170142 A1 | 6/2017 | Edelstein et al. |
| 2017/0189545 A1 | 7/2017 | Lee et al. |
| 2017/0233714 A1 | 8/2017 | Chilkoti et al. |
| 2017/0239363 A1 | 8/2017 | Chilkoti et al. |
| 2017/0369651 A1 | 12/2017 | Cheng et al. |
| 2018/0135060 A1 | 5/2018 | Romero Ramos et al. |
| 2018/0161772 A1 | 6/2018 | Rammohan et al. |
| 2018/0171337 A1 | 6/2018 | O'Neill et al. |
| 2018/0200196 A1 | 7/2018 | Fahmy et al. |
| 2018/0217136 A1 | 8/2018 | Chilkoti et al. |
| 2018/0231469 A1 | 8/2018 | Gibbons et al. |
| 2018/0238864 A1 | 8/2018 | Burd et al. |
| 2018/0258157 A1 | 9/2018 | Chilkoti et al. |
| 2018/0326044 A1 | 11/2018 | Carter |
| 2018/0327752 A1 | 11/2018 | Pillay et al. |
| 2018/0369399 A1 | 12/2018 | Hershfield et al. |
| 2019/0016763 A1 | 1/2019 | Kitazawa et al. |
| 2019/0204309 A1 | 7/2019 | Gibbs |
| 2019/0285623 A1 | 9/2019 | Chilkoti et al. |
| 2019/0292549 A1 | 9/2019 | Zhang et al. |
| 2019/0345228 A1 | 11/2019 | Chilkoti et al. |
| 2020/0078313 A1 | 3/2020 | Roy et al. |
| 2020/0121809 A1 | 4/2020 | Hope et al. |
| 2020/0148724 A1 | 5/2020 | Chilkoti et al. |
| 2020/0163878 A1 | 5/2020 | Baumhof et al. |
| 2020/0181555 A1 | 6/2020 | Hinojosa et al. |
| 2021/0128734 A1 | 5/2021 | Chilkoti et al. |
| 2021/0154143 A1 | 5/2021 | Chilkoti et al. |

FOREIGN PATENT DOCUMENTS

| | | |
|---|---|---|
| CA | 2423488 A1 | 4/2002 |
| CN | 104725628 B | 4/2018 |
| CN | 112961065 A | 6/2021 |
| EP | 1670315 B1 | 4/2017 |
| EP | 2664340 B1 | 2/2020 |
| JP | 2014-156428 A | 8/2014 |
| JP | 2014-534265 A | 12/2014 |
| WO | WO1991/019813 A1 | 12/1991 |
| WO | WO2003/040165 A2 | 10/2002 |
| WO | WO2004/096124 A2 | 11/2004 |
| WO | WO2006/004778 A2 | 1/2006 |
| WO | 2006/110292 A2 | 10/2006 |
| WO | WO2007/073486 A2 | 6/2007 |
| WO | WO2007/108013 A2 | 9/2007 |

(56) References Cited

FOREIGN PATENT DOCUMENTS

| | | |
|---|---|---|
| WO | WO2007/134245 A2 | 11/2007 |
| WO | WO2008/012543 A1 | 1/2008 |
| WO | WO2008/030968 A2 | 3/2008 |
| WO | WO2009/067584 A1 | 5/2009 |
| WO | WO2010/054699 A1 | 5/2010 |
| WO | WO2010/057154 A1 | 5/2010 |
| WO | WO2010/096422 A1 | 8/2010 |
| WO | WO2011/025572 A1 | 3/2011 |
| WO | WO2011/123813 A2 | 10/2011 |
| WO | 2012/162426 A1 | 11/2012 |
| WO | WO2013/049234 A2 | 4/2013 |
| WO | WO2013/065009 A1 | 5/2013 |
| WO | 2013/106715 A1 | 7/2013 |
| WO | WO2014/037373 A1 | 3/2014 |
| WO | WO2014/194244 A1 | 12/2014 |
| WO | 2015/011231 A1 | 1/2015 |
| WO | WO2015/130846 A2 | 9/2015 |
| WO | 2016/065300 A1 | 4/2016 |
| WO | WO2016/065273 A1 | 4/2016 |
| WO | WO2016/090103 A1 | 6/2016 |
| WO | WO2016/154530 A1 | 9/2016 |
| WO | WO2017/015132 A1 | 1/2017 |
| WO | WO2017/024182 A1 | 2/2017 |
| WO | WO2017/112825 A2 | 6/2017 |
| WO | WO2017/112826 A2 | 6/2017 |
| WO | WO2017/192449 A1 | 11/2017 |
| WO | WO2018/115401 A1 | 6/2018 |
| WO | WO2018/144854 A1 | 8/2018 |
| WO | 2019/103744 A1 | 5/2019 |
| WO | WO2019/147954 A1 | 8/2019 |
| WO | 2020/037214 A1 | 2/2020 |
| WO | 2020/051223 A1 | 3/2020 |
| WO | 2020/160472 A1 | 8/2020 |
| WO | 2021/178898 A1 | 9/2021 |
| WO | 2022/016089 A2 | 1/2022 |
| WO | 2022/178438 A1 | 8/2022 |

OTHER PUBLICATIONS

Abbaspourrad et al., "Controlling release from pH-responsive microcapsules," Langmuir, 2013, 29: 12697-12702.

Abbaspourrad et al., "Polymer microcapsules with programmable active release," J Am Chem Soc, 2013, 135: 7744-7750.

Agarwal et al., "One-step microfluidic generation of pre-hatching embryo-like core-shell microcapsules for miniaturized 3D culture of pluripotent stem cells," Lab Chip, 2013, 13:4525-4533.

Amiram et al., "Evolution of translation machinery in recoded bacteria enables multi-site incorporation of nonstandard amino acids," Nat Biotechnol, 2015, 33: 1272-1279.

Appleyard et al., "Multiplexed protein quantification with barcoded hydrogel microparticles," Anal Chem, 2011, 83 193-199.

Bain et al., "Formation of monolayer films by the spontaneous assembly of organic thiols from solution onto gold," Journal of the American Chemical Society, 1989, 111: 321-335.

Boeynaems et al., "Spontaneous driving forces give rise to protein-RNA condensates with coexisting phases and complex material properties," Proc Natl Acad Sci U S A, 2019, 116: 7889-7898.

Cha et al., "Microfluidics-assisted fabrication of gelatin-silica core-shell microgels for injectable tissue constructs," Biomacromolecules, 2014, 15:283-290.

Chapin et al., "Rapid microRNA profiling on encoded gel microparticles," Angew Chem Int Ed Engl, 2011, 50: 2289-2293.

Chin et al., "Addition of p-azido-I-phenylalanine to the genetic code of *Escherichia coli*," Journal of the American Chemical Society, 2002, 124: 9026-9027.

Choi et al., "Multiplexed detection of mRNA using porosity-tuned hydrogel microparticles," Anal Chem, 2012, 84: 9370-9378.

Choi et al., "Recent advances in engineering microparticles and their nascent utilization in biomedical delivery and diagnostic applications," Lab Chip, 2017, 17: 591-613.

Chu et al., "Controllable monodisperse multiple emulsions," Angew Chem Int Ed Engl, 2007, 46: 8970-8974.

Costa et al., "Photo-crosslinkable unnatural amino acids enable facile synthesis of thermoresponsive nano- to microgels of intrinsically disordered polypeptides," Adv Mater, 2018, 30(5): 1704878.

Darling et al., "Viscoelastic properties of zonal articular chondrocytes measured by atomic force microscopy," Osteoarthritis Cartilage, 2006, 14: 571-579.

Griffin et al., "Accelerated wound healing by injectable microporous gel scaffolds assembled from annealed building blocks," Nat Mater, 2015, 14: 737-744.

Hutter et al., "Calibration of atomic-force microscope tips," Review of Scientific Instruments, 1993, 64: 1868-1873.

Hwang et al., "Differentially degradable janus particles for controlled release applications," Macromol Rapid Commun, 2012, 33: 1178-1183.

Jang et al., "Engineering Globular Protein Vesicles through Tunable Self-Assembly of Recombinant Fusion Proteins," Small, 2017, 13(36): 1700399.

Khademhosseini et al., "Micromolding of photocrosslinkable hyaluronic acid for cell encapsulation and entrapment," J Biomed Mater Res A, 2006, 79: 522-532.

Kim et al., "Generation of core-shell microcapsules with three-dimensional focusing device for efficient formation of cell spheroid," Lab Chip, 2011, 11: 246-252.

Liu, L. et al., "Monodisperse core-shell chitosan microcapsules for pH-responsive burst release of hydrophobic drugs," Soft Matter, 2011, 7:4821-4827.

Ma et al., "Core-shell hydrogel microcapsules for improved islets encapsulation," Adv Healthc Mater, 2013, 2: 667-672.

Matsunaga et al., "Molding cell beads for rapid construction of macroscopic 3D tissue architecture," Adv Mater, 2011, 23: H90-94.

Oh et al., "The development of microgels/nanogels for drug delivery applications," Progress in Polymer Science, 2008, 33(4): 448-477.

Panda et al., "Stop-flow lithography to generate cell-laden microgel particles," Lab Chip, 2008, 8: 1056-1061.

Paulsen et al., "Optofluidic fabrication for 3D-shaped particles," Nat Commun, 2015, 6: 6976.

Roberts et al., "Injectable tissue integrating networks from recombinant polypeptides with tunable order," Nature Materials, 2018, 17(12): 1154-1163.

Rodriguez-Cabello et al., "Elastin-like polypeptides in drug delivery," Adv Drug Deliv Rev, 2016, 97: 85-100.

Song et al., "Budding-like division of all-aqueous emulsion droplets modulated by networks of protein nanofibrils," Nat Commun, 2018, 9: 2110.

Srinivas et al., "Aptamer-functionalized microgel particles for protein detection," Anal Chem, 2011, 83: 9138-9145.

Tsuda et al., "Monodisperse cell-encapsulating peptide microgel beads for 3D cell culture," Langmuir, 2010, 26 2645-2649.

Utada et al., "Monodisperse double emulsions generated from a microcapillary device," Science, 2005, 308: 537-541.

Uversky, "Protein intrinsic disorder-based liquid-liquid phase transitions in biological systems: Complex coacervates and membrane-less organelles," Adv Colloid Interface Sci, 2017, 239: 97-114.

Volodkin et al., "One-Step Formulation of Protein Microparticles with Tailored Properties: Hard Templating at Soft Conditions," Advanced Functional Materials, 2012, 22:1914-1922.

Wang et al., "Functional polymeric microparticles engineered from controllable microfluidic emulsions," Acc Chem Res, 2014, 47: 373-384.

Yeh et al., "Micromolding of shape-controlled, harvestable cell-laden hydrogels," Biomaterials, 2006, 27: 5391-5398.

United States Patent Office Action for U.S. Appl. No. 16/305,696 dated Jan. 28, 2021 (15 pages).

United States Patent Office Notice of Allowance for U.S. Appl. No. 16/332,865 dated Apr. 2, 2021 (10 pages).

Resh, "Covalent Lipid Modifications of Proteins," Curr Biol., May 2013, 23(10): R431-R435.

United States Patent Office Action for Application No. 16/477,229 dated Apr. 12, 2021 (14 pages).

(56) References Cited

OTHER PUBLICATIONS

Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.
Amanat et al., "A serological assay to detect SARS-CoV-2 seroconversion in humans," Nat Med, 2020, 26(7): 1033-1036.
American Hospital Association, "AHA Hospital Statistics," 2020 edition. Available at: <https://www.aha.org/statistics/fast-facts-US-hospitals>.
Armbruster et al., "Limit of blank, limit of detection and limit of quantitation," Clin Biochem Rev, 2008, 29 Suppl 1: S49-52.
Arshavsky-Graham et al., "Lab-on-a-Chip Devices for Point-of-Care Medical Diagnostics," Advances in Biochemical Engineering/Biotechnology, 2020, 19 pages.
Atyeo et al., "Distinct Early Serological Signatures Track with SARS-CoV-2 Survival," Immunity, 2020, 53: 524-532.
Baraf et al., "Infusion-related reactions with pegloticase, a recombinant uricase for the treatment of chronic gout refractory to conventional therapy," J Clin Rheumatol, 2014, 20: 427-432.
Benn et al., "Physiology of Hyperuricemia and Urate-Lowering Treatments," Front Med (Lausanne), 2018, 5: 160, 28 pages.
Berry et al., "Development and characterisation of neutralising monoclonal antibody to the SARS-coronavirus," J Virol Methods, 2004, 120: 87-96.
Bryant et al., "Serology for SARS-CoV-2: Apprehensions, opportunities, and the path forward," Sci Immunol, 2020, 5: eabc6347, 4 pages.
Calabrese et al., "Frequency, distribution and immunologic nature of infusion reactions in subjects receiving pegloticase for chronic refractory gout," Arthritis Res Ther, 2017, 19: 191, 7 pages.
Caves et al., "Thermal inactivation of uricase (urate oxidase): mechanism and effects of additives," Biochemistry, 2013, 52: 497-507.
Chae et al., "Pharmacokinetic and pharmacodynamic evaluation of site-specific PEGylated glucagon-like peptide-1 analogs as flexible postprandial-glucose controllers," J Pharm Sci, 2009, 98(4): 1556-1567.
Chen et al., "Real-world patterns of pegloticase use for treatment of gout: descriptive multidatabase cohort study," BMJ Open, 2020, 10: e041167, 6 pages.
Chen et al., "The influence of polymer topology on pharmacokinetics: differences between cyclic and linear PEGylated poly(acrylic acid) comb polymers," J Control Release, 2009, 140: 203-209.
Chu et al., "Molecular Diagnosis of a Novel Coronavirus (2019-nCoV) Causing an Outbreak of Pneumonia," Clin Chem, 2020, 66(4): 549-555.
Cong et al., "Nucleocapsid Protein Recruitment to Replication-Transcription Complexes Plays a Crucial Role in Coronaviral Life Cycle," J Virol, 2020, 94: e01925-19, 21 pages.
Crowther, "The ELISA guidebook," Methods Mol Biol, 2000, 149(III-IV): 1-413.
Dincer et al., "Multiplexed Point-of-Care Testing—xPOCT," Trends Biotechnol, 2017, 35(8): 728-742.
Dong et al., "An interactive web-based dashboard to track COVID-19 in real time," Lancet Infect Dis, 2020, 20: 533-534.
Dutta et al., "The Nucleocapsid Protein of SARS-CoV-2: a Target for Vaccine Development," J Virol, 2020, 94(13): e00647-20, 2 pages.
Ekladious et al., "Polymer-drug conjugate therapeutics: advances, insights and prospects," Nature Reviews Drug Discovery, 2019, 18: 273-294.
Fathallah et al., "Immunogenicity of Subcutaneously Administered Therapeutic Proteins—a Mechanistic Perspective," The AAPS Journal, 2013, 15(4): 897-900.
Fox et al., "Soluble polymer carriers for the treatment of cancer: the importance of molecular architecture," Acc Chem Res, 2009, 42(8): 1141-1151.
Garay et al., "Therapeutic perspectives on uricases for gout," Joint Bone Spine, 2012, 79: 237-242.
Harris et al., "Effect of pegylation on pharmaceuticals," Nature Reviews Drug Discovery, 2003, 2: 214-221.
Heggestad et al., "In Pursuit of Zero 2.0: Recent Developments in Nonfouling Polymer Brushes for Immunoassays," Adv Mater, 2020, 32: e1903285.
Hermanson et al., "Peginesatide for the treatment of anemia due to chronic kidney disease—an unfulfilled promise," Expert Opin Drug Saf, 2016, 15(10): 1421-1426.
Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.
Huang et al., "Clinical features of patients infected with 2019 novel coronavirus in Wuhan," China. Lancet, 2020, 395: 497-506.
Hucknall et al., "Simple Fabrication of Antibody Microarrays on Nonfouling Polymer Brushes with Femtomolar Sensitivity for Protein Analytes in Serum and Blood," Adv Mater, 2009, 21(19): 1968-1971.
Jiang et al., "Neutralizing Antibodies against SARS-CoV-2 and Other Human Coronaviruses," Trends Immunol, 2020, 41(5): 355-359.
Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.
Joh et al., "Inkjet-printed point-of-care immunoassay on a nanoscale polymer brush enables subpicomolar detection of analytes in blood," Proc Natl Acad Sci U S A, 2017, 114: E7054-E7062.
Kang et al., "Crystal structure of SARS-CoV-2 nucleocapsid protein RNA binding domain reveals potential unique drug targeting sites," Acta Pharm Sin B, 2020, 10(7): 1228-1238.
Khailany et al., "Genomic characterization of a novel SARS-CoV-2," Gene Rep, 2020, 9: 100682, 6 pages.
Kozel et al., "Point-of-care testing for infectious diseases: past, present, and future," J Clin Microbiol, 2017, 55: 2313-2320.
Kozma et al., "Anti-PEG antibodies: Properties, formation, testing and role in adverse immune reactions to PEGylated nano-biopharmaceuticals," Adv Drug Deliv Rev, 2020, 154-155, 163-175.
Krammer et al., "Serology assays to manage COVID-19," Science, 2020, 368: 1060-1061.
Kuo et al., "Global epidemiology of gout: prevalence, incidence and risk factors," Nature Reviews Rheumatology, 2015, 11: 649-662.
Laing et al., "A dynamic COVID-19 immune signature includes associations with poor prognosis," Nat Med, 2020, 26:1623-1635.
Lieberman et al., "Comparison of Commercially Available and Laboratory-Developed Assays for In Vitro Detection of SARS-CoV-2 in Clinical Laboratories," J Clin Microbiol, 2020, 58(8):e00821-20.
Lipsitch et al., "Antibody testing will enhance the power and accuracy of COVID-19-prevention trials," Nat Med, 2020, 26: 818-819.
Lipsky et al., "Pegloticase immunogenicity: the relationship between efficacy and antibody development in patients treated for refractory chronic gout," Arthritis Res Ther, 2014, 16: R60.
Lisboa Bastos et al., "Diagnostic accuracy of serological tests for covid-19: systematic review and meta-analysis," BMJ, 2020, 370: m2516.
Liu et al., "High neutralizing antibody titer in intensive care unit patients with COVID-19," Emerg Microbes Infect, 2020, 9: 1664-1670.
Liu et al., "Semi-permeable coatings fabricated from comb-polymers efficiently protect proteins in vivo," Nature Communications, 2014, 5: 5526.
Liu et al., "The experiences of health-care providers during the COVID-19 crisis in China: a qualitative study," Lancet Glob Health, 2020, 8: e790-e798.
Lu et al., "Genomic characterisation and epidemiology of 2019 novel coronavirus: implications for virus origins and receptor binding," Lancet, 2020, 395: 565-574.

(56) References Cited

OTHER PUBLICATIONS

McAndrews et al., "Heterogeneous antibodies against SARS-CoV-2 spike receptor binding domain and nucleocapsid with implications for COVID-19 immunity," JCI Insight, 2020, 5(18):e142386, 14 pages.

McElvaney et al., "A linear prognostic score based on the ratio of interleukin-6 to interleukin-10 predicts outcomes in COVID-19," EBioMedicine, 2020, 61: 103026, 8 pages.

Mejia-Salazar et al., "Microfluidic Point-of-Care Devices: New Trends and Future Prospects for eHealth Diagnostics," Sensors, 2020, 20: 1951, 19 pages.

Miller et al., "Disease and healthcare burden of COVID-19 in the United States," Nat Med, 2020, 26: 1212-1217.

Nalla et al., "Comparative Performance of SARS-CoV-2 Detection Assays Using Seven Different Primer-Probe Sets and One Assay Kit," J Clin Microbiol, 2020, 58: e00557-20, 6 pages.

Norman et al., "Ultrasensitive high-resolution profiling of early seroconversion in patients with COVID-19," Nat Biomed Eng, 2020, 11 pages.

Nunn et al., "Crystal Structure of Tobacco Etch Virus Protease Shows the Protein C Terminus Bound within the Active Site," Journal of Molecular Biology, 2005, 350: 145-155.

Nyborg et al., "A Therapeutic Uricase with Reduced Immunogenicity Risk and Improved Development Properties," PLoS One, 2016, 11(12): e0167935, 23 pages.

Okba et al., "Severe Acute Respiratory Syndrome Coronavirus 2-Specific Antibody Responses in Coronavirus Disease Patients," Emerg Infect Dis, 2020, 26: 1478-1488.

Ozer et al., "Effect of Molecular Architecture on Cell Interactions and Stealth Properties of PEG," Biomacromolecules, 2017, 18: 2699-2710.

Pecoraro et al., "A systematic evaluation of immunoassay point-of-care testing to define impact on patients' outcomes," Ann Clin Biochem, 2017, 54(4): 420-431.

Ponti et al., "Biomarkers associated with COVID-19 disease progression," Crit Rev Clin Lab Sci, 2020, 57, 11 pages.

Posthuma-Trumpie et al., "Lateral flow (immuno)assay: its strengths, weaknesses, opportunities and threats. A literature survey," Anal Bioanal Chem, 2009, 393: 569-582.

Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.

Ravichandran et al., "Antibody signature induced by SARS-CoV-2 spike protein immunogens in rabbits," Sci Transl Med, 2020, 10.1126/scitranslmed.abc3539, 9 pages.

Rogers et al., "Isolation of potent SARS-CoV-2 neutralizing antibodies and protection from disease in a small animal model," Science, 2020, 369: 956-963.

Rosadas et al., "Testing for responses to the wrong SARS-CoV-2 antigen," Lancet, 2020, 396: e23.

Rothe et al., "Transmission of 2019-nCoV Infection from an Asymptomatic Contact in Germany," N Engl J Med, 2020, 382: 10, 2 pages.

Seow et al., "Longitudinal evaluation and decline of antibody responses in SARS-CoV-2 infection," medRxiv, 2020, 24 pages.

Sundy et al., "Efficacy and tolerability of pegloticase for the treatment of chronic gout in patients refractory to conventional treatment: two randomized controlled trials," Jama, 2011, 306(7): 711-720.

Sundy et al., "Pharmacokinetics and pharmacodynamics of intravenous PEGylated recombinant mammalian urate oxidase in patients with refractory gout," Arthritis Rheum, 2007, 56(3): 1021-1028.

Tang et al., "Laboratory Diagnosis of COVID-19: Current Issues and Challenges," J Clin Microbiol, 2020, 58: e00512-20, 9 pages.

Turner et al., "Challenges and Opportunities for the Subcutaneous Delivery of Therapeutic Proteins," Journal of Pharmaceutical Sciences, 2018, 107(5): 1247-1260.

U.S. FDA—Classify your medical devices. Updated as of: Feb. 7, 2020. Available at: <https://www.fda.gov/medical-devices/overview-device-regulation/classify-your-medical-device>.

U.S. FDA—In Vitro Diagnostics. Updated as of: Oct. 25, 2019. Available at: <https://www.fda.gov/medical-devices/products-and-medical-procedures/vitro-diagnostics>.

Vaninov, "In the eye of the COVID-19 cytokine storm," Nat Rev Immunol, 2020, 20: 277, 1 page.

Vashist et al., "Emerging Technologies for Next-Generation Point-of-Care Testing," Trends Biotechnol, 2015, 33(11): 692-705.

Verhoef et al., "Potential induction of anti-PEG antibodies and complement activation toward PEGylated therapeutics," Drug Discov Today, 2014, 19(12): 1945-1952.

Vugmeyster et al., "Pharmacokinetics and toxicology of therapeutic proteins: Advances and challenges," World J Biol Chem, 2012, 3(4): 73-92.

Waterboer et al., "Suppression of non-specific binding in serological Luminex assays," J Immunol Methods, 2006, 309: 200-204.

Weinhandl et al., "Relative safety of peginesatide and epoetin alfa," Pharmacoepidemiology and Drug Safety, 2014, 23(10): 1003-1011.

Whitman et al., "Evaluation of SARS-CoV-2 serology assays reveals a range of test performance," Nat Biotechnol, 2020, 38: 1174-1183.

Wiersinga et al., "Pathophysiology, Transmission, Diagnosis, and Treatment of Coronavirus Disease 2019 (COVID-19): A Review," JAMA, 2020, 324(8): 782-793.

Winter et al., "The important role of serology for COVID-19 control," Lancet Infect Dis, 2020, 20: 758-759.

Wölfel et al., "Virological assessment of hospitalized patients with COVID-2019," Nature, 2020, 581: 465-469.

Yang et al., "Analysis of Pre-existing IgG and IgM Antibodies against Polyethylene Glycol (PEG) in the General Population," Analytical Chemistry, 2016, 88(23): 11804-11812.

Yang et al., "Anti-PEG immunity: emergence, characteristics, and unaddressed questions," Wiley Interdiscip Rev Nanomed Nanobiotechnol, 2015, 7(5): 655-677.

Yang et al., "Plasma IP-10 and MCP-3 levels are highly associated with disease severity and predict the progression of COVID-19," J Allergy Clin Immunol, 2020, 146: 119-127.

Yang et al., "Uricases as therapeutic agents to treat refractory gout: Current states and future directions," Drug Dev Res, 2012, 73(2): 66-72.

Yong et al., "Connecting clusters of COVID-19: an epidemiological and serological investigation," Lancet Infect Dis, 2020, 20: 809-815.

Zhang et al., "Anti-PEG antibodies in the clinic: Current issues and beyond PEGylation," J Control Release, 2016, 244(Pt B): 184-193.

Zhang et al., "Impact of Large Aggregated Uricases and PEG Diol on Accelerated Blood Clearance of PEGylated Canine Uricase," PLoS ONE, 2012, 7(6): e39659.

Zhao et al., "Antibody responses to SARS-CoV-2 in patients of novel coronavirus disease 2019," Clin Infect Dis, 2020, 22 pages.

International Search Report and Written Opinion for Application No. PCT/US2021/020591 dated Oct. 7, 2021 (14 pages).

United States Patent Office Action for U.S. Appl. No. 16/614,282 dated Oct. 21, 2021 (14 pages).

United States Patent Office Action for U.S. Appl. No. 15/749,797 dated Nov. 29, 2021 (10 pages).

United States Patent Office Action for U.S. Appl. No. 16/477,229 dated Oct. 26, 2021 (10 pages).

United States Patent Office Action for U.S. Appl. No. 15/749,797 dated Oct. 20, 2020 (16 pages).

Da Pieve Chiara et al., "Modification of Thiol Functionalized Aptamers by Conjugation of Synthetic Polymers," Bioconjugate Chemistry, 2009, 1(1): 169-174.

International Search Report and Written Opinion for Application No. PCT2022/023158 dated Jun. 21, 2022 (7 pages).

International Search Report and Written Opinion for Application No. PCT/US2022/017349 dated Jun. 3, 2022 (20 pages).

United States Patent Office Action for U.S. Appl. No. 16/964,832 dated Jul. 14, 2022 (6 pages).

United States Patent Office Notice of Allowance for U.S. Appl. No. 16/927,982 dated Jul. 15, 2022 (8 pages).

(56) References Cited

OTHER PUBLICATIONS

United States Patent Office Notice of Allowance for U.S. Appl. No. 16/614,282 dated Aug. 23, 2022 (7 pages).
Alghoul et al., "The effect of hyaluronan hydrogel on fat graft survival," Aesthet Surg J, 2012, 32: 622-633.
American Society of Plastic Surgeons, "2017 Plastic Surgery Statistics Report," Oct. 2018, 25 pages.
Balaji, "Subdermal fat grafting for Parry-Romberg syndrome," Ann Maxillofac Surg, 2014, 4: 55-59.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.
Bennett et al., "Association of Fat Grafting With Patient-Reported Outcomes in Postmastectomy Breast Reconstruction," JAMA Surg, 2017, 152: 944-950.
Brzezienski et al., "Autologous Fat Grafting to the Breast Using REVOLVE System to Reduce Clinical Costs," Ann Plast Surg, 2016, 77: 286-289.
Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.
De Leon-Rodriguez et al., "Multifunctional thermoresponsive designer peptide hydrogels," Acta Biomaterialia, 2017, 47: 40-49.
Eom et al., "The number of operations required for completing breast reconstruction," Plast Reconstr Surg Glob Open, 2012, 2: e242.
Frandsen et al., "Recombinant protein-based polymers for advanced drug delivery," Chem Soc Rev, 2012, 41: 2696-2706.
Gabriel et al., "Fat grafting and breast reconstruction: tips for ensuring predictability," Gland Surg, 2015, 4:232-243.
Gylbert, "Applanation tonometry for the evaluation of breast compressibility," Scand J Plast Reconstr Surg Hand Surg, 1989, 23: 223-229.
Hess et al., "Graphene Transistors for Multifunctional Polymer Brushes for Biosensing Applications," Applied Materials & Interfaces, 2014, 6: 9705-9710.
Hsu et al., "Fat grafting's past, present, and future: why adipose tissue is emerging as a critical link to the advancement of regenerative medicine," Aesthet Surg J, 2015, 32: 892-899.
Hwang et al., "Synthesis and Characterization of Polystyrene Brushes for Organic Thin Film Transistors," Journal of Nanoscience and Nanotechnology, 2012, 12: 4137-4141.
Kronowitz et al., "Delayed-Immediate Breast Reconstruction," Plastic and Reconstructive Surgery, 2004, 113: 1617-1628.
Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Pan et al., "A Pig Model for the Histological Analysis of Adipocytes after Co-injections of Autologous Fat with Fillers," International Journal of Surgery & Surgical Techniques, 2016, 2: 7 pages.
Park et al., "Polymer Brush As a Facile Dielectric Surface Treatment for High-Performance, Stable, Soluble Acene-Based Transistors," Chemistry of Materials, 2010, 22: 5377-5382.
Rasmussen et al., "A Novel Porcine Model for Future Studies of Cell-enriched Fat Grafting," Plast Reconstr Surg Glob Open, 2018, 6: e1735.
Roca et al., "Autologous Fat Grafting for Treatment of Breast Implant Capsular Contracture: A Study in Pigs," Aesthet Surg J, 2014, 34: 769-775.
Sandberg et al., "The Structure of the Elastic Fiber: An Overview," The Journal of Investigative Dermatology, 1982, 79(S1): 128s-132s.
Simonacci et al., "Procedure, applications, and outcomes of autologous fat grafting," Ann Med Surg (Lond), 2017, 20: 49-60.
Strong et al., "The Current State of Fat Grafting: A Review of Harvesting, Processing, and Injection Techniques," Plast Reconstr Surg, 2015, 136: 897-912.
Tamburro et al., "Fractal aspects of elastin supramolecular organization," J Biomol Struct Dyn, 1995, 12: 1161-1172.
Toshima et al., "Three-dimensional architecture of elastin and collagen fiber networks in the human and rat lung," Arch Histol Cytol, 2004, 67: 31-40.
UniProtKB—P15214 (GST_PROMI) acessed online at <https://www.uniprot.org/uniprot/P152146/> on Jun. 8, 2021, 7 pages.
Wang et al., "Pigs Can Be Used as a Large Animal Model for Autologous Fat Grafting," Ophthalmic Plast Reconstr Surg, 2016, 32: 73-74.
Wu et al., "An injectable adipose matrix for soft-tissue reconstruction," Plast Reconstr Surg, 2012, 129: 1247-1257.
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).
Chan et al., "A randomized, repeat-dose, pharmacodynamic and safety study of an antidote-controlled factor IXa inhibitor," J Thromb Haemost, 2008, 6(5): 789-796.
Chan et al., "Phase 1b randomized study of antidote-controlled modulation of factor IXa activity in patients with stable coronary artery disease," Circulation, 2008, 117(22): 2865-2874.
Chappell et al., "Computational design of small transcription activating RNAs for versatile and dynamic gene regulation," Nat Commun, 2017, 8(1): 1051.
Chappell et al., "Creating small transcription activating RNAs," Nat Chem Biol, 2015, 11(3): 214-220.
Chase et al., "Single-Stranded DNA Binding Proteins Required for DNA Replication," Ann. Rev. Biochem., 1986, 55: 103-136.
Cohen et al., "First clinical application of an actively reversible direct factor IXa inhibitor as an anticoagulation strategy in patients undergoing percutaneous coronary intervention," Circulation, 2010, 122(6): 614-622.
Dale et al., "Direct covalent mercuration of nucleotides and polynucleotides," Biochemistry, 1975, 14(11): 2447-2457.
Davis et al., "Antibodies and the RNA World: A Role for Low-molecular-weight Effectors in Biochemical Evolution," RNA World, 1993, Chapter 8, p. 185-204.
Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.
Eichhorn et al., "Interactions of metal ions with polynucleotides and related compounds. XII. The relative effect of various metal ions on DNA helicity," J. Am. Chem. Soc, 1968, 90: 7323-7328.
Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.
Gold et al., "Aptamers and the RNA World, Past and Present," Cold Spiing Harbor Perspect. Biol., 2012, 4: a003582, 9 pages.
Heus, "RNA aptamers," Nat Struct Biol, 1997, 4(8): 597-600.
Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.
Hwang et al., "Inhibition of gene expression in human cells through small molecule-RNA interactions," Proc. Natl. Acad. Sci. USA, 1999, 96(23): 12997-13002.
Keefe et al., "Aptamers as therapeutics," Nature Reviews Drug Discovery, 2010, 9: 537-550.
Korte et al., "Short activated partial thromboplastin times are related to increased thrombin generation and an increased risk for thromboembolism," Am J Clin Pathol, 2000, 113(1): 123-127.
Li et al., "Ferric Chloride-induced Murine Thrombosis Models," J. Vis. Exp., 2016, 115: e54479, 12 pages.
Lincoff et al., "Effect of the REG1 anticoagulation system versus bivalirudin on outcomes after percutaneous coronary intervention (REGULATE-PCI): a randomised clinical trial," Lancet, 2016, 387(10016): 349-356.

(56) References Cited

OTHER PUBLICATIONS

Lippard et al., "Platinum complexes: probes of polynucleotide structure and antitumor drugs," Acc. Chem. Res., 1978, 11(5): 211-217.
Maier et al., "From selection hits to clinical leads: progress in aptamer discovery," Mol. Ther. Methods Clin. Dev., 2016, 3: 16014, 10 pages.
McManus et al., "Gene silencing in mammals by small interfering RNAs," Nat Rev Genet, 2002, 3(10): 737-747.
Moreno et al., "Anti-PEG Antibodies Inhibit the Anticoagulant Activity of PEGylated Aptamers," Cell Chem Biol, 2019, 26(5): 634-644.e3.
Nimjee et al., "Aptamers as Therapeutics," Annu Rev Pharmacol Toxicol, 2017, 57: 61-79.
Pisal et al., "Delivery of therapeutic proteins," Journal of Pharmaceutical Sciences, 2010, 99(6): 2557-2575.
Povsic et al., "A Phase 2, randomized, partially blinded, active-controlled study assessing the efficacy and safety of variable anticoagulation reversal using the REG1 system in patients with acute coronary syndromes: results of the RADAR trial," Eur Heart J, 2013, 34(31): 2481-2489.
Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Purtell et al., "Isoelectric point of albumin: effect on renal handling of albumin," Kidney Int, 1979, 16(3): 366-376.
Richter et al., "Mechanistic determinants of biotherapeutics absorption following SC administration," AAPS J, 2012, 14(3): 559-570.
Rinaldi et al., "Antisense oligonucleotides: the next frontier for treatment of neurological disorders," Nat Rev Neurol, 2018, 14(1): 9-21.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor Ixa," Nature, 2002, 19(6902): 90-94.
Shu et al., "GISAID: Global initiative on sharing all influenza data—from vision to reality," Euro Surveill 22, 2017, 22(13): 30494, 3 pages.
Smith et al., "Coronaviruses lacking exoribonuclease activity are susceptible to lethal mutagenesis: evidence for proofreading and potential therapeutics," PLoS Pathog, 2013, 9: e1003565, 11 pages.
Tuerk et al., "Systematic evolution of ligands by exponential enrichment: RNA ligands to bacteriophage T4 DNA polymerase," Science, 1990, 249(4968): 505-510.
Werstuck et al., "Controlling gene expression in living cells through small molecule-RNA interactions," Science, 1998, 282(5387): 296-298.
Woodruff et al., "Modulation of the Coagulation Cascade Using Aptamers," Arterioscler Thromb Vasc Biol, 2015, 35(10): 2083-2091.
Yamaoka et al., "Distribution and tissue uptake of poly (ethylene glycol) with different molecular weights after intravenous administration to mice," Journal of Pharmaceutical Sciences, 1994, 83(4): 601-606.
Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.
Zhou et al., "Aptamers as targeted therapeutics: current potential and challenges," Nat Rev Drug Discov, 2017, 16(3): 181-202.
Gilroy et al., "Sustained release of a GLP-1 and FGF21 dual agonist from an injectable depot protects mice from obesity and hyperglycemia," Science Advances, 2020, 6(35): eaaz9890, 12 pages.
United States Patent Office Notice of Allowance for U.S. Appl. No. 15/749,797 dated Mar. 16, 2022 (6 pages).
United States Patent Office Action for U.S. Appl. No. 16/477,229 dated Mar. 3, 2022 (10 pages).
Ren et al., "Stimulus-Responsive Polymer Prodrugs," Progress in Chemistry, 2013,25(5): 10 pages.

United States Patent Office Action for U.S. Appl. No. 16/614,282 dated Apr. 27, 2022 (15 pages).
United States Patent Office Notice of Allowance for U.S. Appl. No. 16/305,696 dated May 23, 2022 (10 pages).
United States Patent Office Notice of Allowance for U.S. Appl. No. 16/305,696 dated Jun. 10, 2022 (4 pages).
United States Patent Office Notice of Allowance for U.S. Appl. No. 15/749,797 dated Jun. 2, 2022 (6 pages).
United States Patent Office Action for U.S. Appl. No. 16/477,229 dated Jun. 13, 2022 (11 pages).
AACR, "AACR Cancer Progress Report 2016," Clin Cancer Res, Oct. 2016, vol. 22, Issue 19, 143 pages.
Aaron et al., "Elastin as a Random-Network Elastomer—a Mechanical and Optical Analysis of Single Elastin Fibers," Biopolymers, 1981, 20(6):1247-1260.
Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, Jul. 2009, vol. 90B, Issue 1, pp. 67-74.
Adamska et al., "Pancreatic ductal adenocarcinoma: Current and evolving therapies," J Mol Sci, Jun. 2017, vol. 18, Issue 7, pp. 1338-1380.
Adiseshaiah et al., "Nanomedicine strategies to overcome the pathophysiological barriers of pancreatic cancer," Nat Rev Clin Oncol, Dec. 2016, vol. 13, Issue 12, pp. 750-765.
Aladini et al., "Chemical Synthesis and Characterization of Elastin-Like Polypeptides (ELPs) With Variable Guest Residues," J Pept Sci, May 2016, vol. 22, Issue 5, pp. 334-342.
Alarcon et al., "Exendin 4 controls insulin production in rat islet beta cells predominantly by potentiation of glucose-stimulated proinsulin biosynthesis at the translational level," Diabetologia, 2006, 49(12):2920-2929.
Albanese et al., "The effect of nanoparticle size, shape, and surface chemistry on biological systems," Annu. Rev. Biomed. Eng., Aug. 2012, vol. 14, pp. 1-16.
Alconcel et al., "FDA-approved poly(ethylene glycol)-protein conjugate drugs," Polym. Chem., vol. 2, Apr. 2011, Issue 7, pp. 1442-1448.
Allen et al., "Liposomal drug delivery systems: from concept to clinical applications," Adv Drug Deliv Rev, Elsevier, Jan. 2013, 65(1):36-48.
Alley et al., "Feasibility of drug screening with panels of human tumor cell lines using a microculture tetrazolium assay," Cancer Res., 1988, 48, 589-601.
Aluri et al., "Elastin-like peptide amphiphiles Form nanofibers with tunable length," Biomacromolecules, Sep. 2012, vol. 13, Issue 9, pp. 2645-2654.
American Diabetes Association, Standards of medical care in diabetes—2018. Diabetes Care, Jan. 2018, vol. 41, Supplement 1, pp. S1-S159.
Amiram et al., "A depot-forming glucagon-like peptide-1 fusion protein reduces blood glucose for five days with a single injection," J. Control. Release, Nov. 2013, vol. 172, Issue, pp. 144-151.
Amiram et al., "Injectable protease-operated depots of glucagon-like peptide-1 provide extended and tunable glucose control," Proc. Natl. Acad. Sci., Feb. 2013, vol. 110, Issue 8, pp. 2792-2797.
Andersen et al., "Extending Half-life by Indirect Targeting of the Neonatal Fc Receptor (FcRn) Using a Minimal Albumin Binding Domain," Journal of Biological Chemistry, Feb. 2011, vol. 286, Issue 7, pp. 5234-5241.
Anselmo et al., "Nanoparticles in the clinic, " Bioeng Transl Med, Jun. 2016, 1(1):10-29.
Antos et al., "Lipid Modification of Proteins through Sortase-Catalyzed Transpeptidation," J. Am. Chem. Soc., Dec. 2008, vol. 130, Issue 48, pp. 16338-16343.
Antos et al., "Site-Specific N- and C-Terminal Labeling of a Single Polypeptide Using Sortases of Different Specificity," J. Am. Chem. Soc., Aug. 2009, vol. 131, Issue 31, pp. 10800-10801.

(56) References Cited

OTHER PUBLICATIONS

Arami et al., "In vivo delivery, pharmacokinetics, biodistribution and toxicity of iron oxide nanoparticles," Chem Soc Rev, Dec. 2015, 44(23):8576-8607.
Arias et al., "Superior preclinical efficacy of gemcitabine developed as chitosan nanoparticulate system," Biomacromolecules, Jan. 2011, vol. 12, Issue 1, pp. 97-104.
Armstrong et al., "Antibody against poly(ethylene glycol) adversely affects PEG-asparaginase therapy in acute lymphoblastic leukemia patients," Cancer, Jul. 2007, vol. 110, Issue 1, pp. 103-111.
Armstrong et al., "The Hydrodynamic Radii of Macromolecules and Their Effect on Red Blood Cell Aggregation," Biophys. J., 2004, 87, 4259-4270.
Arner et al., "FGF21 attenuates lipolysis in human adipocytes—a possible link to improved insulin sensitivity," FEBS Lett, May 2008, vol. 582, Issue 12, pp. 1725-1730.
Arnida et al., "Geometry and surface characteristics of gold nanoparticles influence their biodistribution and uptake by macrophages," Eur J Pharm Biopharm, Apr. 2011, vol. 77, Issue 3, pp. 417-423.
Asai et al., "Protein polymer hydrogels by in situ, rapid and reversible self-gelation," Biomaterials, Jul. 2012, vol. 33, Issue 21, pp. 5451-5458.
Astete et al., "Synthesis and characterization of PLGA nanoparticles," Journal of Biomaterials Science, Polymer Edition 2006, 17(3):247-289.
Atun et al., "Expanding global access to radiotherapy," Lancet Oncol, Sep. 2015, vol. 16, Issue 10, pp. 1153-1186.
Averick et al., "ATRP under biologically relevant conditions: grafting from a protein," ACS Macro. Lett., Jan. 2012, vol. 1, Issue 1, pp. 6-10.
Averick et al., "Protein-polymer hybrids: conducting ARGET ATRP from a genetically encoded cleavable ATRP initiator," Eur. Polym. J., Oct. 2013, vol. 49, Issue 10, pp. 2919-2924.
Awai et al., "Studies of the metabolism of I-131-labeled human transferrin," J. Lab. Clin. Med. 61, 1963, 363-396.
Awasthi et al., "Comparative benefits of Nab-paclitaxel over gemcitabine or polysorbate-based docetaxel in experimental pancreatic cancer," Carcinogenesis, Oct. 2013, vol. 34, Issue 10, pp. 2361-2369.
Awasthi et al., "Evaluation of combination treatment benefits of nab-paclitaxel in experimental pancreatic cancer," Journal of Clinical Oncology, 2012, 30, 170.
Axup et al., "Synthesis of site-specific antibody-drug conjugates using unnatural amino acids," Proc Natl Acad Sci USA, Feb. 2012, vol. 109, Issue 40, pp. 16101-16106.
Azhdarinia et al., "Regional radiochemotherapy using in situ hydrogel," Pharm Res., 2005, 22, 776-783.
Babu, "The contribution of intrinsically disordered regions to protein function, cellular complexity, and human disease," Biochem Soc Trans, Oct. 2016, 44(5):1185-1200.
Bache et al., "Investigating the accuracy of microstereotactic-body-radiotherapy utilizing anatomically accurate 3D printed rodent-morphic dosimeters," Medical Physics, Feb. 2015, vol. 42, Issue 2, pp. 846-855.
Badi, "Non-linear PEG-based thermoresponsive polymer systems," Progress in Polymer Science, Mar. 2017, vol. 66, pp. 54-79.
Bae et al., "Targeted drug delivery to tumors: myths, reality and possibility," J Control Release, Elsevier, Aug. 2011, 153(3):198-205.
Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.
Baggio et al., "Biology of Incretins: GLP-1 and GIP," Gastroenterology, May 2007, vol. 132, Issue 6, pp. 2131-2157.
Bailey et al., "Genomic analyses identify molecular subtypes of pancreatic cancer," Nature, Mar. 2016, vol. 531, Issue 7592, pp. 47-52.
Balu et al., "An16-resilin: an advanced multi-stimuli-responsive resilin-mimetic protein polymer," Acta Biomater, Nov. 2014, 10:4768-4777.
Bamford et al., "The COSMIC (Catalogue of Somatic Mutations in Cancer) database and website," British Journal of Cancer, 2004, 91, 355-358.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, Elsevier, Nov. 2011, 104:489-507.
Banga et al., "Parenteral controlled delivery and parmacokinetics of therapeutic peptides and proteins," (CRC Press, Boca Raton, FL, 2005).
Banjade et al., "Phase transitions of multivalent proteins can promote clustering of membrane receptors," Elife, Oct. 2014, 3:e04123.
Bansal et al., "PEGylation improves pharmacokinetic profile, liver uptake and efficacy of Interferon gamma in liver fibrosis," J. Control. Release, Sep. 2011, vol. 154, Issue 3, pp. 233-240.
Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.
Barbuti et al., "Paclitaxel through the ages of anticancer therapy: Exploring its role in chemoresistance and radiation therapy," Cancers, Dec. 2015, vol. 7, Issue 4, pp. 2360-2371.
Barnett et al., "Normal tissue reactions to radiotherapy: towards tailoring treatment dose by genotype," Nat Rev Cancer, Feb. 2009, vol. 9, Issue 2, pp. 134-142.
Barton et al., "Estimating the demand for radiotherapy form the evidence: A review of changes from 2003 to 2012," Radiother Oncol, Jul. 2014, vol. 112, Issue 1, pp. 140-144.
Baskar et al., "Cancer and Radiation Therapy: Current Advances and Future Directions," Int. J. Med. Sci., Feb. 2012, vol. 9, Issue 3, pp. 193-199.
Bates et al., "Block copolymer thermodynamics: theory and experiment," Annu Rev. Phys. Chem., 1990, 41:525-57.
Bedford et al., "WW domain-mediated interactions reveal a spliceosome-associated protein that binds a third class of proline-rich motif: The proline glycine and methionine-rich motif," PNAS, 1998, 95: 10602-10607.
Beenken et al., "The FGF family: biology, pathophysiology and therapy," Nat Rev Drug Discov, Mar. 2009, vol. 8, Issue 3, pp. 235-253.
Begg et al., "Strategies to improve radiotherapy with targeted drugs," Nat Rev Cancer, Apr. 2011, vol. 11, Issue 4, pp. 239-253.
Bellucci et al., "A noncanonical function of sortase enables site-specific conjugation of small molecules to lysine residues in proteins," Angew. Chem. Int. Ed. 54, Jan. 2015, vol. 54, Issue 2, pp. 441-445.
Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, Mar. 2013, vol. 52, Issue 13, pp. 3703-3708.
Bender et al., "Synthesis, Crystallization, and Biological Evaluation of an Orally Active Prodrug of Gemcitabine," J. Med. Chem., Nov. 2009, vol. 52, Issue 22, pp. 6958-6961.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.
Bernacki et al., "Length-dependent aggregation of uninterrupted polyalanine peptides," Biochemistry, Sep. 2011, vol. 50, Issue 43, pp. 9200-9211.
Berndt et al., "Synthetic lipidation of peptides and amino acids: Monolayer structure and properties," J. Am. Chem. Soc., 1995, 117, 9515-9522.
Bessa et al., "Thermoresponsive self-assembled elastin-based nanoparticles for delivery of BMPs," Journal of Controlled Release, Mar. 2010, vol. 142, Issue 3, pp. 312-318.
Best, "Computational and theoretical advances in studies of intrinsically disordered proteins," Curr Opin Struct Biol, Feb. 2017, 42:147-154.
Bhattacharyya et al., "A paclitaxel-loaded recombinant polypeptide nanoparticle outperforms Abraxane in multiple murine cancer models," Nat. Commun., Aug. 2015, Issue 6, Article 7939, 30 pages.

(56) References Cited

OTHER PUBLICATIONS

Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, Mar. 2017, vol. 27, Issue 12, Article 1605421, 9 pages.
Bidwell et al., "Development of elastin-like polypeptide for thermally targeted delivery of doxorubicin," Biochemical Pharmacology, Mar. 2007, vol. 73, Issue 5, pp. 620-631.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9):941-51.
Blasko et al., "Brachytherapy for carcinoma of the prostate: Techniques, patient selection, and clinical outcomes," Seminars in Radiation Oncology, 2002, 12, 81-94.
Blasko et al., "The role of external beam radiotherapy with I-125/Pd-103 brachytherapy for prostate carcinoma," Radiother Oncol, 2000, 57, 273-278.
Blasko et al., "Transperineal percutaneous iodine-125 implantation for prostatic carcinoma using transrectal ultrasound and template guidance," Endocurietherapy/Hyperthermia Oncology, 1987, 3, 131-139.
Bley et al., "Microtubule stabilising agents and ionising radiation: Multiple exploitable mechanisms for combined treatment," Eur J Cancer, Jan. 2013, vol. 49, Issue 1, pp. 245-253.
Bobo et al., "Nanoparticle-based medicines: a review of FDA-approved materials and clinical trials to date." Pharmaceutical research, Oct. 2016, vol. 33, Issue 10, pp. 2373-2387.
Bocci et al., "The pharmacological bases of the antiangiogenic activity of paclitaxel," Angiogenesis, Jul. 2013, vol. 16, Issue 3, pp. 481-492.
Bochicchio et al., "Investigating by CD the molecular mechanism of elasticity of elastomeric proteins," Chirality, Sep. 2008, vol. 20, Issue 9, pp. 985-994.
Boekhorst et al., "Genome-wide detection and analysis of cell wall-bound proteins with LPxTG-like sorting motifs," J. Bacteriol. 187, 2005, 4928-4934.
Boeynaems et al., "Protein Phase Separation: A New Phase in Cell Biology," Trends Cell Biol, Jun. 2018, 28(6):420-435.
Boldt, "Use of albumin: an update," Br J. Anaesth., Mar. 2010, vol. 104, Issue 3, pp. 276-284.
Bond, "Exenatide (Byetta) as a novel treatment option for type 2 diabetes mellitus," Proc. (Bayl. Univ. Med. Cent.), Jul. 2006, vol. 19, Issue 3, pp. 281-284.
Bontempo et al., "Streptavidin as a macroinitiator for polymerization: in situ protein-polymer conjugate formation," J. Am. Chem. Soc., 2005, 6508-6509.
Borst et al., "The Therapeutic Antibody LM609 Selectively Inhibits Ligand Binding to Human αVβ3 Integrin via Steric Hindrance," Structure, Nov. 2017, 25(11):1732-1739.e5.
Bowditch et al., "Identification of a novel integrin binding site in fibronectin. Differential utilization by β3 integrins," Journal of Biological Chemistry, 1994, 269(14):10856-10863.
Boyer et al., "Well-Defined Protein-Polymer Conjugates via in Situ RAFT Polymerization," J. Am. Chem. Soc., Jun. 2007, vol. 129, Issue 22, pp. 7145-7154.
Branco et al., "Self-assembling materials for therapeutic delivery," Acta Biomaterialia, Mar. 2009, vol. 5, Issue 3, pp. 817-831.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, Elsevier, Sep. 2012, 64(11):206-212.
Broome et al., "Expanding the utility of beta-galactosidase complementation: piece by piece," Mol Pharm, ACS Publications, Feb. 2010, 7(1):60-74.
Broyer et al., "Emerging synthetic approaches for protein-polymer conjugations," Chem. Commun., Feb. 2011, vol. 47, Issue 8, pp. 2212-2226.
Brusa et al., "Antitumor activity and pharmacokinetics of liposomes containing lipophilic gemcitabine prodrugs," Anticancer Res., Jan. 2007, vol. 27, Issue 1A, pp. 195-199.
Burchard, "Light Scattering Techniques," Physical techniques for the study of food biopolymers, 1994, 151-213.
Burke et al., "Multimodal nanoparticle imaging agents: design and applications," Philos Trans A Math Phys Eng Sci, Nov. 2017, 375:20170261.
Burnouf, "Modern plasma fractionation," Transfus. Med. Rev., Apr. 2007, vol. 21, Issue 2, pp. 101-117.
Buteau et al., "Glucagon-like peptide-1 prevents beta cell glucolipotoxicity," Diabetologia, 2004, 47(5):806-815.
Butler et al., "β-Cell Deficit and Increased β-Cell Apoptosis in Humans With Type 2 Diabetes," Diabetes, 2003, 52(1):102-110.
Cabral et al., "Accumulation of sub-100 nm polymeric micelles in poorly permeable tumours depends on size," Nature Nanotechnology, Oct. 2011, vol. 6, Issue 12, pp. 815-823.
Cabrera et al., "Automated, High-Throughput Assays for Evaluation of Human Pancreatic Islet Function," Cell Transplant, First published Nov. 2007, vol. 16, Issue 10, pp. 1039-1048.
Cabrera et al., "Glutamate Is a Positive Autocrine Signal for Glucagon Release," Cell Metab, Jun. 2008, vol. 7, Issue 6, pp. 545-554.
Cai et al., "Long-acting preparations of exenatide," Drug Des. Devel. Ther., Sep. 2013, vol. 7, pp. 963-970.
Caliceti et al., "Pharmacokinetic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, Mar. 2012, vol. 12, Issue 4, pp. 2165-2170.
Camilloni et al., "Determination of secondary structure populations in disordered states of proteins using nuclear magnetic resonance chemical shifts," Biochemistry, Feb. 2012, vol. 51, Issue 11, pp. 2224-2231.
Campbell et al., "Pegylated peptides V. Carboxy-terminal PEGlyted analogs of growth hormone-releasing factor (GRF) display enhanced duration of biological activity in vivo," J. Peptide Res., 1997, 49:527-537.
Cao et al., "Monitoring the effects of anti-angiogenesis on the radiation sensitivity of pancreatic cancer xenografts using dynamic contrast-enhanced computed tomography," Int J Radiation Oncol Biol Phys, Feb. 2014, vol. 88, Issue 2, pp. 412-418.
Cardenes et al., "Locally advanced pancreatic cancer: Current therapeutic approach," The Oncologist, Jun. 2006, vol. 11, Issue 6, pp. 612-623.
Carreiras et al., "Expression and localization of alpha v integrins and their ligand vitronectin in normal ovarian epithelium and in ovarian carcinoma," Gynecol Oncol, 1996, 62(2):260-7.
Carrico et al., "Introducing genetically encoded aldehydes into proteins," Nat Chem Biol, Jun. 2007, vol. 3, Issue 6, pp. 321-322.
Cataldo et al., "Radiation-induced crosslinking of collagen gelatin into a stable hydrogel," Journal of Radioanalytical and Nuclear Chemistry, Sep. 2008, vol. 275, Issue 1, pp. 125-131.
Centers for Disease Control and Prevention, "National Diabetes Statistics Report, 2017," Atlanta, GA: Centers for Disease Control and Prevention, US Department of Health and Human Services; 2017. Reviewed: Feb. 24, 2018.
Ceska et al., "A new and rapid method for the clinical determination of α-amylase activities in human serum and urine. Optimal conditions," Clinica Chimica Acta, 1969, 26, 437-444.
Chakrabartty et al., "Stability of α-Helices," Adv Protein Chem, 1995, 46, 141-176.
Champion et al., "Particle shape: a new design parameter for micro- and nanoscale drug delivery carriers," J Control Release, Elsevier, Aug. 2007, 121(1-2):3-9.
Champion et al., "Role of particle size in phagocytosis of polymeric microspheres," Pharm Res, Srpinger, Mar. 2008, 25(8):1815-21.

(56) References Cited

OTHER PUBLICATIONS

Champion et al., "Role of target geometry in phagocytosis," Proc Natl Acad Sci U S A, The National Academy of Sciences of the USA, Mar. 2006, 103(13):4930-4.

Champion et al., "Shape induced inhibition of phagocytosis of polymer particles," Pharm Res, Springer, Jan. 2009, 26(1):244-9.

Chang et al., "Tumor-stroma interaction in orthotopic primary pancreatic cancer xenografts during hedgehog pathway inhibition," Int. J. Cancer, Jul. 2013, vol. 133, Issue 1, pp. 225-235.

Chatterjee et al., "Type 2 diabetes," The Lancet, Jun. 2017, vol. 389, Issue 10085, pp. 2239-2251.

Chaudhury et al., "The major histocompatibility complex-related Fc receptor for IgG (FcRn) binds albumin and prolongs its lifespan," J Exp Med, 2003, 197(3): p. 315-22.

Chen et al., "Anisotropic hydrogels fabricated with directional freezing and radiation-induced polymerization and crosslinking method," Materials Letters, Dec. 2012, vol. 89, pp. 104-107.

Chen et al., "Anti-hypervariable region antibody induced by a defined peptide: An approach for studying the structural correlates of idiotypes," PNAS, 1984, 81:1784-1788.

Chen et al., "Bioinspired Modular Synthesis of Elastin-Mimic Polymers To Probe the Mechanism of Elastin Elasticity," J. Am. Chem. Soc., Mar. 2010, vol. 132, Issue 13, pp. 4577-4579.

Chen et al., "Rheology of Soft Materials," Annual Review of Condensed Matter Physics, May 2010, vol. 1, pp. 301-322.

Chen et al., "Site-specific labeling of cell surface proteins with biophysical probes using biotin ligase," Nat Methods, 2005, 2(2):99-104.

Chen et al., "The use of self-adjuvanting nanofiber vaccines to elicit high-affinity B cell responses to peptide antigens without inflammation," Biomaterials, Nov. 2013, vol. 34, Issue 34, pp. 8776-8785.

Chen, "Small-molecule delivery by nanoparticles for anticancer therapy," Trends Mol Med, Cell Press, Dec. 2010, 16(12):594-602.

Chilkoti et al., "Design of thermally responsive, recombinant polypeptide carriers for targeted drug delivery," Advance Drug Delivery Reviews, 2002, 54:1093-1111.

Chilkoti et al., "Stimulus responsive elastin biopolymers: applications in medicine and biotechnology," Curr Opin Chem Biol, Dec. 2006, vol. 10, Issue 6, pp. 652-657.

Chilkoti et al., "Targeted drug delivery by thermally responsive polymers," Advanced Drug Delivery Reviews, 2002, 54:613-630.

Chithrani et al., "Determining the size and shape dependence of gold nanoparticle uptake into mammalian cells," Nano Lett, Apr. 2006, vol. 6, Issue 4, pp. 662-668.

Chithrani et al., "Elucidating the mechanism of cellular uptake and removal of protein-coated gold nanoparticles of different sizes and shapes," Nano letters, ACS Publications, Jun. 2007, 7(6):1542-1550.

Chitkara et al., "Self-Assembling, Amphiphilic Polymer-Gemcitabine Conjugate Shows Enhanced Antitumor Efficacy Against Human Pancreatic Adenocarcinoma," Bioconjug. Chem., Jun. 2013, vol. 24, Issue 7, pp. 1161-1173.

Cho et al., "Effects of hofmeister anions on the phase transition temperature of elastin-like polypeptides," J. Phys. Chem. B., Nov. 2008, vol. 112, Issue 44, pp. 13765-13771.

Cho et al., "Hydrogen bonding of β-turn structure is stabilized in D(2)O," J Am Chem Soc, Oct. 2009, vol. 131, Issue 42, pp. 15188-15193.

Cho et al., "Therapeutic nanoparticles for drug delivery in cancer," Clin. Cancer Res., Mar. 2008, vol. 14, Issue 5, pp. 1310-1316.

Chockalingam et al., "Design and application of stimulus-responsive peptide systems," Protein Engineering, Design & Selection, Apr. 2007, 20(4):155-161.

Choi et al., "Renal Clearance of Nanoparticles," Nature biotechnology, Oct. 2007, vol. 25, Issue 10, pp. 1165-1170.

Chow et al., "Peptide-based biopolymers in biomedicine and biotechnology," Mater. Sci. Eng. R Reports, Jan. 2008, vol. 62, Issue 4, pp. 125-155.

Chow et al., "Ultra-High Expression of a Thermally Responsive Recombinant Fusion Protein in E. coli," Biotechnology Progress, Sep. 2006, vol. 22, Issue 3, pp. 638-646.

Choy et al., "Investigation oftaxol as a potential radiation sensitizer," Cancer, 1993, 71, 3774-3778.

Christensen et al., "Fusion order controls expression level and activity of elastin-like polypeptide fusion proteins," Protein Science, Jul. 2009, vol. 18, Issue 7, pp. 1377-1387.

Christensen et al., "Predicting Transition Temperatures of Elastin-Like Polypeptide Fusion Proteins," Biomacromolecules, Mar. 2013, vol. 14, Issue 5, pp. 1514-1519.

Cid-Arregui et al., "Perspectives in the treatment of pancreatic adenocarcinoma," World Journal of Gastroenterology, Aug. 2015, vol. 21, Issue 31, pp. 9297-9316.

Ciezki et al., "Brachytherapy or surgery? A composite view," Oncology, Oct. 2009, vol. 23, Issue 11, pp. 960-964.

Cima, "AVMA Guidelines for the Euthanasia of Animal: 2013 Edition," Journal of the American Veterinary Medical Association, Jan. 2013, vol. 242, 102 pages.

Cirulis et al., "Viscoelastic properties and gelation of an elastin-like polypeptide," Journal of Rheology, Sep. 2009, vol. 53, Issue 5, pp. 1215-1228.

Clarke et al., "Tropoelastin massively associates during coacervation to form quantized protein spheres," Biochemistry, Jul. 2006, vol. 45, Issue 33, pp. 9989-9996.

Clavé et al., "Amylase, lipase, pancreatic isoamylase, and phospholipase A in diagnosis of acute pancreatitis," Clinical Chemistry, 1995, 41, 1129-1134.

Coin et al., "Solid-phase peptide synthesis: from standard procedures to the synthesis of difficult sequences," Nat. Protoc., Dec. 2007, vol. 2, Issue 12, 3247-3256.

Colomb et al., "Radiation-Convertible Polymers from Norbornenyl Derivatives. Crosslinking with Ionizing Radiation," Journal of Applied Polymer Science, 1970, 14, 1659-1670.

Conner et al., "Regulated portals of entry into the cell," Nature, 2003, 422(6927):37-44.

Conrad et al., "ELPylated anti-human TNF therapeutic single-domain antibodies for prevention of lethal septic shock," Plant Biotechnology Journal, Jan. 2011, vol. 9, Issue 1, pp. 22-31.

Coskun et al., "Fibroblast Growth Factor 21 Corrects Obesity in Mice," Endocrinology, Dec. 2008, vol. 149, Issue 12, pp. 6018-6027.

Costa et al., "Active Targeting of Cancer Cells by Nanobody Decorated Polypeptide Micelle with Bio-orthogonally Conjugated Drug," Nano letters, Dec. 2018, 19(1):247-254.

Craik et al., "The future of peptide-based drugs," Chemical biology & drug design 81, Dec. 2013, vol. 81, Issue 1, pp. 136-147.

Cui et al., "Amino acid sequence in constitutionally isomeric tetrapeptide amphiphiles dictates architecture of one-dimensional nanostructures," J. Am. Chem. Soc., Aug. 2014, vol. 136, Issue 35, 12461-12468.

Cui et al., "Self-assembly of peptide amphiphiles: from molecules to nanostructures to biomaterials," Biopolymers, Jan. 2010, vol. 94, Issue 1, pp. 1-18.

Dai et al., "Versatile biomanufacturing through stimulus-responsive cell-material feedback," Nature chemical biology, Sep. 2019, 15(10):1017-1024.

Dalhaimer et al., "Single Molecule Visualization of Stable, Stiffness-Tunable, Flow-Conforming Worm Micelles," Macromolecules, 2003, 36(18):6873-6877.

Dalia Poza et al., "Targeting gemcitabine containing liposomes to CD44 expressing pancreatic adenocarcinoma cells causes an increase in the antitumoral activity," Biochim. Biophys. Acta, May 2013, vol. 1828, Issue 5, pp. 1396-1404.

Darzynkiewicz et al., "DNA content measurement for DNA ploidy and cell cycle analysis," Current Protocols in Cytometry, 2001, 7.5.1-7.5.24.

Das et al., "Conformations of intrinsically disordered proteins are influenced by linear sequence distributions of oppositely charged residues," Proc Natl Acad Sci U S A, National Academy of Sciences, Aug. 2013, 110(33):13392-13397.

Dasgupta et al., "Isopeptide Ligation Catalyzed by Quintessential Sortase A: Mechanistic Cues From Cyclic and Branched Oligomers

(56) References Cited

OTHER PUBLICATIONS of Indolicidin," The Journal of Biological Chemistry, May 2011, vol. 286, No. 27, pp. 23996-24006, Supplemental Information.
Day et al., "A new glucagon and GLP-1 co-agonist eliminates obesity in rodents," Nat Chem Biol, Oct. 2009, 5:749.
De et al., "Temperature-Regulated Activity of Responsive Polymer-Protein Conjugates Prepared by Grafting-from via RAFT Polymerization," J. Am. Chem. Soc. Jul. 2008, 130, 11288-11289.
De Simone et al., "Accurate random coil chemical shifts from an analysis of loop regions in native states of proteins," J Am Chem Soc, Nov. 2009, 131, 16332-16333.
Deer et al., "Phenotype and genotype of pancreatic cancer cell lines," Pancreas, May 2010, 39, 425-435.
Dejana et al., "The role of adherens junctions and VE-cadherin in the control of vascular permeability," J Cell Sci, Jul. 2008, 121, 2115-2122.
Delaglio et al., "NMRPipe: A multidimensional spectral processing system based on UNIX pipes," Journal of Biomolecular NMR 6, 1995, 277-293.
DeLisser et al., "Vascular endothelial platelet endothelial cell adhesion molecule 1 (PECAM-1) regulates advanced metastatic progression," PNAS, Oct. 2010, 107, 18616-18621.
Dennis et al., "Albumin binding as a general strategy for improving the pharmacokinetics of proteins," J Biol Chem, 2002, 277(38): p. 35035-43.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: A viable and potentially superior alternative to PEGylation for stabilizing biologies," Acta Biomater. Feb. 2009, 5, 560-569.
Deshayes et al., "Radium 223 dichloride for prostate cancer treatment," Drug Des Devel Ther, Sep. 2017, 11, 2643-2651.
DeYoung et al.,"Encapsulation of exenatide in poly-(D,L-lactide-co-glycolide) microspheres produced an investigational long-acting once-weekly formulation for type 2 diabetes," Diabetes Technol Ther, Nov. 2011, 13, 1145-1154.
Diana et al., "Prognostic role and correlation of CA9, CD31, CD68 and CD20 with the desmoplastic stroma in pancreatic ductal adenocarcinoma," Oncotarget, Nov. 2016, 7, 72819-72832.
Diehl et al., "A Good Practice Guide to the Administration of Substances and Removal of Blood Including Routes and Volumes," J Appl Toxicol, 2001, 21, 15-23.
Dignon et al., "Relation between single-molecule properties and phase behavior of intrinsically disordered proteins," Proc Natl Acad Sci U S A, Oct. 2018, 115(40):9929-9934.
Dignon et al., "Sequence determinants of protein phase behavior from a coarse-grained model," PLoS Comput Biol, Jan. 2018, 14(1):e1005941.
Ding et al., "Mechanism for the alpha-helix to beta-hairpin transition," Proteins, 2003, 53, 220-228.
Ding et al., "βKlotho Is Required for Fibroblast Growth Factor 21 Effects on Growth and Metabolism," Cell Metab, Sep. 2012, 16(3):387-393.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. Jan. 2008, 130, 687-694.
Dreher et al., "Thermal cycling enhances the accumulation of a temperature-sensitive biopolymer in solid tumors," Cancer Res, May 2007, 67, 4418-4424.
Dreher, M. R. Ph.D. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm., Aug. 2007, 341, 207-214.

Drucker "Mechanisms of Action and Therapeutic Application of Glucagon-like Peptide-1," Cell Metab, Apr. 2018, 27(4):740-756.
Drucker et al., "The incretin system: glucagon-like peptide-1 receptor agonists and dipeptidyl peptidase-4 inhibitors in type 2 diabetes," Lancet 368, Nov. 2006, 1696-1705.
Drucker, "Glucagon-like peptides," Diabetes 47, 1998, 159-169.
Drucker, "Incretin action in the pancreas: potential promise, possible perils, and pathological pitfalls," Diabetes, Oct. 2013, 62, 3316-3323.
Du et al., "Endoscope-assisted brachytherapy for pancreatic cancer: From tumor killing to pain relief and drainage," Journal of interventional gastroenterology, Jan. 2011, 1, 23-27.
Du et al., "Tailor-made dual pH-sensitive polymer-doxorubicin nanoparticles for efficient anticancer drug delivery," J. Am. Chem. Soc., Oct. 2011, 133, 17560-17563.
Duan et al., "Fibronectin type III domain based monobody with high activity," Biochemistry, Oct. 2007 46(44):12656-12664.
Duan et al., "Improving the thermostability and catalytic efficiency of Bacillus deramificans pullulanase by site-directed mutagenesis," Appl Environ Microbiol, American Society for Microbiology, Jul. 2013, 79(13):4072-4077.
Dubey et al., "Development and evaluation of folate functionalized albumin nanoparticles for targeted delivery of gemcitabine," Int J Pharm., Aug. 2015, 492(1-2):80-91.
Ducreux et al., "Radiation plus docetaxel and cisplatin in locally advanced pancreatic carcinoma: A non-comparative randomized phase II trial," Digestive and Liver Disease, Oct. 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Webpage accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer, Sep. 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
Ehlerding et al., "Biodegradable and Renal Clearable Inorganic Nanoparticles," Adv Sci (Weinh), Feb. 2016, 3(2):1500223.
Eisenhaber et al., "Prediction of lipid posttranslational modifications and localization signals from protein sequences: Big-Π, NMT and PTS1," Nucleic Acids Res., 2003, 31, 3631-3634.
Eisenhauer et al., "New response evaluation criteria in solid tumours: Revised RECIST guideline (version 1.1)," Eur J Cancer, Jan. 2009, 45(2):228-247.
El-Assaad et al., "Saturated Fatty Acids Synergize with Elevated Glucose to Cause Pancreatic β-Cell Death," Endocrinology, 2003, 144(9):4154-4163.
Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.
Ellis, "Macromolecular crowding: obvious but underappreciated," Trends Biochem. Sci., 2001, 26 (10), 597-604.
Elsabahy et al., "Design of polymeric nanoparticles for biomedical delivery applications," Chem Soc Rev, Royal Society of Chemistry, Apr. 2012, 41(7):2545-61.
Elvin et al., "Synthesis and properties of crosslinked recombinant pro-resilin," Nature, 2005, 437(7061):999-1002.

(56) References Cited

OTHER PUBLICATIONS

Elzoghby et al., "Implications of Protein- and Peptide-Based Nanoparticles as Potential Vehicles for Anticancer Drugs," Advances in Protein Chemistry and Structural Biology, Academic Press, Elsevier, Mar. 2015, Chapter Six, vol. 98, pp. 169-221.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, Jun. 2010, 7(4):1015-1026.
Falk et al., "Hyperthermia in oncology," Int J Hyperthermia, 2001, 17, 1-18.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.
Farokhzad et al., "Targeted nanoparticle-aptamer bioconjugates for cancer chemotherapy in vivo," Proc Natl Acad Sci U S A, The National Academy of Sciences of the USA, Apr. 2006, 103(16):6315-20.
Feng et al., "Protein resistant surfaces: comparison of acrylate graft polymers bearing oligoethylene oxide and phosphorylcholine side chains," Biointerphases, Mar. 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, Sep. 2015, 16, 3389-3398.
Finan et al., "A rationally designed monomeric peptide triagonist corrects obesity and diabetes in rodents," Nat Med, Jan. 2015, 21:27-36.
Finan et al., "Unimolecular Dual Incretins Maximize Metabolic Benefits in Rodents, Monkeys, and Humans," Sci Transl Med, Oct. 2013, 5(209):209ra151.
Fluegel et al., "Chain stiffness of elastin-like polypeptides," Biomacromolecules, Oct. 2010, 11, 3216-3218.
Fosgerau et al., "Peptide therapeutics: current status and future directions," Drug Discovery Today, Jan. 2015, 20, 122-128.
Franzmann et al., "Phase separation of a yeast prion protein promotes cellular fitness," Science, Jan. 2018, 359(6371):eaao5654.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, Mar. 2018, 130:A19112.
Friedman et al., "Directed Evolution to Low Nanomolar Affinity of a Tumor-Targeting Epidermal Growth Factor Receptor-Binding Affibody Molecule," J. Mol. Biol., Mar. 2008, 376, 1388-1402.
Frilling et al., "Recommendations for management of patients with neuroendocrine liver metastases," The lancet oncology, Jan. 2014, 15, e8-21.
Fu et al., "Nanoparticle Albumin—Bond (NAB) Technology is a Promising Method for AntiCancer Drug Delivery," Recent Patents on Anti-Cancer Drug Discovery, Nov. 2009. 4(3):262-272.
Fujiwara et al., "Modulating effect of the PI3-kinase inhibitor LY294002 on cisplatin in human pancreatic cancer cells," Journal of Experimental & Clinical Cancer Research, Nov. 2008, 27, 76.
Furgeson et al., "Structural optimization of a "smart" doxorubicin-polypeptide conjugate for thermally targeted delivery to solid tumors," Journal of Controlled Release, Jan. 2006, 110:362-369.
Furumoto et al., "Effect of coupling of albumin onto surface of PEG liposome on its In vivo disposition," International Journal of Pharmaceutics, Mar. 2007, 329(1-2): p. 110-116.

Gaberc-Porekar et al., "Obstacles and pitfalls in the PEGylation of therapeutic proteins," Curr. Opin. Drug Discov. Devel. 11, Mar. 2008, 242-250.
Gabizon et al., "Prolonged circulation time and enhanced accumulation in malignant exudates of doxorubicin encapsulated in polyethylene-glycol coated liposomes," Cancer Res., Feb. 1994, 54, 987-992.
Gaich et al., "The Effects of LY2405319, an FGF21 Analog, in Obese Human Subjects with Type 2 Diabetes," Cell Metab, Sep. 2013, 18(3):333-340.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, Feb. 2006, R12-R22.
Ganson et al., "Pre-existing anti-polyethylene glycol antibody linked to first-exposure allergic reactions to pegnivacogin, a PEGylated RNA aptamer," J Allergy Clin Immunol, May 2016, 137(5): 1610-1613, e1617.
Gao et al., "In situ growth of a PEG-like polymer from the C terminus of an intein fusion protein improves pharmacokinetics and tumor accumulation" PNAS Early Edition, Jul. 2010, vol. 107, 1-6.
Gao et al., "In situ growth of a PEG-like polymer from the C terminus of an intein fusion protein improves pharmacokinetics and tumor accumulation," Proc. Natl. Acad. Sci., Sep. 2010, 107(38):16432-16437.
Gao et al., "In situ growth of a stoichiometric PEG-like conjugate at a protein's N-terminus with significantly improved pharmacokinetics," Proc. Natl. Acad. Sci., Sep. 2009, 15231-15236.
Gao, "Site-specific and in situ growth of stealth polymer conjugates of proteins with significally improved pharmacology," Journal of Controlled Release, Nov. 2013, 172(1):e116-e117.
Garanger et al., "Structural Evolution of a Stimulus-Responsive Diblock Polypeptide Micelle by Temperature Tunable Compaction of its Core," Macromolecules, Sep. 2015, 48, 6617-6627.
Garay et al., "Antibodies against polyethylene glycol in healthy subjects and in patients treated with PEG-conjugated agents," Expert Opinion. Drug Deliv. 9, Nov. 2012, 1319-1323.
Garcia Quiroz et al., "Syntax of Phase Transition Peptide Polymers with LCST and UCST Behavior," Jan. 1, 2013, Retrieved from the Internet: URL:https://dukespace.lib.duke.edu/dspace/bitstream/handle/10161/7256/GarciaQuirozduke0066D 11972.pdf?sequence=1 &isAllowed=y.
Gauthier et al., "Peptide/protein-polymer conjugates: synthetic strategies and design concepts," Chem. Commun., Jul. 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (Mar. 2017).
Geng et al., Shape effects of filaments versus spherical particles in flow and drug delivery, Nat Nanotechnol, Nature Research, Apr. 2007, 2(4):249-55.
Ghoorchian et al., "Molecular architecture influences the thermally induced aggregation behavior of elastin-like polypeptides," Biomacromolecules, Oct. 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.
Giberti et al., "Radical retropubic prostatectomy versus brachytherapy for low-risk prostatic cancer: a prospective study," World J Urol, Oct. 2009, 27, 607-612.
Gibson et al., "Enzymatic assembly of DNA molecules up to several hundred kilobases," Nat Methods, May 2009, 6, 343-345.
Gilbreth et al., "Structural insights for engineering binding proteins based on non-antibody scaffolds," Curr Opin Struct Biol, Elsevier, Jun. 2012, 22(4):413-20.
Gillies et al., "Dendrimers and dendritic polymers in drug delivery," Drug Discovery Today, 2005, 10(1):35-43.
Gilroy et al., "Fusion of fibroblast growth factor 21 to a thermally responsive biopolymer forms an injectable depot with sustained anti-diabetic action," J Control Release, May 2018, 277:154-164.
Glassman et al., "Toughening of Thermoresponsive Arrested Networks of Elastin-Like Polypeptides To Engineer Cytocompatible Tissue Scaffolds," Biomacromolecules, Feb. 2016, 17, 415-426.

(56) References Cited

OTHER PUBLICATIONS

Gluck et al., "Single Vector System for Efficient N-myristoylation of Recombinant Proteins in *E. coli*," Plos One, Apr. 2010, 5(4) e100881.
Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Goldsmith et al., "Enzyme engineering: reaching the maximal catalytic efficiency peak," Curr Opin Struct Biol, Dec. 2017, 47:140-150.
Gordon et al., "Protein N-myristoylation," J. Biol. Chem., 1991, 266, 8647-8650.
Gosline et al., "Elastic proteins: biological roles and mechanical properties," Philos Trans R Soc Lond B Biol Sci, 2002, 357, 121-132.
Gottlieb et al., "NMR chemical shifts of common laboratory solvents as trace impurities," J. Org. Chem., 1997, 62, 7512-7515.
Goutelle et al., "The Hill equation: a review of its capabilities in pharmacological modelling. Fundam," Clin. Pharmacol. 22, Dec. 2008, 633-648.
Graff et al., "Theoretical analysis of antibody targeting of tumor spheroids: importance of dosage for penetration, and affinity for retention," Cancer Research, 2003, 63(6):1288-1296.
Gratton et al., "The effect of particle design on cellular internalization pathways," Proc Natl Acad Sci U S A, The National Academy of Sciences of the USA, Aug. 2008, 105(33):11613-8.
Greco et al., "The search for synergy: a critical review from a response surface perspective," Pharmacological Reviews, 1995, 24, 331-385.
Green et al., "Abraxane®, a novel Cremophor®-free, albumin-bound particle form of paclitaxel for the treatment of advanced non-small-cell lung cancer," Annals of Oncology, Aug. 2006, 17, 1263-1268.
Green et al., "Novel dipeptidyl peptidase IV resistant analogues of glucagon-like peptide-1(7-36)amide have preserved biological activities in vitro conferring improved glucose-lowering action in vivo" J. of Mol. Endocrin., 2003, 31(3): 529-540.
Greenfield, "Using circular dichroism spectra to estimate protein secondary structure," Nat. Protoc., Dec. 2006, 1(6):2876-90.
Grimm et al., "Advances in Brachytherapy," Reviews in Urology, 2004, 6, S37-S48.
Grover et al., "Protein-Polymer Conjugates: Synthetic Approaches by Controlled Radical Polymerizations & Interesting Applications", Curr Opin Chem Bioi., Dec. 2010; 14(6): 818-827.
Gu et al., "Enzymatic Synthesis of Nucleobase-Modified Single-Stranded DNA Offers Turnable Resistance to Nuclease Degradation," Biomacromolecules, Jul. 2018, 19, 3525-3535.
Gu et al., "Photocontrolled micellar aggregation of amphiphilic DNA-azobenzene conjugates," Colloids Surfaces B: Biointerfaces, Nov. 2015, 135, 126-132.
Gu et al., "Precise engineering of targeted nanoparticles by using self-assembled biointegrated block copolymers," Proc Natl Acad Sci U S A, The National Academy of Sciences of the USA, Feb. 2008, 105(7):2586-91.
Güngör et al., "Pancreatic cancer," British Journal of Pharmacology, Jan. 2014, 171, 849-858.
Guo et al., "Nanoparticles escaping RES and endosome: challenges for siRNA delivery for cancer therapy," J. Nanomaterials, Aug. 2011, 2011: 1-12.
Gustafsson, "Nonlinear structured-illumination microscopy: widefield fluorescence imaging with theoretically unlimited resolution," Proc Natl Acad Sci U S A, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, Nov. 2016, 139, 2116-2126.

Ha et al., "Immunoglobulin Fc Heterodimer Platform Technology: From Design to Applications in Therapeutic Antibodies and Proteins," Front Immunol, Oct. 2016, 7(394) (in English).
Haider et al., "Genetically engineered polymers: Status and prospects for controlled release," J. Control. Release, 2004, 95, 1-26.
Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.
Hamada et al., "Novel therapeutic strategies targeting tumor-stromal interactions in pancreatic cancer," Frontiers in Physiology, Nov. 2013, vol. 4, Article 331, 7 pages.
Hamidi et al., "Pharmacokinetic Consequences of Pegylation," Drug Deliv., Dec. 2006, 13, 399-409.
Hamley, "Self-assembly of amphiphilic peptides," Soft Matter, Feb. 2011, 7, 4122.
Hampp et al., "Use of Antidiabetic Drugs in the U.S., 2003-2012," Diabetes Care, May 2014, 37: 1367-1374.
Han et al., "Survival of patients with advanced pancreatic cancer after iodine$^{125}$ seeds implantation brachytherapy: A meta-analysis," Medicine, Feb. 2017, 96, e5719.
Harmon et al., "A Model for Hysteresis Observed in Phase Transitions of Thermally Responsive Intrinsically Disordered Protein Polymers," Biophysical Journal, Feb. 2017, 112(3):207a.
Harries et al., "Nanoparticle Albumin-Bound Paclitaxel for Metastatic Breast Cancer," J. Clin. Oncol., 2005, 23(31):7768-7771.
Harris et al., "Pegylation," Clinical Pharmacokinetics, 2001, 40(7):539-551.
Hart et al., "Attenuation of FGF signalling in mouse B-cells leads to diabetes," Nature, 2000, 408:864.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, Jun. 2015, 48, 4183-4195.
Hassouneh et al., "Elastin-Like Polypeptides as a Purification Tag for Recombinant Proteins," Curr Protoc Protein Sci., Aug. 2010, Chapter 6. Unit 6.11. 10.1002/0471140864.ps0611s61.
Hassouneh et al., "Fusions of elastin-like polypeptides to pharmaceutical proteins," Methods Enzymol., Jan. 2012, 502, 215-37.
Hassouneh et al., "Unexpected Multivalent Display of Proteins by Temperature Triggered Selfassembly of Elastin-like Polypeptide Block Copolymers," Biomacromolecules, Apr. 2012, vol. 13, Issue 4, pp. 1598-1605.
Hathout et al., "Analysis of seed loss and pulmonary seed migration in patients treated with virtual needle guidance and robotic seed delivery," American journal of clinical oncology, Oct. 2011, 34, 449-453.
He et al., "Comparative genomics of elastin: Sequence analysis of a highly repetitive protein," Matrix Biology, Sep. 2007, 26:524-540.
He et al., "Improving protein resistance of α-Al2O3 membranes by modification with POEGMA brushes," Applied Surface Science, Nov. 2011, 258(3):1038-1044.
Heagerty et al., Biometrics, "Time-dependent ROC curves for censored survival data and a diagnostic marker," Jun. 2000, 56(2):337-44.
Heal et al., "N-Myristoyl transferase-mediated protein labelling in vivo," Org. Biomol. Chem., Aug. 2008, 6(13):2308-2315.
Heal et al., "Site-specific N-terminal labelling of proteins in vitro and in vivo using N-myristoyl transferase and bioorthogonal ligation chemistry," Chem. Commun., Jan. 2008, 3, 480-482.
Heredia et al., "In Situ Preparation of Protein-"Smart" Polymer Conjugates with Retention of Bioactivity," J. Am. Chem. Soc. Jan. 2006, 127, 16955-16960.
Herrero-Vanrell et al., "Self-assembled particles of an elastin-like polymer as vehicles for controlled drug release," J Control Release, 2005, 102, 113-122.
Hershfield et al., "Induced and pre-existing anti-polyethylene glycol antibody in a trial of every 3-week dosing of pegloticase for refractory gout, including in organ transplant recipients," Arthritis Res. Ther. 16, Mar. 2014, R63.

(56) References Cited

OTHER PUBLICATIONS

Hidalgo, "Pancreatic Cancer," N Engl J Med, Apr. 2010, 362, 1605-1617.
Hingorani et al., "Phase Ib Study of PEGylated Recombinant Human Hyaluronidase and Gemcitabine in Patients with Advanced Pancreatic Cancer," Clinical Cancer Research, Jun. 2016, 22, 2848-2854.
Ho et al., "Chemoenzymatic Labeling of Proteins for Imaging in Bacterial Cells," J. Am. Chem. Soc., Nov. 2016, 138(46):15098-15101.
Ho et al., "Internal radiation therapy for patients with primary or metastatic hepatic cancer: a review," Cancer, 1998, 83, 1894-1907.
Hober et al., "Protein A chromatography for antibody purification," Journal of Chromatography B 848, Mar. 2007, pp. 40-47.
Hochkoeppler, "Expanding the landscape of recombinant protein production in *Escherichia coli*," Biotechnol. Lett., Dec. 2013, 35, 1971-1981.
Hofmann et al., "A kinetic study on the enzymatic hydrolysis of fluoresceindiacetate and fluorescein-di-β-D-galactopyranoside," Analytical biochemistry, 1983, 131(1):180-186.
Holehouse et al., "CIDER: Classification of Intrinsically Disordered Ensemble Regions," Biophysical Journal, Feb. 2015, vol. 108, Issue 2, Supplement 1, p. 228a.
Holehouse et al.,"Functional Implications of Intracellular Phase Transitions," Biochemistry, May 2018, 57(17):2415-2423.
Holm et al., "Transperineal $^{125}$iodine seed implantation in prostatic cancer guided by transrectal ultrasonography," The Journal of urology, 2002, 167, 985-988.
Hopp et al., "The effects of affinity and valency of an albumin-binding domain (ABD) on the half-life of a single-chain diabody-ABD fusion protein," Protein Engineering Design and Selection, Sep. 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, May 2007, 119, 25-33.
Hruby et al., "Thermoresponsive polymeric radionuclide delivery system—an injectable brachytherapy," Eur J Pharm Sci., Feb. 2011, 42, 484-488.
Hrycushko et al., "Direct intratumoral infusion of liposome encapsulated rhenium radionuclides for cancer therapy: effects of non-uniform intratumoral dose distribution," Med Phys, Mar. 2011, 38, 1339-1347.
Hu et al., "Design of tumor-homing and pH-responsive polypeptide-doxorubicin nanoparticles with enhanced anticancer efficacy and reduced side effects," Chemical Communications, Jun. 2015, 51, 11405-11408.
Hu et al., "Nanografting De Novo Proteins onto Gold Surfaces," Langmuir, 2005, vol. 21:9103-9109.
Huang et al., "Photodynamic Therapy Synergizes with Irinotecan to Overcome Compensatory Mechanisms and Improve Treatment Outcomes in Pancreatic Cancer," Cancer Research, Mar. 2016, 76, 1066-1077.
Huber et al., "Designer amphiphilic proteins as building blocks for the intracellular formation of organelle-like compartments," Nat Mater, Jan. 2015, 14(1):125-132.
Huotari et al., "Endosome maturation," EMBO J, Aug. 2011, 30 (17), 3481-3500.
Hwang et al., "Caprolactonic poloxamer analog: PEG-PCL-PEG," Biomacromolecules, 2005, 6, 885-890.
Hwang et al., "Gene therapy for primary and metastatic pancreatic cancer with intraperitoneal retroviral vector bearing the wild-type p53 gene," Surgery, 1998, 124, 143-151.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., Nov. 2015, 7, 1-8.
Ishida et al., "Accelerated blood clearance (ABC) phenomenon upon repeated injection of PEGylated liposomes," International Journal of Pharmaceutics, May 2008, 354(1-2):56-62.
Ito et al., "Impaired negative feedback suppression of bile acid synthesis in mice lacking pKlotho," J Clin Invest, 2005, 115(8):2202-2208.
Ito et al., "In vivo antitumor effect of the mTOR inhibitor CCI-779 and gemcitabine in xenograft models of human pancreatic cancer," International Journal of Cancer, May 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., Jun. 2006, 4482-4486.
Janes et al., "Chitosan nanoparticles as delivery systems for doxorubicin," J. Control Release, 2001, 73, 255-267.
Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, Feb. 2012, 13, 206-215.
Jia et al., "Preparation, physicochemical characterization and cytotoxicity in vitro of gemcitabine-loaded PEG-PDLLA nanovesicles," World J. Gastroenterol., Feb. 2010, 16(8):1008-1013.
Jiang et al., "Nanoparticle-mediated cellular response is size-dependent," Nat Nanotechnol, Nature Research, Mar. 2008, 3(3):145-50.
Jiang et al., "The internal structure of self-assembled peptide amphiphiles nanofibers," Soft Matter, Feb. 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, Apr. 2009, 70 (1), 53-9.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Johnson et al., "Fibroblast Growth Factor 21 Reduces the Severity of Cerulein-Induced Pancreatitis in Mice," Gastroenterology, Nov. 2009, 137(5):1795-1804.
Jokerst et al., "Nanoparticle PEGylation for imaging and therapy," Nanomedicine (Lond), Future Medicine, Jun. 2011, 6(4):715-28.
Jonsson et al., "Engineering of a femtomolar affinity binding protein to human serum albumin," Protein Engineering Design and Selection, Aug. 2008, 21(8): 515-527.
Junutula et al., "Site-specific conjugation of a cytotoxic drug to an antibody improves the therapeutic index," Nat Biotechnol, Aug. 2008, 26(8):925-932.
Jurney et al., "Unique size and shape-dependent uptake behaviors of non-spherical nanoparticles by endothelial cells due to a shearing flow," J Control Release, Jan. 2017, 245:170-176.
Kaighn et al., "Establishment and characterization of a human prostatic carcinoma cell line (PC-3)," Investigative urology, 1979, 17, 16-23.
Kaitin et al., "Pharmaceutical innovation in the 21st century: new drug approvals in the first decade, 2000-2009," Clin Pharmacol Ther, Feb. 2011, 89, 183-188.

(56) References Cited

OTHER PUBLICATIONS

Kamaly et al., "Targeted polymeric therapeutic nanoparticles: design, development and clinical translation," Chem Soc Rev, Royal Society of Chemistry, Apr. 2012, 41(7):2971-3010.
Kamisawa et al., "Pancreatic cancer," Lancet, Jul. 2016, 388, 73-85.
Kanoski et al., "The role of nausea in food intake and body weight suppression by peripheral GLP-1 receptor agonists, exendin-4 and liraglutide," Neuropharmacology 62, Apr. 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karagoz et al., "Polymerization-Induced Self-Assembly (PISA)—control over the morphology of nanoparticles for drug delivery applications," Polym. Chem., Jan. 2014, 5(2):350-355.
Karamanolis et al., "Increased expression of VEGF and CD31 in postradiation rectal tissue: implications for radiation proctitis," Mediators Inflamm, May 2013, 515048.
Karperien, A. FracLac for Image J, version 2.5 <http://rsb.info.nih.gov/ij/plugins/fraclac/FLHelp/Introduction.htm> 1999-2012.
Kaspar et al., "Future directions for peptide therapeutics development," Drug Discovery Today, Sep. 2013, 18, 807-817.
Katakura, "Nuclear Data Sheets for A = 125," Nuclear Data Sheets, Mar. 2011, 112, 495-705.
Kataoka et al., "Block copolymer micelles for drug delivery: Design, characterization and biological significance," Advanced Drug Delivery Reviews, 2001, 47:113-131.
Kato et al., "Acidic extracellular microenvironment and cancer," Cancer Cell Int, Sep. 2013, 13, 89, 8 pages.
Katti et al., "Amino acid repeat patterns in protein sequences: Their diversity and structural-functional implications," Protein Science, 2000, 9: 1203-1209.
Keefe et al., "Poly(zwitterionic)protein conjugates offer increased stability without sacrificing binding affinity or bioactivity," Nat Chem, Jan. 2012, 4(1):59-63.
Keller et al., "Empirical Statistical Model To Estimate the Accuracy of Peptide Identifications Made by MS/MS and Database Search," Anal. Chem. 2002, 74, 5383-5392.
Kelly et al., "How to study proteins by circular dichroism," Biochim. Byophys. Acta—Proteins Proteomics, 2005, 1751(2):119-39.
Kelly et al., "Shape-specific, monodisperse nano-molding of protein particles," J Am Chem Soc, ACS Publications, Apr. 2008, 130(16):5438-9.
Kesharwani et al., "Dendrimer as nanocarrier for drug delivery," Progress in Polymer Science, Feb. 2014, 39(2):268-307.
Keten et al., "Nanoconfinement controls stiffness, strength and mechanical toughness of 3-sheet crystals in silk," Nat Mater, Mar. 2010, 9, 359-367.
Khandare et al., "Polymer-drug conjugates: Progress in polymeric drugs," Prog. Polym. Sci., 2005, vol. 31, pp. 359-397.
Khanna et al., "The dog as a cancer model," Nat. Biotechnol., Sep. 2006, 24, 1065-1066.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, Nov. 2015, 26(11):608-617.
Kharitonenkov et al., "Fibroblast growth factor 21 night watch: advances and uncertainties in the field," J Intern Med, Nov. 2016, 281(3):233-246.
Kharitonenkov et al., "Inventing new medicines: The FGF21 story," Mol Metab, Jun. 2014, 3(3):221-229.
Khazov et al., "Nuclear Data Sheets for A = 131," Nuclear Data Sheets, 2006, 107, 2715-2930.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic β Cells," J Biol Chem, 2003, 278(35):32969-32977.

Kim et al., "Effects of Once-Weekly Dosing of a Long-Acting Release Formulation of Exenatide on Glucose Control and Body Weight in Subjects With Type 2 Diabetes," Diabetes Care, Jun. 2007, 30, 1487-93.
Kim et al., "Recombinant elastin-mimetic biomaterials: Emerging applications in medicine," Adv Drug Deliv Rev, Dec. 2010, 62, 1468-1478.
Kim et al., "Site-Specific PEGylated Exend in-4 Modified with a High Molecular Weight Trimeric PEG Reduces Steric Hindrance and Increases Type 2 Antidiabetic Therapeutic Effects," Bioconjugate Chem., Nov. 2012, 23, 2214-2220.
Kim et al., "Ultrasensitive Carbon nanotube-based biosensors using antibody-binding fragments," Analytical Biochemistry, Jul. 2008, 381, 193-198.
Knop et al., "Poly(ethylene glycol) in Drug Delivery: Pros and Cons as Well as Potential Alternatives," Angewandte Chemie International Edition, Aug. 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment Of An NMR-Invisible Solubility Enhancement Tag Using A Sortase-Mediated Protein Ligation Method," J Biomol NMR. Mar. 2009, vol. 43, No. 3; pp. 145-150.
Kobayashi et al., "Summary of recombinant human serum albumin development," Biologicals, Mar. 2006, 34(1): 55-59.
Koehler et al., "Albumin affinity tags increase peptide half-life In vivo," Bioorganic & Medicinal Chemistry Letters, 2002, 12(20): 2883-2886.
Kontos et al., "Drug development: longer-lived proteins," Chemical Society Reviews, Feb. 2012, 41(7):2686-2695.
Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.
Kothare et al., "Pharmacokinetics, pharmacodynamics, tolerability, and safety of exenatide in Japanese patients with type 2 diabetes mellitus," J. Clin. Pharmacol. 48, Jan. 2009, 1389-1399.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
Kramer et al., "Quantitative Side-Chain Modifications of Methionine-Containing Elastin-Like Polypeptides as a Versatile Tool to Tune Their Properties," ACS Macro Lett., Nov. 2015, 4(11):1283-1286.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, Mar. 2008, 1778, 631-645.
Krempien et al., "Neoadjuvant chemoradiation in patients with pancreatic adenocarcinoma," HPB (Oxford), Feb. 2006, 8(1):22-28.
Kruger et al., "Analysis of the Substrate Specificity of the *Staphylococcus aureus* Sortase Transpeptidase SrtAt," Biochemistry, 2004, 43, 1541-1551.
Kulkarni et al., "Bioorthogonal Chemoenzymatic Functionalization of Calmodulin for Bioconjugation Applications," Bioconjug. Chem., Oct. 2015, 26(10):2153-2160.
Kulkarni et al., "Design of lipid nanoparticles for in vitro and in vivo delivery of plasmid DNA," Nanomedicine, May 2017, 13(4):1377-1387.
Kulkarni et al., "Selective functionalization of the protein N terminus with N-myristoyl transferase for bioconjugation in cell lysate," ChemBioChem, Oct. 2013, 14, 1958-1962.
Kumar et al., "N-Terminal Region of the Catalytic Domain of Human N-Myristoyltransferase 1 Acts as an Inhibitory Module," PLoS One, May 2015, 10(5):e0127661.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.

(56) References Cited

OTHER PUBLICATIONS

Kurosu et al., "Tissue-specific Expression of βKlotho and Fibroblast Growth Factor (FGF) Receptor Isoforms Determines Metabolic Activity of FGF19 and FGF21," J Biol Chem, Sep. 2007, 282(37):26687-26695.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling," Cancer Res, Mar. 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Langer et al., "Designing materials for biology and medicine," Nature, 2004, 428, 487-92.
Laybutt et al., "Endoplasmic reticulum stress contributes to beta cell apoptosis in type 2 diabetes," Diabetologia, Apr. 2007, 50(4):752-763.
Le Droumaguet et al., "Recent advances in the design of bioconjugates from controlled/living radical polymerization," Polym. Chem. Jan. 2010, 1, 563-598.
Le Meins et al., "Hybrid polymer/lipid vesicles: State of the art and future perspectives," Mater. Today, Oct. 2013, 16, 397-402.
Leader et al., "Protein therapeutics: a summary and pharmacological classification," Nat. Rev. Drug Discov. 7, Jan. 2008, 21-39.
Lee et al., "Atomistic molecular dynamics simulations of peptide amphiphile self-assembly into cylindrical nanofibers," J. Am. Chem. Soc., Feb. 2011, 133, 3677-3683.
Lee et al., "Immunohistochemical analysis of claudin expression in pancreatic cystic tumors," Oncology Reports, Apr. 2011, 25(4): 971-978.
Lee et al., "In vivo bioluminescent imaging of irradiated orthotopic pancreatic cancer xenografts in nonobese diabetic-severe combined immunodeficient mice: a novel method for targeting and assaying efficacy of ionizing radiation," Transl. Oncol., Jun. 2010, 3, 153-159.
Lee et al., "Mechanical properties of cross-linked syntheti elastomeric polypentapeptides," Macromolecules, 2001, 34, 5968-5974.
Lee et al., "Nanoparticle-Delivered Chemotherapy: Old Drugs in New Packages." Oncology (Williston Park, NY) 31.3 (Mar. 2017): 198-208.
Lee et al., "Phase transition and elasticity of protein-based hydrogels," J. Biomater. Sci. Polymer Edn, 2001, 12, 229-242.
Lee et al., "Polymersomes for drug delivery: design, formation and characterization," J Control Release, Elsevier, Jul. 2012, 161(2):473-83.
Lee et al., "Structures of β-klotho reveal a 'zip code'-like mechanism for endocrine FGF signaling," Nature, Jan. 2018, 553:501-505.
Lee et al., "Theranostic nanoparticles with controlled release of gemcitabine for targeted therapy and MRI of pancreatic cancer," ACS Nano, Mar. 2013, 7(3):2078-2089.
Leibowitz et al., "Glucose-Regulated Proinsulin Gene Expression Is Required for Adequate Insulin Production during Chronic Glucose Exposure," Endocrinology, 2002, 143(9):3214-3220.
Lele et al., "Synthesis of uniform protein-polymer conjugates," Biomacromolecules 6, 2005, 3380-3387.
Lennen et al., "Membrane Stresses Induced by Overproduction of Free Fatty Acids in *Escherichia coli*," Appl Environ Microb., Nov. 2011, 77(22):8114-28.
Leung et al., "Bio-Click Chemistry: Enzymatic Functionalization of PEGylated Capsules for Targeting Applications**," Angew. Chem. Int. Ed. Jul. 2012, 51, 7132-7136.
LeVine et al., "Thioflavine T interaction with synthetic Alzheimer's disease beta-amyloid peptides: detection of amyloid aggregation in solution," Protein Sci., 1993, 2, 404-10.
Levy et al., "Novel Exenatide Analogs with Peptidic Albumin Binding Domains: Potent Anti-Diabetic Agents with Extended Duration of Action," PLoS ONE, Feb. 2014, 9(2): e87704, 9 pages.

Lewis et al., "Use of digitized video microscopy with a fluorogenic enzyme substrate to demonstrate cell-and compartment-specific gene expression in *Salmonella enteritidis* and Bacillus subtilis," Molecular microbiology, 1994, 13:655-662.
Li et al., "Elastin is an essential determinant of arterial morphogenesis," Nature, 1998, 393, 276-280.
Li et al., "FGF21 Is Not a Major Mediator for Bone Homeostasis or Metabolic Actions of PPARα and PPARγ Agonists," J Bone Miner Res, Apr. 2017, 32(4):834-845.
Li et al., "Molecular description of the LCST behavior of an elastin-like polypeptide," Biomacromolecules, Aug. 2014, 15, 3522-3530.
Li et al., "Nanoparticles Evading The Reticuloendothelial System: Role of The Supported Bilayer," Biochim. Biophys. Acta, Oct. 2009, 1788 (10), 2259-2266.
Li et al., "Pancreatic cancer," Lancet, 2004, 363, 1049-1057.
Li et al., "Phase transitions in the assembly of multivalent signalling proteins," Nature, Nature Research, Mar. 2012, 483(7389):336-340.
Li et al., "Prediction of solvent-induced morphological changes of polyelectrolyte diblock copolymer micelles," Soft Matter, Nov. 2015, 11(42): 8236-45.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macramol. Rapid Commun., Jan. 2015, 36(1):90-95.
Li et al., "Tunable Assembly of Protein-Microdomains in Living Vertebrate Embryos," Advanced Biosystems, Oct. 2018, 2(10):1800112.
Liao et al., "Removal of N-terminal methionine from recombinant proteins by engineered *E. coli* methionine aminopeptidase," Prot. Sci. 13, 2004, 1802-1810.
Liechty et al., "Polymers for Drug Delivery Systems," Annual review of chemical and biomolecular engineering, Aug. 2010, 1:149-173.
Lillie et al., "The viscoelastic basis for the tensile strength of elastin," Int J Biol Macromol, 2002, 30, 119-127.
Lim et al., "Improved Non-Chromatographic Purification of a Recombinant Protein by Cationic Elastin-like Polypeptides" Biomacromolecules, May 2007, 8(5): 1417-1424.
Lim et al., "In situ cross-linking of elastin-like polypeptide block copolymers for tissue repair," Biomacromolecules, Feb. 2008, 9, 222-230.
Lim et al., "In vivo post-translational modifications of recombinant mussel adhesive protein in insect cells," Biotechnol. Prog., Sep.-Oct. 2011, 27(5):1390-1396.
Lin et al., "Adiponectin Mediates the Metabolic Effects of FGF21 on Glucose Homeostasis and Insulin Sensitivity in Mice," Cell Metab, May 2013, 17(5):779-789.
Lin et al., "Formation and Maturation of Phase-Separated Liquid Droplets by RNA-Binding Proteins," Mol Cell, Oct. 2015, 60(2):208-219.
Lin et al., "Functional expression of a biologically active fragment of soluble gp130 as an ELP-fusion protein in transgenic plants: purification via inverse transition cycling," Biochem J, Sep. 2006, 398(3):577-583.
Lin et al., "Intrinsically disordered sequences enable modulation of protein phase separation through distributed tyrosine motifs," J Biol Chem, Nov. 2017, 292(46):19110-19120.
Lin et al., "Phase Separation and Single-Chain Compactness of Charged Disordered Proteins Are Strongly Correlated," Biophys J, May 2017, 112(10):2043-2046.
Lin et al., "Sequence-Specific Polyampholyte Phase Separation in Membraneless Organelles," Phys Rev Lett, Oct. 2016, 117(17):178101.
Lin et al., "Statistical properties of the traditional algorithm-based designs for phase I cancer clinical trials," Biostatistics, 2001, 2(2):203-215.
Lin et al., "Utility of immunohistochemistry in the pancreatobiliary tract," Arch Pathol Lab Med, Jan. 2015, 139, 24-38.
Linder et al., "Lipid Modifications of G Protein Subunits," J. Biol. Chem., 1991, 266(7):4654-4659.

(56) References Cited

OTHER PUBLICATIONS

Ling et al., "Protein thioester synthesis enabled by sortase," J. Am Chem Soc, Jul. 2012, 134(26):10749-10752.

Liong et al., "Multifunctional inorganic nanoparticles for imaging, targeting, and drug delivery," ACS Nano, ACS Publications, May 2008, 2(5):889-96.

Litiere et al., "RECIST—learning from the past to build the future," Nat Rev Clin Oncol, Mar. 2017, 14, 187-192.

Liu et al., "Brachytherapy using injectable seeds that are self-assembled from genetically encoded polypeptides in situ," Cancer Res, Nov. 2012, 72, 5956-5965.

Liu et al., "Hydrophobic modifications of cationic polymers for gene delivery," Prog. In Polym. Sci., Sep. 2010, 35, 1144-1162.

Liu et al., "In Situ Formation of Protein-Polymer Conjugates through Reversible Addition Fragmentation Chain Transfer Polymerization**," Angew. Chem. Int. Ed. Apr. 2007, 46, 3099-3103.

Liu et al., "Injectable intratumoral depot of thermally responsive polypeptide-radionuclide conjugates delays tumor progression in a mouse model," J. Control Release, May 2010, 144(1):2-9.

Liu et al., "Integrin $\alpha_v\beta_3$-Targeted Cancer Therapy," Drug Dev Res, Wiley, Sep. 2008, 69(6):329-339.

Liu et al., "Tracking the in vivo fate of recombinant polypeptides by isotopic labeling," Journal of Controlled Release, Sep. 2006, 114, 184-192.

Liu et al., "Tumor accumulation, degradation and pharmacokinetics of elastin-like polypeptides in nude mice," Journal of Controlled Release, Nov. 2006, 116, 170-178.

Livingstone, "Theoretical property predictions. Curr Top Med Chem FIELD Full Journal Title: Current topics in medicinal chemistry," Curr. Top. Med. Chem. 2003, 3, 1171-1192.

Loh et al., "Utilising inorganic nanocarriers for gene delivery," Biomater Sci, Jan. 2016, 4(1):70-86.

LoPresti et al., "Polymersomes: nature inspired nanometer sized compartments," Journal of Materials Chemistry, RSC Publishing, Jun. 2009, 19(22):3576-3590.

Lovshin et al., "Incretin-based therapies for type 2 diabetes mellitus," Nat. Rev. Endocrinol. 5, Jun. 2009, 262-269.

Ludden, "Nonlinear pharmacokinetics: clinical Implications," Clin. Pharmacokinet., 1991, 20 (6), 429-446.

Luginbuhl et al., "One-week glucose control via zero-order release kinetics from an injectable depot of glucagon-like peptide-1 fused to a thermosensitive biopolymer," Nat. Biomed. Eng. 1, Jun. 2017, Article No. 0078.

Luginbuhl et al., "Recombinant Synthesis of Hybrid Lipid-Peptide Polymer Fusions that SelfAssemble and Encapsulate Hydrophobic Drugs," Angew Chem Int Ed Engl., Nov. 2017, 56(45):13979-13984.

Lukyanov et al., "Micelles From Lipid Derivatives of Water-Soluble Polymers as Delivery Systems for Poorly Soluble Drugs," Adv. Drug Deliver. Rev., 2004, 56(9):1273-1289.

Lukyanov et al., "Tumor-targeted liposomes: doxorubicin-loaded long-circulating liposomes modified with anti-cancer antibody," J Control Release, 2004, 100(1):135-44.

Lund et al., "Phase II study of gemcitabine (2',2'-difluorodeoxycytidine) in previously treated ovarian cancer patients," J. Natl. Cancer. Inst. 1994, 86(20):1530-1533.

Luo et al., "Noncovalent Modulation of the Inverse Temperature Transition and Self-Assembly of Elastin-b-Collagen-like Peptide Bioconjugates," J Am Chem Soc, Dec. 2015, 137, 15362-15365.

Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, Mar. 2007, 40, 2503-2508.

Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, Jan. 2006, 39, 893-896.

Lyons et al., "Comparisons of Recombinant Resilin-like Proteins: Repetitive Domains Are Sufficient to Confer Resilin-like Properties," Biomacromolecules, ACS Publications, Oct. 2009, 10(11):3009-3014.

Lyons et al., "Design and facile production of recombinant resilin-like polypeptides: Gene construction and a rapid protein purification method," Protein Engineering Design & Selection, Oxford university Press, Jan. 2007, 20(1):25-32.

Ma et al., "Non-fouling" oligo(ethylene glycol)-functionalized polymer brushes synthesized by surface-initiated atom transfer radical polymerization, Advanced Materials 2004, 16 (4), 338.

Ma et al., "Protein-resistant polymer coatings on silicon oxide by surface-initiated atom transfer radical polymerization," Langmuir: the ACS journal of surfaces and colloids, Mar. 2006, 22 (8), 3751-6.

Ma et al., "Surface-Initiated Atom Transfer Radical Polymerization of Oligo(ethylene glycol) Methyl Methacrylate from a Mixed Self-Assembled Monolayer on Gold," Advanced Functional Materials, Mar. 2006, 16 (5), 640-648.

MacEwan et al., "Applications of elastin-like polypeptides in drug delivery," Journal of Controlled Release, Sep. 2014, 190: p. 314-330.

MacEwan et al., "Controlled apoptosis by a thermally toggled nanoscale amplifier of cellular uptake," Nano Letters, Apr. 2014, 14, 2058-2064.

MacEwan et al., "Digital switching of local arginine density in a genetically encoded selfassembled polypeptide nanoparticle controls cellular uptake," Nano Lett., Jun. 2012, 12, 3322-3328.

MacEwan et al., "Elastin-like polypeptides: Biomedical applications of tunable biopolymers," Biopolymers, Jan. 2010, 94, 60-77.

MacEwan et al., "Non-chromatographic Purification of Recombinant Elastin-like Polypeptides and their Fusions with Peptides and Proteins from *Escherichia coli*," Jun. 2014, 88, p. e51583.

MacEwan et al., "Phase Behavior and Self-Assembly of Perfectly Sequence-Defined and Monodisperse Multiblock Copolypeptides," Biomacromolecules, Jan. 2017, 18(2):599-609.

Mack et al., "Antiobesity action of peripheral exenatide (exendin-4) in rodents: effects on food intake, body weight, metabolic status and side-effect measures," Int. J. Obes. 30, Sep. 2006, 1332-1340.

MacKay et al., "Self-assembling chimeric polypeptide-doxorubicin conjugate nanoparticles the abolish tumors after single injection," Nat Mater, Dec. 2009, 8(12):993-999.

Maeda et al., "Tumor vascular permeability and the EPR effect in macromolecular therapeutics: a review," J. Control. Release, Mar. 2000, 65(1-2)271-284.

Maeda et al., "Tumoritropic and lymphotropic principles of macromolecular drugs," Critical reviews in therapeutic drug carrier systems, 1989, 6(3):193-210.

Maeda, "The enhanced permeability and retention (EPR) effect in tumor vasculature: the key role of tumor-selective macromolecular drug targeting," Advances in Enzyme Regulation, 2001, 41(1):189-207.

Magnusson et al., "In Situ Growth of Side-Chain PEG Polymers from Functionalized Human Growth Hormone—A New Technique for Preparation of Enhanced Protein-Polymer Conjugates," Bioconjugate Chem. 21, Mar. 2010, 671-678.

Magnusson et al., "Ion-Sensitive "Isothermal" Responsive Polymers Prepared in Water," Journal of the American Chemical Society, Aug. 2008, 130, 10852-10853.

Maitra et al., "Pancreatic Cancer," Annu Rev Pathol Mech Dis, Feb. 2008, 3, 157-188.

Malam et al., "Liposomes and nanoparticles: nanosized vehicles for drug delivery in cancer," Trends Pharmacol Sci, Cell Press, Nov. 2009, 30(11):592-9.

Malik et al., "Recent advances in protein and peptide drug delivery systems," Curr. Drug Deliv. 2, Apr. 2007, 141-151.

Manders et al., "Dynamics of three-dimensional replication patterns during the S-phase, analysed by double labelling of DNA and confocal microscopy," Journal of cell science, 1992, 103(Pt 3):857-862.

Mann et al., "Proteomic analysis of post-translational modifications," Nat. Biotechnol., 2003, 21, 255-61.

(56) References Cited

OTHER PUBLICATIONS

Manzoor et al., "Overcoming limitations in nanoparticle drug delivery: triggered, intravascular release to improve drug penetration into tumors," Cancer Res, Nov. 2012, 72, 5566-5575.
Mao et al., "DNA repair by nonhomologous end joining and homologous recombination during cell cycle in human cells," Cell cycle, Sep. 2008, 7, 2902-2906.
Mao et al., "Net charge per residue modulates conformational ensembles of intrinsically disordered proteins," Proc Natl Acad Sci U S A, 2010, 107(18):8183-8188.
Mao et al., "Sortase-mediated protein ligation: a new method for protein engineering," J. Am. Chem. Soc., 2004, 126(9):2670-2671.
Maraffini et al., "Sortases and the art of anchoring proteins to the envelopes of Gram-positive bacteria," Microbiol Mol Biol Rev, Mar. 2006, 70(1):192-221.
Mariam et al., "Albumin corona on nanoparticles—a strategic approach in drug delivery," Drug Deliv., Oct. 2016, 23 (8), 2668-2676.
Marr et al., "Effect of Temperature on the Composition of Fatty Acids in *Escherichia coli*," J Bacteriol., 1962, 84(6):1260-7.
Marten et al., "A randomized multicentre phase II trial comparing adjuvant therapy in patients with interferon alpha-2b and 5-FU alone or in combination with either external radiation treatment and cisplatin (CapRI) or radiation alone regarding event-free survival—CapRI-2," BMC Cancer, Feb. 2009, 9, 1-8.
Maskarinec et al., "Protein engineering approaches to biomaterials design," Curr. Opin. Biotechnol., 2005, 16, 422-426.
Masood, "Polymeric nanoparticles for targeted drug delivery system for cancer therapy," Mater Sci Eng C Mater Biol Appl, Mar. 2016, 60:569-578.
Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.
Mastria et al., "Doxorubicin-conjugated polypeptide nanoparticles inhibit metastasis in two murine models of carcinoma," J Control Release, Jun. 2015, 208:52-8.
Mastria et al., "Nanoparticle formulation improves doxorubicin efficacy by enhancing host antitumor immunity," J Control Release, Jan. 2018, 269:364-373.
Matsumura et al., "A new concept for macromolecular therapeutics in cancer chemotherapy: mechanism of tumoritropic accumulation of proteins and the antitumor agent smancs," Cancer Res. 1986, 46, 6387-6392.
Matsumura, "Cancer stromal targeting (CAST) therapy," Advanced Drug Delivery Reviews, Jun. 2012, 64, 710-719.
Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, Dec. 2008, 93(12):4810-4817.
Matyjaszewski et al., "Atom transfer radical polymerization," Chem. Rev. 101, Sep. 2001, 2921-2990.
Matyjaszewski et al., "Macromolecular engineering by atom transfer radical polymerization," J. Am. Chem. Soc. 136, 2014, 6513-6533.
Maurer-Stroh et al., "N-terminal N-myristoylation of proteins: prediction of substrate proteins from amino acid sequence" J Mol Biol., 2002, 317(4):541-557.
Maurer-Stroh et al., "N-terminal N-myristoylation of proteins: Refinement of the sequence motif and its taxon-specific differences," J Mol Biol., 2002, 317(4):523-540.
Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.
McConkey et al., "Molecular Characterization of Pancreatic Cancer Cell Lines," Pancreatic Cancer, Jan. 2010, 457-469.
McDaniel et al., "A unified model for de novo design of elastin-like polypeptides with tunable inverse transition temperatures," Biomacromolecules, Aug. 2013, 14(8):2866-2872.
McDaniel et al., "Actively targeting solid tumours with thermoresponsive drug delivery systems that respond to mild hyperthermia," Int J Hyperthermia, Aug. 2013, 29, 501-510.
McDaniel et al., "Doxorubicin-conjugated chimeric polypeptide nanoparticles that respond to mild hyperthermia," Control. Release, May 2012, 159 (3), 362-367.
McDaniel et al., "Drug delivery to solid tumors by elastin-like polypeptides," Adc. Drug Deliver. Rev., Dec. 2010, 62(15):1456-1467.
McDaniel et al., "Noncanonical Self-Assembly of Highly Asymmetric Genetically Encoded Polypeptide Amphiphiles into Cylindrical Micelles," Nano Lett., Sep. 2014, 14(11):6590-6598.
McDaniel et al., "Rational design of "heat seeking" drug loaded polypeptide nanoparticles that thermally target solid tumors," Nano Letters, Apr. 2014, 14, 2890-2895.
McDaniel et al., "Recursive Directional Ligation by Plasmid Reconstruction Allows Rapid and Seamless Cloning of Oligomeric Genes," Biomacromolecules, Feb. 2010, 11(4):944-952.
McDaniel et al., "Self-assembly of thermally responsive nanoparticles of a genetically encoded peptide polymer by drug conjugation," Chem. Int. Ed. Feb. 2013, 52, 1683-1687.
McDaniel, "Assembly of Highly Asymmetric Genetically-Encoded Amphiphiles for Thermally Targeted Delivery of Therapeutics," Dissertation, 2013, 295 pages, Published Mar. 1, 2014.
McHale et al., "Synthesis and in vitro evaluation of enzymatically cross-linked elastin-like polypeptide gels for cartilaginous tissue repair," Tissue Eng., 2005, 11, 1768-1779.
McIlhinney et al., "Characterization of a polyhistidine-tagged form of human myristoyl-CoA: protein N-myristoyltransferase produced in *Escherichia coli*," European Journal of Biochemistry, 1994, 222(1):137-146.
McKenzie et al., "Multivalent Binding of a Ligand-Coated Particle: Role of Shape, Size, and Ligand Heterogeneity," Biophys J, Apr. 2018, 114(8):1830-1846.
Meier et al., "Determination of Optimal Sample Size for Quantification of α-Cell Area, Amyloid Area and α-Cell Apoptosis in Isolated Islets," J Histochem Cytochem, Aug. 2015, 63(8):663-673.
Mejuch et al., "Synthesis of lipidated proteins," Bioconjug. Chem. 27, Jul. 2016, 1771-1783.
Meng et al., "Stimuli-responsive polymersomes for programmed drug delivery," Biomacromolecules, ACS Publications, Feb. 2009, 10(2):197-209.
Merkel et al., "Using mechanobiological mimicry of red blood cells to extend circulation times of hydrogel microparticles," Proc Natl Acad Sci U S A, The National Academy of Sciences of the USA, Jan. 2011, 108(2):586-91.
Mero et al., "Transglutaminase-mediated PEGylation of proteins: direct identification of the sites protein medification by mass spectrometry using a novel monodisperse PEG," Bioconjug Chem, Feb. 2009, 20(2):384-389.
Merriam Webster Dictionary, "Plurality," <https://www.merriam-webster.com/dictionary/plurality> webpage accessed Jun. 25, 2020.
Merrick et al., "Seed fixity in the prostate/periprostatic region following brachytherapy," International journal of radiation oncology, biology, physics, 2000, 46, 215-220.
Meyer et al., "Drug targeting using thermally responsive polymers and local hyperthermia," Journal of Controlled Release, 2001, 74, 213-224.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol., 1999, 17(11):1112-1115.
Meyer et al., "Quantification of the effects of chain length and concentration on the thermal behavior of elastin-like polypeptides," Biomacromolecules, 2004, 5(3):846-51.

(56) References Cited

OTHER PUBLICATIONS

Meyer et al., "Targeting a Genetically Engineered Elastin-Like Polypeptide to Solid Tumors by Local Hyperthermia," Cancer Res., 2001, 61(4):1548-1554.
Miao et al., "Sequence and domain arrangements influence mechanical properties of elastin-like polymeric elastomers," Biopolymers, Jun. 2013, 99, 392-407.
Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, Jan. 2013, 62, 317-326.
Micsonai et al. "Accurate secondary structure prediction and fold recognition for circular dichroism spectroscopy," Proc Natl Acad Sci U S A, Jun. 2015, 112, E3095-3103.
Milenic et al., "Antibody-targeted radiation cancer therapy," Nature Reviews Drug Discovery, 2004, 3, 488-498.
Miller et al., "Solubilized, Spaced Polyalanines: A Context-Free System for Determining Amino Acid α-Helix Propensities," Journal of the American Chemical Society, 2002, 124, 945-962.
Mitragotri et al., "Physical approaches to biomaterial design," J. Nat Mater, Nature Publishing Group, Jan. 2009, 8(1):15-23.
Miyata et al., "Polymeric micelles for nano-scale drug delivery," Reaction & Functional Polymers, Mar. 2011, 71, 227-234.
Mjelle et al., "Cell cycle regulation of human DNA repair and chromatin remodeling genes," DNA Repair, Jun. 2015, 30, 53-67.
Modery et al., "Heteromultivalent liposomal nanoconstructs for enhanced targeting and shearstable binding to active platelets for site-selective vascular drug delivery," Biomaterials, Elsevier, Dec. 2011, 32(35):9504-9514.
Molliex et al., "Phase separation by low complexity domains promotes stress granule assembly and drives pathological fibrillization," Cell, Sep. 2015, 163(1):123-133.
Moosmann et al., "Alpha complementation of LacZ in mammalian cells," Nucleic Acids Res, 1996, 24(6):1171-1172.
Morgan et al., "The combination of epidermal growth factor receptor inhibitors with gemcitabine and radiation in pancreatic cancer," Clin Cancer Res, Aug. 2008, 14, 5142-5149.
Mosbach et al., "Formation of proinsulin by immobilized Bacillus subtilis," Nature, 1983, 302, 543-545.
Mozhdehi et al., "Genetically Encoded Cholesterol-Modified Polypeptides," Journal of the American Chemical Society, Jan. 2019, 141(2):945-951.
Mozhdehi et al., "Genetically encoded lipid-polypeptide hybrid biomaterials that exhibit temperature-triggered hierarchical self-assembly," Nature chemistry, May 2018, 10(5):496-505.
Mu et al., "FGF21 Analogs of Sustained Action Enabled by Orthogonal Biosynthesis Demonstrate Enhanced Antidiabetic Pharmacology in Rodents," Diabetes, Feb. 2012, 61(2):505-512.
Muiznieks et al., "Modulated growth, stability and interactions of liquid-like coacervate assemblies of elastin," Matrix Biology 36, Jun. 2014, pp. 39-50.
Muiznieks et al., "Proline periodicity modulates the self-assembly properties of elastin-like polypeptides," J Biol Chem, The American Society for Biochemistry and Molecular Biology, Inc, Dec. 2010, 285(51):39779-39789.
Muiznieks et al., "Structural changes and facilitated association of tropoelastin," Archives of Biochemistry and Biophysics, 2003, 410, 317-323.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Muralidharan et al., "Protein Ligation: an Enabling Technology for the Biophysical Analysis of Proteins," Nature Methods, Jun. 2006, vol. 3, No. 6, pp. 429-438.
Muro, "Challenges in design and characterization of ligand-targeted drug delivery systems," J Control Release, Elsevier, Dec. 2012, 164(2):125-37.
Murphy et al., "A dosimetric model of duodenal toxicity after stereotactic body radiotherapy for pancreatic cancer," Int J Radiation Oncology Biol Phys, Dec. 2010, 78, 1420-1426.
Na et al., "Thermoresponsive pore structure of biopolymer microspheres for a smart drug carrier," Langmuir, Jun. 2010, 26, 11165-11169.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials, Aug. 2014, 35(24):6482-6497.
Nairn et al., "A Synthetic Resilin Is Largely Unstructured," Biophysical Journal, Oct. 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Nanoprecision Medical, "Pipeline, Type II Diabetes," <http://www.nanoprecisionmedical.com/pipeline/diabetes> webpage available as early as Aug. 2018.
Napier et al., "Nanoparticle drug delivery platform," Journal of Macromolecular Science, Part C: Polymer Reviews, Taylor & Francis Group, LLC, Aug. 2007, 47(3):321-327.
National Institute of Mental Health, "Methods and Welfare Considerations in Behavioral Research with Animals: Report of a National Institutes of Health Workshop," NIH Publication No. 02-54083, Washington, DC: U.S. Government Printing Office. (Mar. 2002).
Nauck "Glucagon-like Peptide 1 (GLP-1) in the Treatment of Diabetes," Horm Metab Res, 2004, 36(11/12):852-858 (in English).
Nayeem et al., "Engineering enzymes for improved catalytic efficiency: a computational study of site mutagenesis in epothilone-B hydroxylase," Protein Eng Des Sel, Oxford Academy, Apr. 2009, 22(4):257-266.
Neidigh et al., "Exendin-4 and glucagon-like-peptide-q: NMR structural comparisons in the solution and micelle-associated states," Biochemistry 40, 2001, 13188-13200.
Nettles et al., "Applications of elastin-like polypeptides in tissue engineering," Adv Drug Deliv Rev, Dec. 2010, 62, 1479-1485.
Nettles et al., "In situ crosslinking elastin-like polypeptide gels for application to articular cartilage repair in a goat osteochondral defect model," Tissue Eng Part A, Jul. 2008, 14, 1133-1140.
Newcomb et al., "Advances in cryogenic transmission electron microscopy for the characterization of dynamic self-assembling nanostructures," Current Opinion in Colloid and Interface Science, Dec. 2012, 17, 350-359.
Newton et al., "Commissioning a small-field biological irradiator using point, 2D, and 3D dosimetry techniques," Medical Physics, Dec. 2011, 38, 6754-6762.
Ni et al., "Engineering of inorganic nanoparticles as magnetic resonance imaging contrast agents," Chem Soc Rev, Nov. 2017, 46(23):7438-7468.
Nichols et al., "Claudin 4 protein expression in primary and metastatic pancreatic cancer," Am J Clin Pathol, 2004, 121, 226-230.
Nicolas et al., "Fluorescently tagged polymer bioconjugates from protein derived macroinitiators," Chem. Commun. Jan. 2007, 45, 4697-4699.
Nie, "Understanding and overcoming major barriers in cancer nanomedicine," Nanomedicine (Lond) Jun. 2010, 5 (4), 523-528.
Nielsen, "Incretin mimetics and DPP-IV inhibitors for the treatment of type 2 diabetes," Drug Discov. Today 10, 2005, 703-710.
Nies et al., "Fibroblast Growth Factor Signaling in Metabolic Regulation," Front Endocrinol, Jan. 2016, 6(193) (in English).
Nilvebrant et al., "The albumin-binding domain as a scaffold for protein engineering," Computational and Structural Biotechnology Journal, Mar. 2013, 6: e201303009, 8 pages.

(56) References Cited

OTHER PUBLICATIONS

Niu et al., "The role of adhesion molecules, avβ3, avβ5 and their ligands in the tumor cell and endothelial cell adhesion," Eur J Cancer Prev, Wolters Kluwer, Dec. 2007, 16(6):517-27.
Nott et al., "Phase transition of a disordered nuage protein generates environmentally responsive membraneless organelles," Mol Cell, Mar. 2015, 57(5):936-947.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, Sep. 2008, 9, 2755-2763.
O'Day et al., "Therapeutic Protein-polymer Conjugates: Advancing beyond PEGylation," J. Am. Chem. Soc., Sep. 2014, vol. 136, pp. 14323-14332.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.
Olafsen et al., "Covalent disulfide-linked anti-CEA diabody allows site-specific conjugation and radiolabeling for tumor targeting applications," Protein Engineering, Design & Selection, 2004, 17(1):21-27.
Ortega et al., "Hydrodynamic properties of rodlike and dislike particles in dilute solution," The Journal of Chemical Physics, 2003, 119(18):9914-9919.
Ortony et al., "Internal dynamics of a supramolecular nanofibre," Nat. Mater., Aug. 2014, 13, 1-5.
Ozer et al., "Site-Specific and Stoichiometric Stealth Polymer Conjugates of Therapeutic Peptides and Proteins," Bioconjug Chem, Mar. 2017, 28(3):713-723.
Pace et al., "How to measure and predict the molar absorption coefficient of a protein" Protein Science 1995, 4: 2411-2423.
Pagani et al., "International guidelines for management of metastatic breast cancer: can metastatic breast cancer be cured?," Journal of the National Cancer Institute, Apr. 2010, 102, 456-463.
Pak et al., "Sequence Determinants of Intracellular Phase Separation by Complex Coacervation of a Disordered Protein," Mol Cell, Jul. 2016, 63(1):72-85.
Palmerston Mendes et al., "Dendrimers as Nanocarriers for Nucleic Acid and Drug Delivery in Cancer Therapy," Molecules, Aug. 2017, 22(9):1401.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, Oct. 2016, 96, S204-S205.
Palva et al., "Secretion of interferon by Bacillus subtilis," Gene, 1983, 22, 229-235.
Pang et al., "A Modular Method for the High-Yield Synthesis of Site-Specific Protein-Polymer Therapeutics," Angew Chem Int Ed Engl, Jul. 2016, 55, 10296-10300.
Paolino et al., "Folate-targeted supramolecular vesicular aggregates as a new frontier for effective anticancer treatment in in vivo model," Eur. J. Pharm. Biopharm., Jun. 2012, 82(1):94-102.
Paolino et al., "Gemcitabine-loaded PEGylated unilamellar liposomes vs GEMZAR: biodistribution, pharmacokinetic features and in vivo antitumor activity," J. Control. Release Jun. 2010, 144(2):144-150.
Paoloni et al., "Translation of new cancer treatments from pet dogs to humans," Nat. Rev. Cancer Feb. 2008, 8 (2), 147-156.
Papa et al., "PEGylated Liposomal Gemcitabine: Insights Into a Potential Breast Cancer Therapeutic," Cell Oncol. (Dordr), Oct. 2013, 36(6):449-457.
Paramonov et al., "Self-assembly of peptide-amphiphile nanofibers: The roles of hydrogen bonding and amphiphilic packing," J. Am. Chem. Soc., May 2006, 128, 7291-7298.
Pardridge, "The blood-brain barrier: bottleneck in brain drug development," NeuroRx, 2005, 2(1):3-14.

Park et al., "Exendin-4 and exercise improve hepatic glucose homeostasis by promoting insulin signaling in diabetic rats," Metabolism, Jan. 2010, 59, 123-133.
Park et al., "Formulation optimization and in vivo proof-of-concept study of thermosensitive liposomes balanced by phospholipid, elastin-like polypeptide, and cholesterol," PLoS One, Jul. 2014, 9: e103116, 13 pages.
Park et al., "Protein stitchery: Design of a protein for selective binding to a specific DNA sequence," PNAS, 1992, vol. 89:9094-9096.
Parker et al., "Antibody mimics based on human fibronectin type three domain engineered for thermostability and high-affinity binding to vascular endothelial growth factor receptor two," Protein Eng Des Sei, 2005, 18(9):435-44.
Parkes et al. "Discovery and development of exenatide: the first antidiabetic agent to leverage the multiple benefits of the incretin hormone, GLP-1," Expert Opinion. Drug Deliv., Feb. 2013, 8(2):219-244.
Parveen et al., "Nanomedicine," Clinical Pharmacokinetics, Oct. 2006, 45(10):965-988.
Pastuszka et al., "A tunable and reversible platform for the intracellular formation of genetically engineered protein microdomains," Biomacromolecules, ACS Publications, Oct. 2012, 13(11):3439-3444.
Patil et al., "Cellular delivery of doxorubicin via pH-controlled hydrazone linkage using multifunctional nano vehicle based on poly(beta-I-malic acid)," Int J Mol Sci, Sep. 2012, 13, 11681-11693.
Peeler et al., "Genetically encoded initiator for polymer growth from proteins," J. Am. Chem. Soc. 132, Oct. 2010, 13575-13577.
Peng et al., "Length-dependent prediction of protein intrinsic disorder," BMC Bioinformatics, Springer Nature, Apr. 2006, 7:208.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., May 2017, 28(5):1403-1412.
Petros et al., "Strategies in the design of nanoparticles for therapeutic applications," Nat Rev Drug Discov, Nature Research, Aug. 2010, 9(8):615-27.
Phan et al., "Temperature-responsive self-assembly of charged and uncharged hydroxyethylcellulose-graft-poly(N-isopropylacrylamide) copolymer in aqueous solution," Colloid Polym. Sci., Apr. 2011, 289 (9), 993-1003.
Pinkas et al., "Tunable, post-translational hydroxylation of collagen domains in *Escherichia coli*," ACS Chem. Biol., Apr. 2011, 6(4):320-324.
Pliarchopoulou et al., "Pancreatic cancer: Current and future treatment strategies," Cancer Treatment Reviews, Aug. 2009, 35, 431-436.
Poitout et al., "Glucolipotoxicity: Fuel Excess and α-Cell Dysfunction," Endocr Rev, May 2008, 29(3):351-366.
Pometun et al., "Quantitative observation of backbone disorder in native elastin," J Biol Chem, 2004, 279, 7982-7987.
Popp et al., "Site-specific labeling via sortase-mediated transpeptidation," Curr. Protoc. Protein Sci. 56, Apr. 2009, 15.13.1-15.13.9.
Popp et al., "Sortase-Catalyzed Transformations That Improve The Properties Of Cytokines," PNAS, Feb. 2011, vol. 108, No. 8, pp. 3169-3174.
Potters et al., "12-year outcomes following permanent prostate brachytherapy in patients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Potthoff et al., "Endocrine fibroblast growth factors 15/19 and 21: from feast to famine," Genes Dev, Feb. 2012, 26(4):312-324.
Prestwich et al., "Beta dose point kernels for radionuclides of potential use in radioimmunotherapy," J Nucl Med, 1989, 30, 1036-1046.

(56) References Cited

OTHER PUBLICATIONS

Privratsky et al., "PECAM-1: regulator of endothelial junctional integrity," Cell Tissue Res, Mar. 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, Mar. 2012, 21, 418-429.
Provenzano et al., "Hyaluronan, fluid pressure, and stromal resistance in pancreas cancer," Br J Cancer, Jan. 2013, 108, 1-8.
Pulaski et al., "Mouse 4T1 breast tumor model," Curr. Protoc. Immunol., 2001, Chapter 20, Unit 20.2.
Qamar et al., "FUS Phase Separation Is Modulated by a Molecular Chaperone and Methylation of Arginine Cation-pi Interactions," Cell, Apr. 2018, 173(3):720-734.e15.
Qi et al., "A brush-polymer conjugate of exendin-4 reduces blood glucose for up to five days and eliminates poly(ethylene glycol) antigenicity," Nat Biomed Eng, Nov. 2016, 1:0002.
Qi et al., Dataset for A brush-polymer conjugate of exendin-4 reduces blood glucose for up to five days and eliminates poly(ethylene glycol) antigenicity. Figshare, Nov. 2016, <http://dx.doi.org/10.6084/m9.figshare.3976761>.
Qi et al., "Growing polymers from peptides and proteins: a biomedical perspective," Polym. Chem., Jan. 2014, 5(2):266-276.
Qi et al., "Protein-polymer conjugation—moving beyond PEGylation," Curr. Opin. Chem. Biol. 28, Oct. 2015, 181-193.
Qi et al., "Sortase-catalyzed initiator attachment enables high yield growth of a stealth polymer from the C terminus of a protein," Macromol. Rapid Commun., Aug. 2013, 34(15):1256-1260.
Qiu et al., "Development of Orthotopic Pancreatic Tumor Mouse Models," Methods Mol Biol, Jan. 2013, 980: 215-223.
Qiu et al., "Polymer Architecture and Drug Delivery," Pharmaceutical Research, Feb. 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Intrinsically disordered proteins access a range of hysteretic phase separation behaviors," Scientific advances, Oct. 2019, 5(10):eaax5177.
Quiroz et al., "Sequence heuristics to encode phase behaviour in intrinsically disordered protein polymers," Nat. Mater., Nov. 2015, 14(11):1164-1171.
Rabotyagova et al., "Protein-based block copolymers," Biomacromolecules, Feb. 2011, 12(2): 269-289.
Radivojac et al., "Intrinsic Disorder and Functional Proteomics," Biophysical Journal, Mar. 2007, vol. 92, Issue 5, pp. 1439-1456.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, Dec. 2016, 76.
Rankine et al., "Investigating end-to-end accuracy of image guided radiation treatment delivery using a micro-irradiator," Physics in Medicine and Biology, Nov. 2013, 58(21): 7791-7801.
Rao et al., "Synthetic nanoparticles camouflaged with biometric erythrocyte membranes for reduced reticuloendothelial system uptake," Nanotechnology, Jan. 2016, 27 (8), 85106, 9 pages.
Rapaka et al., "Coacervation of Sequential Polypeptide Models of Tropoelastin," Int J Peptide Protein Res, 1978, 11: 97-108.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, Feb. 2016, 3(2):107-110.
Rauscher et al. "Proline and Glycine Control Protein Self-Organization into Elastomeric or Amyloid Fibrils," Structure, Nov. 2006, 14(11):1667-1676.

Ravikumar et al., "Mimicking adhesive functionalities of blood platelets using ligand-decorated liposomes," Bioconjugate chemistry, ACS Publications, May 2012, 23(6):1266-1275.
Ray et al., "Aptamer-mediated delivery of chemotherapy to pancreatic cancer cells." Nucleic acid therapeutics, Oct. 2012, 22(5): 295-305.
Regier et al., American Heart Association 2014 Scientific Sessions, May 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, Feb. 2008, 2(2): p. 141-150.
Ribeiro et al., "Influence of the amino-acid sequence on the inverse temperature transition of elastin-like polypeptides," Biophysical Journal, Jul. 2009, 97(1):312-320.
Richards et al., "Engineered fibronectin type III domain with a RGDWE sequence binds with enhanced affinity and specificity to human avβ3 integrin," J Mol Biol, 2003, 326(5):1475-1488.
Richards et al., "Man's best friend: what can pet dogs teach us about non-Hodgkin lymphoma?" Inmunol Rev., Jan. 2015, 263 (1): 173-191.
Riddles et al., "Ellman's reagent: 5,5'-dithiobis(2-nitrobenzoic acid)—a reexamination," Anal Biochem. 1979, 94(1):75-81.
Riedel et al., "Engineered glucagon-like peptide-1-producing hepatocytes lower plasma glucose levels in mice," Am J Physiol Endocrinol Metab, Apr. 2009, 296(4):E936-E944.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, Aug. 2015, 17(8):661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., Sep. 2015, 589, 2477-2486.
Robinet et al. "Elastin-derived peptides enhance angiogenesis by promoting endothelial cell migration and tubulogenesis through upregulation of MT1-MMP," J. Cell Science, 2005, 118:343-356.
Rodriguez-Diaz et al., "Alpha cells secrete acetylcholine as a non-neuronal paracrine signal priming beta cell function in humans," Nat Med, Jun. 2011, 17:888-892.
Rolland et al., "Direct fabrication and harvesting of monodisperse, shape-specific nanobiomaterials," J Am Chem Soc, 2005, 127(28):10096-100.
Römer et al., "The elaborate structure of spider silk: structure and function of a natural high performance fiber," Prion, Nov. 2008, 2(4):154-161.
Roopenian et al., "FcRn: the neonatal Fc receptor comes of age," Nat. Rev. Immunol., Sep. 2007, vol. 7, No. 9, 715-725.
Rosenberg et al., "Present and future innovations in radiation oncology," Surg Oncol Clin N Am, Jul. 2013, 22(3):599-618.
Rosenholm et al., "Towards multifunctional, targeted drug delivery systems using mesoporous silica nanoparticles—opportunities & challenges," Nanoscale, Royal Society of Chemistry, Oct. 2010, 2(10):1870-83.
Rösler et al., "Advanced drug delivery devices via self-assembly of amphiphilic block copolymers," Advanced Drug Delivery Reviews, 2001, 53:95-108.

(56) References Cited

OTHER PUBLICATIONS

Rozak et al., "G148-GA3: a streptococcal virulence module with atypical thermodynamics of folding optimally binds human serum albumin at physiological temperatures," Biochim Biophys Acta, 2005, 1753(2): p. 226-33.
Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem. Pharmacol. 1996, 51(7):911-908.
Russo et al., "The role of neoadjuvant therapy in pancreatic cancer: a review," Future Oncol, Mar. 2016, 12(5):669-685.
Ryerson et al., "Annual report to the nation on the status of cancer, 1975-2012, featuring the Increasing incidence of liver cancer," Cancer, May 2016, 122(9): 1312-1337.
Ryu et al., "Elastin-like polypeptide for improved drug delivery for anticancer therapy: preclinical studies and future applications," Expert Opinion on Drug Delivery, Informa Healthcare, Oct. 2014, 12(4):653-667.
Saba et al., "A Comparative Oncology Study of Iniparib Defines Its Pharmacokinetic Profile and Biological Activity in a Naturally-Occurring Canine Cancer Model," PLoS One, Feb. 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, Jun. 2009, 131(26): 9304-9310.
Saifer et al., "Selectivity of binding of PEGs and PEG-like oligomers to anti-PEG antibodies induced by methoxyPEG-proteins," Molecular Immunology, Feb. 2014, 57(2):236-246.
Sandler et al., "Gemcitabine: Single-Agent and Combination Therapy in Non-Small Cell Lung Cancer," Oncologist 1999, 4(3)241-251.
Sanna et al., "Targeted therapy using nanotechnology: focus on cancer," Int J Nanomedicine, Jan. 2014, 9:467-83.
Schaal et al., "Biopolymer β-brachytherapy delivered with concomitant paclitaxel outperforms traditional x-ray radiation to include complete regression in multiple pancreatic tumor xenograft models through synergistic modulation of the tumor microenvironment," Poster #5831, 2018.
Schaal et al., "Injectable polypeptide micelles that form radiation crosslinked hydrogels in situ for intratumoral radiotherapy," Journal of Controlled Release, Apr. 2016, 228, 58-66.
Schellenberg et al., "Gemcitabine chemotherapy and single-fraction stereotactic body radiotherapy for locally advanced pancreatic cancer," Int J Radiation Oncol Biol Phys,Nov. 2008, 72(3): 678-686.
Schellenberg et al., "Single-fraction stereotactic body radiation therapy and sequential gemcitabine for the treatment of locally advanced pancreatic cancer," Int J Radiation Oncology Biol Phys, Sep. 2011, 81(1): 181-188.
Schellenberger et al., "A recombinant polypeptide extends the in vivo half-life of peptides and proteins in a tunable manner," Nat. Biotechnol., Dec. 2009, 27(12):1186-1188.
Schlaff et al., "Bringing the heavy: carbon ion therapy in the radiobiological clinical context," Radiation Oncology, Mar. 2014, 9, Article 88, 1-18.
Schneider et al., "NIH Image to ImageJ: 25 years of image analysis," Nature Methods, Jul. 2012, 9(7): 671-675.
Schnell et al., "Expression of integrin αvβ3 in gliomas correlates with tumor grade and is not restricted to tumor vasculature," Brain Pathol, International Society of Neuropathology, Aug. 2008, 18(3):378-86.
Schwendeman et al., "Injectable controlled release depots for large molecules," J Control Release, Sep. 2014, 190, 240-253.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.

Serrano et al., "An infrared spectroscopic study of the conformational transition of elastin-like polypeptides," Biophys. J., Oct. 2007, 93(7):2429-2435.
Shadwick, "Mechanical design in arteries," J Exp Biol, 1999, 202, 3305-3313.
Shang et al., "pH-Dependent Protein Conformational Changes in Albumin:Gold Nanoparticle Bioconjugates: A Spectroscopic Study," Langmuir, Feb. 2007, 23 (5), 2714-2721.
Shao et al., "Super-resolution 3D microscopy of live whole cells using structured illumination," Nat Methods, Oct. 2011, 8(12): 1044-1046.
Sharma et al., "Dendrimer nanoarchitectures for cancer diagnosis and anticancer drug delivery," Drug Discov Today, Feb. 2017, 22(2):314-326.
Sharma et al., "PLGA-based nanoparticles: A new paradigm in biomedical applications," TrAC Trends in Analytical Chemistry, Jun. 2016, 80:30-40.
Sharma et al., "Polymer particle shape independently influences binding and internalization by macrophages," Journal of Controlled Release, Elsevier, Nov. 2010, 147(3):408-412.
Shen et al., "Conjugation site modulates the in vivo stability and thearpeutic activity of antibody-drug conjugates," Nat Biotechnol, Jan. 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, Jul. 2009, 10:1955-1961.
Sherman et al., "Next-Generation PEGylation Enables Reduced Immunoreactivity of PEG-Protein Conjugates," Drug and Development & Delivery, Jun. 2012, vol. 12, No. 5, 36-42.
Sherman et al., "Role of the Methoxy Group in Immune Responses to mPEG-Protein Conjugates," Bioconjugate Chemistry, Mar. 2012, 23(3): 485-499.
Shi et al., "Cell adhesion on a POEGMA-modified topographical surface," Langmuir: the ACS journal of surfaces and colloids, Dec. 2012, 28 (49), 17011-8.
Shi et al., "Triggered sorting and co-assembly of genetically engineered protein microdomains in the cytoplasm," Adv Mater, Wiley, Jan. 2014, 26(3):449-454.
Shimoboji et al., "Temperature-Induced Switching of Enzyme Activity with Smart Polymer-Enzyme Conjugates," Bioconjugate Chem. 2003, 14, 517-525.
Shin et al., "Liquid phase condensation in cell physiology and disease," Science, Sep. 2017, 357(6357):eaaf4382.
Shusharina et al., "Micelles of Diblock Copolymers with Charged and Neutral Blocks: Scaling and Mean-Field Lattice Approaches," Macromolecules, 2000, 33(10): 3892-3901.
Sickmeier et al., "DisProt: the Database of Disordered Proteins," Nucleic Acids Res, Oxford Academy, Jan. 2007, 35:D786-793.
Siegel et al., "Absorbed fractions for electrons and beta particles in spheres of various sizes," J Nucl Med, 1994, 35, 152-156.
Siegwart et al., "ATRP In The Design Of Functional Materials For Biomedical Applications," Prog Polymer Science, Jan. 2012, vol. 37, No. 1, pp. 18-37.
Silberstein et al., "The SNM Practice Guideline for Therapy of Thyroid Disease with $^{131}$I, 3.0," J Nucl Med, Jul. 2012, 53, 1-19.
Silva et al., "Selective differentiation of neural progenitor cells by high-epitope density nanofibers," Science, 2004, 303, 1352-5.
Simakova et al., "Aqueous ARGET ATRP," Macromolecules, Aug. 2012, 45(16):6371-6379.
Simnick et al., "In vivo tumor targeting by a NGR-decorated micelle of a recombinant diblock copolypeptide," J Control Release, Oct. 2011, 155(2): 144-151.
Simnick et al., "Morphing low-affinity ligands into high-avidity nanoparticles by thermally triggered self-assembly of a genetically encoded polymer," ACS Nano, Apr. 2010, 4(4):2217-2227.
Simon et al., "Engineered Ribonucleoprotein Granules Inhibit Translation in Protocells," Molecular cell, Jul. 2019, 75(1):66-75.
Simon et al., "Programming molecular self-assembly of intrinsically disordered proteins containing sequences of low complexity," Nat Chem, Jun. 2017, 9(6):509-515.

(56) References Cited

OTHER PUBLICATIONS

Singhal et al., "Fibroblast Growth Factor 21 (FGF21) Protects against High Fat Diet Induced Inflammation and Islet Hyperplasia in Pancreas," PLoS One, Feb. 2016, 11(2):e0148252.
Sisson et al., "Radiation safety in the treatment of patients with thyroid diseases by radioiodine 131I: practice recommendations of the American Thyroid Association," Thyroid, Apr. 2011, 21(4):335-346.
Skerra, "Alternative non-antibody scaffolds for molecular recognition," Curr Opin Biotechnol, Elsevier, Aug. 2007, 18(4):295-304.
Smith et al., "The Role of Beta Cell Glucagon-like Peptide-1 Signaling in Glucose Regulation and Response to Diabetes Drugs," Cell Metab, Jun. 2014, 19(6):1050-1057.
Smits et al., "Elastin-Like Polypeptide Based Nanoparticled: Design Rationale Toward Nanomedicine," Macromolecular Bioscience, Macromolecular Journals, Jan. 2015, 15(1):36-51.
Sonawane et al., "Hydrazo linkages in pH responsive drug delivery systems," European Journal Pharmaceutical Sciences, Mar. 2017, 99, 45-65.
Sorkin et al., "Signal transduction and endocytosis: close encounters of many kinds," Nat Rev Mol Cell Biol, 2002, 3(8):600-614.
Sousa et al., "Production of a polar fish antimicrobial peptide in *Escherichia coli* using an ELP-intein tag," J Biotechnol, Sep. 2016, 234:83-89.
Sriraman et al., "Barriers to drug delivery in solid tumors," Tissue Barriers, Jul. 2014, 2(3): 2-10.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, May 2017, 158(5):1314-1327.
Stefl et al., "RNA sequence-and shape-dependent recognition by proteins in the ribonucleoprotein particle" EMBO reports (2005) 6(1):33-38.
Steichen et al., "A Review of Current Nanoparticle and Targeting Moieties for the Delivery of Cancer Therapeutics," Eur J Pharm Sci, Elsevier, Feb. 2013, 48(3):416-27.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, Nov. 2007, 20(11): p. 569-576.
Strohmaier et al., "Comparison of $^{60}$Co and $^{192}$Ir sources in HDR brachytherapy," J Contemp Brachyther, Dec. 2011, 3(4): 199-208.
Strulson et al., "RNA catalysis through compartmentalization," Nat Chem, Nature Publishing Group, Nov. 2012, 4(11):941-946.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human antitransferring receptor monoclonal antibody in pancreatic cancer mouse models," PLoS One, Apr. 2015, 10, 1-17.
Suk et al., "PEGylation as a Strategy for Improving Nanoparticle-Based Drug and Gene Delivery," Adv Drug Deliv Rev, Apr. 2016, 99(Pt A):28-51.
Sumerlin, "Proteins as Initiators of Controlled Radical Polymerization: Grafting-from via ATRP and Raft," ACS Macro Lett. Jan. 2012, 1(1): 141-145.
Sun et al., "Autofluorescence Imaging of Living Pancreatic Islets Reveals Fibroblast Growth Factor-21 (FGF21)-Induced Metabolism," Biophys J, Dec. 2012, 103(11):2379-2388.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, Feb. 2015, 16(3): 438-449.
Sun et al., "EUS-guided interstitial brachytherapy of the pancreas: a feasibility study," Gastrointestinal Endoscopy, 2005, 62, 775-779.
Sun et al., "On the Thermally Reversible Dynamic Hydration Behavior of Oligo(ethylene glycol) Methacrylate-Based Polymers in Water," Macromolecules, Jan. 2013, 46(1): 236-246.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng, Jul. 2014, 42(7): 1508-1516.
Swee et al., "Sortase-mediated modification of αDEC205 affords optimization of antigen presentation and immunization against a set of viral epitopes," Proc Natl Acad Sci USA, Jan. 2013, 110(4): 1428-1433.
Swers et al., Multivalent Scaffold Proteins as Superagonists of TRAIL Receptor 2-Induced Apoptosis, Mol Cancer Ther, Jul. 2013, 12(7): 1235-1244.
Swider et al., "Customizing Poly(lactic-Co-Glycolic Acid) Particles for Biomedical Applications," Acta Biomater, Jun. 2018, 73:38-51.
Takalkar et al., "Radium-223 dichloride bone-targeted alpha particle therapy for hormone-refractory breast cancer metastatic to bone," Exp Hematol Oncol, Sep. 2014, 8, Article No. 23.
Talelli et al., "Core-Crosslinked Polymeric Micelles: Principles, Preparation, Biomedical Applications and Clinical Translation," Nano Today, Feb. 2015, 10(1):93-117.
Tallarida, "Quantitative methods for assessing drug synergism," Genes & Cancer, Nov. 2011, 2(11): 1003-1008.
Talukdar et al., "A Long-Acting FGF21 Molecule, PF-05231023, Decreases Body Weight and Improves Lipid Profile in Non-human Primates and Type 2 Diabetic Subjects," Cell Metab, Mar. 2016, 23(3):427-440.
Tamburro et al., "Dissection of human tropoelastin: exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, Aug. 2006, 45(31): 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., Apr. 2016, 15(4): 419-424.
Tang et al., "Enzymatic Polymerization of High Molecular Weight DNA Amphiphiles That Self-Assemble into Star-Like Micelles," Advanced Materials, Feb. 2014, 26(19): 3050-3054.
Tang et al., "High-Molecular-Weight Polynucleotides by Transferase-Catalyzed Living Chain-Growth Polycondensation," Angew. Chem., Jun. 2017, 56(24): 6778-6782.
Tang et al., "Identification of PECAM-1 in solid tumor cells and its potential involvement in tumor cell adhesion to endothelium," J. Biol. Chem., 1993, 268, 22883-22894.
Tantakitti et al., "Energy landscapes and functions of supramolecular systems," Nat. Mater., Apr. 2016, 15(4): 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, Oct. 2012, 3 (10), 2743-2751.
Teicher, "In vivo/exvivo and in situ assays used in cancer research: a brief review," Toxicol. Pathol., Jan. 2009, 37 (1), 114-122.
Thakor et al., "Clinically Approved Nanoparticle Imaging Agents," J Nucl Med, Oct. 2016, 57(12):1833-1837.
Theillet et al., "The alphabet of intrinsic disorder: I. Act like a Pro: On the abundance and roles of proline residues in intrinsically disordered proteins," Intrinsically Disord Proteins, Taylor & Francis, Apr. 2013, 1(1):e24360.
Therasse et al., "New guidelines to evaluate the response to treatment in solid tumors," J Natl Cancer Inst, 2000, 92, 205-216.

(56) References Cited

OTHER PUBLICATIONS

Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tomiyama et al., "Relevant use of Klotho in FGF19 subfamily signaling system in vivo," Proc Natl Acad Sci USA, Jan. 2010, 107(4):1666-71.
Tompa et al., "Fuzzy complexes: polymorphism and structural disorder in protein-protein interactions," Trends Biochem Sci, Jan. 2008, 33(1): 2-8.
Tong et al., "Protein Modification with Amphiphilic Block Copoly(2-oxazoline)s as a New Platform for Enhanced Cellular Delivery," Mol. Pharm., Aug. 2010, vol. 7, No. 4, pp. 984-992.
Ton-That et al., "Assembly of pili on the surface of Corynebacterium diptheriae," 2003, 50(4):1429-1438.
Ton-That et al., "Purification and characterization of sortase, the transpeptide that cleaves surface proteins of *Staphylococcus aureus* and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Towler et al., "Purification and Characterization of Yeast Myristoyl-Coa—Protein N-13Myristoyltransferase," P Natl Acad Sci USA, 1987, 84(9):2708-12.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trabbic-Carlson et al., "Expression and purification of recombinant proteins from *Escherichia coli*: Comparison of an elastin-like polypeptide fusion with an oligohistidine fusion" Protein Science, 2004, 13: 3274-3284.
Trakul et al., "Stereotactic body radiotherapy in the treatment of pancreatic cancer," Semin Radiat Oncol, Apr. 2014, 24(2): 140-147.
Trieu et al., "P0157 Preclinical evaluation of NBN-paclitaxel in pancreatic cancer xenograft models," Eur J Cancer, May 2014, 50(4): e53.
Triola et al., "Chemical biology of lipidated proteins," ACS Chemical Biology, Jan. 2012, 7(1): 87-99.
Troyanskaya et al., "Nonparametric methods for identifying differentially expressed genes in microarray data," Bioinformatics, 2002, 18(11):1454-61.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, Elsevier, Nov. 2011, 32(33):8462-73.
Tsarevsky et al., "Deactivation efficiency and degree of control over polymerization in ATRP in protic solvents," Macromolecules 37, 2004, 9768-9778.
Tschöp et al., "Unimolecular Polypharmacy for Treatment of Diabetes and Obesity," Cell Metab, Jul. 2016, 24(1):51-62.
Tsume et al., "The development of orally administrable gemcitabine prodrugs with D-enantiomer amino acids: Enhanced membrane permeability and enzymatic stability," Eur. J. Pharm. Biopharm., Apr. 2014, 86(3):514-523.
Tu et al., "Stages in tropoelastin coalescence during synthetic elastin hydrogel formation," Micron, Apr. 2010, 41(3): 268-272.
Turunen et al., "Paclitaxel Succinate Analogs: Anionic Introduction as a Strategy to Impart Blood Brain Barrier Permeability," Bioorg Med Chem Lett, Nov. 2008, 18(22):5971-5974.
Tward et al., "Survival of men with clinically localized prostate cancer treated with prostatectomy, brachytherapy, or no definitive treatment: impact of age at diagnosis," Cancer, Oct. 2006, 107(10): 2392-2400.
Uchida et al., "Potential of adenovirus-mediated REIC/Dkk-3 gene therapy for use in the treatment of pancreatic cancer," Journal of Gastroenterology and Hepatology, Apr. 2014, 29(5):973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am. Chem. Soc., 1991, 113(11):4346-4348.
Urry, "Free energy transduction in polypeptides and proteins based on inverse temperature transitions," Prog Biophys Mol Biol, Jan. 1992, 57(1):23-57.
Urry, "Protein elasticity based on conformations of sequential polypeptides: The biological elastic fiber," J Protein Chemistry, 1984, 3, 403-436.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, Elsevier, Jun. 2010, 1804(6):1231-1264.
Valkenburg et al., "Targeting the tumour stroma to improve cancer therapy," Nature Reviews Clinical Oncology, Jun. 2018, 15, 366-381.
Van der Lee et al., "Classification of intrinsically disordered regions and proteins," Chem Rev, Jul. 2014, 114(13): 6589-6631.
Van Roey et al., "Short linear motifs: ubiquitous and functionally diverse protein interaction modules directing cell regulation," Chem Rev, Jul. 2014, 114(13): 6733-6778.
Van Roy, "Beyond E-cadherin: roles of other cadherin superfamily members in cancer," Nat Rev Cancer, Feb. 2014, 14(2): 121-134.
Vasey et al., "Phase I clinical and Pharmacokinetic study of PK1 (N-(2-Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vazquez-Lombardi et al., "Challenges and Opportunities for Non-Antibody Scaffold Drugs," Drug Discov Today, Oct. 2015, 20(10):1271-83.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Venkataraman et al., "The Effects of Polymeric Nanostructure Shape on Drug Delivery," Adv Drug Deliv Rev, Elsevier, Nov. 2011, 63(14-15):1228-46.
Verma et al., "Effect of surface properties on nanoparticle-cell interactions," Small, Wiley, Jan. 2010, 6(1):12-21.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.

(56) References Cited

OTHER PUBLICATIONS

Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., " Polyoxazoline: Chemistry, properties and applications," Bioconjugate Chem., May 2011, 22(5): 976-986.
Vlieghe et al., "Synthetic therapeutic peptides: science and market," Drug Discovery Today, Jan. 2010, 15(1-2): 40-56.
Voelker et al., "Alteration of the specificity and regulation of fatty acid synthesis of Escherichia coli by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., Nov. 2011, vol. 7, No. 4, pp. 214-220.
Von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, Wiley, Sep. 2006, 78(3):620-8.
Vrhovski et al., "Biochemistry of tropoelastin," Eur J Biochem, 1998, 258, 1-18.
Vrhovski et al., "Coacervation Characteristics of Recombinant Human Tropoelastin," European Journal of Biochemistry, 1997, 250(1):92-98.
Vrignaud et al., "Strategies for the nanoencapsulation of hydrophilic molecules in polymerbased nanoparticles," Biomaterials, Nov. 2011, 32(33):8593-8604.
Walczak, "Death Receptor-Ligand Systems in Cancer, Cell Death, and Inflammation," Cold Spring Harb. Perspect. Biol., May 2013, 5(5): a008698.
Wali et al., "Measuring Death of Pancreatic Beta Cells in Response to Stress and Cytotoxic T Cells," Methods in Molecular Biology, Mar. 2015, 1292:165-176.
Walsh et al., "Post-translational modifications in the context of therapeutic proteins," Nat. Biotechnol., Oct. 2006, 24(10): 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "A Molecular Grammar Governing the Driving Forces for Phase Separation of Prion-like RNA Binding Proteins," Cell, Jul. 2018, 174(3):688-699.e616.
Wang et al., "Enhanced Tumor Delivery of Gemcitabine via PEG-DSPE/TPGS Mixed Micelles," Mol. Pharm., Apr. 2014, 11(4): 1140-1150.
Wang et al., "Extending Half Life of H-Ferritin Nanoparticle by Fusing Albumin Binding Domain for Doxorubicin Encapsulation," Biomacromolecules, Mar. 2018, 19(3):773-781.
Wang et al., "More effective nanomedicines through particle design," Small, Wiley, Jul. 2011, 7(14):1919-31.
Wang et al., "Nanoparticle delivery of cancer drugs," Annu Rev Med, Annual Reviews, Feb. 2012, 63:185-98.
Wang et al., "Quantitative Mapping of the Spatial Distribution of Nanoparticles in Endo-Lysosomes by Local pH," Nano Lett., Feb. 2017, 17(2): 1226-1232.
Wang et al., "Size and dynamics of caveolae studied using nanoparticles in living endothelial cells," ACS nano, Dec. 2009, 3(12): p. 4110-4116.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface To Enhance Cancer Cell Targeting by Polymer Micelles," Nano Lett Oct. 2017, 17(10):5995-6005.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wechsel et al., "Renal Cell Carcinoma: Immunohistological Investigation of Expression of the Integrin $\alpha v\beta 3$," Anticancer research, 1999, 19(2C):1529-1532.
Wei et al., "Anticancer drug nanomicelles formed by self-assembling amphiphilic dendrimer to combat cancer drug resistance," Proceedings of the National Academy of Sciences of the United States of America, Mar. 2015, 112(10): 2978-2983.
Wei et al., "Fibroblast growth factor 21 promotes bone loss by potentiating the effects of peroxisome proliferator-activated receptor $\gamma$," Proc Natl Acad Sci USA, Feb. 2012, 109(8):3143-3148.
Weis et al., "$\alpha$V Integrins in Angiogenesis and Cancer," Cold Spring Harb Perspect Med, Cold Spring Harbor Laboratory Press, Sep. 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wendt et al., "DNA-mediated Folding and Assembly of MyoD-E47 Heterodimers," Journal of Biol. Chem., 1998, 273(10):5735-5743.
Wente et al., "Fibroblast Growth Factor-21 Improves Pancreatic $\beta$-Cell Function and Survival by Activation of Extracellular Signal-Regulated Kinase 1/2 and Akt Signaling Pathways," Diabetes, Sep. 2006, 55(9):2470-2478.
Werle et al., "Strategies to improve plasma half life time of peptide and protein drugs," Amino Acids 30, Jun. 2006, 30(4):351-367.
Wienkers et al., "Predicting in vivo drug interactions from in vitro drug discovery data," Nat. Rev. Drug. Discov. 2005, 4(10):825-833.
Wilkins et al., "Hydrodynamic Radii of Native and Denatured Proteins Measured by Pulse Field Gradient NMR Techniques," Biochemistry, 1999, 38(50):16424-16431.
Williams et al., "Targeted radionuclide therapy," Medical Physics, Jul. 2008, 35(7): 3062-3068.
Williamson et al., "Efficient N-terminal labeling of proteins by use of sortase," Angew Chem Int ed Engl, Sep. 2012, 51(37):9377-9380.
Wimley et al., "Experimentally determined hydrophobicity scale for proteins at membrane interfaces," Nature Structural & Molecular Biology, 1996, 3(10):842-848.
Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu. Rev. Med., 1981, 50, 783-814.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Intrinsically disordered proteins in cellular signalling and regulation," Nat Rev Mol Cell Biol, Jan. 2015, 16(1):18-29.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "Site-specific chemical modification of recombinant proteins produced in mammalian cells by using the genetically encoded aldehyde tag," Proc Natl Acad Sci USA, Mar. 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc., Feb. 2010, 132(5): 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, Apr. 2016, 79(7-8): 405-412.
Xia et al., "Tunable self-assembly of genetically engineered silk—elastin-like protein polymers," Biomacromolecules, Nov. 2011, 12(11): 3844-3850.

(56) References Cited

OTHER PUBLICATIONS

Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, Elsevier, Oct. 2011, 155(2):248-61.
Xu et al., "A quality by design (QbD) case study on liposomes containing hydrophilic API: II. Screening of critical variables, and establishment of design space at laboratory scale," Int. J. Pharm., Feb. 2012, 423(2):543-553.
Xu et al., "Downregulation of GLP-1 and GIP Receptor Expression by Hyperglycemia," Diabetes, Jun. 2007, 56(6):1551-58.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Fibroblast Growth Factor 21 Reverses Hepatic Steatosis, Increases Energy Expenditure, and Improves Insulin Sensitivity in Diet-Induced Obese Mice," Diabetes, Jan. 2009, 58(1):250-259.
Xu et al., "Genetically engineered block copolymers: influence of the length and structure of the coiled-coil blocks on hydrogel self-assembly," Pharm Res, Mar. 2008, 25, 674-682.
Xu et al., "Inorganic nanoparticles as carriers for efficient cellular delivery," Chemical Engineering Science, Elsevier, Feb. 2006, 61(3):1027-1040.
Xu et al., "Role of pancreatic stellate cells in pancreatic cancer metastasis," Am J of Pathology, Nov. 2010, 177(5): 2585-2596.
Xu et al., "Self-assembly behavior of peptide amphiphiles (PAs) with different length of hydrophobic alkyl tails," Colloids Surfaces B Biointerfaces, Nov. 2010, 81(1): 329-335.
Yamamoto et al., "ATRP Synthesis of Thermally Responsive Molecular Brushes from Oligo(ethylene oxide) Methacrylates," Macromolecules, Dec. 2007, 40(26): 9348-9353.
Yang et al., "Long Term Exendin-4 Treatment Reduces Food Intake and Body Weight and Alters Expression of Brain Homeostatic and Reward Markers," Endocrinology, Sep. 2014, 155(9): 3473-3483.
Yang et al., "Poly(carboxybetaine) nanomaterials enable long circulation and prevent polymerspecific antibody production," Nano Today, Feb. 2014, 9(1):10-16.
Yates et al., "Contemporary management of patients with high-risk non-muscle-invasive bladder cancer who fail intravesical BCG therapy," World journal of urology, May 2011, 29(4): 415-422.
Yeo et al., "Coacervation of tropoelastin," Adv Colloid Interface Sci, Sep. 2011, 167(1-2): 94-103.
Yokoe et al., "Albumin-conjugated PEG liposome enhances tumor distribution of liposomal doxorubicin in rats," International Journal of Pharmaceutics, May 2008, 353(1-2): 28-34.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release, Feb. 2007, 117(3):371-379.
Yousefpour et al., "Co-opting biology to deliver drugs," Biotechnol Bioeng, Sep. 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett., Dec. 2018, 18(12): 7784-7793.
Yu et al., "Effectiveness and security of CT-guided percutaneous implantation of (125)I seeds in pancreatic carcinoma," The British journal of radiology, Jul. 2014, 87(1039): 20130642, 7 pages.
Yusta et al., "GLP-1 receptor activation improves β cell function and survival following induction of endoplasmic reticulum stress," Cell Metab, Nov. 2006, 4(5):391-406.

Zhang et al., "A self-assembly pathway to aligned monodomain gels," Nat. Mater., Jul. 2010, 9(7): 594-601.
Zhang et al., "In Depth Analysis on the Unusual Multistep Aggregation Process of Oligo(ethylene glycol) Methacrylate-Based Polymers in Water," Macromolecules, Jul. 2014, 47(14): 4728-4737.
Zhang et al., "Nanoparticles in medicine: therapeutic applications and developments," Clin. Pharmacol. Ther., May 2008, 83(5):761-769.
Zhang et al., "Novel agents for pancreatic ductal adenocarcinoma: emerging therapeutics and future directions," Jounral of Hematology & Oncology, Jan. 2018, 11:14, 17 pages.
Zhang et al., "Shape Effects of Nanoparticles Conjugated with Cell-Penetrating Peptides (HIV Tat PTD) on CHO Cell Uptake," Bioconjugate Chem, Sep. 2008, 19(9):1880-1887.
Zhao et al., "A new Bliss Independence model to analyze drug combination data," J Biomol Screen, Jun. 2014, 19(5): 817-821.
Zhao et al., "Cellular uptake, intracellular trafficking, and cytotoxicity of nanomaterials," Small, Wiley, May 2011, 7(10):1322-37.
Zhao et al., "Fluorescence probe techniques used to study micelle formation in water-soluble block copolymers," Langmuir 1990, 6(2):514-516.
Zhao et al., "Tumor αvβ3 Integrin Is a Therapeutic Target for Breast Cancer Bone Metastases," Cancer Res, AACR Publications, Jun. 2007, 67(12):5821-30.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, Nov. 2011, 60(5): 1055-1065.
Zong et al., "Crystal structures of Staphylococcus aureus sortase A and its substrate complex," J. Biol. Chem. 279, 2004, 31383-31389.
Zununi Vahed et al., "Targeted cancer drug delivery with aptamer-functionalized polymeric nanoparticles," Journal of drug targeting, Mar. 2019, 27(3):292-299.
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
International Search Report and Written Opinion for Application No. PCT/US2019/061144 dated May 21, 2020 (15 pages).

(56) References Cited

OTHER PUBLICATIONS

United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
United States Patent Office Action for U.S. Appl. No. 16/058,924 dated Nov. 26, 2019 (23 pages).
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
International Search Report and Written Opinion for Application No. PCT/US2021/046833 dated Nov. 8, 2021 (12 pages).
International Search Report and Written Opinion for Application No. PCT/US2021/035823 dated Dec. 8, 2021 (16 pages).
United States Patent Office Action for U.S. Appl. No. 17/265,165 dated Dec. 21, 2021 (11 pages).
United States Patent Office Action for U.S. Appl. No. 16/964,832 dated Jan. 19, 2022 (12 pages).
United States Patent Office Action for U.S. Appl. No. 16/625,899 dated Dec. 15, 2021 (12 pages).
United States Patent Office Action for U.S. Appl. No. 16/927,982 dated Jan. 6, 2022 (6 pages).
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.
PCT/US2016/024202, Mar. 25, 2016, WO2016/154530, Sep. 26, 2016.
U.S. Appl. No. 15/561,799, filed Sep. 26, 2017, U.S. Pat. No. 10,385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.
PCT/US2017/052887, Sep. 22, 2017, WO2018/057847, Mar. 29, 2018.
U.S. Appl. No. 16/335,734, filed Mar. 22, 2019, 2020/0017557, Jan. 16, 2020.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, U.S. Pat. No. 10,364,451, Jul. 30, 2019.
U.S. Appl. No. 15/387,540, filed Dec. 21, 2016, U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
U.S. Appl. No. 62/506,593, filed May 15, 2017.
U.S. Appl. No. 62/534,442, filed Jul. 19, 2017.
U.S. Appl. No. 62/544,720, filed Aug. 11, 2017.
U.S. Appl. No. 62/545,313, filed Aug. 14, 2017.
PCT/US20168/032785, May 15, 2018, WO2018/213320, Nov. 22, 2018.
U.S. Appl. No. 16/614,282, filed Nov. 15, 2019.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/394,662, filed Sep. 14, 2016.
PCT/US2017/051661, Sep. 14, 2017, WO2018/053201, Mar. 22, 2018.
U.S. Appl. No. 16/332,865, filed Mar. 13, 2019, 2020/0164082, May 28, 2020.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
U.S. Appl. No. 62/527,836, filed Jun. 30, 2017.
U.S. Appl. No. 62/534,019, filed Jul. 18, 2017.
PCT/US2018/040409, Jun. 29, 2018, WO2019/006374, Jan. 3, 2019.
U.S. Appl. No. 16/625,899, filed Dec. 23, 2019, 2020/0148724, May 14, 2020.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.
U.S. Appl. No. 16/305,696, filed Nov. 29, 2018.
U.S. Appl. No. 62/728,582, filed Sep. 7, 2018.
PCT/US2019/050077, Sep. 6, 2019, WO2020/051541, Mar. 12, 2020.
U.S. Appl. No. 62/767,736, filed Nov. 15, 2018.
PCT/US2019/061144, Nov. 13, 2019, WO2020/102324, May 22, 2020.
U.S. Appl. No. 62/622,249, filed Jan. 26, 2018.
PCT/US2019/015176, Jan. 25, 2019, WO2019/147954, Aug. 1, 2019.
U.S. Appl. No. 16/964,832, filed Jul. 24, 2020.
U.S. Appl. No. 62/647,199, filed Mar. 23, 2018.
PCT/US2019/023583, Mar. 22, 2019, WO2019/183476, Sep. 26, 2019.

(56) References Cited

OTHER PUBLICATIONS

U.S. Appl. No. 62/664,512, filed Apr. 30, 2018.
PCT/US2019/030022, Apr. 30, 2019, WO2019/213150, Nov. 7, 2019.
U.S. Appl. No. 62/700,939, filed Jul. 20, 2018.
U.S. Appl. No. 62/873,306, filed Jul. 12, 2019.
U.S. Appl. No. 16/927,982, filed Jul. 13, 2020.
U.S. Appl. No. 62/713,752, filed Aug. 2, 2018.
PCT/US2019/044911, Aug. 2, 2019, WO2020/028806, Feb. 6, 2020.
U.S. Appl. No. 62/985,174, filed Mar. 4, 2020.
U.S. Appl. No. 62/985,179, filed Mar. 4, 2020.
Nikolic et al., "Structural basis for the recognition of LDL-receptor family members by VSV glycoprotein," Nature Communications, 2018, 9: 1029, 12 pages.
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
Ozer et al., "Injectable non-immunogenic PEG-like conjugate that forms a subcutaneous depot and enables sustained delivery of a peptide drug," Research Square, 2021, 38 pages.
United States Patent Office Notice of Allowance for U.S. Appl. No. 17/265,165 dated Jan. 10, 2023 (7 pages).
International Search Report and Written Opinion for Application No. PCT/US2022/041241 dated Oct. 25, 2022 (10 pages).
United States Patent Office Notice of Allowance for U.S. Appl. No. 16/625,899 dated Jan. 18, 2023 (8 pages).
United States Patent Office Action for U.S. Appl. No. 17/265,165 dated Sep. 2, 2022 (5 pages).
United States Patent Office Notice of Allowance for Application No. 16/477,229 dated Jan. 6, 2023 (8 pages).
Erbacher et al., "Transfection and Physical Properties of Various Saccharide, Poly(ethylene glycol), and Antibody-Derivatized Polyethylenimines (PEI)," The Journal of Gene Medicine, 1999, 1: 210-222.
Alves et al., "Influence of doxorubicin on model cell membrane properties: insight from in vitro and in silico studies," Sci Rep, 2017, 7(1): 6343.
International Search Report and Written Opinion for Application No. PCT/US2022/078659 dated Feb. 1, 2023 (17 pages).
United States Patent Office Action for U.S. Appl. No. 16/964,832 dated Apr. 17, 2023 (17 pages).
Liu et al., "Stable Evans Blue Derived Exendin-4 Peptide for Type 2 Diabetes Treatment," Bioconjugate Chem, 2016, 27: 54058.
United States Patent Office Action for U.S. Appl. No. 17/051,202 dated Jun. 21, 2023 (10 pages).

* cited by examiner

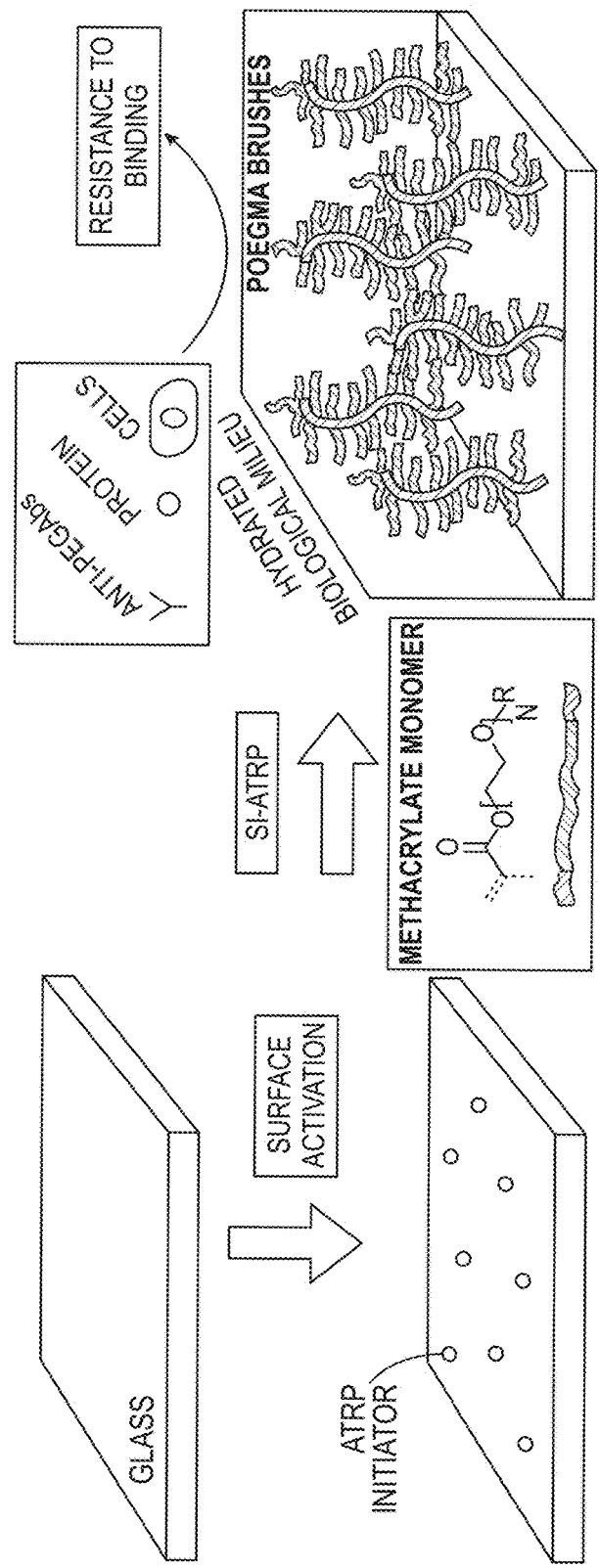

FIG. 18A

| Monomer | MW | n | -R | Abbreviation | Δ (nm) |
|---|---|---|---|---|---|
| Ethylene glycol methyl ether methacrylate | 144 | 1 | -OMe | EG1-OMe | 31.9 ± 4.0 |
| Di(ethylene glycol) methyl ether methacrylate | 188 | 2 | -OMe | EG2-OMe | 31.5 ± 2.1 |
| Tri(ethylene glycol) methyl ether methacrylate | 232 | 3 | -OMe | EG3-OMe | 46.5 ± 5.0 |
| Poly(ethylene glycol) methyl ether methacrylate | 300 | 5 | -OMe | EG5-OMe | 57.9 ± 2.9 |
| Poly(ethylene glycol) methyl ether methacrylate | 500 | 9 | -OMe | EG9-OMe | 28.4 ± 2.4 |
| Poly(ethylene glycol) methacrylate | 360 | 6 | -OH | EG6-OH | 52.0 ± 11.8 |

| Monomer | C | | O | | COOR | | COR | | CH$_3$ | |
|---|---|---|---|---|---|---|---|---|---|---|
| | Expt. | Pred. | Expt. | Pred. | Expt. | Pred. | Expt. | Pred. | Expt. | Pred. |
| EG1-OMe | 70.7 ± 2.2 | 70.0 | 29.3 ± 2.2 | 30.0 | 14.2 ± 0.1 | 14.2 | 43.9 ± 0.5 | 42.9 | 42.0 ± 0.6 | 42.9 |
| EG3-OMe | 70.8 ± 2.3 | 69.2 | 29.2 ± 2.3 | 30.8 | 11.1 ± 0.2 | 11.1 | 57.5 ± 0.4 | 55.6 | 31.4 ± 0.2 | 33.3 |
| EG3-OMe | 73.8 ± 2.0 | 68.8 | 26.2 ± 2.0 | 31.2 | 9.5 ± 0.1 | 9.1 | 64.4 ± 0.7 | 63.6 | 26.2 ± 0.6 | 27.3 |
| EG5-OMe | 69.0 ± 2.4 | 68.3 | 31.0 ± 2.4 | 31.7 | 8.3 ± 0.1 | 6.7 | 70.5 ± 0.1 | 73.3 | 21.3 ± 0.1 | 20.0 |
| EG6-OH | 69.6 ± 2.2 | 66.7 | 30.4 ± 2.2 | 33.3 | 8.6 ± 0.5 | 6.3 | 76.4 ± 8.1 | 75.0 | 151 ± 7.7 | 18.7 |
| EG9-OMe | 68.2 ± 1.4 | 67.6 | 31.8 ± 1.4 | 32.4 | 6.0 ± 0.3 | 4.4 | 80.6 ± 1.5 | 82.6 | 13.4 ± 1.2 | 13.0 |

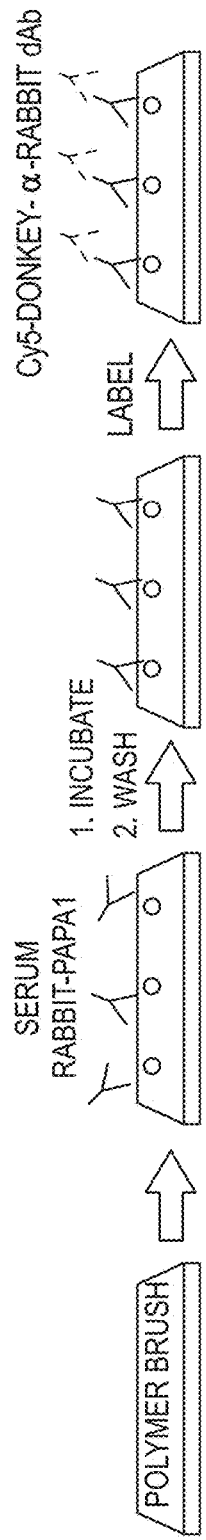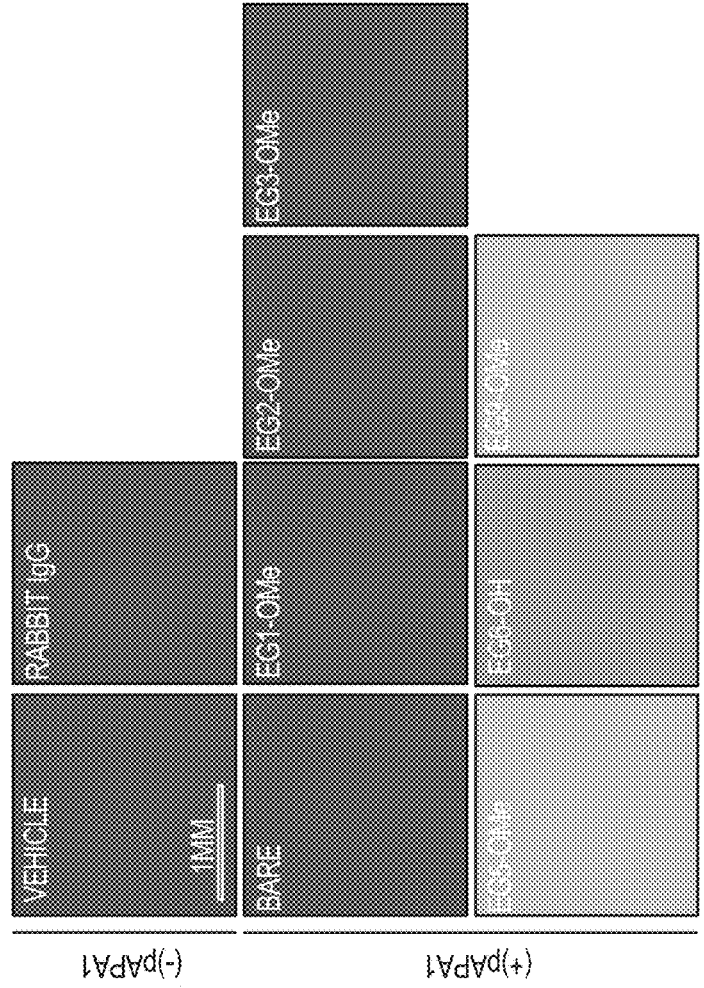
FIG. 20A
FIG. 20B

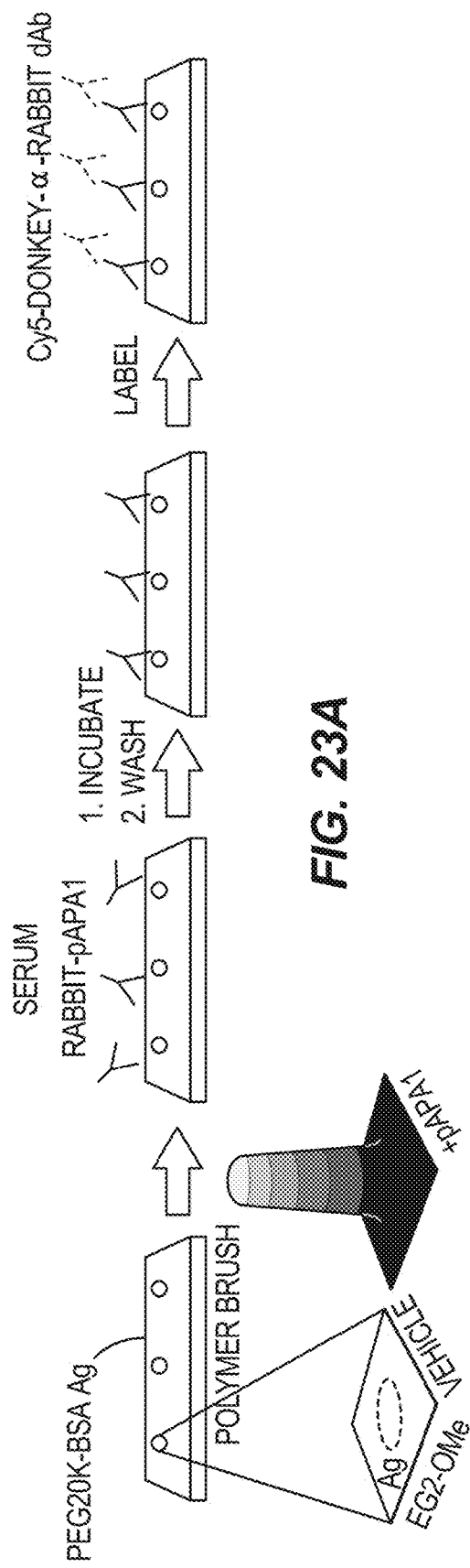
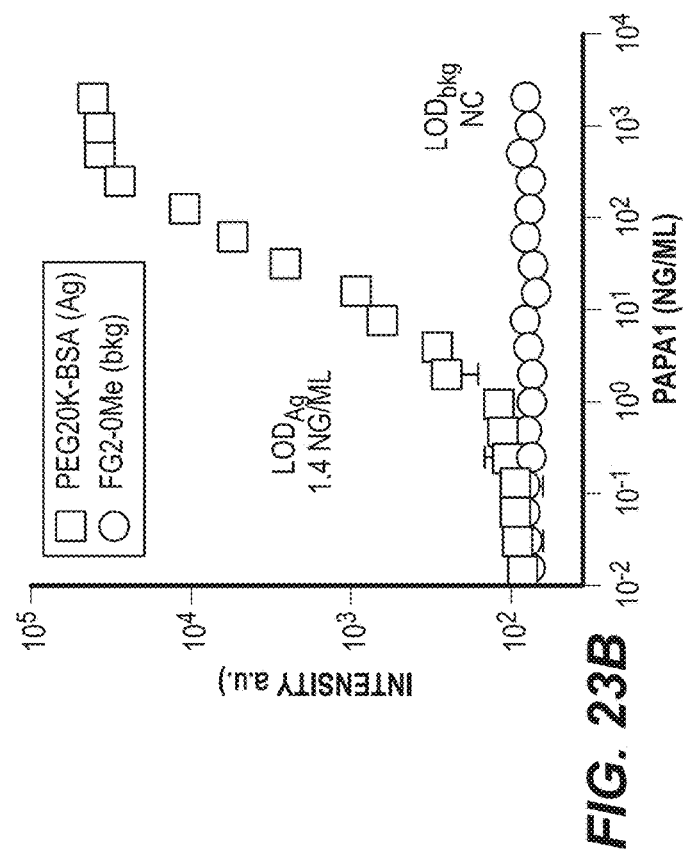
FIG. 23A
FIG. 23B

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (3)..(3)
<223> OTHER INFORMATION: any amino acid

<400> SEQUENCE: 1

Leu Pro Xaa Thr Gly
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic

<400> SEQUENCE: 2

Leu Pro Glu Thr Gly
1               5

<210> SEQ ID NO 3
<211> LENGTH: 5
<212> TYPE: PRT
<213> ORGANISM: Artificial sequence
<220> FEATURE:
```

```
<223> OTHER INFORMATION: Synthetic
<220> FEATURE:
<221> NAME/KEY: Xaa
<222> LOCATION: (3)..(3)
<223> OTHER INFORMATION: any amino acid independent of Xaa located at
      position 4
<220> FEATURE:
<221> NAME/KEY: Xaa
<222> LOCATION: (4)..(4)
<223> OTHER INFORMATION: any amino acid independent of Xaa located at
      position 3

<400> SEQUENCE: 3

Leu Pro Xaa Xaa Gly
1               5

<210> SEQ ID NO 4
<211> LENGTH: 3
<212> TYPE: PRT
<213> ORGANISM: Artificial sequence
<220> FEATURE:
<223> OTHER INFORMATION: Synthetic

<400> SEQUENCE: 4

Gly Gly Cys
1

<210> SEQ ID NO 5
<211> LENGTH: 24
<212> TYPE: PRT
<213> ORGANISM: Artificial sequence
<220> FEATURE:
<223> OTHER INFORMATION: Synthetic

<400> SEQUENCE: 5

Gly Gly Cys Gly Gly Cys Gly Gly Cys Gly Gly Cys Gly Gly Cys Gly
1               5                   10                  15

Gly Cys Gly Gly Cys Gly Gly Cys
            20

<210> SEQ ID NO 6
<211> LENGTH: 15
<212> TYPE: PRT
<213> ORGANISM: Artificial sequence
<220> FEATURE:
<223> OTHER INFORMATION: Synthetic

<400> SEQUENCE: 6

Gly Gly Gly Gly Ser Gly Gly Gly Ser Gly Gly Gly Gly Ser
1               5                   10                  15

<210> SEQ ID NO 7
<211> LENGTH: 80
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (4)..(4)
<223> OTHER INFORMATION: valine or cysteine present in a ratio of 1:1
<220> FEATURE:
<221> NAME/KEY: Xaa
<222> LOCATION: (9)..(9)
<223> OTHER INFORMATION: valine or cysteine present in a ratio of 1:1
<220> FEATURE:
<221> NAME/KEY: Xaa
<222> LOCATION: (14)..(14)
<223> OTHER INFORMATION: valine or cysteine present in a ratio of 1:1
<220> FEATURE:
```

```
<221> NAME/KEY: Xaa
<222> LOCATION: (19)..(19)
<223> OTHER INFORMATION: valine or cysteine present in a ratio of 1:1
<220> FEATURE:
<221> NAME/KEY: Xaa
<222> LOCATION: (24)..(24)
<223> OTHER INFORMATION: valine or cysteine present in a ratio of 1:1
<220> FEATURE:
<221> NAME/KEY: Xaa
<222> LOCATION: (29)..(29)
<223> OTHER INFORMATION: valine or cysteine present in a ratio of 1:1
<220> FEATURE:
<221> NAME/KEY: Xaa
<222> LOCATION: (34)..(34)
<223> OTHER INFORMATION: valine or cysteine present in a ratio of 1:1
<220> FEATURE:
<221> NAME/KEY: Xaa
<222> LOCATION: (39)..(39)
<223> OTHER INFORMATION: valine or cysteine present in a ratio of 1:1
<220> FEATURE:
<221> NAME/KEY: Xaa
<222> LOCATION: (44)..(44)
<223> OTHER INFORMATION: valine or cysteine present in a ratio of 1:1
<220> FEATURE:
<221> NAME/KEY: Xaa
<222> LOCATION: (49)..(49)
<223> OTHER INFORMATION: valine or cysteine present in a ratio of 1:1
<220> FEATURE:
<221> NAME/KEY: Xaa
<222> LOCATION: (54)..(54)
<223> OTHER INFORMATION: valine or cysteine present in a ratio of 1:1
<220> FEATURE:
<221> NAME/KEY: Xaa
<222> LOCATION: (59)..(59)
<223> OTHER INFORMATION: valine or cysteine present in a ratio of 1:1
<220> FEATURE:
<221> NAME/KEY: Xaa
<222> LOCATION: (64)..(64)
<223> OTHER INFORMATION: valine or cysteine present in a ratio of 1:1
<220> FEATURE:
<221> NAME/KEY: Xaa
<222> LOCATION: (69)..(69)
<223> OTHER INFORMATION: valine or cysteine present in a ratio of 1:1
<220> FEATURE:
<221> NAME/KEY: Xaa
<222> LOCATION: (74)..(74)
<223> OTHER INFORMATION: valine or cysteine present in a ratio of 1:1
<220> FEATURE:
<221> NAME/KEY: Xaa
<222> LOCATION: (79)..(79)
<223> OTHER INFORMATION: valine or cysteine present in a ratio of 1:1

<400> SEQUENCE: 7

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

<210> SEQ ID NO 8
<211> LENGTH: 16
<212> TYPE: PRT
<213> ORGANISM: Artificial sequence
```

```
<220> FEATURE:
<223> OTHER INFORMATION: Synthetic

<400> SEQUENCE: 8

Asn Gly Gly Pro Ser Ser Gly Ala Pro Pro Pro Ser Leu Pro Glu Thr
1               5                   10                  15
```

SURFACES HAVING REDUCED NON-SPECIFIC BINDING AND ANTIGENICITY

CROSS-REFERENCE TO RELATED APPLICATIONS

This application claims priority to U.S. Provisional Patent Application No. 62/899,353, filed on Sep. 12, 2019, and is a continuation-in-part of U.S. patent application Ser. No. 16/064,424, filed Jun. 20, 2018, which is a national phase application of International Patent Application No. PCT/US2016/068141, filed Dec. 21, 2016, which claims priority to U.S. Provisional Patent Application No. 62/270,401, filed Dec. 21, 2015; U.S. Provisional Patent Application No. 62/310,534, filed Mar. 18, 2016; U.S. Provisional Patent Application No. 62/329,800, filed Apr. 29, 2016; and U.S. Provisional Patent Application No. 62/407,403, filed Oct. 12, 2016, each of which is incorporated herein by reference in its entirety.

STATEMENT REGARDING FEDERALLY SPONSORED RESEARCH

This invention was made with government support under National Institutes of Health Grant Numbers: R01-DK092665, R01-GM061232, 5T32-GM008487, R01-GM061232, and R01-A146611; National Cancer Institute Grant Number 1UG3CA211232-01; United States Department of Defense Special Operations Command Grant Number W81XWH-16-C-0219; and United States Department of Defense Combat Casualty Care Research Program Grant Number W81XWH-17-2-0045 National Institutes of Health. The government has certain rights in the invention.

REFERENCE TO SEQUENCE LISTING

This application is filed with a Computer Readable Form of a Sequence Listing in accord with 37 C.F.R. § 1.821(c). The text file submitted by EFS, "028193-9357-US02_sequence_listing_9 Sep. 2018_ST25.txt," was created on Sep. 9, 2020, contains 8 sequences, has a file size of 4.39 Kbytes, and is hereby incorporated by reference in its entirety.

TECHNICAL FIELD

Described herein are coatings for surfaces comprising poly(oligoethylene glycol) methacrylate (POEGMA) "bottlebrushes" with sidechain lengths of 1-, 2- or 3-ethylene glycol (EG) repeats as the optimal polymer architecture to minimize binding of anti-PEG antibodies. These polymer coatings minimize nonspecific binding by proteins and cells and have reduced or eliminated antigenicity.

BACKGROUND

With more than a hundred peptides and proteins approved by the FDA to treat various diseases and many more in clinical and pre-clinical development, therapeutic peptides and proteins are an important class of drugs today. However, the clinical use of peptides and proteins is often challenged by their short plasma half-life, which can necessitate frequent injections and cause an undesirable peak-to-valley fluctuation of the drug concentration in vivo as well as reduce patient compliance and increase treatment cost. Other limitations of peptide and protein therapeutics may include poor stability, low solubility, and immunogenicity. To address these limitations, various delivery strategies have been developed for sustained delivery of peptide and protein therapeutics, ranging from particulate systems, depots, to chemical conjugation with long circulating polymers such as poly(ethylene glycol) (PEG), or recombinant fusions with long circulating proteins such as albumin or the Fc domain of antibodies.

PEGylation, or the covalent conjugation of therapeutics with the "stealth" polymer PEG, is one of the most widely used approaches to increase the circulation half-life and stability and to reduce the immunogenicity of biomolecule therapeutics such as polypeptides and polynucleotides. However, after nearly four decades of research and over two decades of clinical use, the drawbacks of PEGylation have begun to emerge. Conventional methods for the synthesis of PEGylated conjugates have significant limitations: (1) conjugation involves the reaction between protein-repulsive PEG chains and biomacromolecules, so that even with a large excess of polymer, steric hindrance still results in a low yield of conjugate, typically in the 10-20% range; (2) the presence of a large excess of unreacted polymer makes product purification non-trivial; and (3) conjugation typically involves reacting the chain-ends of the polymer with reactive side-groups on lysine and cysteine residues, which are often promiscuously distributed on the biomolecule, thus yielding chemically heterogeneous products that can significantly compromise the bioactivity of the drug and greatly complicate regulatory approval.

Furthermore, the immunogenicity of PEG has recently attracted much attention. Anti-PEG antibodies have been induced in patients treated with some PEGylated enzymes, and in clinical trials of PEG-uricase and PEG-asparaginase, these anti-PEG antibodies have markedly accelerated blood clearance, abrogated clinical efficacy, and increased the risk and severity of infusion reactions. Circulating anti-PEG antibodies have also been found in individuals naïve to PEGylated materials, possibly induced by chronic exposure to free PEGs present in commonly used consumer products. High levels of such pre-existing anti-PEG antibodies have recently been linked to serious first-exposure allergic reactions to a PEGylated RNA aptamer, which led to early termination of a clinical trial.

The immune responses that the widely-used polymer, poly(ethylene glycol) (PEG), can trigger is of growing concern. Previously considered non-immunogenic, linear PEG modification ("PEGylation") has become the most popular synthetic strategy to confer materials with "stealth" properties to eliminate protein adsorption and cell adhesion on surfaces, improve the biocompatibility of implanted biomaterials, and when conjugated to "biologics"-typically peptide and protein drugs and more recently aptamers—enhance their blood circulation and reduce their recognition by the immune system.

Products containing linear PEG constitute an estimated multi-billion-dollar market. However, evidence supporting the existence and clinical relevance of anti-PEG immunity, namely in the form of anti-PEG antibodies (APAs), is mounting. PEGylated therapeutics are now known to induce APAs in both animals and humans. Further, APAs are known to be present in much of the general population, presumably from chronic exposure to PEG from consumer products, with approximately 37% showing moderate (100 ng/mL) and 8% showing high levels (500 ng/mL) of APAs. This potentially complicates the development of drugs, devices, or diagnostics modified with PEG (or PEG-derivatives), given the possibility of unwanted interference by APAs. In fact, clinical experience with PEGylated therapeutics has already indicated that APAs can not only cause increased clearance rates and loss of efficacy, but also can lead to serious anaphylactic or hypersensitivity reactions. Notably, the issues posed by APAs has now been recognized by the Food and Drug Administration (FDA), which currently requests testing patients for APAs before treatment with experimental PEGylated compounds.

Several studies have proposed the use of alternative— non-PEG derived—stealth polymers such as polyzwitterions, poly(2-ethyl 2-oxazoline), and polyglycerol to circumvent this issue. However, transitioning to such polymers might offer an incomplete or temporary solution, for two reasons. First, antibodies (Abs) against other natural and synthetic polymers have been reported previously, suggesting that other (non-PEG derived) stealth polymers might be capable of inducing an immune response after repeated administration over time. Second, both animal and human APAs were discovered to cross-react with other synthetic polymers; this "polypharmacy" nature of polymer-reactive Abs likely adds further design constraints on candidate materials proposed as alternatives to PEG.

The large investments already made in PEGylation and its mainstream status underscore a pressing need to thoroughly investigate methods to tackle the emerging problem of 'PEG antigenicity' directly, without replacing PEG itself. Ideally, this would be accomplished without the need for potentially aggressive interventions such as preemptive immunosuppression, pre-injection of large quantities of free PEG to saturate APAs or removing PEG altogether in select situations. While these proposed strategies are intriguing, their downsides include potential additional risk to patients, reduction in therapeutic efficacy, suboptimal assay or device performance, and overall inconvenience.

What is needed are non-fouling coatings for biointerfacial applications that have reduced antigenicity and do not induce anti-PEG antibodies.

SUMMARY

One embodiment described herein is a surface having reduced antigenicity and non-specific biomolecule binding comprising: a surface comprising a plurality of poly[oligo(ethylene glycol) methyl ether methacrylate (POEGMA) polymers comprising a poly(methyl methacrylate) backbone and a plurality of side chains covalently attached to the backbone, each side chain comprising 1 to 9 ethylene glycol monomers repeated in tandem and terminating with an alkoxy moiety. In one aspect, the surface has reduced antigenicity and reduced immunogenicity. In another aspect, the surface is not reactive with anti-PEG antibodies in a subject. In another aspect, the surface does not bind proteins, lipids, or carbohydrates non-specifically. In another aspect, the side chain comprises 1 to 5 ethylene glycol monomers repeated in tandem. In another aspect, the side chain comprises 1 to 3 ethylene glycol monomers repeated in tandem. In another aspect, the side chain comprises 2 to 3 ethylene glycol monomers repeated in tandem. In another aspect, the side chain comprises 2 ethylene glycol monomers repeated in tandem. In another aspect, the side chain comprises 3 ethylene glycol monomers repeated in tandem. In another aspect, the alkoxy is methoxy, ethoxy, or propoxy. In another aspect, the alkoxy is methoxy. In another aspect, the POEGMA comprises monomers of ethylene glycol methyl ether methacrylate (EG-1-OMe). In another aspect, the POEGMA comprises monomers of di(ethylene glycol) methyl ether methacrylate (EG-3-OMe). In another aspect, the POEGMA comprises monomers of tri(ethylene glycol) methyl ether methacrylate (EG-3-OMe). In another aspect, the POEGMA comprises monomers of penta(ethylene glycol) methyl ether methacrylate (EG-5-OMe). In another aspect, the POEGMA comprises monomers of nona(ethylene glycol) methyl ether methacrylate (EG-9-OMe). In another aspect, the surface is a material or a biomolecule. In another aspect, the surface is a protein or a protein complex. In another aspect, the surface is a material comprising glass, plastic, metal, ceramic, textile, or paper.

Another embodiment described herein is a method for reducing antigenicity of and non-specific biomolecule binding to a surface, the method comprising: affixing to a surface a plurality of poly[oligo(ethylene glycol) methyl ether methacrylate (POEGMA) polymers comprising a poly(methyl methacrylate) backbone and a plurality of side chains covalently attached to the backbone, each side chain comprising 1 to 9 ethylene glycol monomers repeated in tandem and terminating with an alkoxy moiety. In one aspect, the plurality of POEGMA polymers are affixed to the surface by contacting the surface with an initiator agent to form a macroinitiator; and incubating the macroinitiator with a monomer under conditions that permit free-radical polymerization and formation of a branched polymer to occur from the initiator agent to form the molecule-polymer conjugate. In another aspect, the side chain comprises 1 to 5 ethylene glycol monomers repeated in tandem. In another aspect, the side chain comprises 1 to 3 ethylene glycol monomers repeated in tandem. In another aspect, the side chain comprises 2 to 3 ethylene glycol monomers repeated in tandem. In another aspect, the side chain comprises 2 ethylene glycol monomers repeated in tandem. In another aspect, the side chain comprises 3 ethylene glycol monomers repeated in tandem. In another aspect, the alkoxy is methoxy, ethoxy, or propoxy. In another aspect, the alkoxy is methoxy. In another aspect, the POEGMA comprises monomers of ethylene glycol methyl ether methacrylate (EG-1-OMe). In another aspect, the POEGMA comprises monomers of di(ethylene glycol) methyl ether methacrylate (EG-3-OMe). In another aspect, the POEGMA comprises monomers of tri(ethylene glycol) methyl ether methacrylate (EG-3-OMe). In another aspect, the POEGMA comprises monomers of penta(ethylene glycol) methyl ether methacrylate (EG-5-OMe). In another aspect, the POEGMA comprises monomers of nona(ethylene glycol) methyl ether methacrylate (EG-9-OMe). In another aspect, the surface is a material or a biomolecule. In another aspect, the surface is a protein or a protein complex. In another aspect, the surface is a protein and one or more POEGMA polymers is affixed to the polypeptide at the C-terminus, the N-terminus, or an internal amino acid of the polypeptide. In another aspect, the surface is a material comprising glass, plastic, metal, ceramic, textile, or paper.

Another embodiment described herein is a surface coated with a plurality of POEGMA polymers by a method described herein. In one aspect, the surface is a biomolecule or a material. In another aspect, the surface has reduced antigenicity and reduced immunogenicity; is not reactive with anti-PEG antibodies in a subject; and does not bind proteins, lipids, or carbohydrates non-specifically.

In another embodiment, the disclosure relates to methods of reducing the antigenicity of a molecule. The methods may include conjugating at least one branched polymer to a molecule to form a molecule-polymer conjugate, wherein the molecule comprises a polypeptide, a polynucleotide, a small molecule, or a combination thereof, wherein the branched polymer comprises a backbone and a plurality of side chains, each side chain is covalently attached to the backbone, wherein the backbone comprises at least one of an acrylate, methacrylate, acrylamide, methacrylamide, carbonate, phosphoester, oxazoline, or a combination thereof, and wherein the molecule-polymer conjugate has reduced or eliminated antigenicity compared to a control. In some embodiments, the molecule is conjugated to the backbone of the branched polymer. In some embodiments, the molecule is conjugated to the backbone of the branched polymer via a linker. In some embodiments, each side chain has a first terminal end and a second terminal end, wherein the first terminal end is covalently attached to the backbone, and wherein the second terminal end independently comprises an alkyl, ester, amine, amide, or carboxyl group. In some embodiments, each side chain has a first terminal end and a second terminal end, wherein the first terminal end is covalently attached to the backbone, and wherein the second terminal end does not include a hydroxyl group. In some embodiments, each side chain is a linear polymer. In some embodiments, at least one side chain comprises 1 monomer. In some embodiments, each side chain comprises at least 2 monomers repeated in tandem. In some embodiments, each side chain comprises less than 25 monomers repeated in tandem. In some embodiments, each side chain comprises 3 to 9 monomers repeated in tandem. In some embodiments, each side chain comprises 3 monomers repeated in tandem. In some embodiments, the monomer of each side chain is independently selected from betaine, phosphorylcholine, phosphorylethanolamine, sarcosine, ethylene glycol, or a combination thereof. In some embodiments, the betaine comprises carboxybetaine, sulfobetaine, or a combination thereof. In some embodiments, the monomer of at least one side chain comprises ethylene glycol. In some embodiments, the monomer of each side chain comprises ethylene glycol. In some embodiments, more than one branched polymer is conjugated to the molecule, each branched polymer conjugated to a different site of the molecule. In some embodiments, the molecule comprises a polypeptide, and wherein one branched polymer is conjugated to the polypeptide at a site selected from the C-terminus, the N-terminus, and an internal amino acid of the polypeptide. In some embodiments, the molecule comprises a polypeptide, and wherein more than one branched polymer is conjugated to the polypeptide, each branched polymer conjugated to a different site of the polypeptide selected from the C-terminus, the N-terminus, an internal amino acid, or a combination thereof.

In some embodiments, the molecule comprises a polypeptide comprising a sortase A recognition site, and wherein the branched polymer and the polypeptide are incubated with sortase A under conditions to conjugate the branched polymer to the sortase recognition site of the polypeptide. In some embodiments, the molecule comprises a polypeptide comprising a sortase A recognition site, and wherein the conjugating comprises: a) contacting the molecule with a sortase A and an initiator agent under conditions that permit attachment of the initiator agent to the sortase A recognition site to form a macroinitiator; and b) incubating the macroinitiator with a monomer under conditions that permit free-radical polymerization and formation of a branched polymer to occur from the initiator agent to form the molecule-polymer conjugate. In some embodiments, the sortase A recognition site comprises LPXTG (SEQ ID NO: 1), wherein X is any amino acid. In some embodiments, the macroinitiator and monomer are incubated with a catalyst in step (b). In some embodiments, the monomer in step (b) comprises at least one of an acrylate, methacrylate, acrylamide, methacrylamide. In some embodiments, the method further includes separating the molecule-polymer conjugate formed in step (b) from the unreacted macroinitiator. In some embodiments, the branched polymer is synthesized and subsequently grafted to the molecule to form the molecule-polymer conjugate. In some embodiments, the conjugating comprises attaching an initiator agent to the molecule to form a macroinitiator; and incubating the macroinitiator with a monomer under conditions that permit free-radical polymerization and formation of a branched polymer to occur from the initiator agent to form the molecule-polymer conjugate. In some embodiments, the branched polymer is synthesized using free-radical polymerization. In some embodiments, the branched polymer is synthesized using at least one method selected from ionic ring-opening polymerization (ionic ROP), ring opening metathesis polymerization, ionic polymerization, condensation polymerization, and coordination polymerization.

In a further aspect, the disclosure relates to methods of making a molecule-polymer conjugate having reduced or eliminated antigenicity compared to a control, from a molecule comprising a polypeptide having a sortase A recognition site. The methods may include a) contacting the molecule with a sortase A and an initiator agent under conditions that permit attachment of the initiator agent to the sortase A recognition site to form a macroinitiator; and b) incubating the macroinitiator with a monomer under conditions that permit free-radical polymerization and formation of a branched polymer to occur from the initiator agent to form the molecule-polymer conjugate, wherein the branched polymer comprises a backbone and a plurality of side chains, each side chain covalently attached to the backbone. In some embodiments, the sortase A recognition site comprises LPXTG (SEQ ID NO: 1), wherein X is any amino acid. In some embodiments, the macroinitiator and monomer are incubated with a catalyst in step (b). In some embodiments, the monomer in step (b) comprises at least one of an acrylate, methacrylate, acrylamide, and methacrylamide. In some embodiments, the method further includes separating the molecule-polymer conjugate formed in step (b) from the unreacted macroinitiator, wherein the yield of molecule-polymer conjugate is at least about 50% of the total conjugates and macroinitiators which are separated. In some embodiments, the molecule-polymer conjugate is separated by chromatography. In some embodiments, the chromatography comprises size-exclusion chromatography, ion exchange chromatography, affinity chromatography, or hydrophobic interaction chromatography, or a combination thereof. In some embodiments, the chromatography comprises size-exclusion chromatography. In some embodiments, the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization. In some embodiments, the molecule comprises a polypeptide, a polynucleotide, a small molecule, or a combination thereof.

Another aspect of the disclosure provides a molecule-polymer conjugate having reduced or eliminated antigenicity compared to a control. The molecule-polymer conjugates may include a branched polymer comprising a backbone and a plurality of side chains, each side chain covalently attached to the backbone; and a molecule conjugated to the backbone of the branched polymer, wherein the molecule comprises a polypeptide, a polynucleotide, a small molecule, or a combination thereof, wherein each side chain is a linear polymer, wherein the backbone comprises at least one of an acrylate, methacrylate, acrylamide, methacrylamide, carbonate, phosphoester, oxazoline, or a combination thereof. In some embodiments, the molecule is conjugated to the backbone of the branched polymer via a linker. In some embodiments, each side chain has a first terminal end and a second terminal end, wherein the first terminal end is covalently attached to the backbone, and wherein the second terminal end independently comprises an alkyl, ester, amine, amide, or carboxyl group. In some embodiments, each side chain has a first terminal end and a second terminal end, wherein the first terminal end is covalently attached to the backbone, and wherein the second terminal end does not include a hydroxyl group. In some embodiment the second terminal end includes an alkoxy group.

In some embodiments, at least one side chain comprises at least 1 monomer. In some embodiments, each side chain comprises at least 2 monomers repeated in tandem. In some embodiments, each side chain comprises less than 25 monomers repeated in tandem. In some embodiments, each side chain comprises less than 10 monomers repeated in tandem. In some embodiments, each side chain comprises less than 5 monomers repeated in tandem. In some embodiments, each side chain comprises less than 4 monomers repeated in tandem. In some embodiments, each side chain comprises less than 3 monomers repeated in tandem. In some embodiments, each side chain comprises 1 to 9 monomers repeated in tandem. In some embodiments, each side chain comprises 3 to 9 monomers repeated in tandem. In some embodiments, each side chain comprises 1 to 3 monomers repeated in tandem. In some embodiments, each side chain comprises 2 to 3 monomers repeated in tandem. In some embodiments, each side chain comprises 3 monomers repeated in tandem. In some embodiments, each side chain comprises 2 monomers repeated in tandem.

In some embodiments, the monomer of each side chain is independently selected from betaine, phosphorylcholine, phosphorylethanolamine, sarcosine, ethylene glycol, or a combination thereof. In some embodiments, the betaine comprises carboxybetaine, sulfobetaine, or a combination thereof. In some embodiments, the monomer of at least one side chain comprises ethylene glycol. In some embodiments, the monomer of each side chain comprises ethylene glycol. In some embodiments, more than one branched polymer is conjugated to the molecule, each branched polymer conjugated to a different site of the molecule. In some embodiments, the molecule comprises a polypeptide, and wherein one branched polymer is conjugated to the polypeptide at a site selected from the C-terminus, the N-terminus, and an internal amino acid of the polypeptide. In some embodiments, the molecule comprises a polypeptide, and wherein more than one branched polymer is conjugated to the polypeptide, each branched polymer conjugated to a different site of the polypeptide selected from the C-terminus, the N-terminus, an internal amino acid, or a combination thereof.

In some embodiments, the branched polymer comprises poly[oligo(ethylene glycol) methyl ether methacrylate] (POEGMA), and wherein the POEGMA comprises: a backbone comprising poly(methyl methacrylate); and a plurality of side chains covalently attached to the backbone, each side chain comprising at least 1 monomer of ethylene glycol (EG) repeated in tandem. In some embodiments, at least one side chain comprises at least 1 monomer of ethylene glycol (EG). In some embodiments, each side chain comprises at least 2 monomers of ethylene glycol (EG) repeated in tandem. In some embodiments, each side chain comprises at least 3 monomers of ethylene glycol (EG) repeated in tandem. In some embodiments, each side chain comprises at least 10 monomers of ethylene glycol (EG) repeated in tandem. In some embodiments, each side chain comprises less than 25 monomers of ethylene glycol (EG) repeated in tandem. In some embodiments, each side chain comprises 1 monomer of ethylene glycol (EG). In some embodiments, each side chain comprises 2 monomers of ethylene glycol (EG) repeated in tandem. In some embodiments, each side chain comprises 3 monomers of ethylene glycol (EG) repeated in tandem. In some embodiments, each side chain comprises 5 monomers of ethylene glycol (EG) repeated in tandem. In some embodiments, each side chain comprises 6 monomers of ethylene glycol (EG) repeated in tandem. In some embodiments, each side chain comprises 9 monomers of ethylene glycol (EG) repeated in tandem. In some embodiments, each side chain comprises 1 to 9 monomers of ethylene glycol (EG) repeated in tandem. In some embodiments, each side chain comprises 3 to 9 monomers of ethylene glycol (EG) repeated in tandem. In some embodiments, each side chain comprises 2 to 3 monomers of ethylene glycol (EG) repeated in tandem. In some embodiments, the molecule-POEGMA conjugate or surface-POEGMA is not reactive with pre-existing anti-PEG antibodies in a subject and does not bind to proteins non-specifically.

In some embodiments, the molecule comprises one or more peptides or protein therapeutic agents selected from a monoclonal antibody, blood factor, betatrophin, exendin, enzyme, asparaginase, glutamase, arginase, arginine deaminase, adenosine deaminase (ADA), ADA-2, ribonuclease, cytosine deaminase, trypsin, chymotrypsin, papain, growth factor, epidermal growth factor (EGF), insulin, insulin-like growth factor (IGF), transforming growth factor (TGF), nerve growth factor (NGF), platelet-derived growth factor (PDGF), bone morphogenic protein (BMP), fibroblast growth factor (FGF), somatostatin, somatotropin, somatropin, somatrem, calcitonin, parathyroid hormone, colony stimulating factors (CSF), clotting factors, tumor necrosis factors (TNF), gastrointestinal peptides, vasoactive intestinal peptide (VIP), cholecystokinin (CCK), gastrin, secretin, erythropoietins, growth hormone, GRF, vasopressins, octreotide, pancreatic enzymes, superoxide dismutase, thyrotropin releasing hormone (TRH), thyroid stimulating hormone, luteinizing hormone, luteinizing hormone-releasing hormone (LHRH), growth hormone releasing hormone (GHRH), tissue plasminogen activators, interleukins, interleukin-1, interleukin-15, interleukin-2, interleukin-10, colony stimulating factor, granulocyte macrophage colony-stimulating factor (GM-CSF), interleukin-1 receptor antagonist (IL-1RA), glucagon-like peptide-1 (GLP-1), exenatide, GLP-1 R multi-agonist, GLP-1 R antagonist, GLP-2, TNF-related apoptosis-inducing ligand (TRAIL), leptin, ghrelin, granulocyte monocyte colony stimulating factor (GM-CSF), interferons, interferon-α, interferon-gamma, human growth hormone (hGH) and antagonist, macrophage activator, chorionic gonadotropin, heparin, atrial natriuretic peptide, hemoglobin, relaxin, cyclosporine, oxytocin, vaccines, monoclonal antibodies, single chain antibodies, ankyrin repeat proteins, affibodies, activin receptor 2A extracellular domain, alpha-2 macroglobulin, alpha-melanocyte, apelin, bradykinin B2 receptor antagonist, cytotoxic T-lymphocyte-associated protein (CTLA-4), elafin, Factor IX, Factor VIIa, Factor VIII, hepcidin, infestin-4, kallikrein inhibitor, L4F peptide, lacritin, parathyroid hormone (PTH), peptide YY (PYY), thioredoxin, thymosin B4, urate oxidase, urodilatin, aptamers, silencing RNA, microRNA, long non-coding RNA, ribozymes, analogs and derivatives thereof, and combinations thereof. In some embodiments, the molecule comprises a polypeptide, and wherein the polypeptide comprises a His-tag, a stimulus-responsive polypeptide, or a combination thereof. In some embodiments, the stimulus-responsive polypeptide is selected from an elastin-like polypeptide, a polypeptide comprising a repeated motif, and a resilin-like polypeptide. In some embodiments, the molecule-polymer conjugate has: an in vivo half-life that is at least 25% greater compared with the in vivo half-life of the molecule itself; or an in vivo biodistribution to a tissue, organ, or disease site that is at least 25% greater than the in vivo biodistribution of the molecule itself; or a reduced binding to anti-PEG antibodies compared to a control; or a reduced immune response compared to a control; or a combination thereof. In some embodiments, the molecule-polymer conjugates have an in vivo half-life that is at least 80% greater than the in vivo half-life of the molecule itself. In some embodiments, the control comprises the molecule conjugated to a polymer that is not branched. In some embodiments, the control comprises the molecule by itself. In some embodiments, the control comprises the molecule conjugated to a linear polymer. In some embodiments, the control comprises the molecule conjugated to unbranched PEG. In some embodiments, the molecule comprises a polypeptide, and wherein at least about 20% of the polypeptides have a conjugated branched polymer solely at the C-terminus. In some embodiments, at least about 75% of the polypeptides have a conjugated branched polymer solely at the C-terminus. In some embodiments, at least about 90% of the polypeptides have a conjugated branched polymer solely at the C-terminus. In some embodiments, the yield of molecule-polymer conjugate is at least about 75%. In some embodiments, the yield of molecule-polymer conjugate is at least about 85%.

The disclosure provides for other aspects and embodiments that will be apparent in light of the following detailed description and accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows Recombinant expression of the sortase A substrate, exendin-srt-His6-ELP, and purification by ITC. FIG. 1B shows sortase-catalyzed site-specific attachment of the ATRP initiator AEBMP to the C-terminus of exendin to generate exendin-C—Br. FIG. 1C shows in situ ATRP of OEGMA from exendin-C—Br yielding exendin-C-POEGMA. ITC: inverse transition cycling, ELP: elastin-like polypeptide, srt: sortase A recognition sequence "LPETG" (SEQ ID NO: 2), AEBMP: N-(2-(2-(2-(2-aminoacetamido) acet-amido)acetamido) ethyl)-2-bromo-2-methylpropanamide. Images from the RCSB PDB (www.rcsb.org) of: PDB ID 1T2P (sortase A); PDB ID 1JRJ (exendin-4).

FIG. 2A shows Coomassie-stained SDS-PAGE analysis of initiator attachment on exendin by sortase A. Lane 1: MW marker, lane 2: sortase reaction mixture after 18 h of reaction, lane 3: purified exendin-C—Br macroinitiator. FIG. 2B shows SEC traces of ATRP reaction mixtures of grafting EG9 POEGMA from exendin-C—Br carried out for 0.5 h, 1 h, 1.25 h, 2 h and 3 h, detected by UV-vis absorbance at 280 nm. FIG. 2C shows cyclic adenosine monophosphate (cAMP) response of native exendin and EG9 exendin-C-POEGMA conjugates with Mns of 25.4 kDa, 54.6 kDa, 66.2 kDa, 97.2 kDa and 155.0 kDa in baby hamster kidney (BHK) cells expressing the GLP-1R. Results are plotted as mean±standard error of the mean (SEM), n=3. Half-maximal effective concentration ($EC_{50}$) values are summarized in Table 3.

FIG. 3F shows the area under the curve (AUC) of blood glucose profiles (0 h to 144 h, with respect to 0% baseline) as a function of conjugate Mn. AUCs were compared using one-way ANOVA followed by post hoc Tukey's multiple comparison test. In all panels, results are plotted as mean±SEM, n=6, *$P<0.05$, $P<0.01$, *$P<0.001$ and ****$P<0.0001$.

FIG. 5A shows a direct ELISA probing 54.6 kDa EG9 exendin-C-POEGMA conjugate, native exendin, adenosine deaminase (ADA), bovine serum albumin (BSA), Krystexxa® (PEG-uricase) and Adagen® (PEG-ADA) with diluent (1% BSA in PBS), an anti-PEG negative patient plasma sample, or one of two anti-PEG positive plasma samples. FIG. 5B shows a competitive ELISA, where various amounts of exendin, 54.6 kDa EG9 exendin-C-POEMGA, ADA and Adagen® were allowed to compete with Krystexxa® for binding with anti-PEG antibodies in a positive plasma sample. FIG. 5C shows direct and FIG. 5D shows competitive assays described in FIG. 5A and FIG. 5B, respectively, performed with a 55.6 kDa EG3 exendin-C-POEGMA conjugate. In all assays, the same unmodified peptide/protein content or similar PEG/OEG content in the case of polymer-modified samples per well were compared. See Methods section for details. Results are plotted as mean±SEM, n=3 in FIG. 5A-B, n=5 in FIG. 5C-D. Data were analyzed by two-way ANOVA, followed by post hoc Dunnett's multiple comparison test ($P<0.01$, and **$P<0.0001$).

FIG. 7A shows a $CuCl_2$-stained SDS-PAGE analysis of exendin-srt-His6-ELP purification by inverse transition cycling (ITC). Lane 1: marker, lane 2: *E. coli* lysate, lanes 3 and 4: soluble protein after one and two ITC cycles (yield: ~60 mg/L of culture). ELP: elastin-like polypeptide. FIG. 7B shows His6-sortase A purification by immobilized metal affinity chromatography (IMAC). Lane 1: marker, lane 2: *E. coli* lysate, lanes 3 and 4: first and second elution washes with imidazole (yield: ~400 mg/L of culture). His6: hexahistidine.

FIG. 9A shows SEC traces of ATRP reaction mixtures of grafting EG9 POEGMA from the exendin-C—Br macroinitiator carried out for various times with RI detection. Due to its small size and low concentration, the signal from the residual exendin-C—Br was too low to be observed by RI detection. FIG. 9B shows Coomassie-stained SDS-PAGE analysis of EG9 exendin-C-POEGMA conjugates purified by a single round of preparative SEC. Lane 1: marker, from left to right in lanes 2-6: purified 155.0 kDa, 97.2 kDa, 66.2 kDa, 54.6 kDa and 25.4 kDa EG9 conjugates.

FIG. 12C shows overlaid weight profiles for all treatment and control groups. Weights are reported as % change from 0 h time point. Weights were not measured for the exendin group at t=144 h. Results in all panels are plotted as mean±SEM.

FIG. 16A shows isotopic distribution of C-terminal peptide [NGGPSSGAPPPSLPET-"AEBMP", SEQ ID NO: 8]2+ detected by LC/MS-MS after trypsin digestion of exendin-C—Br. FIG. 16B shows theoretical isotopic distribution of C-terminal peptide of exendin-C—Br after trypsin digestion generated by Molecular Mass Calculator software (Pacific Northwest National Laboratory).

FIG. 17C shows Coomassie-stained SDS-PAGE analysis of EG3 exendin-C-POEGMA conjugates purified by a single round of preparative SEC. Lane 1: marker, from left to right in lanes 2-4: purified 26.3, 55.6 and 71.6 kDa EG3 conjugates.

FIG. 18A-D. Synthesis of POEGMA bottlebrushes with variable sidechain lengths by surface-initiated atom transfer radical polymerization (SI-ATRP) from planar glass substrates. FIG. 18A shows a stepwise illustration of POEGMA growth strategy. Glass surfaces are first functionalized ("activated") with a brominated ATRP initiator (see Methods). POEGMA bottlebrushes are then "grafted from" surfaces by SI-ATRP of PEG-methacrylate monomers. This study sought to identify polymer brush coatings that not only resist nonspecific binding by proteins and cells, but also recognition by anti-PEG antibodies (APAs) upon exposure to biological fluid. FIG. 18B shows characteristics of PEG-methacrylate monomers, which were all methoxy-terminated except for the EG6 moiety, which was hydroxy-terminated. (MW=molecular weight, EG #=number of ethylene glycol units, t=polymer overlayer thickness in nm). FIG. 18C and FIG. 18D show the contact angle measurement of bottle-brush coatings. Experimental whole water droplet profiles (FIG. 18C) and measured contact angles (FIG. 18D) for each surface. Results are plotted as mean±95% confidence interval. There was a statistically significant difference between groups as determined by one-way ANOVA (F(6, 37)=136.0, p<0.0001). Bars marked with a different letter indicates significant differences (Tukey post hoc test, p≤0.05).

FIG. 19A-H. X-ray photoelectron spectroscopy (XPS) analysis of polymer bottlebrush coatings. FIG. 19A, FIG. 19B, FIG. 19C, FIG. 19D, FIG. 19E, FIG. 19F, and FIG. 19G show survey spectra (left) along with high-resolution O1s (middle) and C1s (right) spectra for each surface are shown. Deconvolution of high-resolution C1s spectrum into individual CHx, COR, and COOR peaks is also shown. FIG. 19H shows a table of predicted and experimental atomic concentrations (%). Total carbon (C) and oxygen (O) content were calculated from survey spectra, and individual carbon species were calculated by curve-fitting deconvolved high-resolution C1s spectra. The following peak positions were used: O1s (530.6 eV); C1s (~284.5 eV); CHx (284.5 eV), COR (286.0 eV), COOR (288.5 eV); Si 2s (154.8 eV), Si 2p (103.5 eV). Results are displayed as mean±s.d. of three separate spectra.

FIG. 20A-C. Screening polymer bottlebrush surfaces for immune reactivity toward polyclonal APAs (pAPA1). FIG. 20A shows a schematic of pAPA1 fluoroimmunoassay. Surfaces were incubated with a solution of rabbit-derived pAPA1 spiked into calf serum, rinsed, and then labeled with Cy5-donkey-α-rabbit dAbs, and then read with a scanner. CHAPS/PBS rinsing buffer was used instead of PEG detergent-containing buffers (e.g., Tween20@/PBS) to prevent potential assay interference. FIG. 20B and FIG. 20C show representative Cy5 channel fluorescence images (FIG. 20B) and quantitation of mean fluorescence intensities (FIG. 20C). Vehicle-only and rabbit-IgG (not specific to PEG) controls are also included to show baseline values. Treating surfaces with pAPA1 leads to considerable fluorescence signal (APA binding) by EG5-OMe, EG6-OH, and EG9-OMe surfaces, but not for bare, EG1-OMe, EG2-OM2, nor EG3-OMe surfaces. Results are plotted as mean±95% confidence interval. There was a statistically significant difference between pAPA1-treated groups, as determined by one-way ANOVA (F(6, 33)=50.05, p<0.0001). Control groups are plotted for comparison. Bars marked with different letters indicate significant differences within the pAPA1-treated groups (Tukey post hoc test, p≤0.05).

FIG. 22A shows a schematic of surface fluorescence assay used to evaluate protein fouling. Cy5-labeled BSA was incubated on surfaces, rinsed, and then read with a scanner for residual fluorescence. FIG. 22B and FIG. 22C show representative Cy5 channel fluorescence images (FIG. 22B) and quantitation of mean±95% CI fluorescence intensities (FIG. 22C) (n=3 for bare glass, and n≥6 for others). Vehicle groups are plotted for comparison. Bars marked with different letters indicate significant differences within the Cy5-BSA-treated groups by multiple comparison testing in one-way ANOVA (Tukey post hoc test, p≤0.05). FIG. 22D shows a schematic of in vitro cell adhesion assay. NIH 3T3 cells expressing GFP (3T3-GFP) were incubated on surfaces in complete medium, washed, and then imaged for residual fluorescence on GFP channel by epifluorescence imaging. FIG. 4E and FIG. 4F show representative epifluorescence images of cells (FIG. 22E) and quantitation of cell adhesion to surfaces (FIG. 22F) expressed as mean % FOV±95% CI (n=6). Bars marked with different letters indicate significantly different groups by multiple comparison testing in one-way ANOVA (Tukey post hoc test, p≤0.05).

FIG. 23A-F. Direct comparison of reactivity of APAs toward POEGMA brushes with different EG sidechain lengths versus linear PEG (MW=20 K). FIG. 23A shows a schematic of printing microspots of PEG20K-BSA Ag onto a background of POEGMA brush surfaces. Surfaces were incubated with a dilution series of rabbit-derived pAPA1 in serum, labeled with Cy5-anti-rabbit dAb, and then read by a fluorescence scanner. The inset shows spatial intensity plots of Cy5 fluorescence from EG2-OMe polymer brush surfaces functionalized by PEG20K-BSA Ag microspots (outlined by white dashes). Shown are 330×330 μm regions corresponding to surfaces (containing a single Ag microspot) exposed to serum alone (left) versus serum spiked with 2 μg/mL pAPA1 (right). FIG. 23B, FIG. 23D, and FIG. 23F show concentration curves of pAPA1 binding measured by fluorescence intensity from PEG20K-BSA Ag microspots (black squares) versus that from EG2-OMe POEGMA background (open circles). Data represent mean±s.d. (n=3). LODs determined from PEG20K-BSA microspots versus polymer background (LODAg vs. LODbkg, respectively) are displayed adjacent to each curve. FIG. 23C and FIG. 23E show spatial intensity plots and concentration curves for EG3-Ome (FIG. 5C) and EG5-OMe (FIG. 23E).

FIG. 26A shows a schematic of backbone-selective (blue) versus endgroup-selective (tan) APA binding to PEG backbone and methoxy terminus of a bottlebrush, respectively. FIG. 26B shows a schematic of surface fluoroimmunoassay for APA binding. Surfaces were incubated with a solution of APA-spiked calf serum, then labeled with Cy5-conjugated dAbs, and then read with a scanner. FIG. 26C, FIG. 26D, FIG. 26E, and FIG. 26F show reactivity of polyclonal APAs toward bottlebrush surfaces with known selectivity for PEG endgroups (pAPA1) versus backbone (pAPA2) (FIG. 26C and FIG. 26D), and similar plots shown for endgroup-selective (e-mAPA) versus backbone-selective (b-mAPA) monoclonal APAs (FIG. 26E and FIG. 26F) as assessed by surface fluoroimmunoassays. Data are plotted as mean fluorescence intensities±s.d. (n=9). Bars marked with different letters indicate significant differences by multiple comparison testing in one-way ANOVA (Tukey post hoc test, $p \leq 0.05$).

FIG. 29A shows a schematic of serological antibody ISIA. ISIAs comprised of p24 Ag spotted onto bottlebrush overlayers were incubated with a dilution series of rabbit anti-HIV p24 polyclonal Ab, either with (bottom pathway) or without (top pathway) the presence of APA interferent (pAPA1). Surfaces were labeled with Cy5-donkey-anti-rabbit dAb, and then read by a scanner. FIG. 29B, FIG. 29C, FIG. 29D, FIG. 29E, and FIG. 29F show concentration binding curves for detecting polyclonal anti-p24 Ab (analyte) on polymer brush-based ISIAs, either with or without 100 ng/mL of APA interferent (black squares and open circles, respectively). LODs for each curve are provided in ng/mL, except for the EG5-OMe curve run with APA interferent, which was not calculated due to high background noise. Each data point represents mean±s.d. from duplicate runs.

DETAILED DESCRIPTION

Figure 1A:
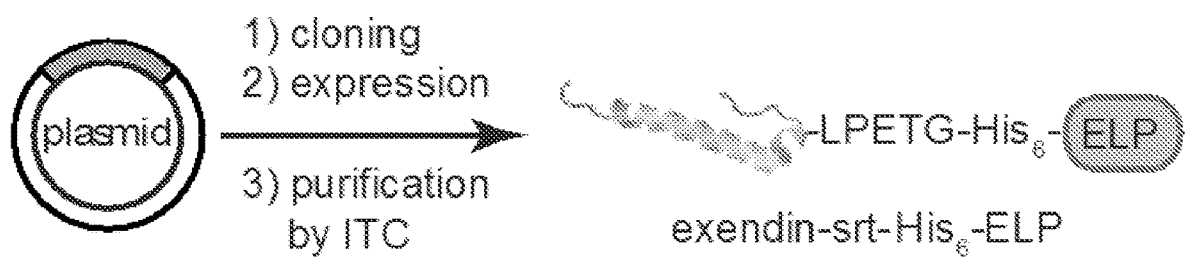
FIG. 1A-C. Synthetic scheme of exendin-C-POEGMA.

Described herein are methods of reducing or eliminating the antigenicity of a molecule by conjugating a branched polymer thereto to form a molecule-polymer conjugate. The branched polymer may be conjugated to the molecule by a variety of ways. As detailed herein, sortase-catalyzed polymer conjugation may be used to generate a molecule-polymer conjugate. This strategy exploits the C-terminal native peptide ligation mechanism of the enzyme sortase A. Breaking up and appending PEG as short oligomeric sidechains of optimized length on the conjugated POEGMA not only retains the long circulation of the POEGMA conjugates, but also eliminates their reactivity toward patient-derived PEG antibodies. These results demonstrate that the architecture of PEG appended to a molecule plays a role in modulating its antigenicity. The compositions and methods detailed here may be used to deliver molecules with reduced or eliminated antigenicity, and thereby address the growing prevalence of pre-existing anti-PEG antibodies in the general population that is increasingly undermining the safety and efficacy of PEGylated therapeutics.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "or" can be conjunctive or disjunctive.

All ranges disclosed include both end points as discrete values as well as all integers and fractions specified within the ranges with the same degree of precision is explicitly contemplated. For example, a range of 0.1-2.0 includes 0.1, 0.2, 0.3, 0.4 . . . 2.0. If the end points are modified by the term "about," the range specified is expanded by a variation of up to ±10% of any value within the range, including the end points.

The term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. The term "about" as used herein refers to any values, including both integers and fractional components that are within a variation of up to ±10% of the value modified by the term "about." In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, in some embodiments within 5-fold, and in some embodiments within 2-fold, of a value. As used herein the symbol "~" preceeding any value means "about."

The term "substantially" as used herein means to a great or significant extent, but not completely.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

"Antigen" refers to a molecule capable of being bound by an antibody or a T cell receptor. The term "antigen," as used herein, also encompasses T-cell epitopes. An antigen is additionally capable of being recognized by the immune system and/or being capable of inducing a humoral immune response and/or cellular immune response leading to the activation of B-lymphocytes and/or T-lymphocytes. In some embodiments, the antigen contains or is linked to a Th cell epitope. An antigen can have one or more epitopes (B-epitopes and T-epitopes). Antigens may include polypeptides, polynucleotides, carbohydrates, lipids, small molecules, and combinations thereof. Antigens may also be mixtures of several individual antigens.

"Antigenicity" refers to the ability of an antigen to specifically bind to a T cell receptor or antibody and includes the reactivity of an antigen toward pre-existing antibodies in a subject.

"Immunogenicity" refers to the ability of any antigen to induce an immune response and includes the intrinsic ability of an antigen to generate antibodies in a subject. As used herein, the terms "antigenicity" and "immunogenicity" are different and not interchangeable.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (Biometrics 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a molecule, or sample comprising a molecule, without having a branched polymer conjugated thereto. A control may be a molecule, or sample comprising a molecule, with a polymer, that is different from a branched polymer as detailed herein, conjugated thereto. A control may be a subject, or a sample therefrom, whose disease state is known. The subject, or sample therefrom, may be healthy, diseased, diseased prior to treatment, diseased during treatment, or diseased after treatment, or a combination thereof. The control may include, for example, the molecule alone or by itself, the molecule conjugated to a different polymer, the molecule conjugated to a non-branched polymer or to a polymer that is not branched, the molecule conjugated to PEG, the molecule conjugated to unbranched PEG, the molecule directly conjugated to a linear polymer, or the molecule conjugated to a side chain directly (without a branched polymer).

The term "expression vector" indicates a plasmid, a virus or another medium, known in the art, into which a nucleic acid sequence for encoding a desired protein can be inserted or introduced.

The term "host cell" is a cell that is susceptible to transformation, transfection, transduction, conjugation, and the like with a nucleic acid construct or expression vector. Host cells can be derived from plants, bacteria, yeast, fungi, insects, animals, etc. In some embodiments, the host cell includes *Escherichia coli*.

"Opsonization" refers to the molecular mechanism whereby molecules, microbes, or apoptotic cells are chemically modified to have stronger interactions with cell surface receptors on phagocytes and natural killer (NK) cells. An antigen on the molecules, microbes, or apoptotic cell is coated in opsonins. The opsonins enhance binding to immune cells such as macrophages and neutrophils. Opsonization also mediates phagocytosis via signal cascades from cell surface receptors.

"Polymer" or "synthetic polymer" refers to a polymer which is produced from at least one monomer by a chemical process. A synthetic polymer is not produced directly by a living organism. Synthetic polymers include a homopolymer, heteropolymer, block polymer, co-polymer, ter-polymer, etc., and blends, combinations, and mixtures thereof. Examples of synthetic polymers include, but are not limited to, functionalized polymers, such as a polymer comprising 5-vinyltetrazole monomer units and having a molecular weight distribution less than 2.0. A synthetic polymer may be or contain one or more of a star block copolymer, a linear polymer, a branched polymer, a hyperbranched polymer, a dendritic polymer, a comb polymer, a graft polymer, a brush polymer, a bottle-brush copolymer and a crosslinked structure, such as a block copolymer comprising a block of 5-vinyltetrazole monomer units. Synthetic polymers include, without limitation, polyesters, poly(meth)acrylamides, poly(meth)acrylates, polyethers, polystyrenes, polynorbornenes and monomers that have unsaturated bonds. For example, amphiphilic comb polymers are described in U.S. Patent Application Publication No. 2007/0087114 and in U.S. Pat. No. 6,207,749 to Mayes et al., the disclosure of each of which is herein incorporated by reference in its entirety. The amphiphilic comb-type polymers may be present in the form of copolymers, containing a backbone formed of a hydrophobic, water-insoluble polymer and side chains formed of short, hydrophilic non-cell binding polymers. Examples of other synthetic polymers include, but are not limited to, polyalkylenes such as polyethylene and polypropylene and polyethyleneglycol (PEG); polychloroprene; polyvinyl ethers; such as poly(vinyl acetate); polyvinyl halides such as poly(vinyl chloride); polysiloxanes; polystyrenes; polyurethanes; polyacrylates; such as poly(methyl (meth)acrylate), poly(ethyl (meth)acrylate), poly(n-butyl(meth)acrylate), poly(isobutyl (meth)acrylate), poly(tert-butyl (meth)acrylate), poly(hexyl(meth)acrylate), poly(isodecyl (meth)acrylate), poly(lauryl (meth) acrylate), poly(phenyl (meth)acrylate), poly(methyl acrylate), poly(isopropyl acrylate), poly(isobutyl acrylate), and poly(octadecyl acrylate); polyacrylamides such as poly (acrylamide), poly(methacrylamide), poly(ethyl acrylamide), poly(ethyl methacrylamide), poly(N-isopropyl acrylamide), poly(n, iso, and tert-butyl acrylamide); and copolymers and mixtures thereof. These synthetic polymers may include useful derivatives, including synthetic polymers having substitutions, additions of chemical groups, for example, alkyl groups, alkylene groups, hydroxylations, oxidations, and other modifications routinely made by those skilled in the art. The synthetic polymers may include zwitterionic polymers such as, for example, polyphosphorycholine, polycarboxybetaine, and polysulfobetaine. The synthetic polymers may have side chains of betaine, carboxybetaine, sulfobetaine, oligoethylene glycol (OEG), sarcosine or polyethyleneglycol (PEG).

"Polynucleotide" as used herein can be single stranded or double stranded or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide," "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three-dimensional structure of a polypeptide monomer. "Quaternary structure" refers to the three-dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids.

"Pharmacokinetics" as used herein refers the circulation of a drug or molecule in the body and its bioavailability, distribution, and excretion.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Sample" or "test sample" as used herein can mean any sample in which the presence and/or level of a target is to be detected or determined or any sample comprising a molecule or conjugate as described herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Sortase" refers to a polypeptide that recognizes a sortase recognition site in a protein and cleaves a peptide bond therein, forming a stable intermediate that joins the catalytic thiol of sortase to the carboxyl group of an amino acid within the recognition site via a thioester bond. This intermediate undergoes nucleophilic attack by the α-amino group of an oligoglycine branch in the peptidoglycan, generating a native peptide bond that anchors the substrate protein to the cell wall. Sortase A (SrtA) may recognize a sortase A recognition site, such as an amino acid sequence consisting of LPXZG (SEQ ID NO: 3, where X and Z are independently any amino acid) and cleave the peptide bond between the Z amino acid and the glycine of LPXZG and form a thioester bond between the catalytic thiol in SrtA and the carboxyl group of the Z amino acid. The thioester bond between the catalytic thiol in SrtA and the carboxyl group of the Z amino acid forms an intermediate, and the intermediate undergoes nucleophilic attack by the ε-amino group of the lysine of first polypeptide to form an isopeptide bond between the ε-amino group of the lysine and the Z amino acid of LPXZG. In some embodiments, SrtA forms an isopeptide bond between the ε-amino group of any solvent-accessible, nucleophilic lysine of the first polypeptide and the Z amino acid of LPXZG. In some embodiments, the sortase A recognition site includes LPXTG (SEQ ID NO: 1, where X is any amino acid). The SrtA may be any SrtA, such as *Staphylococcus aureus* SrtA. SrtA may be from a Gram-positive bacterium, such as, for example, bacteria in a genus selected from *Staphylococcus, Streptococcus, Enterococcus, Bacillus, Corynebacterium, Nocardia, Clostridium*, Actinobacteria, and *Listeria*. In some embodiments, SrtA is from *S. aureus*. The SrtA may be wild-type SrtA or a variant thereof. Sortase is further detailed in International Patent Application No. PCT/US2015/017601, filed Feb. 25, 2015, published as WO 2015/130846, and International Patent Application No. PCT/US2014/040319, filed May 30, 2014, published as WO 2014/194244, which are incorporated herein by reference.

As used herein, the terms "stealth," "stealth polymer," or "stealth functionality" refers to a polymer that can remain undetected by immune cells and undegraded in the bloodstream, at a bio-interface, or in a biological medium for a prolonged period of time. Stealth polymers are at least partially resistant to enzymatic degradation polymer, such as by proteases, and opsonization, which is a common method used by immune system to recognize foreign particles. Accordingly, stealth polymers may have one or more of reduced antigenicity, reduced immunogenicity, increased stability, increased half-life, and increased bioavailability relative to other polymers or non-stealth polymers. The ability to delay, reduce, or prevent opsonization, recognition by the immune system, or clearance of a polymer from the body is referred to herein as a "stealth property" or "stealth functionality."

As used herein, the term "surface" refers to the exterior or outer portion of a one-, two-, or three-dimensional composition of matter. The surface may be the surface of a molecule, macromolecule, or object. In one aspect the surface is a polypeptide, protein, or protein complex. In another aspect, the surface is a bio-interface, i.e., is in contact with a biological system or biological fluid or is in fluid communication with a biological fluid, medium, or solution containing biological molecules, cells, or tissues.

"Subject" as used herein can mean a mammal that wants or is in need of the herein described conjugates. The subject may be a patient. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

"Target" as used herein can refer to an entity that a molecule binds. A target may include, for example, a small molecule, a protein, a polypeptide, a polynucleotide, a carbohydrate, or a combination thereof.

"Treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

Definitions of specific functional groups and chemical terms are described in more detail herein. The chemical elements are identified in accordance with the Periodic Table of the Elements, CAS version, *Handbook of Chemistry and Physics*, 75$^{th}$ ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ ed, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ ed, Cambridge University Press, Cambridge, 1987.

The term "acyl" or "carbonyl" refers to the group —C(O)R wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl, and heterocyclylalkyl, any of which may be optionally substituted, e.g., with one or more substituents. For example, when R is alkyl, such a group may be referred to as an alkylcarbonyl group.

The term "alkoxy" refers to the group —O—R wherein R is alkyl, alkenyl, alkynyl, cycloalkyl or heterocyclyl, any of which may be optionally substituted, e.g., with one or more substituents.

The term "alkyl" refers to a straight or branched hydrocarbon chain, containing the indicated number of carbon atoms. For example, C1-C$_{12}$ alkyl indicates that the alkyl group may have from 1 to 12 (inclusive) carbon atoms, and C1-C4 alkyl indicates that the alkyl group may have from 1 to 4 (inclusive) carbon atoms. An alkyl group may be optionally substituted. Examples of C1-C4 alkyl groups include methyl, ethyl, n-propyl, isopropyl, n-butyl, sec-butyl, and tert-butyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. An alkenyl group may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl. An aromatic amine is an aryl group substituted with one or more amino groups. An aromatic alcohol is an aryl group substituted with one or more hydroxyl groups. Both aromatic amines and aromatic alcohols may be further substituted with other substitutents.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "carboxyl" refers to the group —C(=O)OR, wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl any of which may be optionally substituted, e.g., with one or more substituents.

The term "carboxylate" refers to the group —C(=O)O—.

The term "carbonylamino" or "amido" refers to the group —C(O)NR'R" wherein R' and R" are independently selected from the group consisting of hydrogen, alkyl, alkenyl, alkynyl, aryl, cycloalkyl, heterocyclyl, heteroaryl, arylalkyl, cycloalkylalkyl, heteroarylalkyl, and heterocyclylalkyl, or R' and R" together with the nitrogen to which they are attached, may form a ring. The groups R' and R" may be optionally substituted, e.g., with one or more substituents, or when R' and R" together with the nitrogen to which they are attached form a ring, the ring may be optionally substituted, e.g., with one or more substituents.

The term "amide" refers to the group —C(O)NR wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted, e.g., with one or more substituents.

The term "amine" refers to the group —NH$_2$.

The term "cycloalkyl" as used herein refers to nonaromatic, saturated, or partially unsaturated cyclic, bicyclic, tricyclic or polycyclic hydrocarbon groups having 3 to 12 carbons (e.g., 3, 4, 5, 6, or 7 carbon atoms). Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "ester" refers to the group —C(O)OR wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl, and heterocyclylalkyl, any of which may be optionally substituted, e.g., with one or more substituents.

The term "halo" or "halogen" as used herein refers to any radical of fluorine, chlorine, bromine, or iodine.

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O-alkyl radical. The term "aryloxy" refers to an —O-aryl radical. The term "haloalkoxy" refers to an —O— haloalkyl radical.

Where chemical groups are specified by their conventional chemical formulae, written from left to right, they optionally encompass substituents resulting from writing the structure from right to left, e.g., —CH$_2$O— optionally also recites —OCH$_2$—.

Conjugate

Provided herein is a molecule-polymer conjugate. The molecule-polymer conjugate includes a branched polymer and a molecule covalently attached thereto. The molecule-polymer may include more than one branched polymer conjugated to the molecule. In some embodiments, more than one branched polymer is conjugated to the molecule, each branched polymer conjugated to a different site of the molecule.

Branched Polymer

The branched polymer includes a backbone and a plurality of side chains. Each side chain is covalently attached to the backbone. The branched polymer may include any branched, non-linear structure with a backbone and side chains. For example, the branched polymer includes structures such as a brush polymer, a comb polymer, a star polymer, a dendrimer, or a hyperbranched polymer. Brush polymers may have four-way branch points where the backbone and side chain connect. Comb polymers may have three-way branch points where the backbone and side chain connect. The backbone may be a single point for star polymers, hyperbranched polymers, and dendrimers. Star polymers may have a single point (backbone) to which multiple side chains are connected. Hyperbranched polymers and dendrimers are both repetitively branched polymers, wherein the side chains originate from a single point. Dendrimers may be symmetrical with the same side chains at each branch, whereas hyperbranched polymers may have side chains of random and/or irregular lengths and sizes one or more branches. In some embodiments, the branched polymer comprises poly[oligo(ethylene glycol) methyl ether methacrylate](POEGMA).

Backbone

The backbone comprises any suitable polymer. In some embodiments, the backbone comprises a linear polymer. In some embodiments, the backbone comprises at least one of an acrylate, methacrylate, acrylamide, methacrylamide, carbonate, phosphoester, oxazoline, or a combination thereof. In some embodiments, the backbone comprises poly(methyl methacrylate). The molecule may be conjugated to the backbone of the branched polymer.

Side Chains

The side chains are polymers, each side chain covalently attached to the backbone. In some embodiments, the side chain is a linear polymer. In some embodiments, the side chain is a linear oligomer. In some embodiments, an oligomer is a polymer comprising 25 monomers or less. In some embodiments, each side chain is a linear polymer. In some embodiments, each side chain is an oligomer. In some embodiments, a side chain is a block copolymer comprising two or more oligomers in tandem, wherein the monomers of each oligomer are the same. Each side chain includes at least 1 monomer. The monomers of a single side chain may be the same. The monomers of a single side chain may be different from each other. The monomer of each side chain may be independently selected from at least one of a betaine, phosphorylcholine, phosphorylethanolamine, sarcosine, ethylene glycol, or a combination thereof. The betaine may be any betaine in the art. For example, the betaine may comprise carboxybetaine, sulfobetaine, or a combination thereof.

Each side chain may include about 1 to 20 monomers, about 2 to 20 monomers, about 3 to 20 monomers, about 3 to 9 monomers, about 4 to 20 monomers, about 5 to 20 monomers, about 8 to 20 monomers, about 3 to 10 monomers, about 3 to 9 monomers, or about 3 to 5 monomers repeated in tandem. Each side chain may include at least 3 monomers, at least 4 monomers, at least 5 monomers, at least 6 monomers, at least 7 monomers, at least 8 monomers, at least 9 monomers, or at least 10 monomers repeated in tandem. Each side chain may include less than 25 monomers, less than 20 monomers, less than 15 monomers, less than 10 monomers, less than 9 monomers, less than 8 monomers, less than 7 monomers, less than 6 monomers, less than 5 monomers, less than 4 monomers, or less than 3 monomers repeated in tandem. In some embodiments, each side chain comprises at least 2 monomers repeated in tandem. In some embodiments, each side chain comprises less than 25 monomers repeated in tandem. In some embodiments, each side chain comprises at least 3 monomers repeated in tandem. In some embodiments, each side chain comprises 3 monomers repeated in tandem.

In some embodiments, the monomer of at least one side chain comprises ethylene glycol. In some embodiments, the monomer of each side chain comprises ethylene glycol. In some embodiments, each side chain includes at least 2 monomers of ethylene glycol (EG) repeated in tandem. In some embodiments, each side chain comprises at least 10 monomers of ethylene glycol (EG) repeated in tandem. In some embodiments, each side chain comprises less than 25 monomers of ethylene glycol (EG) repeated in tandem. In some embodiments, each side chain comprises 3 monomers of ethylene glycol (EG) repeated in tandem. In some embodiments, each side chain comprises 3 to 9 monomers of ethylene glycol (EG) repeated in tandem. Adjacent side chains may be the same. Adjacent side chains may be different from each other.

Each side chain has a first terminal end and a second terminal end. The first terminal end is covalently attached to the backbone. The second terminal end is free. In some embodiments, the second terminal end independently comprises an alkyl, ester, amine, amide, or carboxyl group. In some embodiments, the second terminal end of each side chain does not include a hydroxyl group.

In some embodiments, the terminal end of each side chain individually comprises an ester, amine, amide, alkyl, or carboxyl. In some embodiments, the terminal end of each side chain does not include a hydroxyl group. The terminal end may be modified. The terminal end may be natural or unmodified. The terminal end of each side chain may be the same or different from the terminal end of an adjacent side chain. In some embodiments, the terminal end of each side chain is the same as the terminal end of an adjacent side chain. In some embodiments, the terminal end of each side chain is different from the terminal end of an adjacent side chain.

Surface Coatings

In one embodiment, the surface coating comprises a non-fouling polymer that can decrease non-specific binding and/or adsorption of non-target analytes to the surface and simultaneously not react with or induce anti-PEG antibodies. Non-fouling, as used herein with respect to the surface, relates to the inhibition (e.g., reduction or prevention) of growth of an organism as well as to non-specific or adventitious binding interactions between the surface and a biomolecule or organism (e.g., protein, nucleic acid, carbohydrate, lipid, cell, etc.). In a particular aspect, the non-fouling polymer does not non-specifically bind with proteins in general (such as serum proteins, for example) and is non-antigenic and does not bind with or induce antibodies that recognize polyethylene glycol moieties.

The non-fouling property of the polymer layer is due in part to the inclusion of polyoligo(ethylene glycol) methyl methacrylate (POEGMA). POEGMA can instill a non-fouling characteristic to the surface due to its composition and structure. For example, POEGMA can form a "bottlebrush"-like structure on the surface. The bottlebrush-like structure of POEGMA can be achieved through suitable polymerization conditions of growing the polymer on the surface.

POEGMA can have different terminal functional groups. In some embodiments, POEGMA may be alkoxy terminated (e.g., methoxy, ethoxy, propoxy, etc.). In some embodiments, POEGMA can be hydroxy terminated, methoxy terminated, or ethoxy terminated homopolymers. In other embodiments, POEGMA can be a copolymer of alkoxy-terminated POEGMA and hydroxy-terminated POEGMA. In some embodiments, the POEGMA can be a combination of the different homo- and copolymers of POEGMA. In some embodiments, POEGMA can be the only polymer.

The POEGMA may have varying ethylene glycol repeat units within its polymer chains. For example, POEGMA may have an ethylene glycol repeat unit of from about 1 to about 20, such as from about 1 to about 9, from about 1 to about 8, from about 1 to about 7, from about 1 to about 6, from about 1 to about 5, from about 1 to about 4, about 1 to about 3, from about 1 to about 2, about 2 to about 3, or about 1 ethylene glycol units. In some embodiments, POEGMA can have an ethylene glycol repeat unit of greater or equal to 1, greater than or equal to 2, greater than or equal to 3, greater than or equal to 4, greater than or equal to 5, greater than or equal to 6, greater than or equal to 7, greater than or equal to 8, or greater than or equal to 9.

In specific embodiments, the POEGMA comprises side chains comprising 1 to 9, 1 to 8, 1 to 7, 1 to 6, 1 to 5, 1 to 3, 2 to 3, or 3, 2 or 1 ethylene glycol tandem repeats (or repeat units). In one embodiment, the POEGMA comprises monomers of ethylene glycol methyl ether methacrylate (EG1-OMe). In another embodiment, the POEGMA comprises monomers of di(ethylene glycol) methyl ether methacrylate (EG2-OMe). In another embodiment, the POEGMA comprises monomers of tri(ethylene glycol) methyl ether methacrylate (EG3-OMe). In another embodiment, the POEGMA comprises monomers of poly(ethylene glycol) methyl ether methacrylate with 5 ethylene glycol repeat units (EG5-OMe). In another embodiment, the POEGMA comprises monomers of poly(ethylene glycol) methyl ether methacrylate with 6 ethylene glycol repeat units (EG6-OMe). In another embodiment, the POEGMA comprises monomers of poly(ethylene glycol) methyl ether methacrylate with 9 ethylene glycol repeat units (EG9-OMe). In one embodiment, the POEGMA comprises monomers shown in Table 1.

TABLE 1

POEGMA Monomers

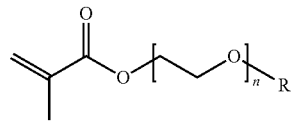

(ethylene glycol)$_n$ methyl ether methacrylate

| Monomer | n | —R | Abbreviation |
|---|---|---|---|
| Ethylene glycol methyl ether methacrylate | 1 | —OMe | EG1-OMe |
| Di(ethylene glycol) methyl ether methacrylate | 2 | —OMe | EG2-OMe |
| Tri(ethylene glycol) methyl ether methacrylate | 3 | —OMe | EG3-OMe |
| Poly(ethylene glycol) methyl ether methacrylate | 5 | —OMe | EG5-OMe |
| Poly(ethylene glycol) methyl ether methacrylate | 9 | —OMe | EG9-OMe |
| Poly(ethylene glycol) methacrylate | 6 | —OH | EG6-OH |

POEGMA is a potential alternative to linear PEG for biomedical applications. POEGMA is a derivative of PEG with a "bottlebrush" architecture. POEGMA brushes show excellent "nonfouling"-protein- and cell-resistant-properties that make it a "stealth" polymer, like PEG. This is because POEGMA's three-dimensional hyperbranched structure presents a high density of oligoethylene glycol (EG) moieties. Studies have shown that drug-POEGMA conjugates having an average polymer sidechain length of nine EG units ("EG9") demonstrated significantly reduced anti-PEG antigenicity in patient plasma compared to two FDA-approved PEGylated protein drugs (Krystexxa® and Adagen®). It was observed that shortening the POEGMA sidechain length from EG9 to EG3 virtually eliminated the reactivity of the drug-POEGMA conjugates to APAs in patient plasma samples and did so without substantially compromising in vivo pharmacokinetics in animal models. It was hypothesized that replacing long, linear PEG structures (typically ≥EG100) used in most PEGylated products with the shorter, hyperbranched structure of POEGMA (sidechains typically s EG9) could offer a successful route towards mitigating antigenicity while simultaneously retaining acceptable stealth behavior. Realization of such a strategy would be a significant advancement, as it might potentially render POEGMA more efficacious than linear PEG for clinical applications. Further, the use of POEGMA—rather than transitioning to non-PEG derived polymers—may be logistically favorable given PEG's long history of use in humans and its pervasive role in commercial, research, and clinical settings.

These considerations motivated the systematically investigation of the length of EG sidechains on POEGMA as a design parameter that could be tuned to mitigate POEGMA's reactivity toward APAs, while retaining its resistance to nonspecific binding. The effects on POEGMA brushes grown as thin films from solid surfaces (FIG. 18A) were used as a model system, as opposed to solution studies of drug-polymer conjugates, for several reasons. First, planar polymer coatings are easy to synthesize and characterize with a variety of tools (e.g., X-ray spectroscopy, ellipsometry, contact angle goniometry). Second, this approach permits straightforward investigation of APA binding and non-specific binding of proteins and cells directly on a POEGMA-grafted surface. Third, in situ growth of POEGMA from surfaces by surface-initiated atom transfer radical polymerization (SI-ATRP) is reliable and high-throughput. Fourth, this approach also enables investigation of how APAs might interfere in clinical devices and in vitro diagnostics (IVDs).

Described herein is the synthesis and characterization of POEGMA surface coatings grown from glass substrates by SI-ATRP, encompassing a range of polymer brush sidechain lengths (EG1 to EG9). These POEGMA brush surfaces were subjected to a battery of screening tests and subsequent down-selection processes aimed at identifying candidates that resist reactivity to APAs, protein adsorption—specifically, bovine serum albumin (BSA)—and adhesion of cultured cells. Next, the structural characteristics of bottlebrushes and their contributions to mitigating binding by polymer endgroup-selective or backbone-selective APAs were examined. Combined, these experiments revealed that POEGMA coatings with EG2—and to a lesser extent, EG3—sidechains exhibit the most favorable performance in minimizing both APA recognition and nonspecific adsorption. As proof-of-concept, these findings were validated by measuring the binding of APAs to the POEGMA brush surfaces from plasma samples from patients previously treated with a PEGylated drug (Krystexxa®) and found to have induced or pre-existing APAs. Given the relevance of POEGMA surfaces to immunodiagnostic applications, the response of protein microarray immunoassays fabricated onto POEGMA surfaces with different EG side-chain lengths were examined in the presence of APAs.

Molecule

The molecule may include any suitable molecule whose antigenicity is to be reduced or eliminated. The molecule may be selected from a nucleotide, polynucleotide, protein, peptide, polypeptide, carbohydrate, lipid, small molecule, or a combination thereof. In some embodiments, the molecule comprises a polypeptide, a polynucleotide, a small molecule, or a combination thereof. In some embodiments, the molecule comprises one or more peptides or protein therapeutic agents. In some embodiments, the molecule comprises a polypeptide. In some embodiments, the molecule comprises a small molecule. In some embodiments, the molecule comprises a protein. In some embodiments, the molecule comprises a drug. In some embodiments, the molecule comprises a therapeutic. In some embodiments, the molecule comprises a cancer therapeutic. In some embodiments, the molecule comprises an antibody. In some embodiments, the molecule comprises exendin.

The molecule may include, for example, a monoclonal antibody, blood factor, betatrophin, exendin, enzyme, asparaginase, glutamase, arginase, arginine deaminase, adenosine deaminase (ADA), ADA-2, ribonuclease, cytosine deaminase, trypsin, chymotrypsin, papain, growth factor, epidermal growth factor (EGF), insulin, insulin-like growth factor (IGF), transforming growth factor (TGF), nerve growth factor (NGF), platelet-derived growth factor (PDGF), bone morphogenic protein (BMP), fibroblast growth factor (FGF), somatostatin, somatotropin, somatropin, somatrem, calcitonin, parathyroid hormone, colony stimulating factors (CSF), clotting factors, tumor necrosis factors (TNF), gastrointestinal peptides, vasoactive intestinal peptide (VIP), cholecystokinin (CCK), gastrin, secretin, erythropoietins, growth hormone, GRF, vasopressins, octreotide, pancreatic enzymes, superoxide dismutase, thyrotropin releasing hormone (TRH), thyroid stimulating hormone, luteinizing hormone, luteinizing hormone-releasing hormone (LHRH), growth hormone releasing hormone (GHRH), tissue plasminogen activators, interleukins, interleukin-1, interleukin-15, interleukin-2, interleukin-10, colony stimulating factor, granulocyte macrophage colony-stimulating factor (GM-CSF), interleukin-1 receptor antagonist (IL-1RA), glucagon-like peptide-1 (GLP-1), exenatide, GLP-1 R multi-agonist, GLP-1 R antagonist, GLP-2, TNF-related apoptosis-inducing ligand (TRAIL), leptin, ghrelin, granulocyte monocyte colony stimulating factor (GM-CSF), interferons, interferon-α, interferon-gamma, human growth hormone (hGH) and antagonist, macrophage activator, chorionic gonadotropin, heparin, atrial natriuretic peptide, hemoglobin, relaxin, cyclosporine, oxytocin, vaccines, monoclonal antibodies, single chain antibodies, ankyrin repeat proteins, affibodies, activin receptor 2A extracellular domain, alpha-2 macroglobulin, alpha-melanocyte, apelin, bradykinin B2 receptor antagonist, cytotoxic T-lymphocyte-associated protein (CTLA-4), elafin, Factor IX, Factor Vlla, Factor VIII, hepcidin, infestin-4, kallikrein inhibitor, L4F peptide, lacritin, parathyroid hormone (PTH), peptide YY (PYY), thioredoxin, thymosin B4, urate oxidase, urodilatin, aptamers, silencing RNA, microRNA, long non-coding RNA, ribozymes, analogs and derivatives thereof, and combinations thereof.

The molecule may include a sortase A recognition site, a His-tag, stimulus-responsive polypeptide, or a combination thereof. Stimulus-responsive polypeptides may include environmentally responsive polypeptides. The stimulus-responsive polypeptide may include, for example, an elastin-like polypeptide, a polypeptide comprising a repeated motif (as disclosed in, for example, US 2015/0112022, filed Dec. 16, 2014, and incorporated herein by reference), or a resilin-like polypeptide, or a combination thereof. In some embodiments, the molecule comprises a polypeptide comprising a sortase A recognition site. In some embodiments, the sortase A recognition site comprises LPXTG (SEQ ID NO: 1), wherein X is any amino acid.

The branched polymer may be conjugated to any site anywhere on the molecule. For example, when the molecule comprises a polypeptide, the branched polymer may be conjugated to the polypeptide at the C-terminus, the N-terminus, or an internal amino acid, or a combination thereof. In some embodiments, the molecule comprises a polypeptide with the branched polymer conjugated to the C-terminus of the polypeptide. One branched polymer may be conjugated to the molecule. More than one branched polymer may be conjugated to the molecule, each branched polymer conjugated to a different site of the molecule. In some embodiments, the molecule comprises a polypeptide, and wherein more than one branched polymer is conjugated to the polypeptide, each branched polymer conjugated to a different site of the polypeptide selected from the C-terminus, the N-terminus, an internal amino acid, or a combination thereof. At least about 50%, at least about 55%, at least about 60%, at least about 65%, at least about 70%, at least about 75%, at least about 80%, at least about 85%, at least about 90%, or at least about 95% of the polypeptides have a conjugated polymer initiated solely from the C-terminus. In some embodiments, at least about 50% of the polypeptides have a conjugated polymer initiated solely from the C-terminus. In some embodiments, at least about 75% of the polypeptides have a conjugated polymer initiated solely from the C-terminus. In some embodiments, at least about 90% of the polypeptides have a conjugated polymer initiated solely from the C-terminus.

Conjugate Properties

The conjugates may have an altered pharmacological property compared to a control. The property may include, for example, reduced antigenicity, eliminated antigenicity, reduced opsonization of the molecule, reduced binding to anti-PEG antibodies, a reduced immune response, lack of reactivity with pre-existing anti-PEG antibodies in a subject, an in vivo half-life that is at least 25% greater, or an in vivo biodistribution to a tissue, organ, or disease site that is at least 25% greater, compared to a control.

In some embodiments, the conjugates have an in vivo half-life that is at least 25% greater compared with the in vivo half-life of the molecule alone or other molecule-polymer conjugates; or an in vivo biodistribution to a tissue, organ, or disease site that is at least 25% greater than the in vivo biodistribution of the molecule alone or other molecule-polymer conjugates. In some embodiments, the antigenicity of the conjugate is reduced compared to the molecule alone or to the molecule conjugated to the linear polymer. In some embodiments, the conjugates have reduced antigenicity compared to other molecule-polymer conjugates. In some embodiments, the conjugates have reduced binding to anti-PEG antibodies compared to other molecule-polymer conjugates or molecules. In some embodiments, the conjugates induce a reduced immune response compared to other molecule-polymer conjugates or molecules. In some embodiments, the conjugate is not reactive with pre-existing anti-PEG antibodies in a subject. In some embodiments, the conjugates have an in vivo half-life that is at least 25% greater compared with the in vivo half-life of the molecule. In some embodiments, the conjugates have an in vivo biodistribution to a tissue, organ, or disease site that is at least 25% greater than the in vivo biodistribution of the molecule. In some embodiments, the conjugates have an in vivo half-life that is at least 80% greater than the in vivo half-life of the molecule. In some embodiments, the branched polymer comprises POEGMA, and the molecule-polymer conjugate is not reactive with pre-existing anti-PEG antibodies in a subject.

The methods detailed herein may enable control over site and stoichiometry of conjugation of the branched polymer to the molecule. The methods detailed herein may enable a high degree of molecular weight tunability and low dispersity of the branched polymer conjugated to the molecule, which may translate to a more predictable therapeutic performance relative to other polymer conjugates of therapeutic biomolecules. The molecule-polymer conjugates detailed herein may be more homogenous than conventional PEGylated molecules, in terms of the conjugation site, the molecular weight of the branched polymer, or a combination thereof.

The molecule-polymer conjugates detailed herein may facilitate less frequent administration, prevent an undesirable peak-to-valley fluctuation of the drug concentration in vivo, increase patient compliance, and reduced treatment cost, or a combination thereof.

Synthesis of the Conjugate

Methods of making the conjugate may include, for example, those detailed in International Patent Application No. PCT/US2014/040319, filed May 30, 2014, published as WO 2014/194244, which is incorporated herein by reference.

In some embodiments, the molecule is conjugated to the backbone of the branched polymer via a linker. The molecule may be conjugated to the backbone of the branched polymer via more than one linker. The molecule may be conjugated to the backbone of the branched polymer via at least 1, at least 2, at least 3, at least 4, at least 5, at least 6, at least 7, at least 8, at least 9, or at least 10 linkers. The molecule may be conjugated to the backbone of the branched polymer via less than 20, less than 15, less than 10, or less than 5 linkers. The molecule may be conjugated to the backbone of the branched polymer via between 1 and 20, between 5 and 15, or between 1 and 5 linkers. The linker may be a polypeptide of any amino acid sequence and length. The linker may act as a spacer peptide. In some embodiments, the linker comprises charged amino acids. In some embodiments, the linker comprises uncharged amino acids. In some embodiments, the linker is flexible. In some embodiments, the linker comprises one or more cysteines. In some embodiments, the linker comprises an amino acid sequence selected from SEQ ID NO: 4 (GGC), SEQ ID NO: 5 ((GGC)8), SEQ ID NO: 6 ((G4S)3), and SEQ ID NO: 7 ((VPGXG)16 wherein X is valine or cysteine present in a ratio of 1:1). The linker may serve as an attachment site for the molecule to the branched polymer. The molecule may attach to the linker by any suitable means known in the art. The molecule may attach to the linker through a thiol reactive linking group. In some embodiments, the molecule is attached to one or more branched polymers via the linker. In some embodiments, the molecule is attached to the branched polymer through a thiol reactive group in the linker.

The conjugate may be made by joining or conjugating a branched polymer to a polypeptide with a sortase. In some embodiments, the molecule comprises a polypeptide that includes a sortase A recognition site, and the branched polymer and the polypeptide are incubated with Sortase A under conditions to conjugate the branched polymer to the sortase A recognition site of the polypeptide. In some embodiments, the conjugating includes contacting the molecule with a sortase A and an initiator agent under conditions that permit attachment of the initiator agent to the sortase A recognition site to form a macroinitiator, and incubating the macroinitiator with a monomer under conditions that permit free-radical polymerization and formation of a branched polymer to occur from the initiator agent to form the molecule-polymer conjugate. In some embodiments, the macroinitiator and monomer are incubated with a catalyst. The monomer may include at least one of an acrylate, methacrylate, acrylamide, and methacrylamide.

In some embodiments, the branched polymer is synthesized and subsequently grafted to the molecule to form the molecule-polymer conjugate. In some embodiments, the branched polymer is synthesized using free-radical polymerization. In some embodiments, the branched polymer is synthesized using at least one method selected from ionic ring-opening polymerization (ionic ROP), ring opening metathesis polymerization, ionic polymerization, condensation polymerization, and coordination polymerization.

In some embodiments, the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization.

The yield of molecule-polymer conjugates may be at least about 50%, at least about 55%, at least about 60%, at least about 65%, at least about 70%, at least about 75%, at least about 80%, at least about 85%, at least about 90%, or at least about 95%. In some embodiments, the yield of molecule-polymer conjugates is at least about 75%. In some embodiments, the yield of molecule-polymer conjugates is at least about 85%.

In some embodiments wherein the molecule comprises a polypeptide, at least about 20% of the polypeptides have a conjugated branched polymer solely at the C-terminus. At least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the polypeptides have a conjugated branched polymer solely at the C-terminus.

In some embodiments, the molecule-polymer conjugates are separated by chromatography, such as size-exclusion chromatography, ion exchange chromatography, affinity chromatography, or hydrophobic interaction chromatography, or a combination thereof. In some embodiments, the chromatography comprises size-exclusion chromatography.

Administration

A composition may comprise the conjugate. The conjugates as detailed above can be formulated into a composition in accordance with standard techniques well known to those skilled in the pharmaceutical art. The composition may be prepared for administration to a subject. Such compositions comprising a conjugate can be administered in dosages and by techniques well known to those skilled in the medical arts taking into consideration such factors as the age, sex, weight, and condition of the particular subject, and the route of administration.

The conjugate can be administered prophylactically or therapeutically. In prophylactic administration, the conjugate can be administered in an amount sufficient to induce a response. In therapeutic applications, the conjugates are administered to a subject in need thereof in an amount sufficient to elicit a therapeutic effect. An amount adequate to accomplish this is defined as "therapeutically effective dose." Amounts effective for this use will depend on, e.g., the particular composition of the conjugate regimen administered, the manner of administration, the stage and severity of the disease, the general state of health of the patient, and the judgment of the prescribing physician.

The conjugate can be administered by methods well known in the art as described in Donnelly et al. (Ann. Rev. Immunol. 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The conjugate can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The conjugates can be delivered via a variety of routes. Typical delivery routes include parenteral administration, e.g., intradermal, intramuscular, or subcutaneous delivery. Other routes include oral administration, intranasal, intravaginal, transdermal, intravenous, intraarterial, intratumoral, intraperitoneal, and epidermal routes. In some embodiments, the conjugate is administered intravenously, intraarterially, or intraperitoneally to the subject.

The conjugate can be a liquid preparation such as a suspension, syrup, or elixir. The conjugate can be incorporated into liposomes, microspheres, or other polymer matrices (such as by a method described in Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The conjugate may be used as a vaccine. The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation can be carried out via a minimally invasive device.

In some embodiments, the conjugate is administered in a controlled release formulation. The conjugate may be released into the circulation or a tumor, for example. In some embodiments, the conjugate may be released over a period of at least about 1 day, at least about 2 days, at least about 3 days, at least about 4 days, at least about 5 days, at least about 6 days, at least about 7 days, at least about 1 week, at least about 1.5 weeks, at least about 2 weeks, at least about 2.5 weeks, at least about 3.5 weeks, at least about 4 weeks, or at least about 1 month.

Methods

Methods of Reducing the Antigenicity of a Molecule

Provided herein are methods of reducing the antigenicity of a molecule. The methods may include conjugating at least one branched polymer to a molecule to form a molecule-polymer conjugate, as detailed herein.

In some embodiments, the molecule comprises a polypeptide comprising a sortase A recognition site, and the branched polymer and the polypeptide are incubated with sortase A under conditions to conjugate the branched polymer to the sortase A recognition site of the polypeptide. In some embodiments, the molecule comprises a polypeptide comprising a sortase A recognition site, and the conjugating includes (a) contacting the molecule with a sortase A and an initiator agent under conditions that permit attachment of the initiator agent to the sortase A recognition site to form a macroinitiator; and (b) incubating the macroinitiator with a monomer under conditions that permit free-radical polymerization and formation of a branched polymer to occur from the initiator agent to form the molecule-polymer conjugate. In some embodiments, the sortase A recognition site comprises LPXTG (SEQ ID NO: 1), wherein X is any amino acid. In some embodiments, the macroinitiator and monomer are incubated with a catalyst in step (b). In some embodiments, the monomer in step (b) comprises at least one of an acrylate, methacrylate, acrylamide, and methacrylamide. In some embodiments, the method further includes separating the molecule-polymer conjugate formed in step (b) from the unreacted macroinitiator.

The methods may further include separating the molecule-polymer conjugate formed in step (b) from the unreacted macroinitiator. In some embodiments, the yield of molecule-polymer conjugate is at least about 50% of the total conjugates and macroinitiators which are separated. In some embodiments, the molecule-polymer conjugate is separated by chromatography. In some embodiments, chromatography comprises size-exclusion chromatography, ion exchange chromatography, affinity chromatography, or hydrophobic interaction chromatography, or a combination thereof. In some embodiments, the chromatography comprises size-exclusion chromatography.

In some embodiments, the branched polymer is synthesized and subsequently grafted to the molecule to form the molecule-polymer conjugate. In some embodiments, the branched polymer is synthesized using free-radical polymerization. In some embodiments, the branched polymer is synthesized using at least one method selected from ionic ring-opening polymerization (ionic ROP), ring opening metathesis polymerization, ionic polymerization, condensation polymerization, and coordination polymerization.

In some embodiments, conjugating at least one branched polymer to a molecule to form a molecule-polymer conjugate comprises attaching an initiator agent to the molecule to form a macroinitiator; and incubating the macroinitiator with a monomer under conditions that permit free-radical polymerization and formation of a branched polymer to occur from the initiator agent to form the molecule-polymer conjugate. In some embodiments, the macroinitiator and monomer are incubated with a catalyst. In some embodiments, the monomer comprises at least one of an acrylate, methacrylate, acrylamide, and methacrylamide. In some embodiments, the method further includes separating the molecule-polymer conjugate from the unreacted macroinitiator.

In some embodiments, the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization.

Methods of Making Molecule-Polymer Conjugates

Provided herein are methods of making molecule-polymer conjugates having reduced or eliminated antigenicity compared to a control. The molecule may include a polypeptide having a sortase A recognition site. The method may include (a) contacting the molecule with a sortase A and an initiator agent under conditions that permit attachment of the initiator agent to the sortase A recognition site to form a macroinitiator; and (b) incubating the macroinitiator with a monomer under conditions that permit free-radical polymerization to occur from the initiator agent to form the molecule-polymer conjugate.

In some embodiments, the sortase A recognition site comprises LPXTG (SEQ ID NO: 1), wherein X is any amino acid. In some embodiments, the macroinitiator and monomer are incubated with a catalyst in step (b). In some embodiments, the monomer in step (b) comprises at least one of an acrylate, methacrylate, acrylamide, and methacrylamide. In some embodiments, the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization. In some embodiments, the free-radical polymerization comprises at least one of ionic ring-opening polymerization (ionic ROP), ring opening metathesis polymerization, ionic polymerization, condensation polymerization, and coordination polymerization.

In some embodiments, the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization.

The methods may further include separating the molecule-polymer conjugate formed in step (b) from the unreacted macroinitiator. In some embodiments, the yield of molecule-polymer conjugate is at least about 50% of the total conjugates and macroinitiators which are separated. In some embodiments, the molecule-polymer conjugate is separated by chromatography. In some embodiments, chromatography comprises size-exclusion chromatography, ion exchange chromatography, affinity chromatography, or hydrophobic interaction chromatography, or a combination thereof. In some embodiments, the chromatography comprises size-exclusion chromatography.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All the various embodiments, aspects, and options disclosed herein can be combined in any variations or iterations. The scope of the compositions, formulations, methods, and processes described herein include all actual or potential combinations of embodiments, aspects, options, examples, and preferences herein described. The compositions, formulations, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the specification discloses and describes merely exemplary embodiments. All patents and publications cited herein are incorporated by reference herein for the specific teachings thereof.

EXAMPLES

Example 1

Materials and Methods

Experimental Design. All in vitro and in vivo experiments include suitable controls; where applicable, PBS served as a negative control and unmodified exendin served as a positive control. The sample sizes for in vivo studies were chosen based on similar studies conducted previously (Amiram, M., et al. Proc. Natl. Acad. Sci. 2013, 110, 2792-2797; Schellenberger, V., et al. Nat. Biotechnol. 2009, 27, 1186-1188). See Animal studies section below for details on the animal model used. Mice were randomly grouped before initiation of each experiment. The investigator was not blinded to group allocation. For the in vivo fed glucose measurement studies, mouse blood glucose levels were measured until all experimental groups no longer showed statistical significance in glucose reduction compared to the PBS control group. All collected data points were included in data analysis.

Cloning, expression, and purification. All molecular biology reagents were purchased from New England Biolabs unless otherwise specified. The gene encoding exendin in a pMA-T vector was codon optimized and synthesized by Life Technologies. The first methionine residue encoding the translational start codon in proteins recombinantly expressed in E. coli needs to be cleaved post-translationally for proper function and stability of the protein. However, the first amino acid of exendin is a histidine, and our past experience and reports in the literature both suggest that having histidine as the residue immediately following methionine prevents proper methionine cleavage. Thus, a di-alanine leader was incorporated at the N-terminus of the peptide to facilitate methionine cleavage. Once in vivo, the di-alanine leader can be cleaved by dipeptidyl peptidase 4 (DPP4), an exopeptidase that cleaves N-terminal dipeptides containing proline or alanine as the second residue, to reveal the N-terminus of exendin for GLP-1R binding. The exendin gene was amplified by polymerase chain reaction (PCR), using forward and reverse primers containing NdeI overhangs and with the sequence for the sortase A recognition motif "LPETG" (named "srt" for brevity) followed by a His6-tag incorporated in the reverse primer. The amplified "exendin-srt-His6" fragment was inserted into a modified pET-24a+ vector at a NdeI restriction site immediately upstream of an ELP with the sequence (VPGVG)60, to yield "exendin-srt-His6-ELP."

Expression and purification of the quaternary fusion protein followed previously described procedures with minor changes (Qi, Y., et al. *Macromol. Rapid Commun.* 2013, 34, 1256-1260). Briefly, cells were cultured in Terrific Broth (TB, Mo Bio Laboratories, Inc.) supplemented with 45 μg/mL of kanamycin at 25° C. Once the optical density at 600 nm (OD600) of the culture reached 0.6, temperature was lowered to 16° C. and isopropyl β-D-1-thiogalactopyranoside (IPTG, AMRESCO) was added to a final concentration of 0.1 mM to induce protein expression. Cells were harvested 15 h post induction by centrifugation at 700×g for 10 min and were lysed by sonication on a Misonex Ultrasonic Liquid Processer (Qsonica, LLC.) at amplitude 85 for 3 min with 10 sec on and 40 sec off cycles. Nucleic acids were removed from the crude extract by addition of 1 vol % polyethyleneimine (PEI, Acros) followed by centrifugation at 4° C. and 21,000×g for 10 min. The ELP tag enables purification of the fusion protein by ITC, a nonchromatographic method that we have previously developed for the purification of ELP fusion proteins that takes advantage of the inverse phase transition behavior imparted by the ELP (Meyer, D. E. & Chilkoti, A. Nat. Biotechnol. 2009, 14, 1112-1115). After triggering the inverse phase transition of the fusion by addition of 0.1 M ammonium sulfate, the aggregated proteins were collected by centrifugation at ~30° C. and 21,000×g for 10 min. The pellet was then resolubilized in cold PBS and the resulting solution was centrifuged at 4° C. and 21,000×g for 10 min to remove any remaining insoluble material. The last two steps were typically repeated one more time to obtain homogeneous protein, as verified by SDS-PAGE. In the final step, the protein was resolubilized in sortase buffer (50 mM Tris, 150 mM NaCl, 10 mM $CaCl_2$, pH adjusted to 7.5) in preparation for sortase-catalyzed initiator attachment.

The gene for sortase A with a 59 N-terminal amino acid truncation (previously shown to not affect its transpeptidase activity) and an N-terminal His6-tag in a pET15b vector was available from a previous study. Expression and purification of His6-sortase A were carried out as previously described (Qi, Y., et al. *Macromol. Rapid Commun.* 2013, 34, 1256-1260).

Sortase-catalyzed initiator attachment and macroinitiator purification. The exendin-C—Br macroinitiator was synthesized and purified following procedures described previously with minor changes (Qi, Y., et al. *Macromol. Rapid Commun.* 2013, 34, 1256-1260). Briefly, a reaction mixture consisting of exendin-srt-His6-ELP, His6-sortase A, and AEBMP at a 2:1:60 ratio in sortase buffer was incubated at 20° C. for 18 h. After reaction, a reverse His-tag purification was used to isolate the exendin-C—Br macroinitiator, by exploiting the fact that it is the only species in the mixture without a His6-tag. Purification was performed on an AKTA Purifier (GE Healthcare) equipped with a photodiode detector set at 280 nm and a HisTrap HP column. Elution through the column with PBS yielded pure exendin-C—Br in the eluent while leaving all other unwanted species bound to the resin. The collected exendin-C—Br was dialyzed overnight in PBS (pH 7.4) to remove residual free initiator.

Macroinitiator characterization. MALDI-MS was performed on a Voyager-DE Pro mass spectrometer (Life Technologies). Samples at ~25 μM in PBS were diluted 1:10 with 10 mg/mL sinapinic acid in 90:10 water/acetonitrile with 0.1 vol % trifluoroacetic acid (TFA) as the ionization matrix. The instrument was operated in linear mode with positive ions generated using a $N_2$ laser. Ubiquitin was used as a molecular weight standard to calibrate the instrument.

For LC/MS-MS analysis to confirm site-specificity of initiator attachment, 100 μL of ~8 μM exendin-C—Br in PBS was solvent exchanged into 50 mM ammonium bicarbonate (pH 8.0) on a ZebaSpin desalting column (Thermo Fisher Scientific) followed by trypsin (sequencing grade, Promega) digestion at 37° C. for 18 h directly in the column. The digestion mixture was collected by centrifugation, dried by vacuum centrifugation, and was then resuspended in 20 μL 2% acetonitrile and 0.1% formic acid in water. 1 μL of the sample was separated on a NanoAquity ultra performance liquid chromatography (UPLC, Waters) system equipped with a BEH130 C18 reversed phase column (Waters) using a mobile phase consisting of (A) 0.1% formic acid in water and (B) 0.1% formic acid in acetonitrile. A linear gradient of 5% B to 40% B was performed over 60 min at 400 nL/min and the separated peptides were ionized by electrospray ionization (ESI) followed by MS analysis on a Synapt G2 HDMS QToF mass spectrometer (Waters). The top four most abundant ions were selected for MS/MS. Mass spectra were processed with Mascot Distiller (Matrix Science) and were then submitted to Mascot searches (Matrix Science) against a SwissProt_Ecoli database appended with the custom exendin-C—Br sequence. Search results were imported into Scaffold (v4.0, Proteome Software) and scoring thresholds were set to yield a minimum of 99% protein confidence for protein identification. Extracted ion chromatograms were performed in MassLynx (v4.1). Experimental isotope distributions of the brominated C-terminal tryptic peptide were compared to a theoretical isotope distribution modeled in Molecular Weight Calculator (v. 6.49, Pacific Northwest National Laboratory, ncrr.pnl.gov/software).

In situ ARGET-ATRP. All chemical reagents were purchased from Sigma Aldrich and used as received, unless otherwise specified. EG9 OEGMA monomer (Mn ~500 Da or ~9 side-chain EG repeats on average, Sigma Aldrich, #447943) and EG3 OEGMA monomer (triethylene glycol methyl ether methacrylate, 232 Da, Sigma Aldrich, #729841) were passed through a column of basic alumina to remove the inhibitors.

In a typical reaction, 216 μmol of OEGMA and 21.6 μL of a stock solution of 200 mM $CuBr_2$ and 1.6 M tris(2-pyridylmethyl)amine (TPMA) pre-complexed in MilliQ water with 5% dimethylformamide (DMF) were mixed with 1 mL of 500 μM exendin-C—Br in PBS in a Schlenk flask. A 3.2 mM solution of ascorbic acid in MilliQ water was prepared in a separate flask. The two solutions were degassed by bubbling with argon for 30 min, after which Activator-Regenerated Electron Transfer (ARGET) ATRP was initiated and maintained by continuously injecting the ascorbic acid solution into the reaction medium using a syringe pump at a rate of 1.6 nmol/min. Polymerization was allowed to proceed for a specified time at 20° C. under argon and was quenched by bubbling with air. Reactions of the EG3 OEGMA were done with 443 μmol of the monomer in 20 v/v % methanol in PBS while all other conditions remained the same. At the end of the reaction, the reaction mixture was dialyzed against PBS overnight to remove residual small molecule reagents in preparation for downstream characterization and purification.

Characterization of OEGMA monomers. Monomers diluted 1:20,000 in methanol were separated on an Agilent 1100 LC system equipped with a Zorbax Eclipse Plus C18 column (Agilent) using a mobile phase consisting of (A) 0.3% formic acid in water and (B) 0.3% formic acid in acetonitrile. A linear gradient of 50% B to 95% B was performed over 10 min at 50° C. Separated samples were ionized by ESI followed by MS analysis on an Agilent MSD ion trap mass spectrometer.

Physical characterization of exendin-C-POEGMA conjugates. Analytical SEC was performed on a Shimadzu high performance liquid chromatography (HPLC) system equipped with a UV-vis detector (SPD-10A VP) operating at 280 nm. 50 μL of samples at ~2 mg/mL were separated on a Protein KW-803 column (Shodex) using 0.1 M Tris-HCl (pH 7.4) as mobile phase at 25° C. with a flow rate of 0.5 mL/min. Conjugation efficiency of in situ ATRP from exendin was calculated by quantifying AUC of peaks detected at 280 nm. Sum of the AUC's of the two peaks corresponding to the unreacted macroinitiator and the conjugate in each chromatogram was regarded as 100% and % fraction of the conjugate peak was calculated as the conjugation efficiency of that particular polymerization reaction.

The fluid line of the analytical HPLC system was connected downstream in series to a DAWN HELEOS II MALS detector followed by an Optilab T-rEX refractometer (both from Wyatt Technology) for conducting SEC-MALS analysis. The system was calibrated with toluene and normalized with 2.0 mg/mL bovine serum albumin (BSA, Pierce). Samples were passed through 0.1 μm filters before injection. dn/dc values of the conjugates were determined on an Anton Paar Abbemat 500 refractometer (Anton Paar). Data were analyzed in ASTRA (v. 6.0, Wyatt Technology) to compute Mw, Mn and D of the conjugates.

Conjugates were purified by a single round of preparative SEC on an AKTA Purifier equipped with a photodiode detector set at 280 nm and a HiLoad 26/600 Superdex 200 PG column using PBS as mobile phase at 4° C. and a flow rate of 2.0 mL/min.

DLS was performed on a DynaPro Plate Reader (Wyatt Technology). Samples were prepared at 25 μM and filtered with 0.1 μm filters before analysis. The instrument was operating at a laser wavelength of 831.95 nm, a scattering angle of 90° and at 25° C. Data were analyzed in Dynals mode using Dynamics 6.12.0.3.

General biochemical analysis. Concentrations of fusion proteins were measured on a ND-1000 Nanodrop spectrophotometer (Thermo Scientific) by UV-vis absorption spectroscopy. Concentration of exendin and conjugates for in vitro assays and in vivo studies was assessed using a Bicinchoninic Acid (BCA, Pierce) assay following manufacturer's instructions. SDS-PAGE analysis of sortase A was performed using precast 4-20% Tris-HCl gels (Bio-Rad). SDS-PAGE analyses of all exendin derivatives were performed using precast Tris/Tricine gels (Bio-Rad). Quantification of sortase reaction conversion was done by gel densitometry analysis using a built-in function in Image Lab (v. 4.0.1, Bio-Rad).

In vitro cAMP ELISA. Activity of native exendin and conjugates was assessed in vitro by quantifying intracellular cAMP release as a result of GLP-1R activation in BHK cells stably transfected with rat GLP-1R (a generous gift of Drucker group, University of Toronto, Toronto, Canada) (Drucker, D. J. & Nauck, M. A. Lancet 2006, 368, 1696-1705). Cells were allowed to reach 70-80% confluence in 24-well plates. Prior to the assay, ~20 μg of peptide or equivalent of conjugates were treated with 0.5 μg DPP4 (ProSpect) overnight to remove the di-alanine leader. On the day of the assay, cells were incubated with 3-isobutyl-1-methylxanthineto (IBMX, EMD Millipore) for 1 h to prevent cAMP degradation, followed by incubation with varying concentrations (0.001-1000 nM in log-scale increments) of exendin (Genscript) or conjugates for 10 min to trigger GLP-1R activation. 0.1 M HCl was then added to disrupt the cells and release intracellular cAMP. cAMP concentration was measured by a competitive cAMP ELISA according to the manufacturer's protocol (Enzo Life Sciences). Each sample was assayed in triplicate and data were analyzed in Igor Pro (v. 6.2, Wavemetrics) using a Hill equation fit to determine the EC50 of each construct (Goutelle, S. et al. *Fundam. Clin. Pharmacol.* 2008, 22, 633-648).

Animal studies. In vivo experiments were performed with 6-week-old male C57BL/6J mice (stock no. 000664) purchased from Jackson Laboratories. Upon arrival, mice were initiated on a 60 kCal % fat diet (#D12492, Research Diets Inc.) to induce a diabetic phenotype. Previous studies have established high fat-fed C57BL/6J mice as an adequate model for type 2 diabetes, as after one week on a high-fat diet, mice exhibit elevated blood glucose, progressively increasing insulin level, and severely compromised insulin response and glucose tolerance (Winzell, M. S. & Ahren, B. *Diabetes* 2004, 53, S215-S219; Surwit, R. S., et al. *Diabetes* 1988, 37, 1163-1167). Mice were housed under controlled light on a 12 h light/12 h dark cycle with free access to food and water. All mice were allowed to acclimate to the high-fat diet and the facility for 10 d before initiation of experiments. Mice used for fed glucose measurement study of EG3 conjugates were maintained on the high-fat diet for 3 weeks and used at the age of 8 weeks. All animal care and experimental procedures were approved by the Duke Institutional Animal Care and Use Committee.

In vivo fed glucose measurements. The effect of native exendin and the conjugates on fed blood glucose levels was measured following a single s.c. injection of each sample. Before blood glucose measurement, the tail was wiped with a sterilizing alcohol solution and wiped dry. A tiny incision was made on the mouse tail vein using a disposable lancet, and the first 1 µL drop of blood was wiped off. The second 1-2 µL blood drop was used for glucose measurement using a hand-held glucometer (AlphaTrack, Abbott). Blood glucose levels were measured 1 d before the experiment. On the day of injection, weights and blood glucose were measured, and a sample solution or PBS control of equivalent volume was injected s.c. Immediately following injection, mice were placed back in the cage with free access to food and water, and blood glucose was measured at 1, 4, 6 (exendin only), 8, 24, 48, 72, 96, 120 and 144 h post-injection. Weights were monitored daily. In the EG9 dose-dependent study, a 66.2 kDa EG9 exendin-C-POEGMA conjugate was injected into mice (n=3) at 25, 50, and 85 nmol/kg mouse body weight. In the EG9 MW-dependent study, EG9 conjugates of 25.4, 54.6, 97.2 and 155.0 kDa Mns were injected into mice (n=6) at 25 nmol/kg. In the EG3 fed glucose study, 55.6 kDa and 71.6 kDa EG3 exendin-C-POEGMA conjugates were injected into mice (n=5) at 25 nmol/kg. Blood glucose levels were normalized by the average glucose levels measured 24 h and immediately before injection to reflect the percent change in blood glucose and to correct for transient variations in glucose.

Figure 4A:
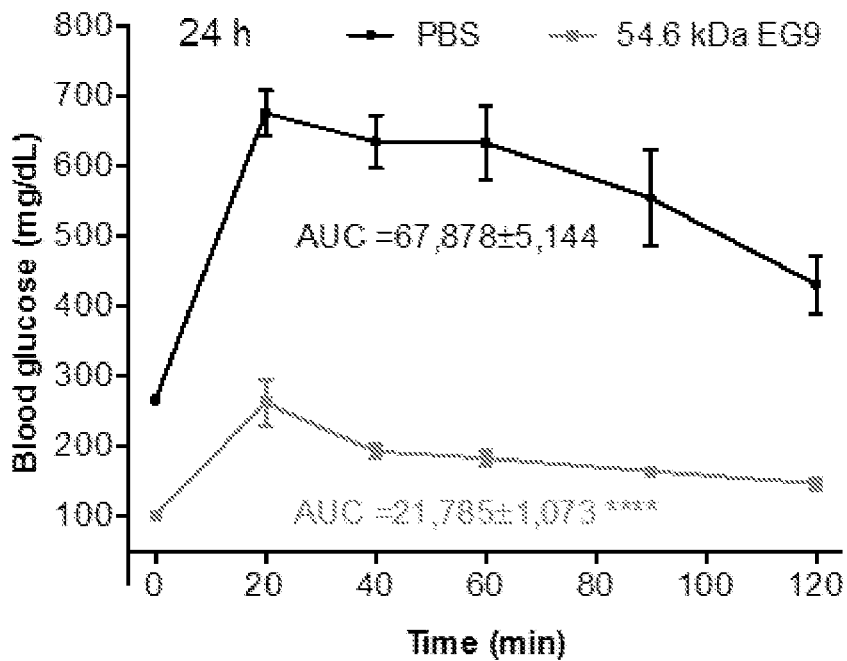
FIG. 4A-D. Intraperitoneal glucose tolerance test (IP-GTT) of an EG9 exendin-POEGMA in mice. Mouse blood glucose levels measured in an IPGTT performed at 24 h and 72 h after a single s.c. injection of the 54.6 kDa EG9 exendin-POEGMA conjugate (24 h, FIG. 4A; 72 h, FIG. 4B) or unmodified exendin at 25 nmol/kg (24 h, FIG. 4C or 72 hr, FIG. 4D), compared to PBS of equivalent volume. Mice were fasted for 6 h prior to glucose challenge by an intraperitoneal (i.p.) injection of 1.5 g/kg of glucose. Results are plotted as mean±SEM, n=5 in FIG. 4A-B, n=3 in FIG. 4C-D. AUCs of treatment and PBS were compared using an unpaired parametric two-tailed t test ($P<0.01$, and **$P<0.0001$). Exendin was not significant at either time point.
Figure 4B:
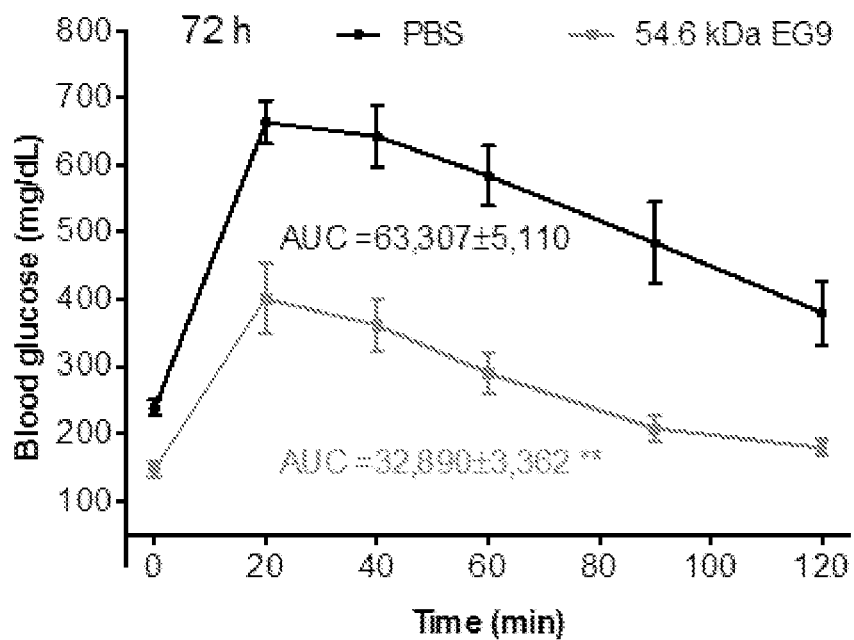

In vivo IPGTT. Mice were randomly divided into groups (n=5 in FIG. 4A and FIG. 4B, n=3 in FIG. 4C and FIG. 4D). On day one, every two groups of mice received a s.c. injection of either 54.6 kDa EG9 exendin-C-POEGMA conjugate, exendin as positive control, or PBS at equivalent volume as negative control. Exendin and the conjugate were injected at 25 nmol/kg. 18 h after injection, one group of mice in each category were fasted by removal of food for 6 h. At the end of the fast period (24 h following injection), mice were given 1.5 g/kg glucose (10 w/v % sterile glucose solution, Sigma) via i.p. injection. Blood glucose levels were monitored by nicking the tail vein and measuring the glucose level in the blood using a glucometer at 0, 20, 40, 60, 90, and 120 min after glucose administration. 66 h after injection, the remaining groups of mice were subjected to the same protocol and an IPGTT was similarly performed 72 h following injection.

In vivo pharmacokinetics. Exendin, 54.6 kDa EG9, 55.6 kDa EG3 and 71.6 kDa EG3 exendin-C-POEGMA conjugates were fluorescently labeled with Alexa Fluor® 488 NHS ester (Thermo Fisher Scientific) via their solvent accessible primary amines on lysine residues and the N-terminus, according to manufacturer's protocol. Unreacted free fluorophore was removed using a ZebaSpin desalting column (Thermo Fisher Scientific). Mice were randomly divided into four groups (n=3). Animals were weighed before injection. Each group of mice received a single s.c. injection of one of the labeled samples at 75 nmol/kg (45 nmol/kg fluorophore). 10 µL of blood samples were collected from the tail vein into 100 µL of a heparin solution (1 kU/ml in PBS, Sigma Aldrich) at 40 s, 40 min, 2.5 h, 4.5 h, 8 h, 24 h, 48 h, 72 h, 96 h and 120 h after injection. Blood samples were centrifuged at 4° C. and 20,000 xg for 10 min to extract the plasma for fluorescence reading at excitation 485 nm and emission 535 nm on a Victor multilabel plate reader (Perkin Elmer). Plasma concentrations of constructs as a function of time were fitted using a non-compartmental analysis (PK Solutions 2.0, Summit Research Services) that characterizes the absorption and elimination phases of the profiles to derive the pharmacokinetic parameters.

In vitro anti-PEG ELISA. In the direct ELISA, columns of a 96-well microtiter plate (CoStar) were coated with Krystexxa® (Crealta Pharmaceuticals), ADA (Sigma-Tau Pharmaceuticals), Adagen® (Sigma-Tau Pharmaceuticals), exendin (Genscript), a 54.6 kDa EG9 exendin-C-POEGMA conjugate, a 55.6 kDa EG3 exendin-C-POEGMA conjugate or BSA (Sigma Aldrich). The antigen solutions for plate coating were prepared in PBS to yield ~2 µg of unmodified peptide/protein or ~5 µg of PEG/OEG in the case of polymer-modified antigens per well upon adding 50 µL to each well. The PEG/OEG contents of the polymer-modified antigens were calculated as follows: Krystexxa® consists of the tetrameric uricase enzyme (125 kDa total) with 10-11 lysine side-chain amino groups on each of its four subunits reacted with 10 kDa PEG p-nitrophenyl carbonate ester, giving a PEG content of ~76%. Adagen® consists of ADA (40.8 kDa) with 11-17 of its side-chain amino groups on solvent-accessible lysines functionalized with 5 kDa monomethoxy succinyl PEG according to the manufacturer's specifications (Sigma-Tau Pharmaceuticals). For our calculation, we assumed 14 PEG chains per Adagen® conjugate on average, giving ~60% PEG content. In the case of the exendin-C-POEGMA conjugates, subtracting the poly(methyl methacrylate) backbone (~17% for EG9 POEGMA and ~37% for EG3 POEGMA) gives an OEG content of ~75% for the 54.6 kDa EG9 conjugate and ~58% for the 55.6 kDa EG3 conjugate. After overnight incubation of the coated plate at 4° C., it was washed with PBS and all wells were blocked with 1% BSA in PBS. One patient plasma sample previously tested negative for PEG antibody and two that were tested positive were diluted 1:400 v/v in 1% BSA in PBS. The two positive patient plasma samples were from two different individuals that developed anti-PEG antibodies during a Phase II clinical trial of Krystexxa®. Following another round of PBS washing, 100 µL of each diluted plasma sample and 1% BSA in PBS were added to replicate wells of each antigen. The plate was then incubated at room temperature for 2 h. Wells were again washed with PBS and 100 µL of alkaline phosphatase-conjugated goat anti-human IgG (Sigma) diluted 1:5250 with 1% BSA in PBS was added to each well. After 1 h incubation at room temperature, wells were washed with PBS followed by Tris-buffered saline. Bound alkaline phosphatase was detected by incubating with p-nitrophenyl phosphate (Sigma) in accordance with the directions of the supplier. The phosphatase reaction was stopped by adding 50 µL/well of 10% NaOH, and the absorbance at 405 nm was measured on a plate reader (Tecan Infinite M200 Pro, Tecan Austria).

In the competitive ELISA, a microtiter plate was coated with 50 µL of 100 µg/mL Krystexxa® per well by overnight incubation at 4° C. Various amounts of ADA, Adagen®, exendin, a 54.6 kDa EG9 exendin-C-POEGMA conjugate, and a 55.6 kDa EG3 exendin-C-POEGMA conjugate were diluted with PBS to yield 0, 0.5, 2, 5, 10, and 20 µg of competing antigen per well upon adding 50 µL to each well. Dilutions of Adagen® and the exendin-C-POEGMA conjugates were prepared such that at each competing antigen concentration, similar PEG/OEG contents were compared as shown in Table 2. The diluted competing antigens were mixed with equal volume of a patient plasma sample that tested positive for PEG antibody (diluted 1:200 v/v in 1% BSA in PBS) and incubated at 4° C. overnight. The following morning, after washing with PBS, all wells were blocked with 1% BSA in PBS. Wells were washed with PBS after blocking, and 100 µL of each concentration of the competing antigen-plasma mixtures was added in replicate wells. After incubation at room temperature for 2 h, alkaline phosphatase-conjugated IgG was added for colorimetric readout at 405 nm as described above.

TABLE 2

Variable amounts of Adagen ® and exendin-C-POEGMA conjugates and their corresponding PEG/OEG contents loaded as competing antigens per well in the competitive ELISA. PEG content of Adagen ® was approximated by assuming 14 PEG chains per Adagen ® conjugate, while OEG content of the exendin-C-POEGMA conjugates was directly calculated by subtracting the poly(methyl methacrylate) backbone.

| Nominal (µg/well) | Adagen ® | | 54.6 kDa EG9 exendin-C-POEGMA | | 55.6 kDa EG3 exendin-C-POEGMA | |
|---|---|---|---|---|---|---|
| | Conjugate (µg/well) | PEG (µg/well) | Conjugate (µg/well) | OEG (µg/well) | Conjugate (µg/well) | OEG (µg/well) |
| 0.5 | 0.6 | 0.4 | 0.5 | 0.4 | 0.7 | 0.4 |
| 2 | 2.6 | 1.6 | 2.0 | 1.5 | 2.8 | 1.6 |
| 5 | 6.4 | 3.8 | 5.0 | 3.8 | 6.9 | 4 |
| 10 | 12.8 | 7.7 | 10.0 | 7.5 | 13.8 | 8 |
| 20 | 25.6 | 15.4 | 20.0 | 15.0 | 27.6 | 16 |

Figure 5A:
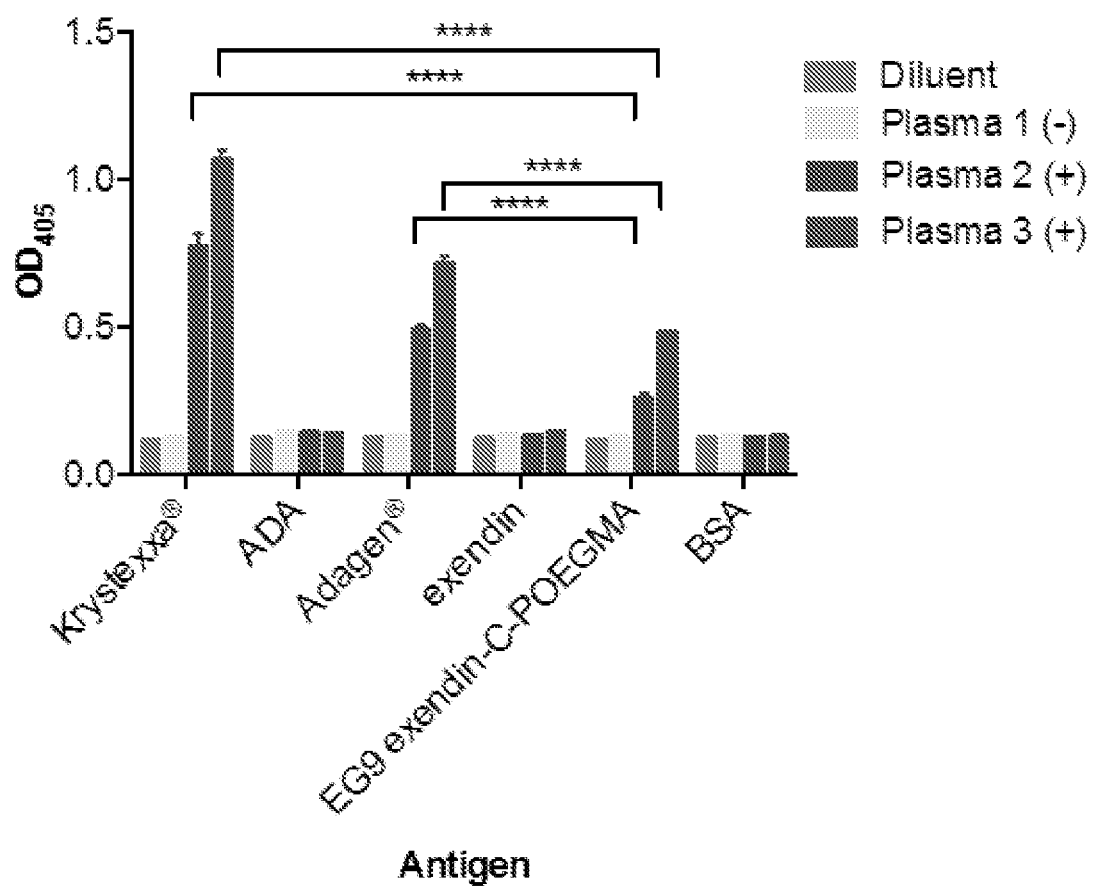
FIG. 5A-D. Assessment of reactivity of exendin-C-POEGMA conjugates toward anti-PEG antibodies in patient plasma samples.
Figure 5B:
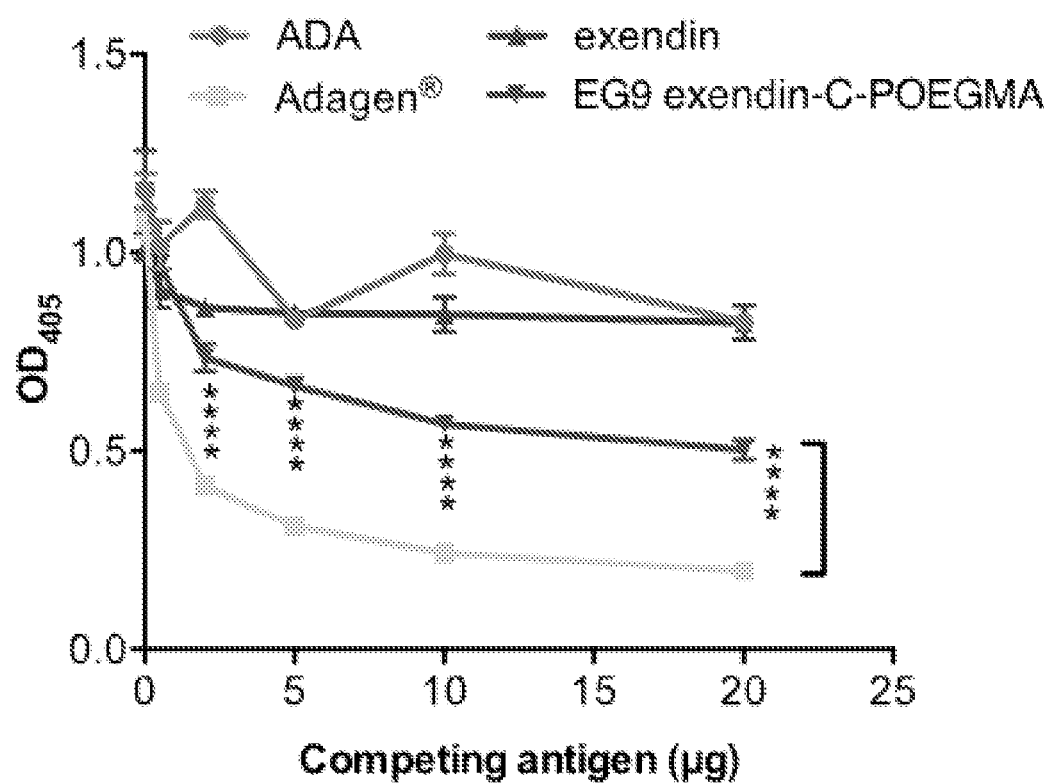
Figure 5C:
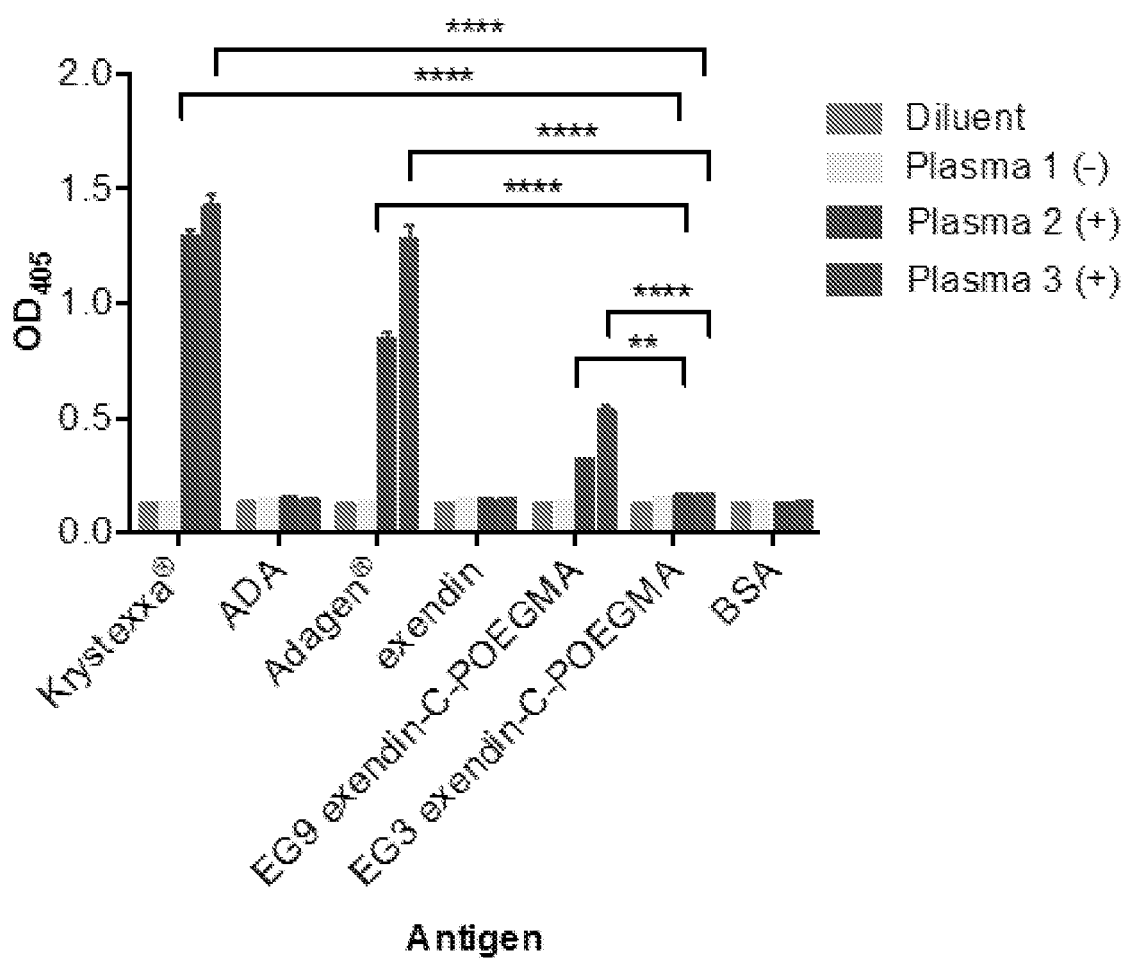
Figure 5D:
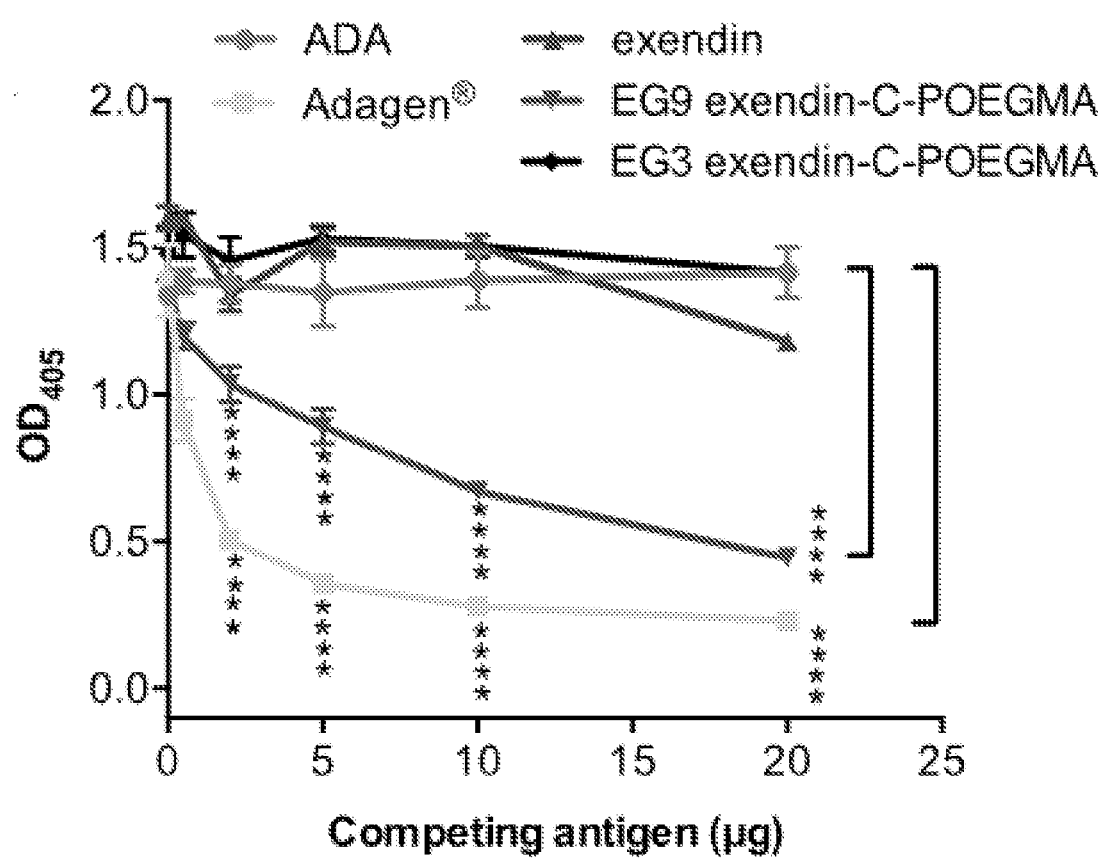
Figure 6A:
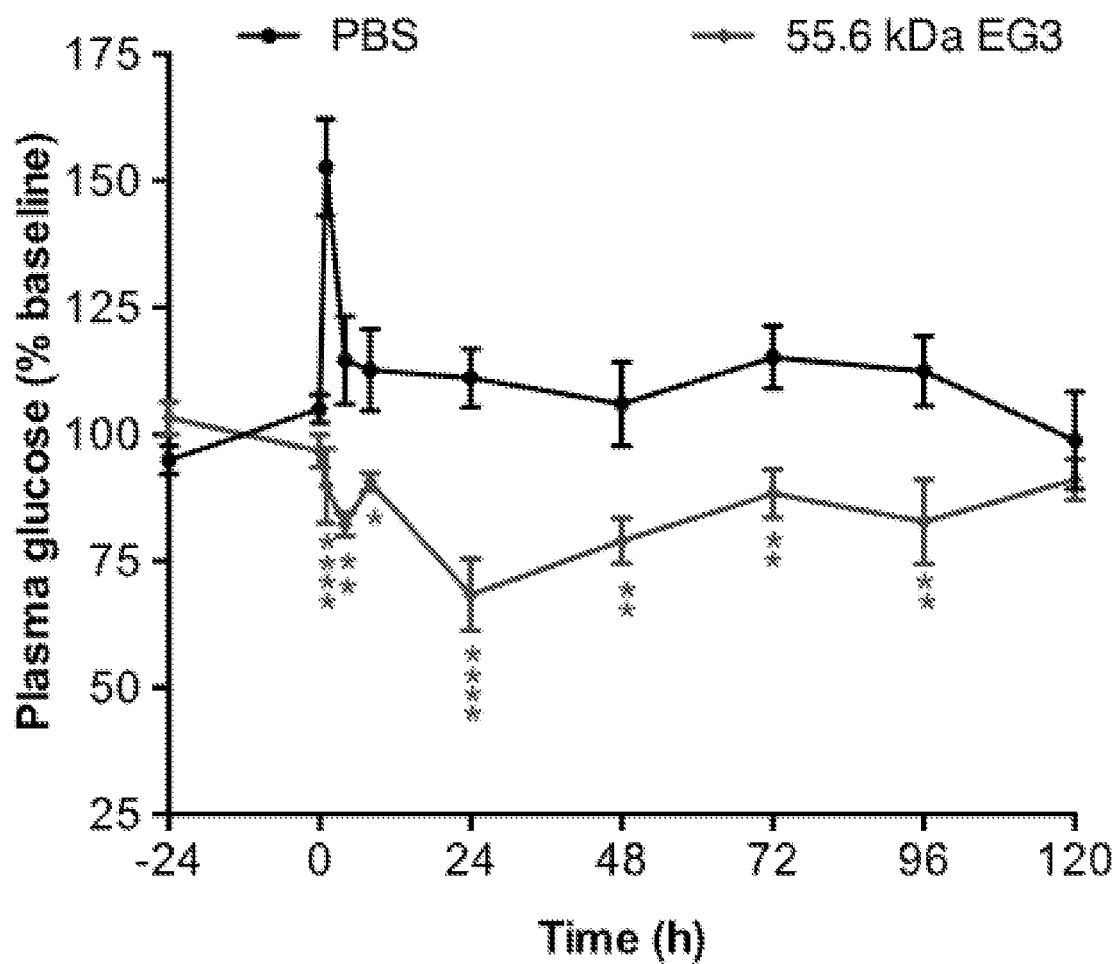
FIG. 6A-D. Assessment of in vivo efficacy and pharmacokinetics of exendin-C-POEGMA conjugates. Blood glucose levels in fed mice measured before and after a single s.c. injection of 55.6 kDa (FIG. 6A) and 71.6 kDa (FIG. 6B) EG3 exendin-C-POEGMA conjugates at 25 nmol/kg or PBS at equivalent volume administered at t=0 h. Blood glucose levels were normalized to the average glucose levels measured 24 h and immediately before injection. Data were analyzed by repeated measures two-way ANOVA, followed by post hoc Dunnett's multiple comparison test (n=5, *P<0.05, P<0.01, and **P<0.0001). Exendin (FIG. 6C) and exendin-C-POEGMA conjugates (54.6 kDa EG9, 55.6 kDa EG3 and 71.6 kDa EG3) (FIG. 6D) were fluorescently labeled with Alexa Fluor® 488 and injected into mice (n=3) s.c. at 75 nmol/kg (45 nmol/kg fluorophore). Blood samples were collected via tail vein at various time points for fluorescence quantification. Data were analyzed using a non-compartmental fit (solid lines) to derive the pharmacokinetic parameters shown in Table 6. Results in all panels are plotted as mean±SEM.
Figure 6B:
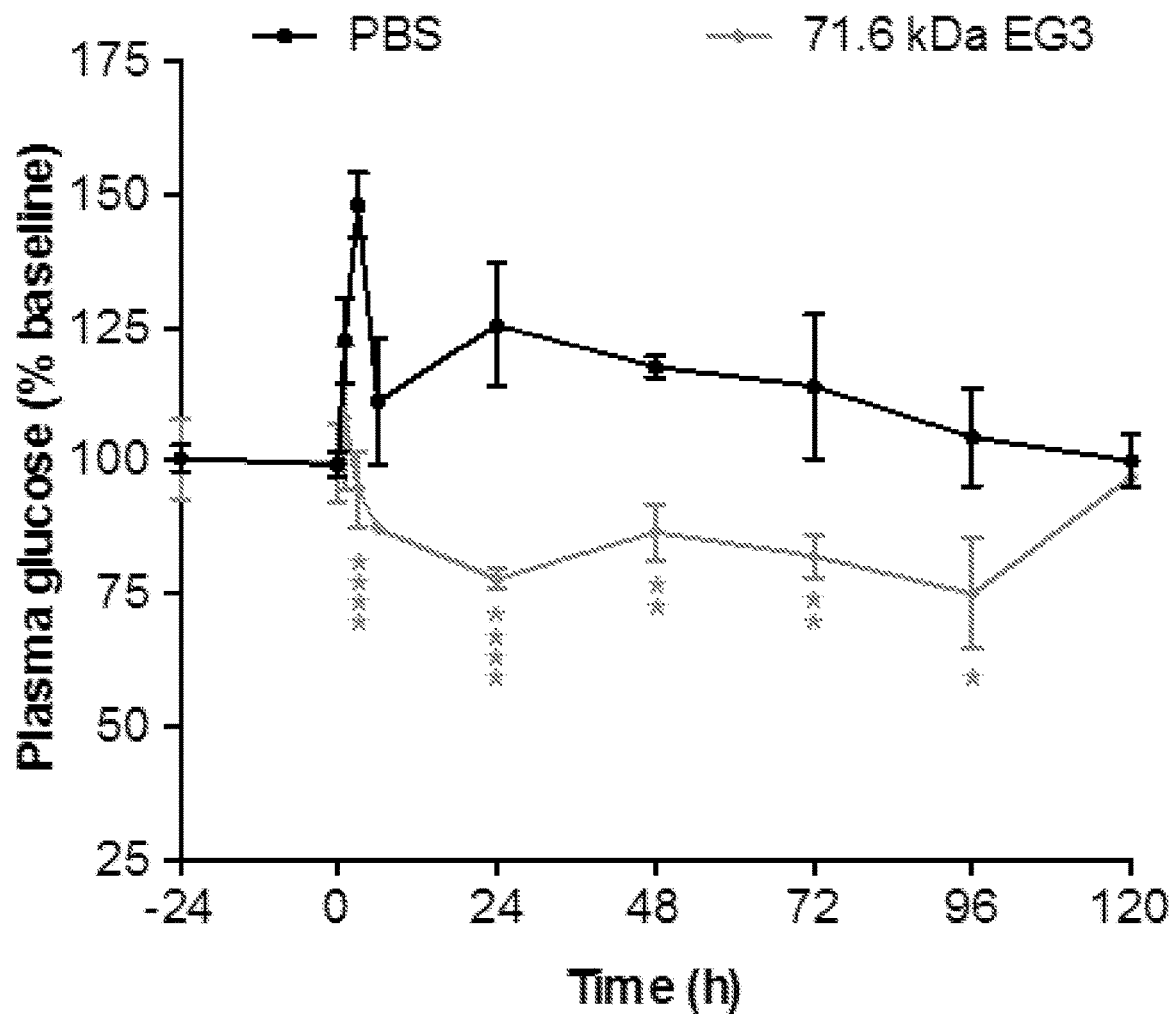
Figure 6C:
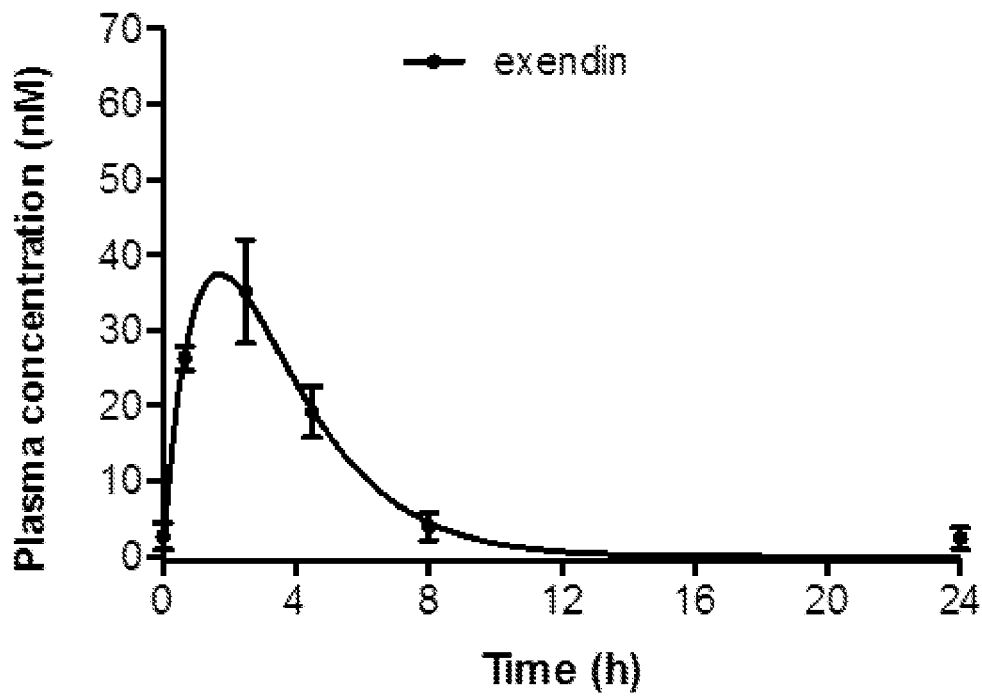
Figure 6D:
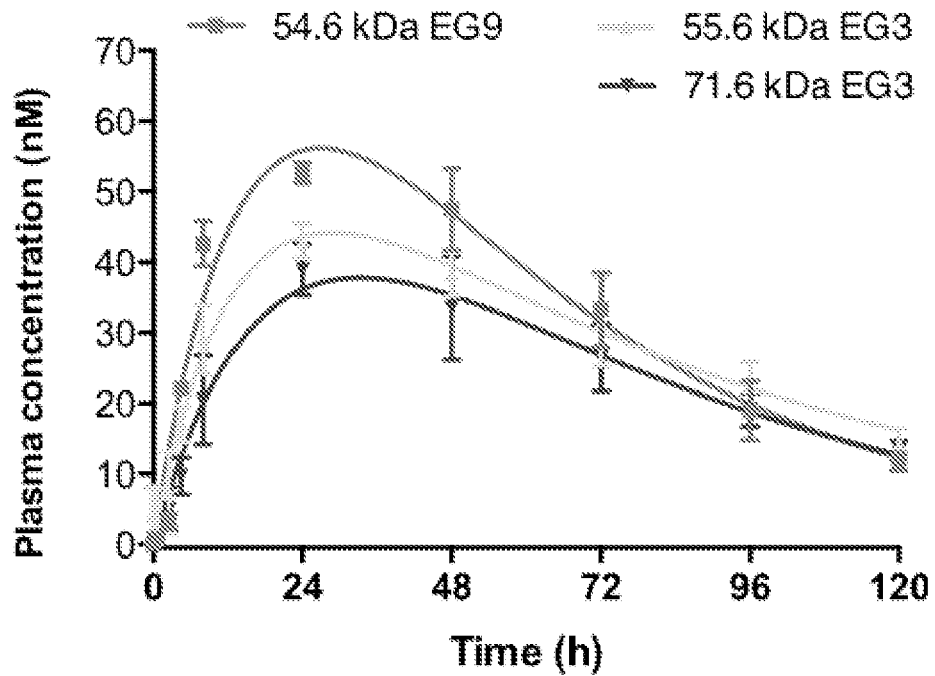

Assays in FIG. 5A and FIG. 5B were performed with n = 3, while those in FIG. 5C and FIG. 5D were performed with n = 5.

Statistical analysis. Data are presented as means±standard errors (SEs). Blood glucose levels in fed glucose measurement studies (n=6) were normalized by the average glucose levels measured 24 h and immediately before injection. Treatment effects on fed glucose levels were analyzed using repeated measures two-way ANOVA, followed by post hoc Dunnett's multiple comparison test to evaluate individual differences between a treatment and PBS control at each time point. AUCs of fed glucose profiles were compared using one-way ANOVA followed by post hoc Tukey's multiple comparison test (n=6). For evaluating AUC of IPGTT (n=5), treatment and PBS were compared using an unpaired parametric two-tailed t test. Both direct and competitive anti-PEG ELISAs (n=3) were analyzed using two-way ANOVA, followed by post hoc Dunnett's multiple comparison test to evaluate individual differences between exendin-C-POEGMA and the other groups for each plasma sample (direct) or antigen concentration (competitive). A test was considered significant if the P value was less than 0.05. Statistical analyses were performed using Prism 6 (GraphPad software Inc.).

Example 2

Sortase-Catalyzed C-Terminal Initiator Attachment to Exendin

Figure 1B:
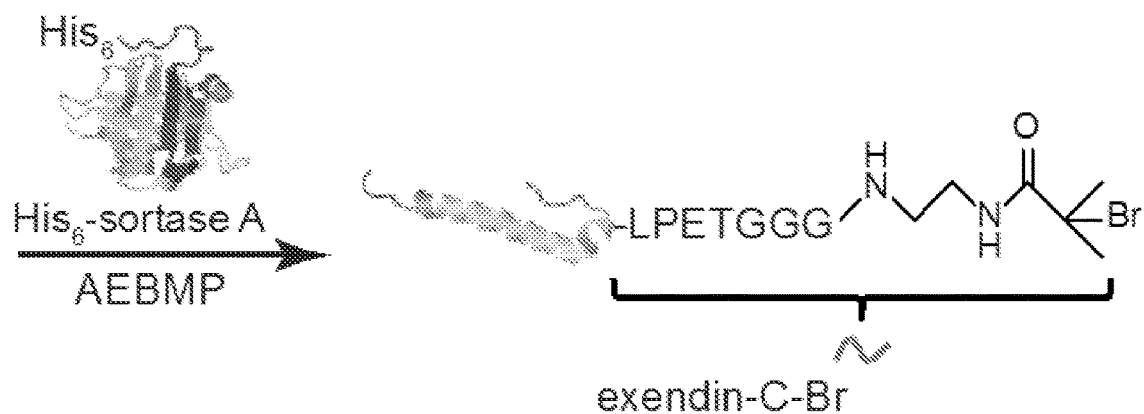
Figure 7A:
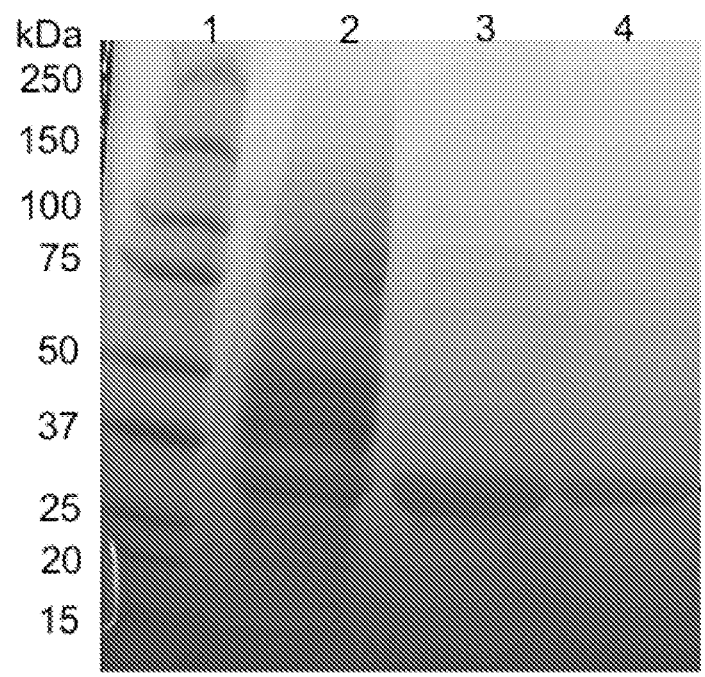
FIG. 7A-B.
Figure 7B:
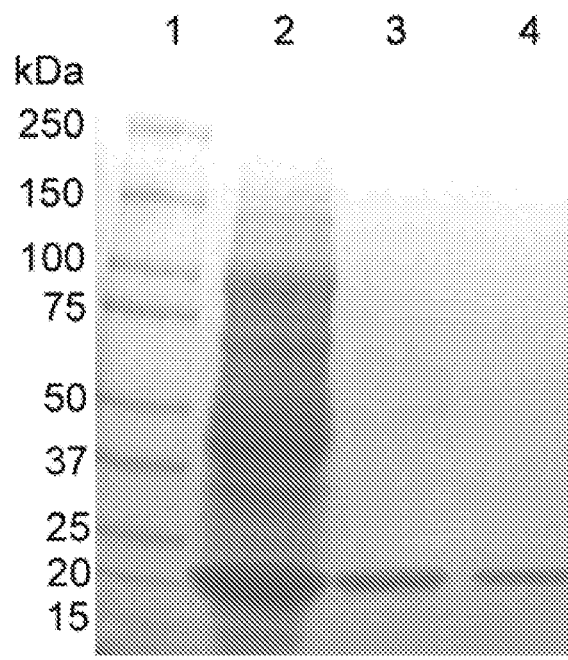

We exploited the C-terminal native peptide ligation mechanism of sortase A to site-specifically attach the ATRP initiator N-(2-(2-(2-(2-aminoacetamido)acet-amido)acet-amido) ethyl)-2-bromo-2-methylpropanamide (AEBMP) to the C-terminus of exendin (FIG. 1). A quaternary fusion protein, abbreviated as "exendin-srt-His6-ELP", was recombinantly expressed to serve as the sortase A substrate (FIG. 1A). As explained in an earlier study, "srt" stands for the native sortase A recognition sequence "LPETG" and ELP refers to a stimulus-responsive elastin-like polypeptide that was incorporated to enable easy purification of the fusion protein by inverse transition cycling (ITC, FIG. 7A), a nonchromatographic protein purification method that we previously developed (Meyer, D. E. & Chilkoti, A. *Nat. Biotechnol.* 1999, 14, 1112-1115). The recognition sequence was deliberately located between the protein and the ELP, so that transpeptidation by sortase A not only attaches the initiator to exendin, but also conveniently liberates the purification tag. Sortase A with an N-terminal hexahistidine tag (His6-tag) was recombinantly expressed from a plasmid constructed in the earlier study and was purified by immobilized metal affinity chromatography (IMAC, FIG. 7B). The ATRP initiator AEBMP (FIG. 1) was chemically synthesized with an N-terminal $(Gly)_3$ motif serving as the nucleophile, as maximum reaction rates for sortase-catalyzed C-terminal ligation have been reported with two or more glycines (Mao, H., et al., *J. Am. Chem. Soc.* 2004, 126).

Figure 2A:
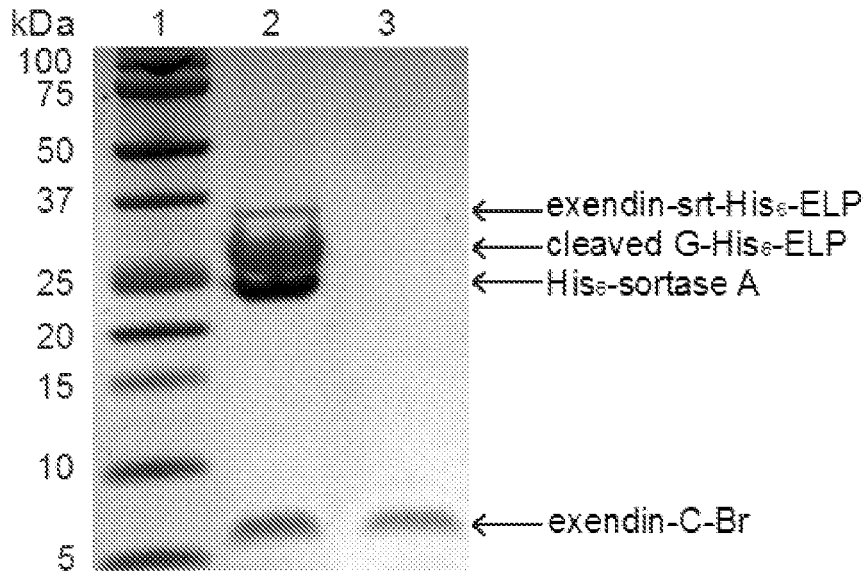
FIG. 2A-C. Characterization of exendin-C—Br macroinitiator and EG9 exendin-C-POEGMA conjugates.

Successful sortase-catalyzed initiator attachment (FIG. 1B) resulted in cleavage of exendin-LPETG-His6-ELP into exendin-LPET and G-His6-ELP, followed by attachment of AEBMP to exendin-LPET to generate the macroinitiator product (exendin-C—Br). Sodium dodecyl sulfate-polyacrylamide gel electrophoresis (SDS-PAGE) analysis of the reaction mixture (FIG. 2A) showed >90% conversion to exendin-C—Br, as assessed by gel densitometry. Similar to the previous study, a His6-tag was intentionally inserted between "srt" and ELP on the exendin-srt-His6-ELP fusion, such that upon transpeptidation by His6-sortase A, all the residual reactants, enzyme and side-products except the desired product-exendin-C—Br-carried a His6-tag. Conse quently, elution through an IMAC column yielded pure exendin-C—Br (FIG. 2A) in the eluent while leaving all other unwanted species bound to the resin.

Example 3

Synthesis and Characterization of Exendin-C-POEGMA Conjugates

Figure 1C:
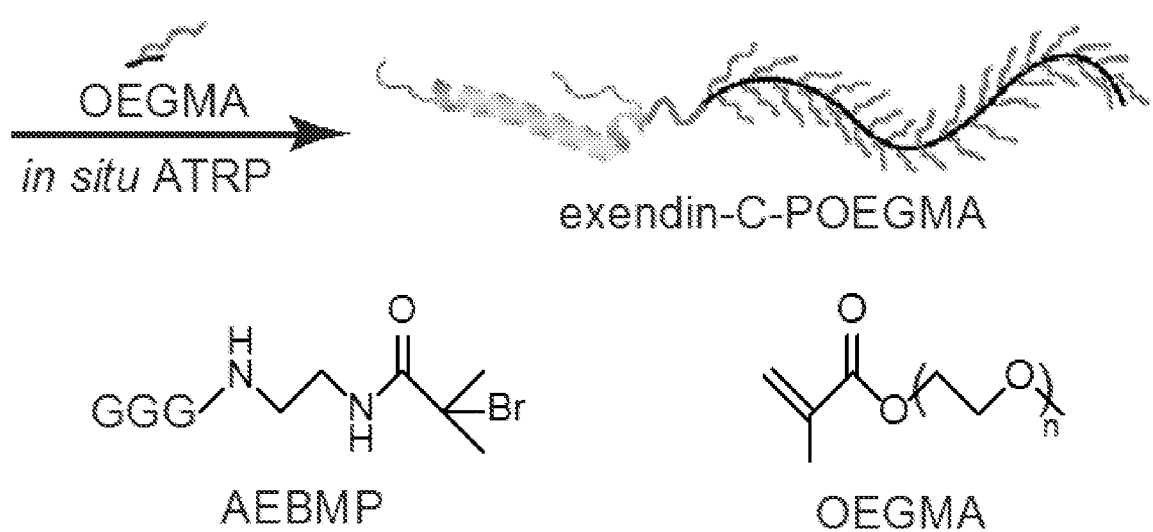
Figure 2B:
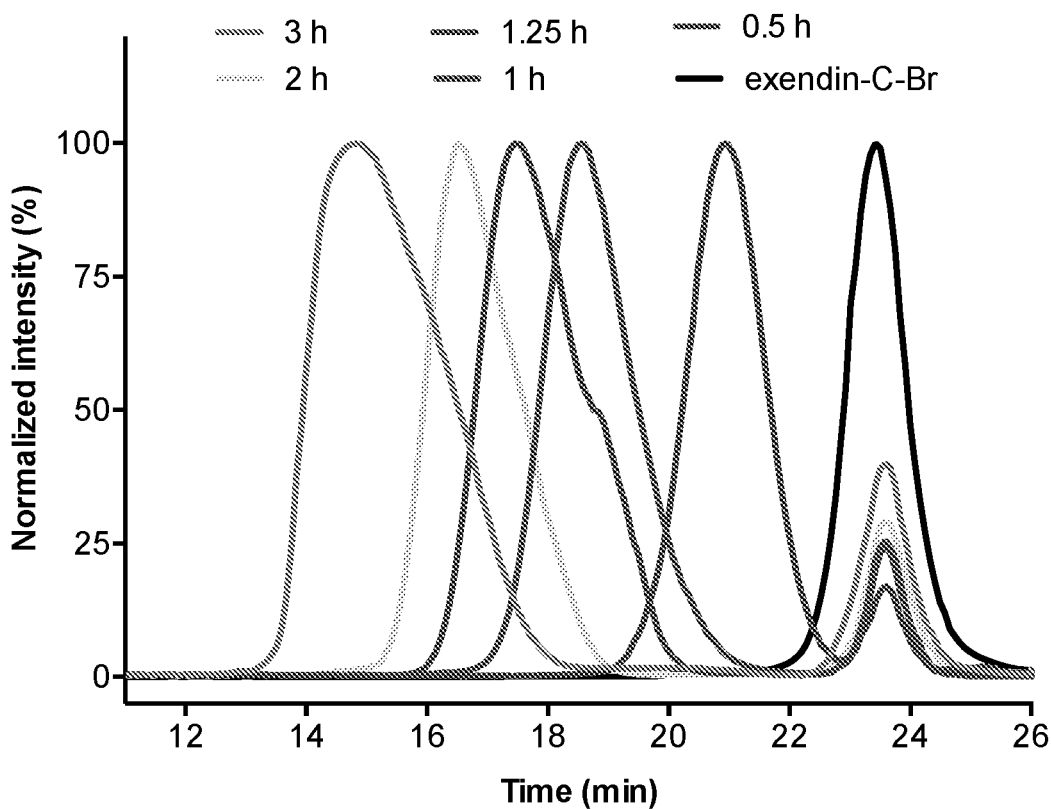
Figure 8A:
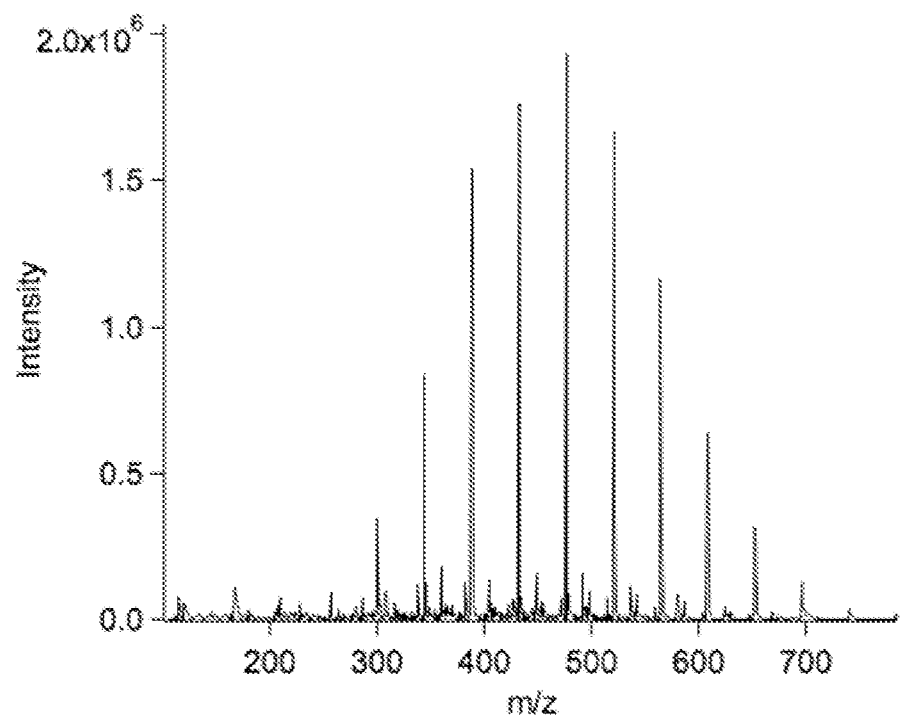
FIG. 8A-B. Liquid chromatography electrospray ionization mass spectrometry (LC/ESI-MS) characterization of OEGMA monomer with (FIG. 8A) an average mass of ~500 Da or ~9 side-chain ethylene glycol repeats (EG9), and (FIG. 8B) a mass of 232 Da or 3 side-chain EG repeats (EG3). Peaks were detected as [M+Na]+.
Figure 9A:
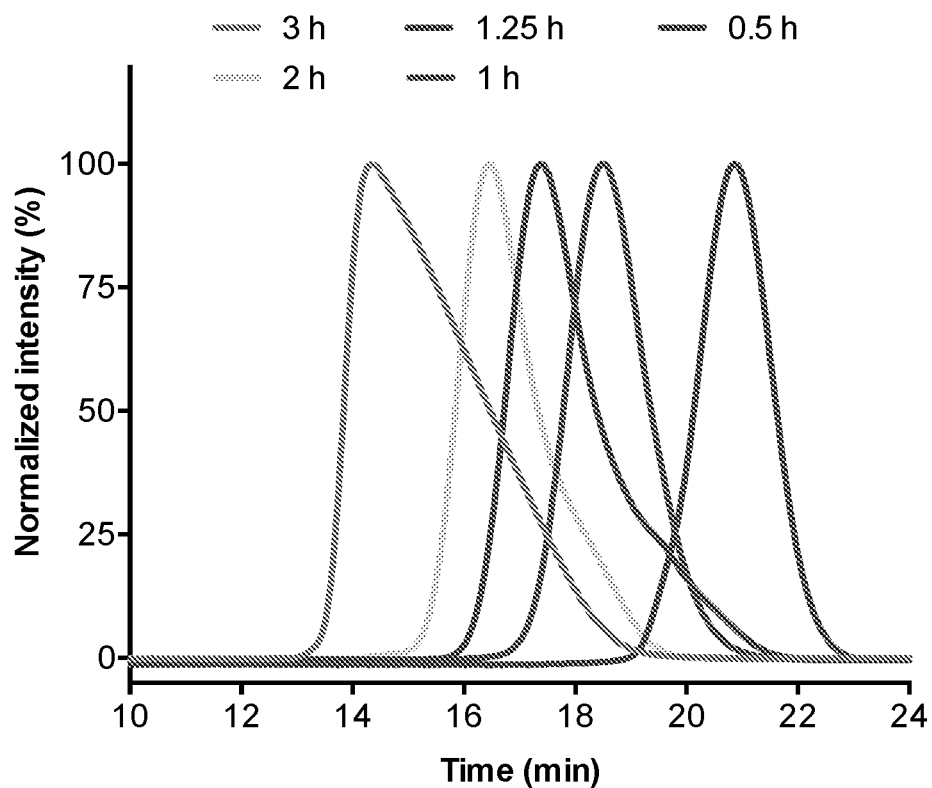
FIG. 9A-B. Physical characterization of EG9 exendin-C-POEGMA conjugates.
Figure 9B:
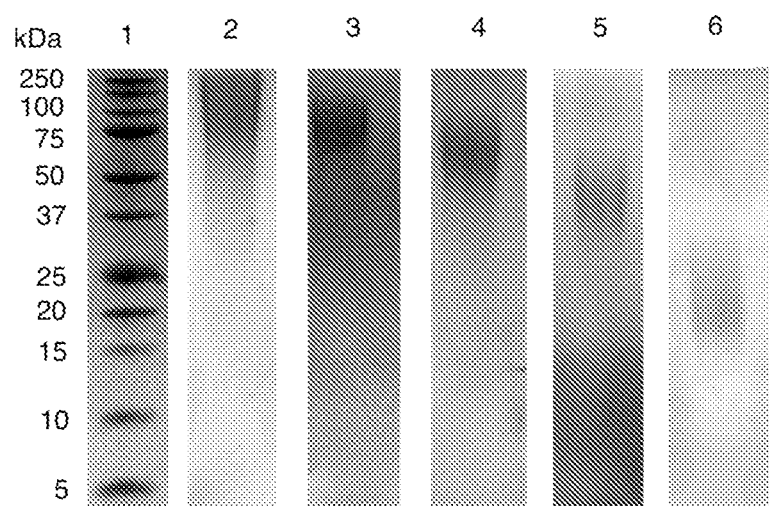

Next, in situ Activator Regenerated by Electron Transfer (ARGET) ATRP (Jakubowski, W. & Matyjaszewski, K. Angew. Chem. Int. Ed. 2006, 45, 4482-4486) was carried out to graft POEGMA from exendin-C—Br (FIG. 1C). An OEGMA monomer with an average mass of ~500 Da or ~9 side-chain EG repeats (EG9) was used, as shown by liquid chromatography electrospray ionization mass spectrometry (LC/ESI-MS) analysis (FIG. 8A). The reaction time was varied to produce EG9 exendin-C-POEGMA conjugates with a range of MWs. Size exclusion chromatography (SEC) analysis of exendin-C—Br before polymerization detected by UV-vis absorbance at 280 nm (FIG. 2B) showed a single peak eluting at 23.7 min. After polymerization, the intensity of the macroinitiator peak greatly diminished, and was accompanied by the appearance of peaks at 21.3, 19.5, 17.8, 16.5, and 15.0 min, corresponding to EG9 exendin-C-POEGMA conjugates with increasing MWs as the reaction time was increased. The results from UV-vis detection were in agreement with those from refractive index (RI) detection (FIG. 9A). Integration of peak areas in the UV-vis chromatograms showed that the average conjugation yield was ~80%. As shown in Table 3, the synthesized conjugates had Mns that ranged from 25.4 to 155.0 kDa and all conjugates had very narrow dispersities (Đ≤1.15). The conjugates could be easily and completely purified by a single round of preparative SEC (FIG. 9B).

Figure 2C:
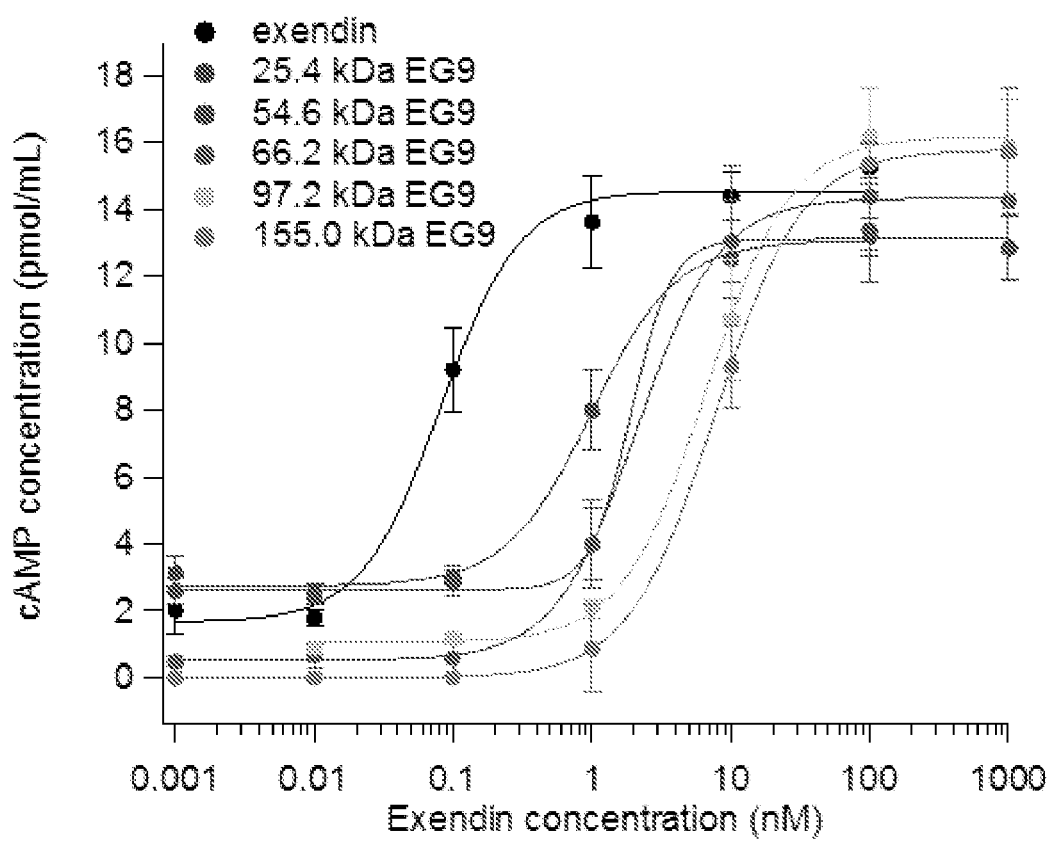

Exendin acts by binding and activating the G protein-coupled GLP-1 receptor (GLP-1R), which results in the release of cyclic adenosine monophosphate (cAMP) as a second messenger in a downstream signaling cascade, ultimately leading to secretion of insulin to regulate blood glucose. The potency of native exendin and the EG9 exendin-C-POEGMA conjugates were next assessed by quantifying intracellular cAMP release as a result of GLP-1R activation in baby hamster kidney (BHK) cells that were stably transfected with rat GLP-1R. As shown in FIG. 2C and Table 3, grafting EG9 POEGMA from exendin increases the EC50 of the peptide in an overall MW-dependent manner, which indicates decreased receptor binding with increasing polymer MW as a result of the steric hindrance im

TABLE 4-continued

Figure 10A:
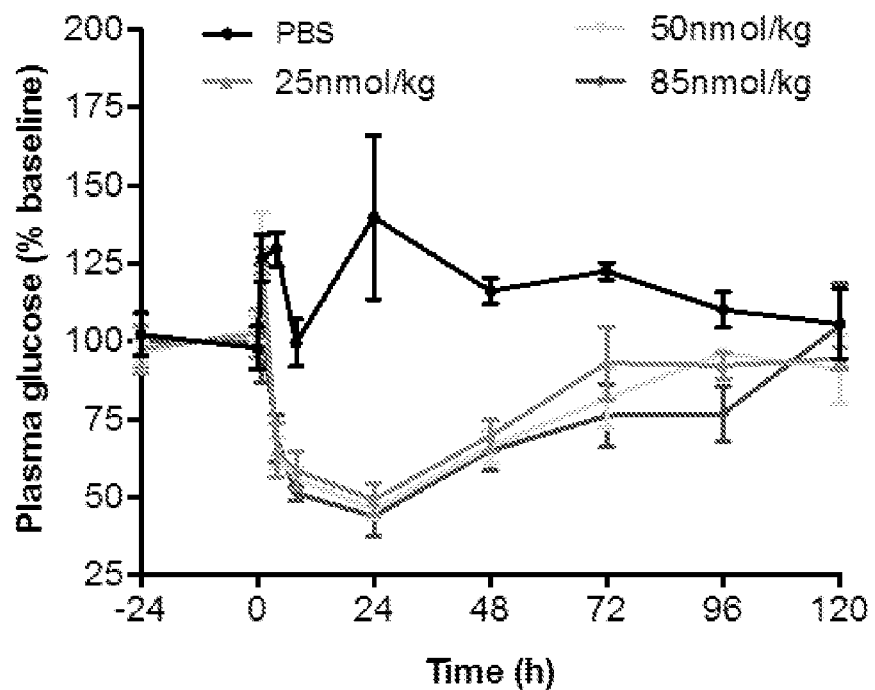
FIG. 10A-B. Assessment of in vivo dose-dependent efficacy of EG9 exendin-C-POEGMA. Overlaid normalized (FIG. 10A) and un-normalized (FIG. 10B) blood glucose levels of 6-wk-old male C57BL/6J mice (n=3) maintained on a 60 kCal % diet measured before and after a single s.c. injection of a 66.2 kDa EG9 exendin-C-POEGMA conjugate at 25, 50, 80 nmol/kg or phosphate buffered saline (PBS) control of equivalent volume administered at t=0 h. Blood glucose levels in panel a were normalized to the average glucose levels measured 24 h prior to and immediately before injection.
Figure 10B:
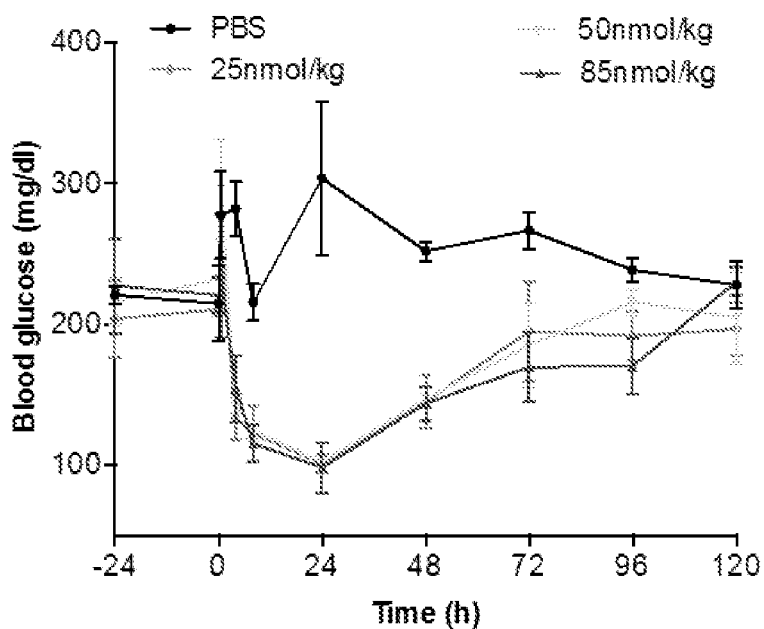
Figure 10C:
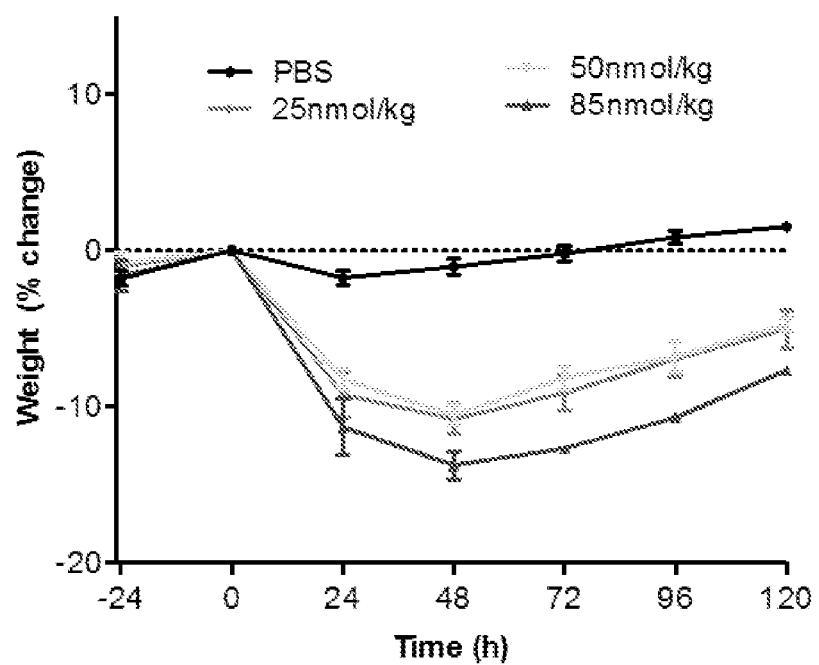
FIG. 10C shows overlaid weight profiles for all treatment and control groups. Weights are reported as % change from 0 h time point. Results in all panels are plotted as mean±SEM.

Summary of statistical significance levels of dose-dependent fed blood glucose measurements of EG9 exendin-C-POEGMA shown in FIG. 10A compared to PBS control.

| Time (h) | Dosage (nmol/kg) | | |
|---|---|---|---|
| | 25 | 50 | 85 |
| 8 | ** | ** | *** |
| 24 | **** | **** | **** |
| 48 | *** | *** | *** |
| 72 | | ** | **** |
| 96 | | | * |

Data were analyzed by repeated measures two-way analysis of variance (ANOVA), followed by post hoc Dunnett's test to evaluate individual differences between a treatment and PBS control at each time point (n = 3, *P < 0.05, P < 0.01, *P < 0.001 and ****P < 0.0001).

Figure 3A:
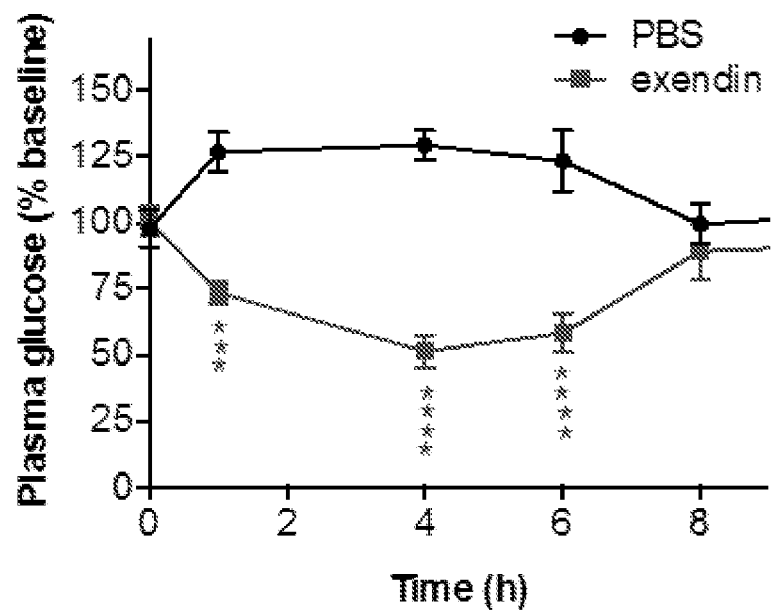
FIG. 3A-F. Assessment of MW-dependent in vivo efficacy of EG9 exendin-C-POEGMA conjugates. Blood glucose levels in fed mice were measured before and after a single s.c. injection of unmodified exendin (FIG. 3A), or 25.4 kDa (FIG. 3B), 54.6 kDa (FIG. 3C), 97.2 kDa (FIG. 3D), and 155.0 kDa (FIG. 3E) EG9 exendin-C-POEGMA conjugates, compared to PBS control. The peptide and conjugates were administered at 25 nmol/kg and PBS was injected at equivalent volume at t=0 h. Blood glucose levels were normalized to the average glucose levels measured 24 h and immediately before injection. Data were analyzed by repeated measures two-way analysis of variance (ANOVA), followed by post hoc Dunnett's multiple comparison test.
Figure 3B:
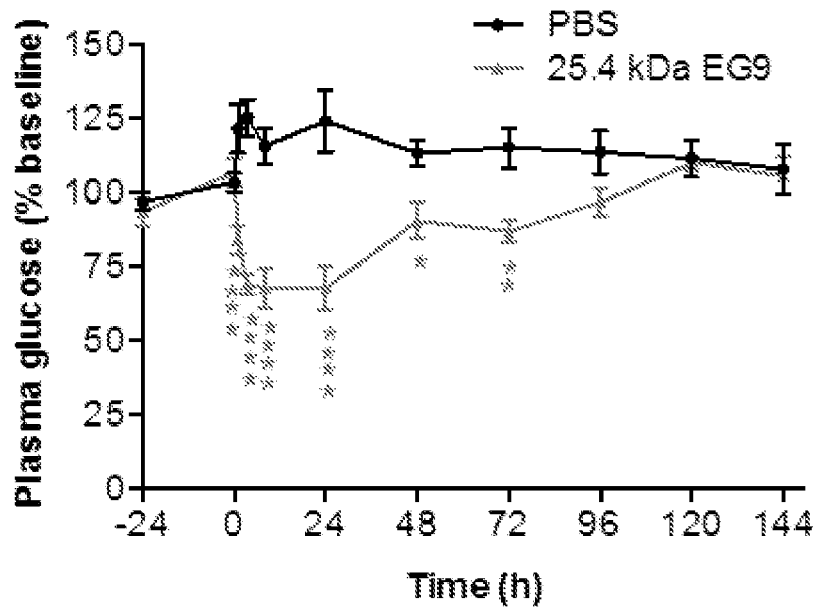
Figure 3C:
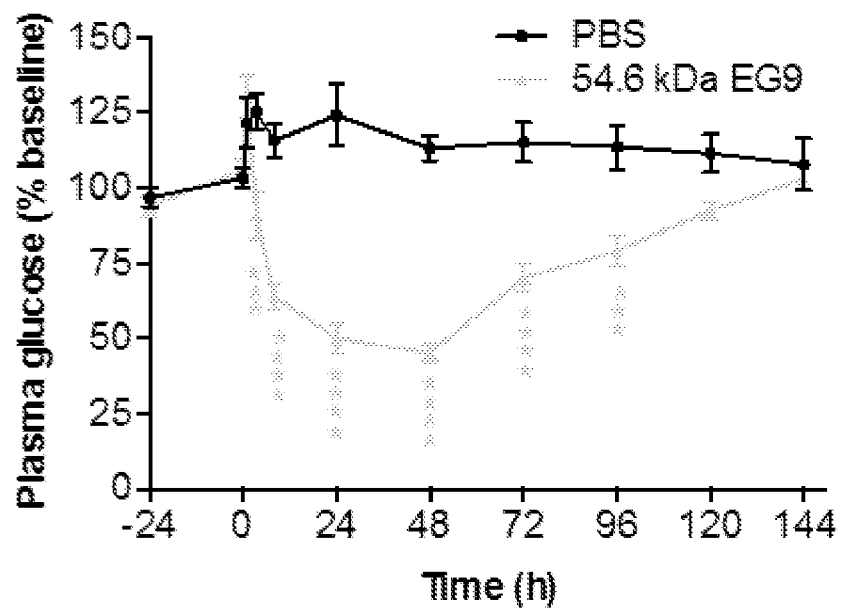
Figure 3D:
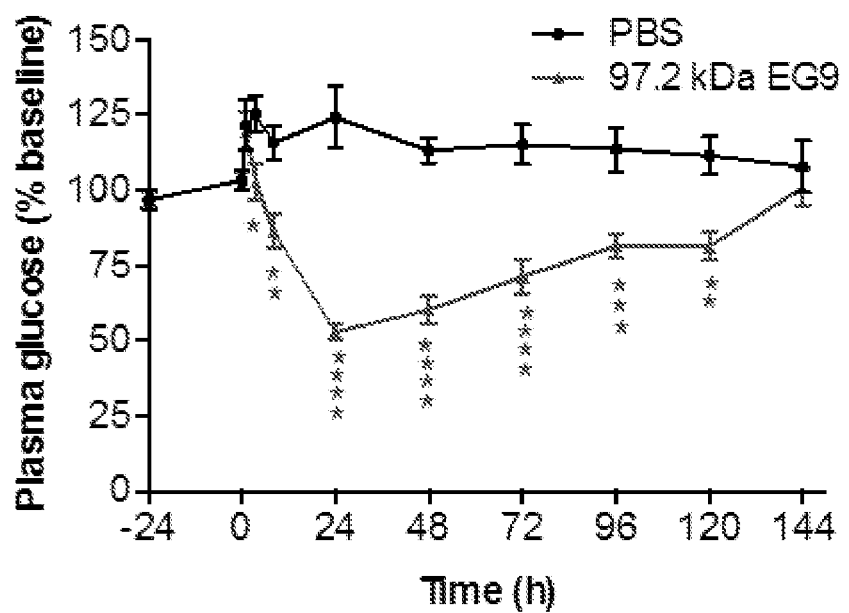
Figure 3E:
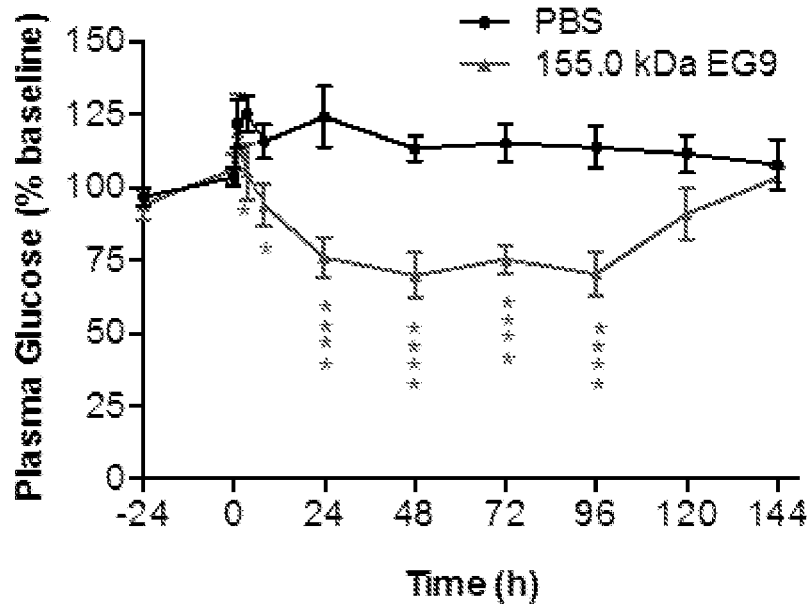
Figure 11A:
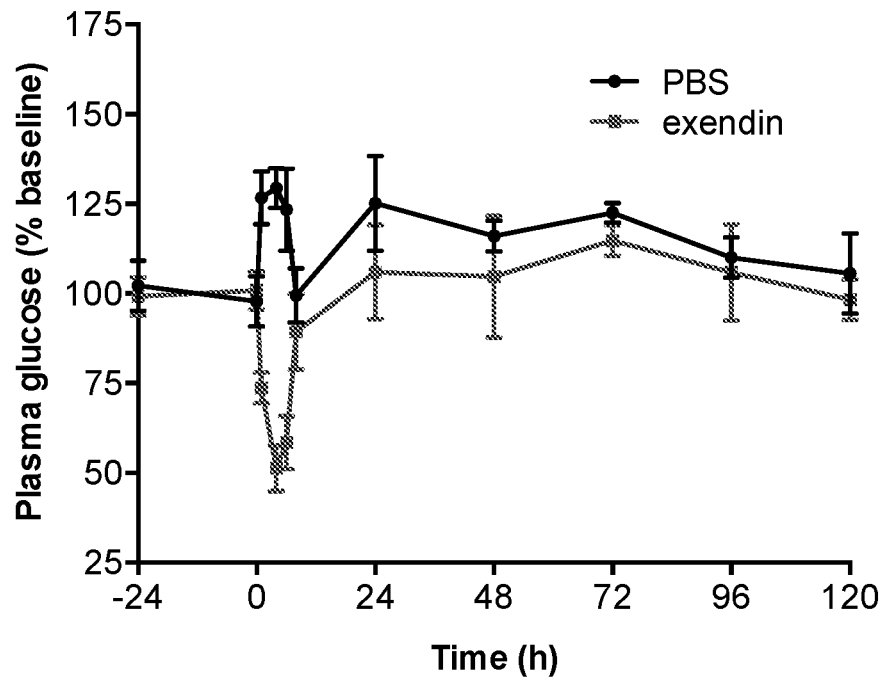
FIG. 11A-B. Assessment of in vivo efficacy of unmodified exendin. Normalized (FIG. 11A) and un-normalized (FIG. 11B) blood glucose profiles of fed mice (n=6) that received a single s.c. injection of unmodified exendin administered at 25 nmol/kg, compared to PBS control at equivalent volume injected at t=0 h. Blood glucose levels in panel a were normalized to the average glucose levels measured 24 h prior to and immediately before injection. Results are plotted as mean±SEM.
Figure 11B:
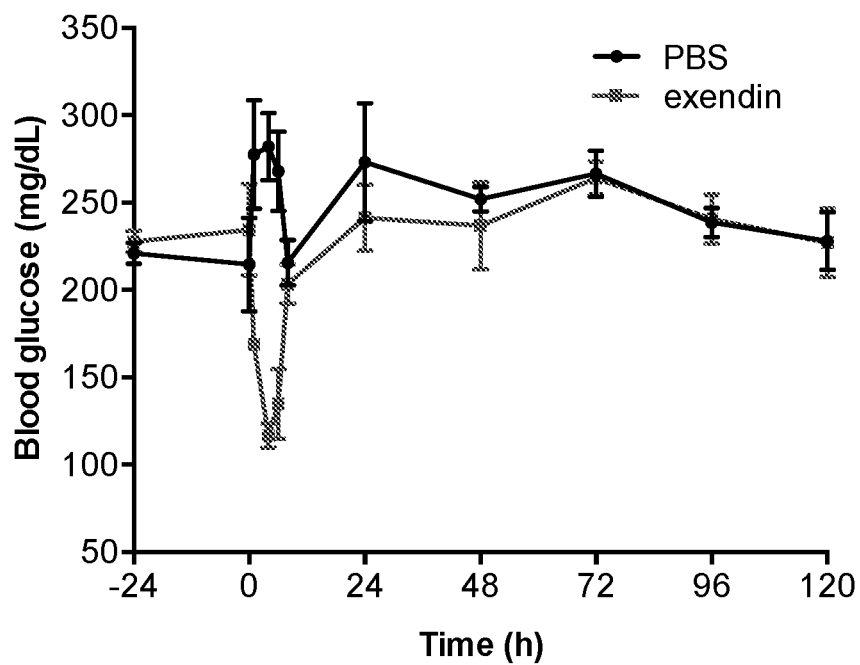
Figure 12A:
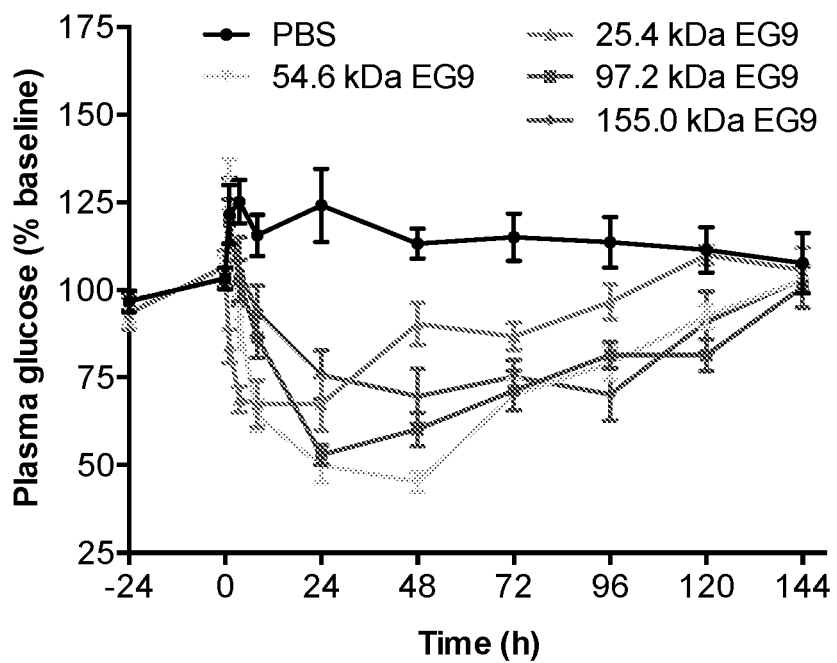
FIG. 12A-C. Assessment of in vivo MW-dependent efficacy of EG9 exendin-C-POEGMA conjugates. Overlaid normalized (FIG. 12A) and un-normalized (FIG. 12B) fed blood glucose levels in mice (n=6) measured before and after receiving a single s.c. injection of 25.4 kDa, 54.6 kDa, 97.2 kDa, 155.0 kDa EG9 exendin-POEGMA conjugates at 25 nmol/kg compared to PBS control at equivalent volume injected at t=0 h. Blood glucose levels in panel a were normalized to the average glucose levels measured 24 h prior to and immediately before injection.
Figure 12B:
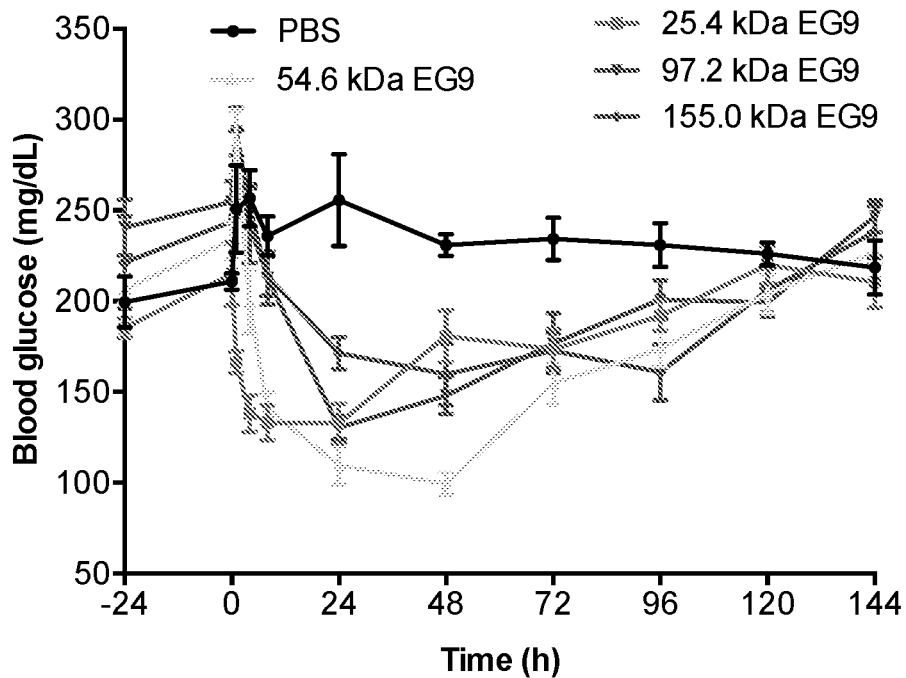
Figure 12C:
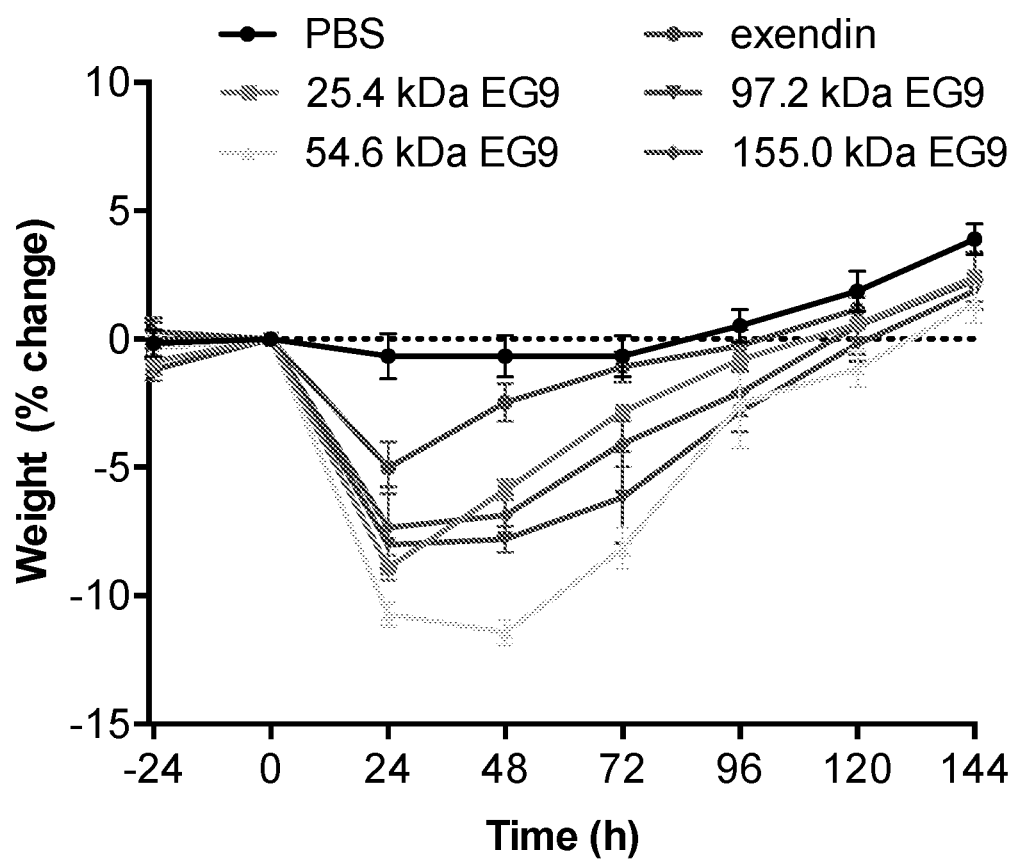

To investigate the effect of MW on the glucose regulatory effect of EG9 exendin-C-POEGMA conjugates, native exendin and conjugates of four different MWs (Mn=25.4, 54.6, 97.2 and 155.0 kDa) were tested at a single s.c. injection at 25 nmol/kg mouse body weight. While unmodified exendin was only able to lower blood glucose for 6 h relative to PBS control (FIG. 3A, full glucose profiles in FIG. 11), modification with EG9 POEGMA significantly extended the glucose-lowering effect of exendin for up to 120 h, with a MW-dependence on the onset, magnitude and duration of the effect (FIG. 3B-E3, Table 5). As is evident from the overlaid glucose profiles in FIG. 12A (overlaid un-normalized glucose profiles in FIG. 12B), an increase in MW delays the onset but prolongs the duration of glucose reduction, and the two higher MW conjugates showed an overall smaller magnitude of glucose reduction. This trend is mirrored by the weight profiles of treated animals as well (FIG. 12C). The two higher MW conjugates also showed much more flat and steady glucose profiles. The glucose profile of the 155.0 kDa conjugate in particular resembled that of a sustained release depot, with no peak-to-valley effect that can cause undesirable side effects.

TABLE 5

Summary of statistical significance levels of MW-dependent fed blood glucose measurements of EG9 exendin-C-POEGMA conjugates shown in FIG. 3 compared to PBS control.

| Time (h) | exendin | EG9 exendin-POEGMA | | | |
|---|---|---|---|---|---|
| | | 25.4 kDa | 54.6 kDa | 97.2 kDa | 155.0 kDa |
| 1 | *** | **** | | | |
| 4 | **** | **** | *** | * | |
| 6 | **** | --- | --- | --- | --- |
| 8 | | **** | **** | ** | * |
| 24 | | **** | **** | **** | **** |
| 48 | | * | **** | **** | **** |
| 72 | | ** | **** | **** | **** |
| 96 | | | **** | *** | **** |
| 120 | | | | | ** |

Data were analyzed by repeated measures two-way ANOVA, followed by post hoc Dunnett's multiple comparison test to evaluate individual differences between a treatment and PBS control at each time point (n = 6, *P < 0.05, P < 0.01, *P < 0.001 and ****P < 0.0001).
--- Groups treated with conjugates were not measured at t = 6 h.

Figure 3F:
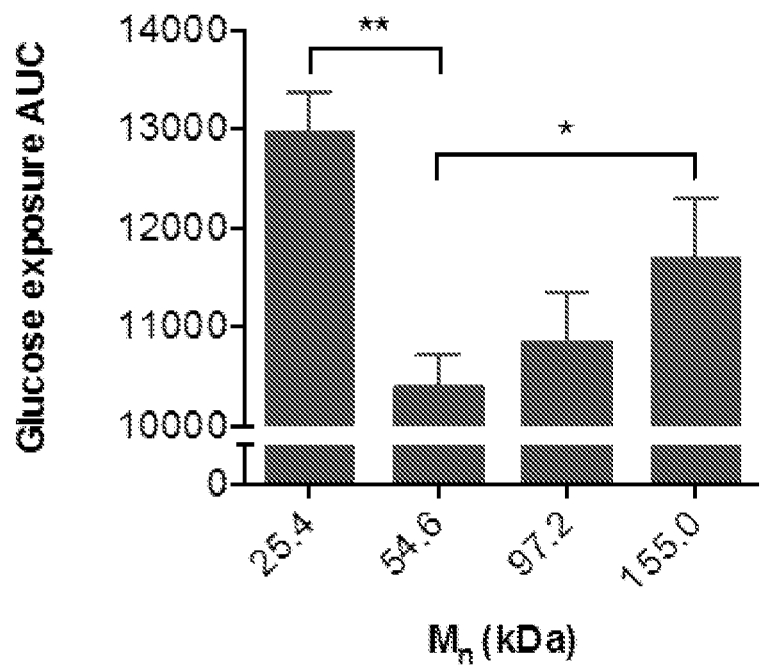

The in vitro cAMP results and the in vivo MW-dependent fed glucose measurements collectively show that an increase in MW of the conjugated polymer decreases the potency but increases the circulation duration of the EG9 exendin-POEGMA conjugate. Therefore, we hypothesize that there exists an optimal MW of the conjugate that best balances these two opposing effects. The area under the curve (AUC) of the fed glucose profiles with respect to 0% baseline signifies total glucose exposure, which accounts for both the magnitude and duration of glucose reduction and is therefore a manifestation of the combined effect of the two opposing factors. Plotting the AUC of fed glucose levels as a function of conjugate Mn indeed yielded a roughly inverted bell-shaped distribution with a minimum at 54.6 kDa (FIG. 3F). This suggests that the 54.6 kDa conjugate is the optimal among the tested EG9 conjugates in terms of balancing receptor activation potency and sustained duration of action. We thus investigated the 54.6 kDa EG9 conjugate further in subsequent experiments.

Figure 4C:
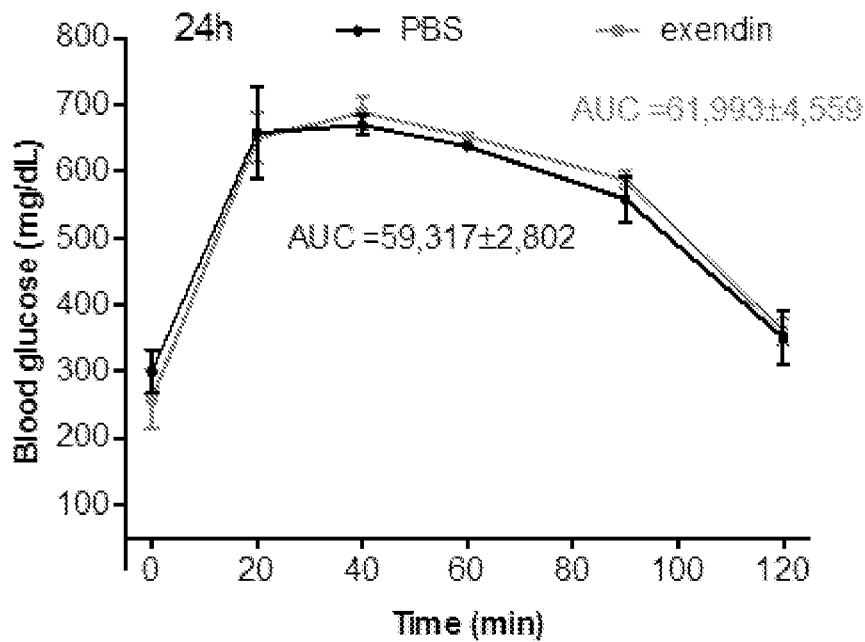
Figure 4D:
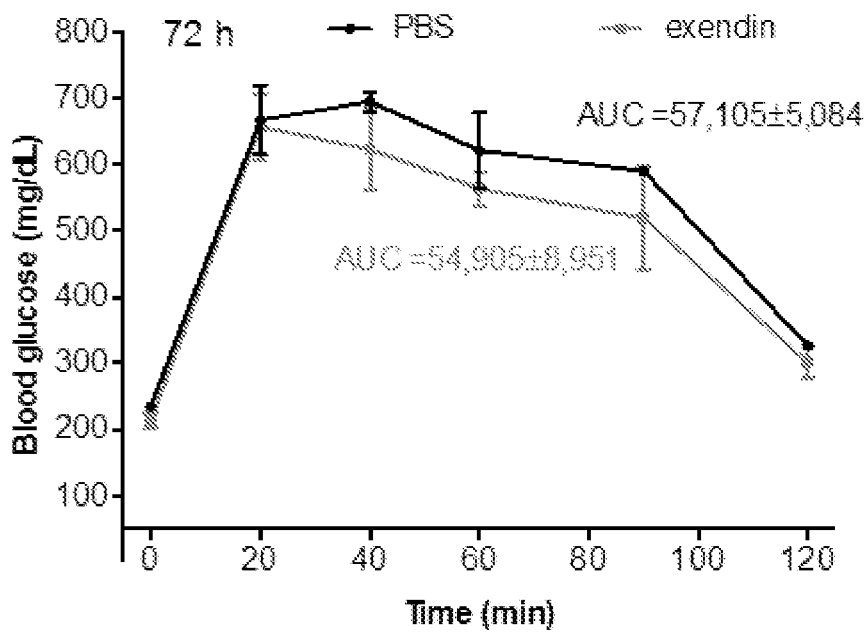

To validate the results from the fed glucose measurements and to obtain further evidence of the efficacy of EG9 exendin-C-POEGMA conjugates, an intraperitoneal glucose tolerance test (IPGTT) was performed 24 h and 72 h after a single s.c. injection of the 54.6 kDa EG9 conjugate or unmodified exendin at 25 nmol/kg. IPGTT confirmed the prolonged presence of the conjugate in circulation and its significant effect on glycemic control: at 24 h post-injection, the AUC of blood glucose level over 2 h after glucose challenge is reduced by 68% (P<0.0001, FIG. 4A), and at 72 h post-injection, the AUC is reduced by 48% for conjugate-treated mice compared with PBS controls (P<0.01, FIG. 4B). This is in stark contrast to the unmodified exendin group, which was insignificant at both time points (FIG. 4C and FIG. 4D).

Example 5

Antigenicity of EG9 Exendin-C-POEGMA Conjugates

We tested the reactivity of the 54.6 kDa EG9 exendin-C-POEGMA conjugate to anti-PEG antibodies in plasma samples of patients previously treated with PEGylated proteins using enzyme-linked immunosorbant assay (ELISA). In a direct ELISA, the 54.6 kDa EG9 exendin-C-POEGMA conjugate and various controls, including two FDA-approved drugs, Adagen®—a PEGylated adenosine deaminase for treating severe combined immunodeficiency disease (SCID) and Krystexxa®—a PEGylated uricase for treating chronic refractory gout, were directly coated on a plate and probed with diluent, an anti-PEG negative patient plasma sample or one of two anti-PEG positive patient plasma samples. As shown in FIG. 5A, while the EG9 exendin-C-POGEMA conjugate did show a small amount of binding to anti-PEG antibodies in the positive plasma samples, the extent of binding is significantly less than those of the two PEGylated positive controls. This result was confirmed by a competitive ELISA, where Krystexxa® was coated on wells, and different amounts of 54.6 kDa EG9 exendin-C-POEGMA and controls were added in solution to compete for binding to anti-PEG antibodies in an anti-PEG positive plasma sample. As can be seen in FIG. 5B, at all tested competing antigen amounts, 54.6 kDa EG9 exendin-C-POEGMA showed significantly reduced antibody binding compared to the positive control, Adagen®.

Example 6

Exendin-C-POEGMA with Shorter Side-Chain Length

Figure 8B:
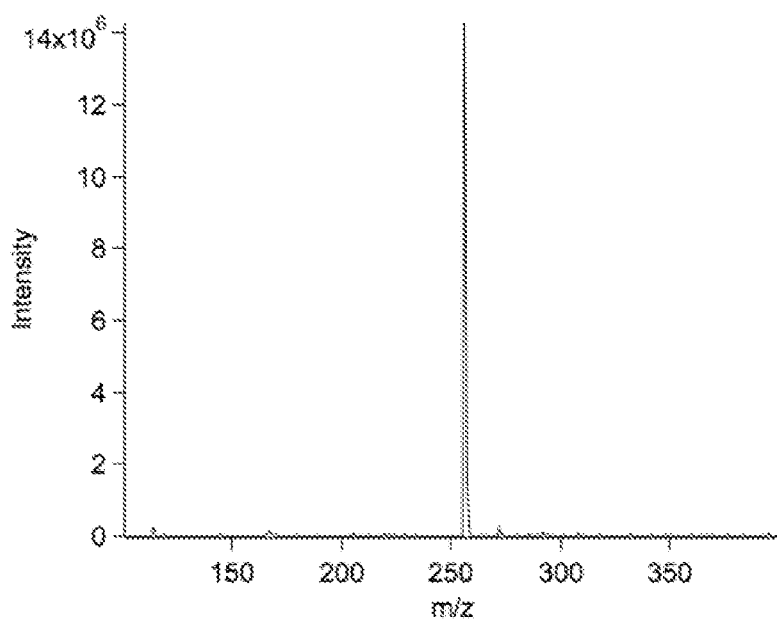
Figure 13:
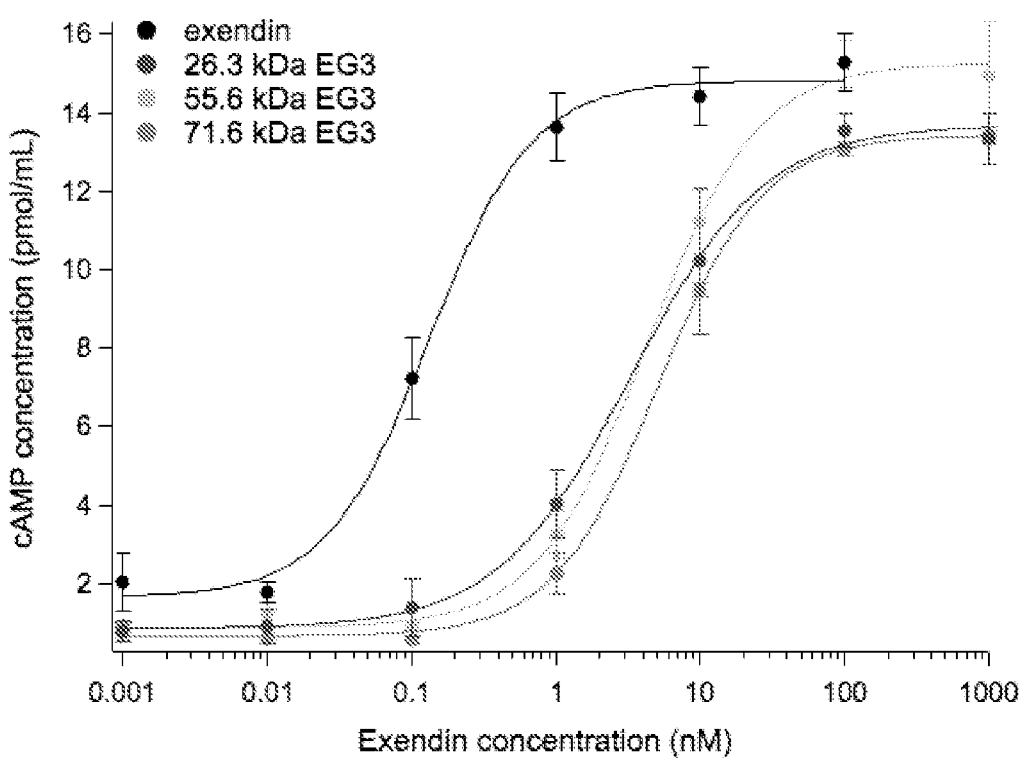
FIG. 13. Cyclic adenosine monophosphate (cAMP) response of native exendin and EG3 exendin-C-POEGMA conjugates with Mns of 26.3 kDa, 55.6 kDa and 71.6 kDa in baby hamster kidney (BHK) cells expressing the glucagon-like peptide-1 receptor (GLP-1R). Results are plotted as mean±SEM. Half-maximal effective concentration ($EC_{50}$) values are summarized in Table 3.
Figure 14A:
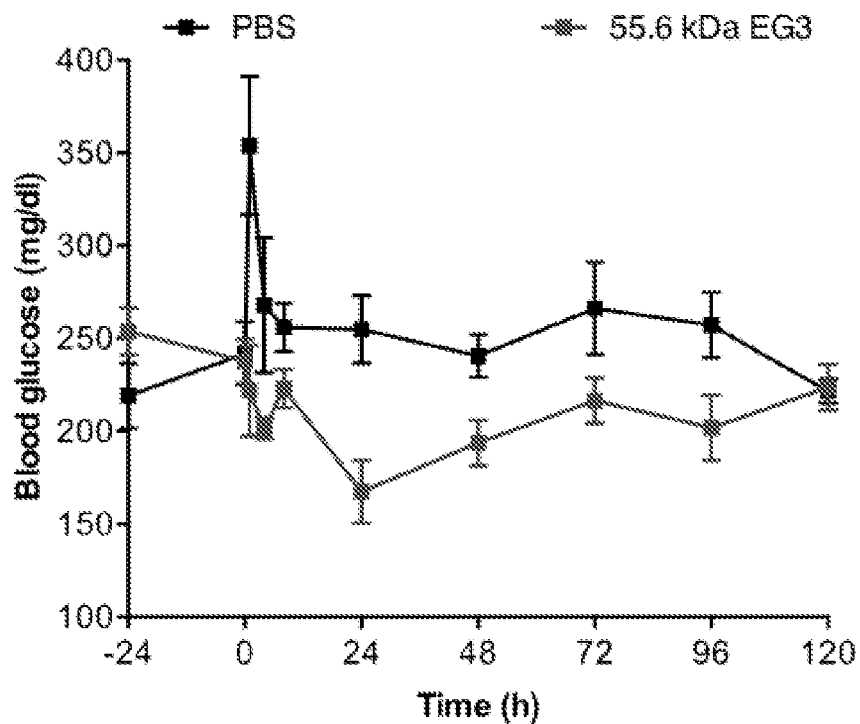
FIG. 14A-D. Assessment of in vivo efficacy of an EG3 exendin-C-POEGMA conjugate. Un-normalized blood glucose levels in fed mice (n=3) measured before and after receiving a single s.c. injection of 55.6 kDa (FIG. 14A) and 71.6 kDa (FIG. 14B) EG3 exendin-POEGMA conjugate at 25 nmol/kg compared to PBS control at equivalent volume administered at t=0 h. Weight profiles for c) 55.6 kDa (FIG. 14C) and 71.6 kDa (FIG. 14D) EG3 exendin-C-POEGMA and PBS control groups. Weights are reported as % change from 0 h time point. Results in all panels are plotted as mean±SEM.
Figure 14B:
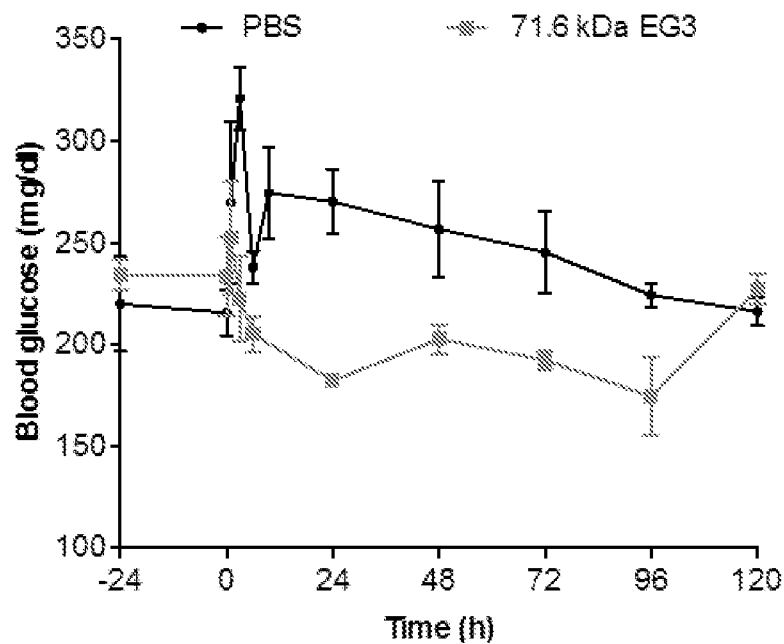
Figure 14C:
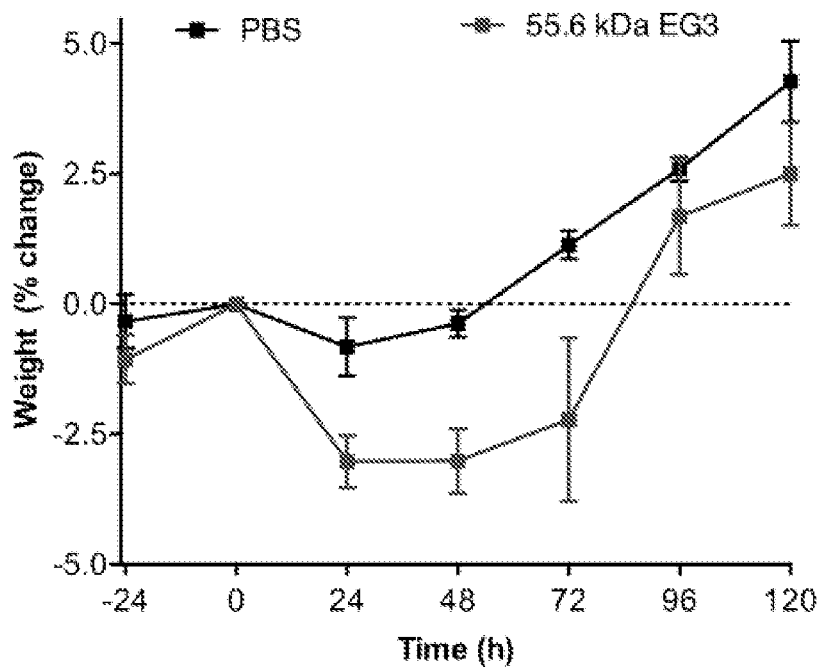
Figure 14D:
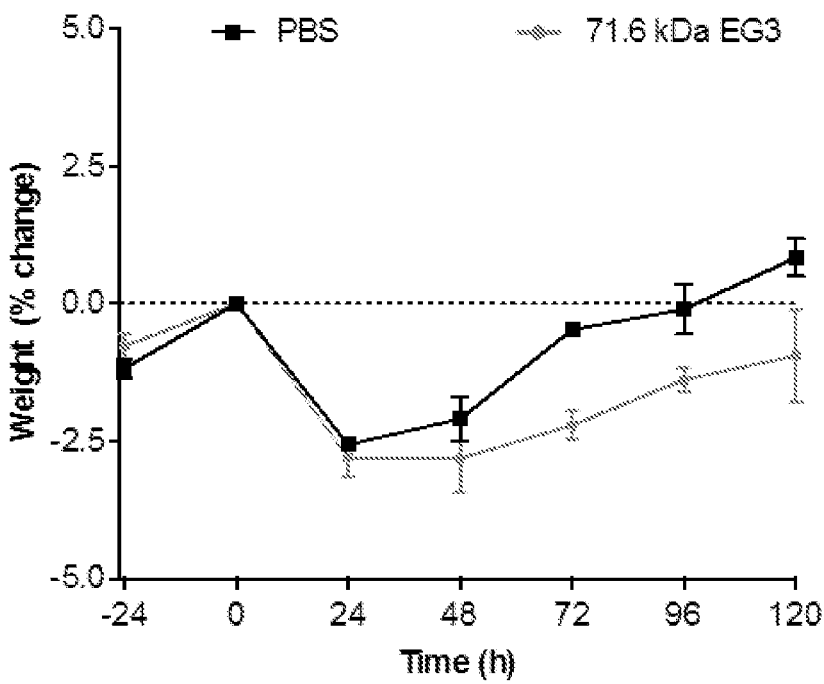
Figure 15:
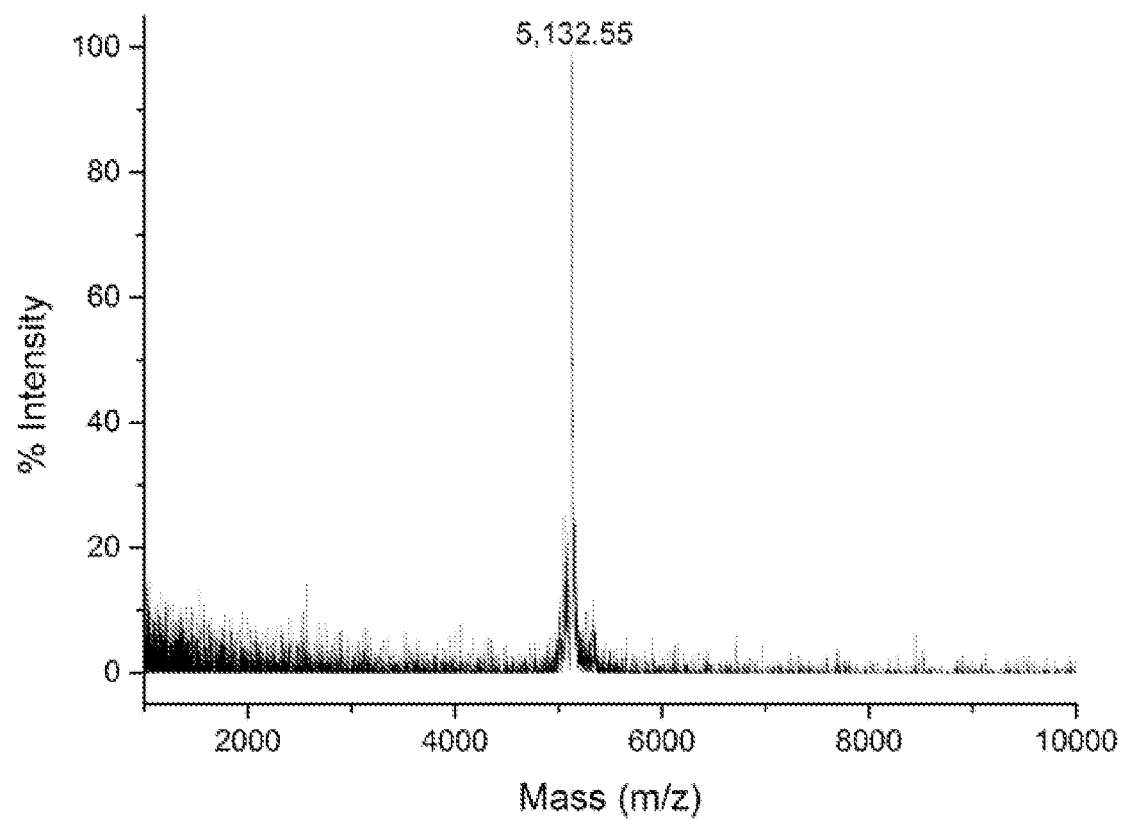
FIG. 15. MALDI-MS spectrum of exendin-C—Br macroinitiator. Major peak at 5,132.55 Da agrees well with theoretical mass of 5,131.44 Da corresponding to a single AEBMP initiator attached to exendin.

These results led us to hypothesize that the reduced PEG antigenicity of the EG9 exendin-C-POEGMA conjugate is due to both the branched architecture and the short sidechain length of the conjugated POEGMA. As a minimum length of PEG is presumably needed for antibody recognition and binding, we hypothesized that optimizing the side-chain OEG length may further reduce or possibly eliminate the antigenicity of POEGMA conjugates to anti-PEG antibodies. To test this hypothesis, we next synthesized exendin-C-POEGMA conjugates using OEGMA monomer with precisely 3 EG side-chain repeats as seen by LC/ESI-MS (FIG. 8B), as evidence in the literature suggests that the antigenic determinant of PEG may be ~6-7 EG repeats. Three different EG3 exendin-C-POEGMA conjugates with Mns of 26.3, 55.6, and 71.6 kDa (Table 3) were synthesized. Assessment of conjugate potency by intracellular cAMP ELISA (FIG. 13) showed that similar to the EG9 conjugates, conjugation of EG3 POEGMA to the C-terminus of exendin caused an increase in the $EC_{50}$ (Table 3), indicating a decrease in the receptor activation of the conjugates, though with a less pronounced MW-dependence.

Example 7

Antigenicity and Efficacy of EG3 Exendin-C-POEGMA Conjugates

Figure 16A:
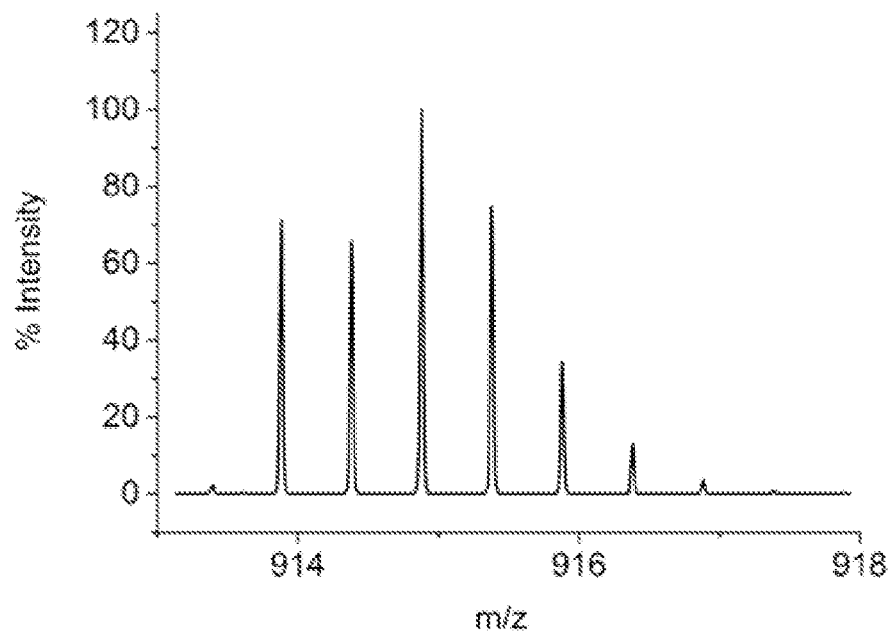
FIG. 16A-B. LC/MS-MS analysis of exendin-C—Br.
Figure 16B:
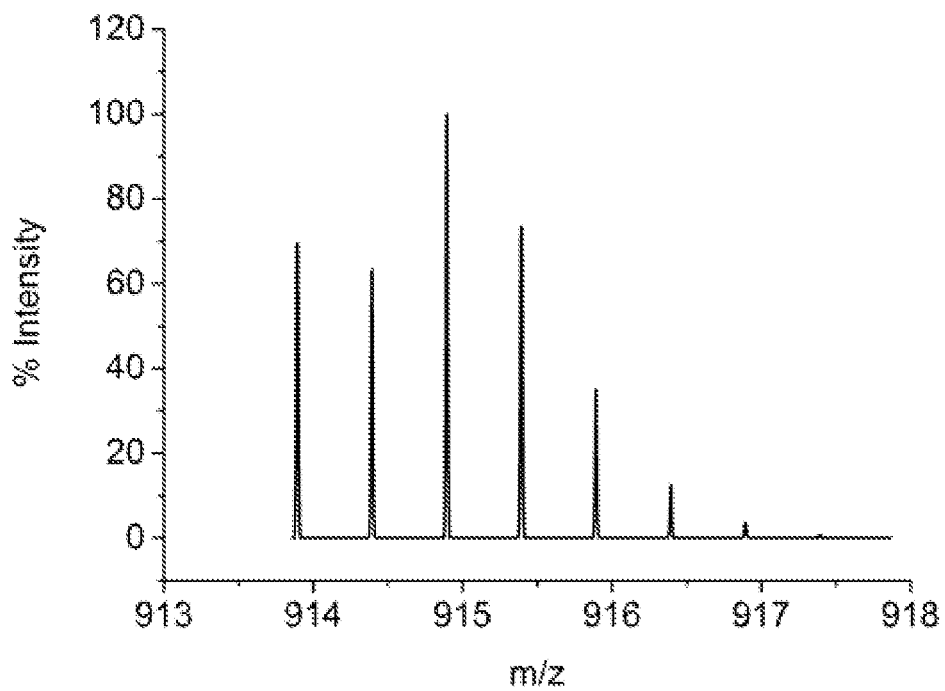

We next tested the reactivity of a 55.6 kDa EG3 exendin-C-POEGMA conjugate to anti-PEG antibodies in patient plasma samples. The 54.6 kDa EG9 conjugate was included as a control to confirm the repeatability of the assays. Remarkably, both direct and competitive anti-PEG ELISAs (FIG. 5C and FIG. 5D) showed that reducing the side-chain length of the conjugated POEGMA down to 3 EG repeats completely eliminated the reactivity of the conjugate toward anti-PEG antibodies present in the patient plasma samples.

As the OEG side-chains on POEGMA are largely responsible for the "stealth" behavior of the polymer and its conjugates, alteration on the side-chain length can thus have an impact on the in vivo behavior of POEGMA conjugates. Therefore, we next investigated the in vivo efficacy of EG3 exendin-C-POEGMA. The 55.6 kDa and 71.6 kDa EG3 exendin-C-POEGMA conjugates were administered into fed mice via a single s.c. injection at 25 nmol/kg mouse body weight. As can be seen from the post-injection glucose profiles in FIG. 6A and FIG. 6B (unnormalized glucose profiles and weight profiles in FIG. 14), both conjugates significantly reduced mouse blood glucose for up to 96 h compared to PBS control. The EG3 conjugates appear to have slightly lower magnitudes of glucose reduction and more flat glucose profiles compared to their EG9 counterparts.

Example 8

Pharmacokinetics of Exendin-C-POEGMA Conjugates

To further confirm the prolonged circulation of exendin-C-POEGMA conjugates and to seek some answers to the difference between the glucose profiles of EG9 and EG3 conjugates, a pharmacokinetics study was performed with fluorescently labeled exendin, the 54.6 kDa EG9, 55.6 kDa EG3 and 71.6 kDa EG3 conjugates. Two MWs of the EG3 conjugate were tested, as the EG3 and EG9 conjugates have different Rhs at the same MW. The MWs were chosen such that the 54.6 kDa EG9 conjugate (Rh=5.4±0.6 nm) has similar MW as the 55.6 kDa EG3 conjugate and similar Rh as the 71.6 kDa EG3 conjugate (Rh=5.6±0.5 nm). The plasma concentration-time courses (FIG. 6C and FIG. 6D) were analyzed using a non-compartmental fit characterizing the absorption and elimination phases of the pharmacokinetic profiles, to approximate the parameters shown in Table 6.

TABLE 6

Pharmacokinetic parameters of exendin and exendin-C-POEGMA conjugates injected s.c. derived from data analyzed with a non-compartmental fit in FIG. 6C and FIG. 6D.

| | $T_{1/2}$ a (h) | $t_{1/2}$ el (h) | $C_{ma}x$ (nM)[a] | $t_{max}$ (nM)[a] | AUC (h*nM)[b] |
|---|---|---|---|---|---|
| Exendin | 0.7 ± 0.1 | 1.7 ± 0.2 | 37.1 ± 3.8 | 1.78 ± 0.1 | 217.5 ± 36.5 |
| 54.6 kDa EG9 | 6.2 ± 0.5 | 42.4 ± 2.9 | 56.4 ± 3.9 | 20.1 ± 0.4 | 4,795.5 ± 440.7 |
| 55.6 kDa EG3 | 7.6 ± 0.7 | 61.2 ± 5.0 | 44.0 ± 2.7 | 28.5 ± 2.3 | 4,775.0 ± 482.9 |
| 71.6 kDa EG3 | 9.0 ± 1.7 | 61.5 ± 3.2 | 37.7 ± 5.0 | 32.4 ± 3.9 | 4,411.2 ± 499.6 |

Values are reported as mean ± SEM. $T_{1/2}$ a: absorption half-life, $t_{1/2}$ el: elimination half-life, $C_{max}$: maximum plasma concentration, $t_{max}$: time to attain $C_{max}$.
[a]Derived from curve fitting.
[b]Calculated from t = 0 to ∞ from curve fitting.

After s.c. injection, unmodified exendin had a very short residence time in circulation, with a rapid absorption phase ($t_{1/2}$a=0.7±0.1 h) and a short terminal elimination phase ($t_{1/2}$ el=1.7±0.2 h). In contrast, the exendin-C-POEGMA conjugates tested increased the absorption time by ~9 to 13-fold, with the two EG3 conjugates taking longer than the EG9 conjugate to absorb into circulation. Similarly, the 54.6 kDa EG9 conjugate prolonged the elimination phase of exendin by ~25-fold, while the two EG3 conjugates afforded a bigger increase of ~36-fold. These differences in the pharmacokinetics resulted in ~20-fold increase in AUC for the conjugates compared to unmodified exendin, indicating that conjugation of POEGMA to the C-terminus of exendin significantly enhanced the cumulative exposure of the peptide in circulation. While the Cmax of the two EG3 conjugates were considerably lower than that of the EG9 conjugate, consistent with the lower magnitude of glucose reduction seen for the EG3 conjugates in the fed blood glucose studies (FIG. 6*a* and FIG. 6*b*), the AUC of the three tested conjugates were comparable given the longer absorption and elimination half-lives of the EG3 conjugates.

Example 9

Macroinitiator Characterization

The purified exendin-C—Br macroinitiator was characterized by matrix assisted laser desorption ionization-mass spectrometry (MALDI-MS) to confirm initiator attachment (FIG. 15). A major peak was detected at 5,132.55 Da, which closely agrees with the theoretical mass of 5,131.44 Da corresponding to a single N-(2-(2-(2-(2-aminoacetamido) acet-amido)acetamido) ethyl)-2-bromo-2-methylpropanamide (AEBMP) initiator molecule attached to exendin. To verify the site-specificity of initiator attachment, exendin-C—Br was subjected to trypsin digestion and the peptide fragments were analyzed by liquid chromatography/tandem mass spectrometry (LC-MS/MS). Only the C-terminal peptide fragment was detected as a singly brominated cation and its experimental isotope distribution (FIG. 16A) showed nearly perfect overlap with its theoretical distribution (FIG. 16B), proving that a single initiator molecule was attached exclusively to the C-terminus of exendin.

Example 10

Characterization of EG3 Exendin-C-POEGMA Conjugates

Figure 17A:
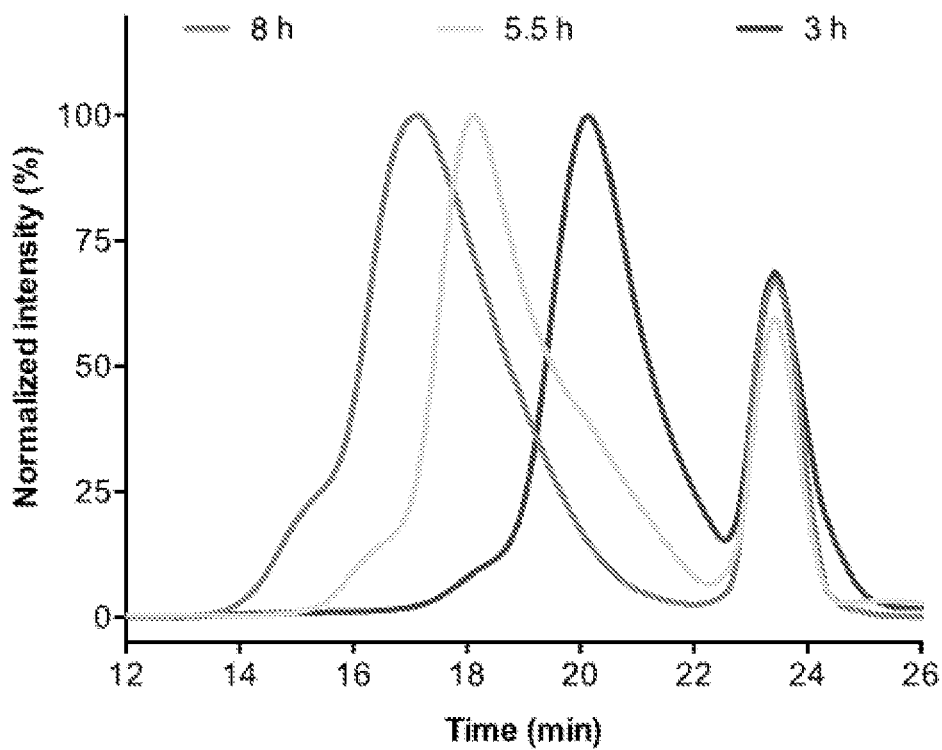
FIG. 17A-C. Physical characterization of EG3 exendin-C-POEGMA conjugates. SEC traces of EG3 exendin-C-POEGMA conjugates synthesized by in situ ATRP carried out for 2.5 h, 5.5 h, and 8 h, detected by UV-vis absorbance at 280 nm (FIG. 17A) and RI (FIG. 17B). The signal from the residual exendin-C—Br was too low to be observed by RI detection due to its small size and low concentration.
Figure 17B:
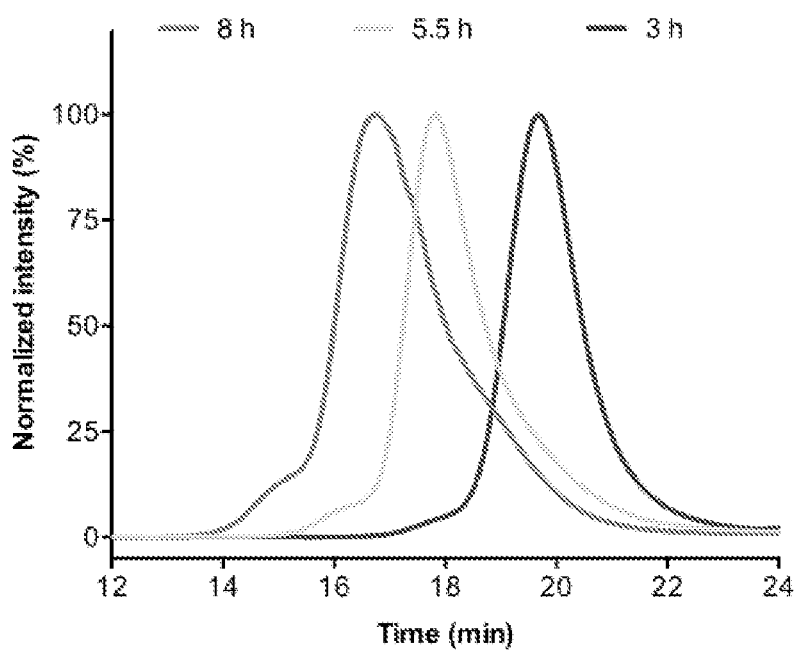
Figure 17C:
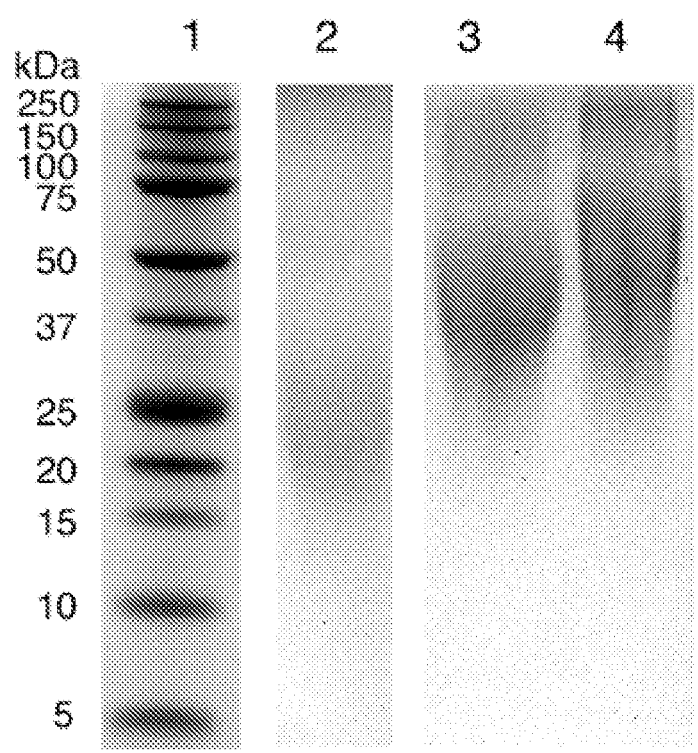

Three EG3 exendin-C-POEGMA conjugates of different molecular weights (MWs) were synthesized by varying Atom Transfer Radical Polymerization (ATRP) reaction times. The different MWs of the conjugates are evident from the Size Exclusion Chromatography (SEC) peaks eluting at 17.2, 18.2 and 20.3 min, detected by UV-vis absorbance at 280 nm (FIG. 17A) and refractive index (RI, FIG. 17B). Integration of peak areas in the UV-vis chromatograms showed that the conjugates constituted ~65% of the polymerization products on average. The relatively lower conjugation efficiency of the EG3 conjugates compared to their EG9 counterparts is speculated to be due to the considerably lower water solubility of the EG3 OEGMA monomer, though such a yield is still well above the yield that is typically achieved with conventional PEGylation. The conjugates were purified by a single round of preparative SEC (FIG. 17C).

Example 11

General Methods

Surface-Initiated Atom Transfer Radical Polymerization

Surface functionalization with APTES and installation of bromide initiator: Unless otherwise stated, steps were performed under ambient conditions. Glass slides (Nexterion Glass B, Schott AG, Mainz, Germany) were immersed in a 10% solution of 3-aminopropyltriethoxysilane (APTES) (Gelest, Inc.; Morrisville, Pa.) in ethanol overnight, and subsequently rinsed with fresh ethanol and then with deionized water. Chips were spun dry at 150 rcf for 5 minutes and then cured in an oven at 110° C. for 2 h. Next, the chips were cooled to room temperature then placed in a dichloromethane solution containing 1% α-bromoisobutyryl bromide (BIB) and 1% triethylamine (TEA) (Sigma Aldrich; St. Louis, Mo.) for 45 min, followed by rinsing in fresh dichloromethane, then ethanol, and then in deionized water. The chips were spun dry 150 rcf for 5 minutes and then stored under ambient conditions.

Preparation of Polymerization Solutions

Degassed polymerization solutions were prepared as described Table 7 and then transferred into an inert (Ar environment) glovebox.

TABLE 7

Si-ATRP Polymerization Conditions for Solution-based Synthesis of POEGMA Bottlebrush Surfaces on Glass

| Monomer | Sigma-Aldrich Cat. No. | Polymerization Solution | Polymerization Conditions |
|---|---|---|---|
| EG1-OMe | 415332 | 50 mL monomer, 300 mL methanol, 100 mL ddH$_2$O, 347 µL HMTETA, 100 mg Cu(II)Br | 1000 mg sodium ascorbate, 46 min |
| EG3-OMe | 447927 | 50 mL monomer, 300 mL methanol, 100 mL ddH$_2$O, 347 µL HMTETA, 100 mg Cu(II)Br | 1000 mg sodium ascorbate, 2 h |
| EG3-OMe | 729841 | 50 mL monomer, 300 mL methanol, 100 mL ddH$_2$O, 347 µL HMTETA, 100 mg Cu(II)Br | 1000 mg sodium ascorbate, 2 h |
| EG5-OMe | 447935 | 75 mL monomer, 350 mL ddH$_2$O, 50 µL HMTETA, 25 mg Cu(II)Br | 800 mg sodium ascorbate, 3 hr |
| EG9-OMe | 447643 | 50 mL monomer, 350 mL ddH$_2$O, 50 µL HMTETA, 25 mg Cu(II)Br | 800 mg sodium ascorbate, 3 hr |
| EG6-OH | 409537 | 75 mL monomer, 350 mL ddH$_2$O, 50 µL HMTETA, 25 mg Cu(II)Br | 800 mg sodium ascorbate, 3.5 hr |

HMTETA: 1,1,4,7,10,10-hexamethyltriethylenetetramine

Surface-initiated atom-transfer radical polymerization was conducted by adding sodium ascorbate (Sigma Aldrich; St. Louis, Mo.) to the polymerization solution described in Table 7 in an Ar environment and gently stirred for 1 min (specific amounts of sodium ascorbate for each monomer is listed in Table 7), at which point the solution changed color from blue to violet. Initiator-functionalized glass slides were then placed in this solution for polymerization (without stirring). After allowing polymerization to proceed for the desired time points (Table 7), the slides were rinsed three times with deionized water, then centrifuged at 150 rcf for 6 minutes and allowed to dry under ambient conditions. The thickness of polymer brushes was determined by reflective-mode ellipsometry, as described below.

Reflective Mode Ellipsometry

The thickness of thin films was measured using an M-88 spectroscopic ellipsometer (J.A. Woollam Co) at angles of 65, 70, and 75 degrees at wavelengths of 400 to 800 nm. Polymer film thicknesses were then determined using a Cauchy layer algorithm. For all ellipsometric measurements, the thickness is the mean standard error between the predicted response from the model and the experimental response from the sample reached a global minimum. Only those data that yielded good fitting results (mean square error s 0.9) were used to determine film thicknesses.

X-Ray Photoelectron Spectroscopy

All XPS experiments were performed on an AXIS Ultra photoelectron spectrometer (Kratos Analytical, NY) operating at 15 kV and 10 mA using monochromatic Kα1 X-rays. The X-ray spot size was 400 µm (full-width at half maximum). Survey scans and high-resolution core-level spectra were recorded with the following pass energy, energy step, dwell time, and number of sweeps: survey spectra—160 eV, 1 eV, 200 msec, and 10 sweeps; high-resolution core-level spectra—20 eV, 0.1 eV, 269.7 msec, and 20 sweeps. The operating pressure of the instrument was ~$1\times10^{-8}$ torr. The spectral data were analyzed using CasaXPS software.

Surface Fluoroimmunoassays for Anti-PEG Reactivity in Simulated Samples

The commercial APAs used in these studies were the following: pAPA1—polyclonal rabbit-anti-PEG Abs (ThermoFisher PA5-32247); pAPA2—polyclonal rabbit-anti-PEG (Life Diagnostics PEGPAB-O1); e-mAPA—monoclonal mouse anti-PEG IgG Ab (Life Diagnostics 5D6-3); b-mAPA—monoclonal mouse anti-PEG IgG Ab (Life Diagnostics 1D9-6); and a monoclonal rabbit-anti-PEG IgM Ab (abcam AB133471). Surfaces were first exposed to a 2 µg/mL solution of APA-spiked calf serum and incubated for 1 h, and then washed 3 times with wash buffer (0.5% CHAPS in PBS). Next, the surfaces were exposed to a 2 µg/mL solution of Cy5 labeled dAb in PBS for 30 mins (donkey-anti-rabbit dAb or goat-anti-mouse dAb, R & D Systems, Inc.). Surfaces were then rinsed again to remove any loosely-bound proteins with 0.1% CHAPS in PBS, centrifuged at 4800 rpm for 15 s to wick away excess liquid, then allowed to dry under ambient conditions. Fluorescence imaging of all samples was performed using an Axon Genepix 4400 tabletop scanner (Molecular Devices, LLC; Sunnyvale, Calif.) under identical imaging conditions with an exciting wavelength of 635 nm; fluorescence intensity analysis was performed using ImageJ Fiji.

Surface Adsorption of Proteins

Surfaces were exposed to a 1 mg/mL solution of Cy5-BSA (ThermoFisher) in 1×PBS buffer (phosphate buffered saline: 137 mM NaCl, 2.7 mM KCl, 10 mM dibasic sodium phosphate; 1.8 mM monobasic potassium phosphate, pH 7.4) for 2 hours. Substrates were then rinsed with a PBS solution containing 0.1% Tween20 to remove any loosely-bound proteins, centrifuged at 4800 rpm for 15 seconds to wick away excess liquid, then allowed to dry under ambient conditions. Fluorescence imaging and analysis of all samples was performed using an Axon Genepix 4400 tabletop scanner and ImageJ Fiji as described above.

Surface Binding of Cells

NIH 3T3 cells stably expressing GFP (3T3-GFP) were acquired from Cell BioLabs Inc. (AKR-214). Cells were cultured in Dulbecco's Modified Eagle Medium (DMEM) supplemented with 10% fetal bovine serum and kept in a tissue culture incubator at 37° C. and 5% $CO_2$. Cells were harvested by trypsinization, counted, and then $3\times10^6$ cells were re-seeded onto the polymer brush-coated slides placed in quadriPERM® slide cell culture chambers (Sarstedt AG & Co). After a 24-hour incubation period, the surfaces were gently rinsed 3 times and placed in culture dishes containing fresh growth medium. Epifluorescence imaging under the GFP channel was performed using a Nikon TE2000 inverted microscope. Images were analyzed with ImageJ Fiji via intensity thresholding to calculate the percentage of pixels in the field of view showing positive signal in the GFP channel (% FOV) as a metric for surface coverage by 3T3-GFP cells.

Microarray-Based Indirect Sandwich Immunoassays (ISIAs) Against Anti-HIV p24 Abs on POEGMA Anti-APA ISIA Microarrays of PEGylated BSA (Life Diagnostics PBSA-00) were prepared by printing onto surfaces with a noncontact microarray printer (Scienion sciFIEXARRAYER S11) at a concentration of 1 mg/mL as microspots and then placed in a vacuum dessicator overnight. Next, these assays were run against serial dilutions of pAPA1 (ThermoFisher PA5-32247) spiked into calf serum and incubated for 1 h. The surfaces were then washed 3 times and then exposed to a 1 µg/mL solution of Cy5-donkey-anti-rabbit antibody (R&D Systems) for 30 min. Surfaces were then rinsed again to remove any unbound proteins, centrifuged at 4800 rpm for 15 s to wick away excess liquid, then allowed to dry under ambient conditions. Fluorescence imaging of all samples was performed using an Axon Genepix 4400 tabletop scanner as described above.

Anti-HIV p24 ISIA

Recombinant HIV p24 Ag (Advanced Biotechnologies Inc. #14-101-050) was printed onto surfaces with a noncontact microarray printer as described above. Next, serial dilutions of rabbit-anti-p24 Abs (Sigma Aldrich SAB3500946) spiked into calf serum were applied to printed microarrays and incubated for 1 h. Simultaneously, a similar set of dilution series was run in parallel, except here the samples also contained 100 ng/mL of rabbit-derived pAPA1 (ThermoFisher PA5-32247) acting as an interferent. Samples were subsequently processed and imaged as described above.

Assessment of Anti-PEG Reactivity in Patient Samples

The patients from whom these samples were obtained were in a clinical trial conducted under Duke University IRB Protocol #577-04-4. Informed signed consent was obtained from either the patient or from next of kin. (A) ELISA detection of APAs: Plasma samples diluted 1:21 in 1% BSA in PBS were tested by ELISA for IgG Ab to PEG, but using Adagen® (Sigma Tau Pharmaceuticals, Gaithersburg, Md.) rather than Krystexxa® as the antigen. (B) Surface fluoroimmunoassay against patient APAs: Polymer-coated surfaces were incubated with patient plasma samples diluted 1:3 in PBS for 1 h, and then washed 3 times with wash buffer (0.5% CHAPS in PBS). Next, the surfaces were exposed to a 1 µg/mL solution of Cy5-goat-anti-human IgG detection Ab (R & D Systems, Inc.) for 30 min. Surfaces were then rinsed again to remove any loosely-bound proteins, centrifuged at 4800 rpm for 15 s to wick away excess liquid, then allowed to dry under ambient conditions. Fluorescence imaging and analysis of all samples was performed using an Axon Genepix 4400 tabletop scanner and ImageJ Fiji as described above.

Surface Fluoroimmunoassay Against Patient APAs

Polymer-coated surfaces were incubated with patient plasma samples diluted 1:3 in PBS for 1 hour, and then washed 3 times with wash buffer (0.5% CHAPS in PBS). Next, the surfaces were exposed to a 1 µg/mL solution of Cy5-goat-anti-human IgG detection Ab (R & D Systems, Inc.) for 30 minutes. Surfaces were then rinsed again to remove any loosely-bound proteins, centrifuged at 4800 rpm for 15 seconds to wick away excess liquid, then allowed to dry under ambient conditions. Fluorescence imaging and analysis of all samples was performed using an Axon Genepix 4400 tabletop scanner and ImageJ Fiji as described above.

Statistical Analysis.

Statistical analyses were performed by GraphPad Prism 6 (San Diego, Calif.). Results are plotted as mean±95% CI (FIG. 18D, 20C, 22C, 22F, 24B) or as mean±s.d. (FIGS. 21, 23C, 23E, 23G, 24A, 25, 26C-26F, and 28). Sample sizes are included in figure captions. Differences between groups were analyzed by one-way or two-way ANOVA analysis (as

Example 12

Growth and characterization of POEGMA brushes with varying sidechain lengths. The strategy to coat planar surfaces with POEGMA bottlebrushes by SI-ATRP is illustrated in FIG. 18A. Glass surfaces were first functionalized with a brominated ATRP initiator, followed by SI-ATRP of PEG methacrylate monomers via activators regenerated by electron transfer (ARGET) to achieve the desired polymer surface coatings. This synthesis strategy has been previously shown to result in uniform POEGMA coatings with controllable film thicknesses under relatively mild experimental conditions. To systematically tune the sidechain length of POEGMA bottlebrushes, surface polymerizations were carried out using different commercially-available PEG methacrylate monomers with varying number of EG repeat units. The characteristics of each monomer are shown in Table 1 and in FIG. 18B, which on average ranged from 1 to 9 EG repeats. The specific SI-ATRP reaction conditions used to synthesize each of these polymer brush surfaces can be found in Table 7. Each was terminated by methoxy (—OMe) endgroups, except the ~360 Da monomer which had a hydroxy (—OH) endgroup. Each surface will be referenced herein by both their average EG repeat lengths and endgroup (i.e., EG2-OMe indicates di(ethylene glycol) methyl ether methacrylate).

Figure 18C:
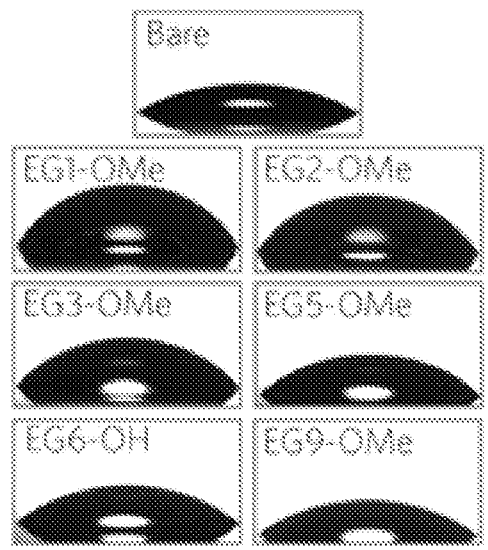
Figure 18D:
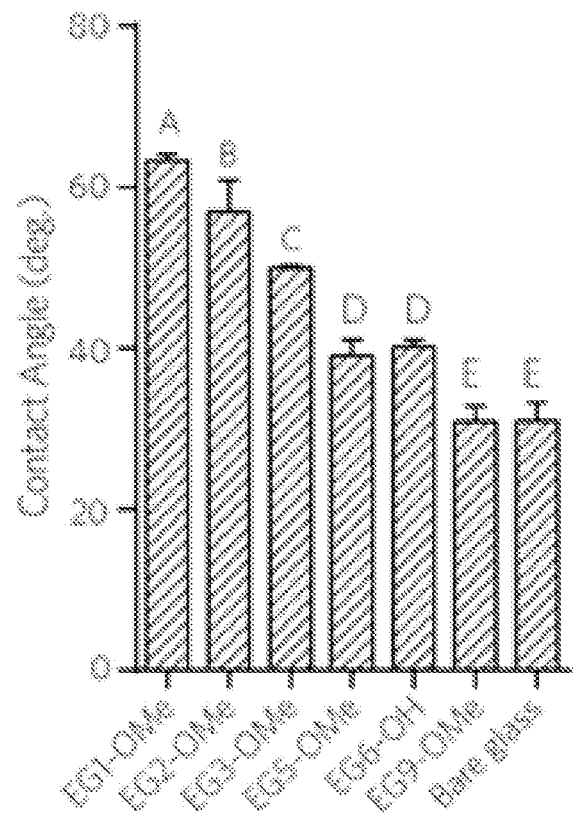
Figure 19A:
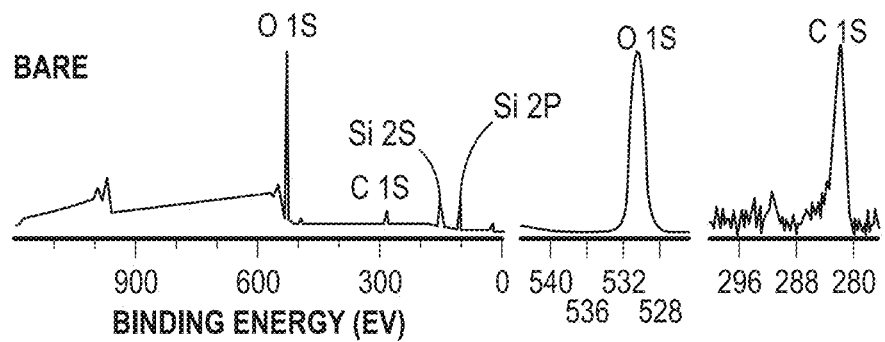
Figure 19B:
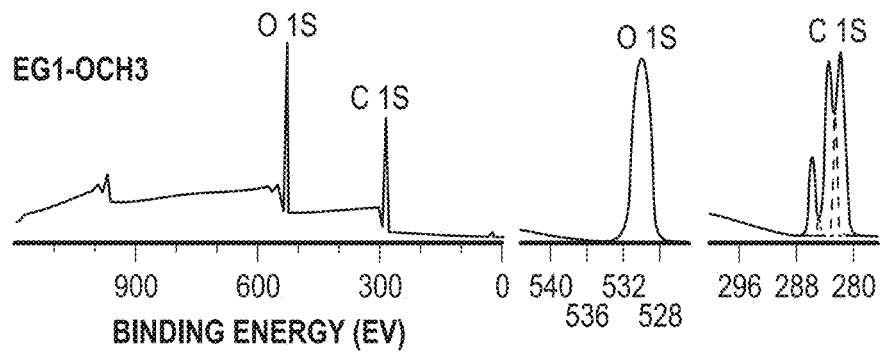
Figure 19C:
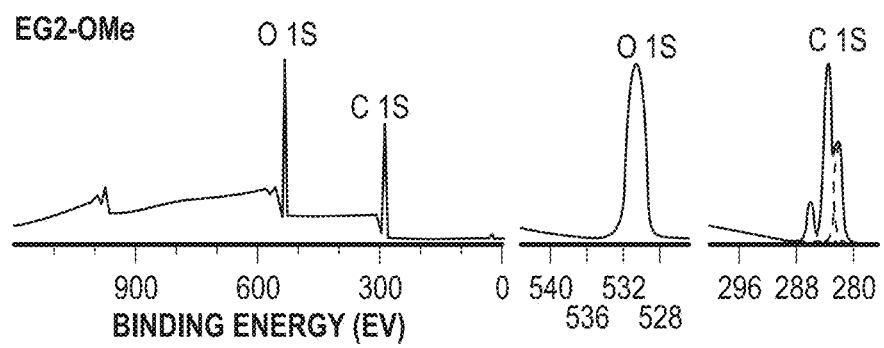
Figure 19D:
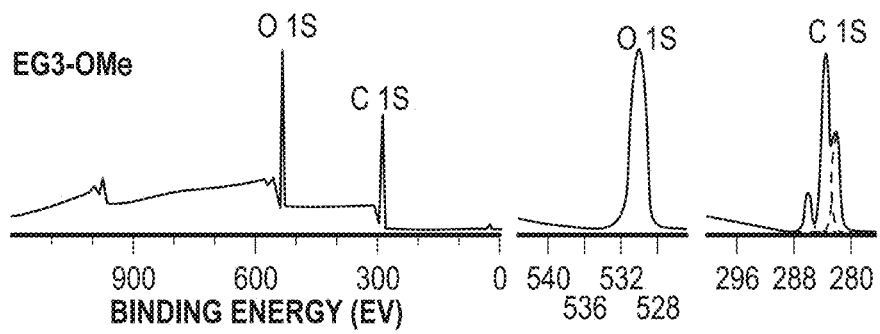
Figure 19E:
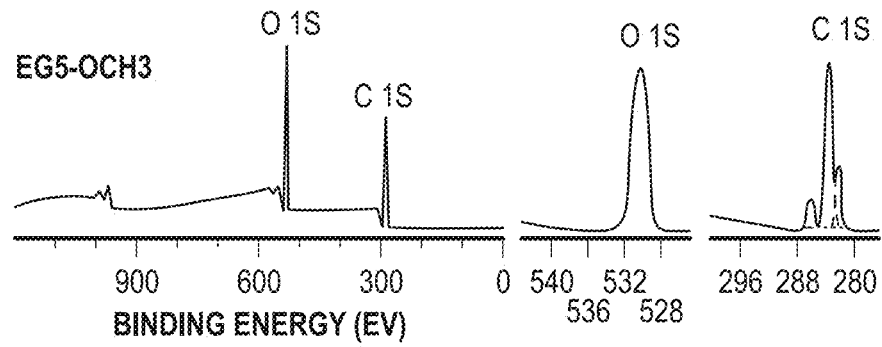
Figure 19F:
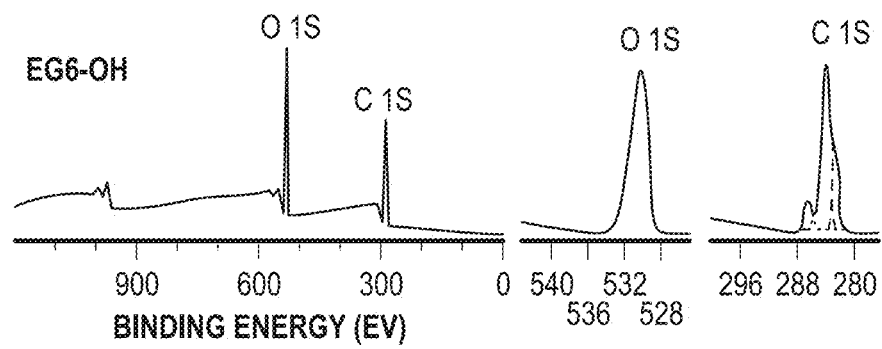
Figure 19G:
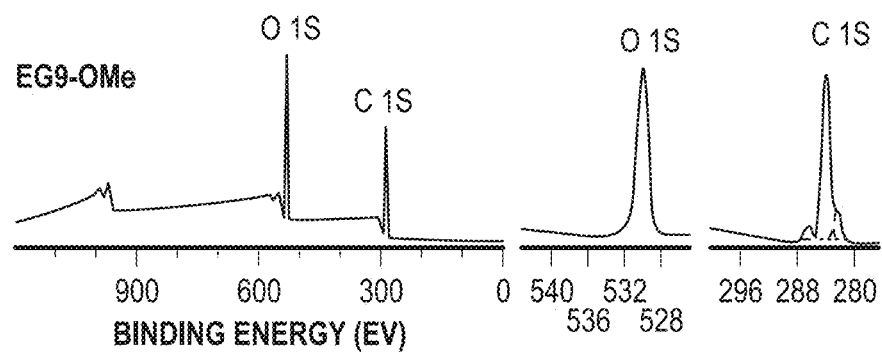

Following growth of the polymer overlayers by SI-ATRP, characterization of the POEGMA bottlebrushes was performed in three ways. First, the thicknesses of the POEGMA overlayers were investigated by reflective mode spectroscopic ellipsometry. Polymer coatings with film thicknesses greater than ~9.5 nm, were examined because this was thought to be the minimum thickness required to achieve ample surface coverage and consistent nonfouling behavior. As indicated in FIG. 18C, the experimental thicknesses were consistently ~25 nm or greater, and thus well above this minimum reported value. Second, the wettability of each surface was assessed by contact angle goniometry (FIG. 18D). There was a statistically significant difference between groups, as determined by one-way ANOVA ($F_{(6, 37)}=136.0$, $p<0.0001$). Bars marked with a different letter indicates significant differences (Tukey post hoc test, p s 0.05). A progressive increase in wettability of each polymer surface (evidenced by decreasing contact angles) was observed with increasing number of EG repeats. This result is consistent with the expectation that monomers with longer EG repeats would present greater densities of oligo(ethylene glycol) functional groups at the solid/water interface.

Third, the molecular composition of the films was investigated by X-ray photoelectron spectroscopy (XPS) (FIG. 19). In all cases, the survey spectra of the polymer-coated samples demonstrated the absence of Si peaks (from the underlying glass) after polymerization (FIG. 19A). This observation is consistent with film thicknesses being greater than the sampling depth of the XPS—typically up to ~10 nm for Al Kα radiation—resulting in the vast majority of detected photoelectrons originating from polymer overlayers (instead of underlying $SiO_2$). The observed carbon and oxygen atomic concentrations obtained from survey spectra for each POEGMA surface agreed with those expected from their stoichiometry (FIG. 19B). Furthermore, analysis of the high-resolution O1s and C1s photoemission spectra in FIG. 19B indicated the presence of a sole oxygen species singly-bonded to an aliphatic carbon (532.8 eV), and three distinct carbon moieties: CHx (284.5 eV), COR (286.7 eV), COOR (289.1 eV). Deconvolution of the C1s envelopes to each of these carbon species also showed agreement between experimental and predicted values (FIG. 19H).

Combined, these experiments confirmed that the fabrication methods produced POEGMA coatings with adequate thicknesses, tunable responses to surface hydration, and appropriate chemical compositions. The next series of experiments focused on screening and downselecting POEGMA surfaces in favor of those that minimize both (1) reactivity to APAs and (2) nonspecific binding of proteins and cells.

Preliminary screening reveals EG2-OMe and EG3-OMe bottlebrushes as those most favorable for minimizing both APA reactivity and biofouling. The reactivity of the polymer coatings toward a rabbit-derived polyclonal APA ("pAPA1") was examined using a surface fluoroimmunoassay approach as shown in FIG. 20A.

Each polymer coating was first incubated with 2 µg/mL pAPA1 spiked into calf serum (to simulate circulating APAs), which was applied directly to the surface, and then rinsed with a standard PEG-free wash buffer (0.5% 3-[(3-Cholamidopropyl)-dimethylammonio]-1-propane sulfonate (CHAPS) detergent in phosphate-buffered saline (PBS)) to remove loosely bound pAPA1. Surfaces were then labeled with a Cy-5-anti(α)-rabbit detection Ab (dAb), and fluorescence intensities were quantified by a tabletop fluorescence scanner to quantify the Cy5 signal from the surface-bound dAb, whose intensities are expected to scale with the surface concentration of APA bound to the polymer surface (FIG. S2). Vehicle controls (serum only) established baseline fluorescence values, and negative controls comprised of control rabbit IgG in serum (in lieu of rabbit-derived pAPA1) showed that adventitious binding of rabbit IgG did not noticeably contribute to nonspecific background noise under these experimental conditions (top row, FIG. 30B and FIG. 30C). This was true even for bare glass; detergent-containing PBS wash buffer was able to remove loosely bound rabbit IgG from the surface (but PBS alone was not, FIG. 24A).

Figure 20C:
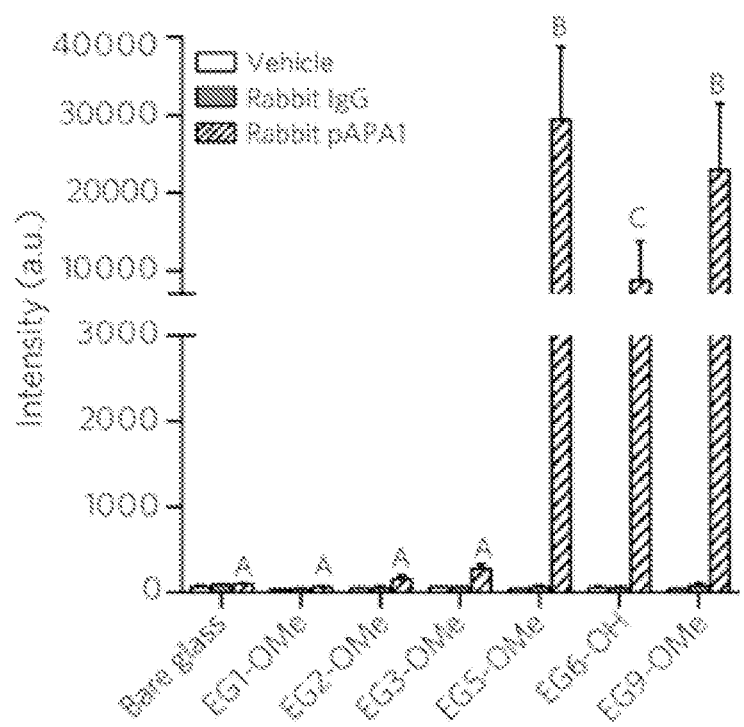
Figure 21:
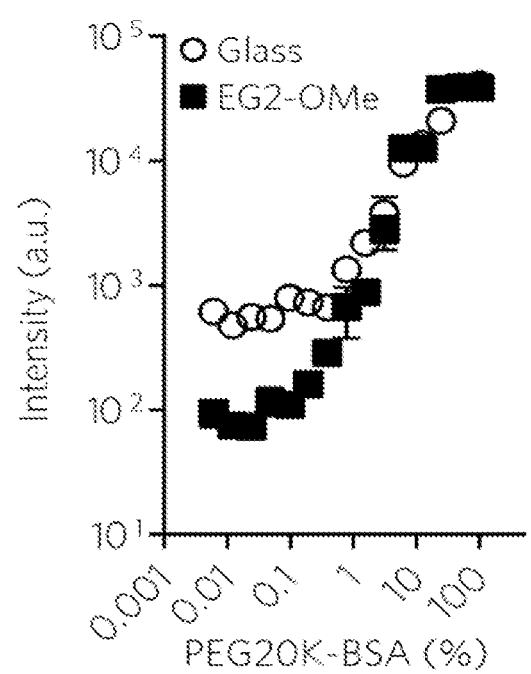
FIG. 21. Fluorescence intensity of APA surface fluoroimmunoassay scales with PEG content. The intensity of the fluorescence readout scaled with the amount of surface PEG available to bind Cy5-labeled APAs. Microspots with adjusted PEG content were inkjet printed onto surfaces using biological "inks" having varied ratios of PEG20K-BSA to free BSA (from 0% to 100% PEG20K-BSA, with total protein content of the ink kept at 1 mg/mL). PEG-protein conjugates were used here (rather than free PEG) as the protein component improves immobilization and retention of the PEG to the surface. These surface-immobilized microspots were then treated as described in the Methods section titled "Surface fluoroimmunoassays for anti-PEG reactivity in simulated samples" using pAPA1. Data plotted as mean±s.d. in triplicate. Comparing assay behavior when the surface is bare glass versus polymer brush film (EG2-OMe shown here), the major difference observed was that the polymer brush-coated surface showed a lower limit-of-detection as a result of a reduction in background noise.

Subsequently, when exposing surfaces to pAPA1 and labeling, large responses in Cy5 fluorescence were observed for EG5-OMe, EG6-OH, and EG9-OMe surfaces, but near-baseline response for EG1-OMe, EG2-OMe, and EG3-OMe surfaces (FIG. 20B-C). One-way ANOVA indicated that there was a statistically significant difference between pAPA1-treated groups ($F_{(6, 33)}=50.05$, $p<0.0001$). Bars marked with different letters in FIG. 20C indicate significant differences within the pAPA1-treated groups (Tukey post hoc test, p s 0.05) indicating that reactivity to pAPA1 is significantly lower for POEGMA brush surfaces with EG3 and smaller sidechains. This suggests that reactivity to pAPA1 is considerably mitigated for POEGMA bearing EG3 and smaller sidechains, generally consistent with previous observations with linear PEG.

A decreasing trend in fluorescence was observed between the smaller sidechain moieties, namely EG3-OMe (276 a.u.)>EG2-OMe (157 a.u.)>EG1-OMe (63 a.u.); while notable, the difference between these groups was not statistically significant by one-way ANOVA analysis. Additionally, while the hydroxy-terminated EG6-OH surface was clearly reactive to pAPA1, we observed a lower response when compared to that of methoxy-terminated EG5-OMe and EG9-OMe. This finding is consistent with previous studies showing that hydroxy-terminated PEG is less antigenic than methoxy-terminated PEG against APAs derived from methoxy-PEG immunogens. This is indeed the case for pAPA1, which is a polyclonal Ab (pAb) generated by immunization with methoxy-terminated linear PEG with 24 EG repeats that shows considerable reactivity to PEG endgroups.

Next, the stealth functionality of the polymer films was examined by evaluating their ability to prevent nonspecific binding of proteins and cells onto surfaces (FIG. 22). Protein adsorption was assessed using bovine serum albumin (BSA), a hydrophobic protein well-known for its tendency to nonspecifically "stick" to surfaces. Surfaces were incubated with Cy5-labeled BSA (Cy5-BSA), rinsed with wash buffer (in this case, 0.1% Tween20 in PBS) to remove any loosely-bound proteins, and then imaged with a fluorescence scanner to detect residual Cy5-BSA avidly bound to the surface (FIG. 22A). The raw fluorescence intensity for each surface is shown in FIG. 3b and are quantified in FIG. 3c as mean±95% confidence interval (CI). There was a statistically significant difference between Cy5-BSA-treated groups in FIG. 22C, as determined by one-way ANOVA ($F(5, 31)=390.2$, $p<0.0001$). Bars marked with different letters indicate significant differences (Tukey post hoc test, $p \leq 0.05$). The uncoated glass surface showed the highest level of nonspecific adsorption of Cy5-BSA (FIG. 22B-C). Next, while EG1-OMe coatings reduced overall binding to some extent, we observed considerable fluorescence response from residually-bound Cy5-BSA on the EG1-OMe brush. In contrast, POEGMA brushes with average sidechain lengths of EG2 or greater showed considerably lower nonspecific BSA adsorption.

Figure 22A:
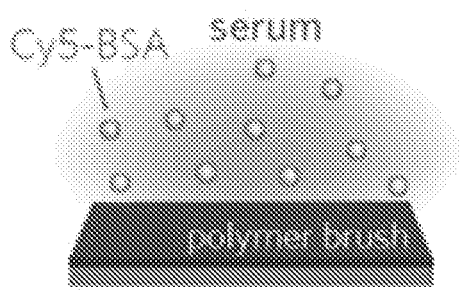
FIG. 22A-F. Screening POEGMA brush surfaces for protein adsorption and cell adhesion.
Figure 22A:
Figure 22B:
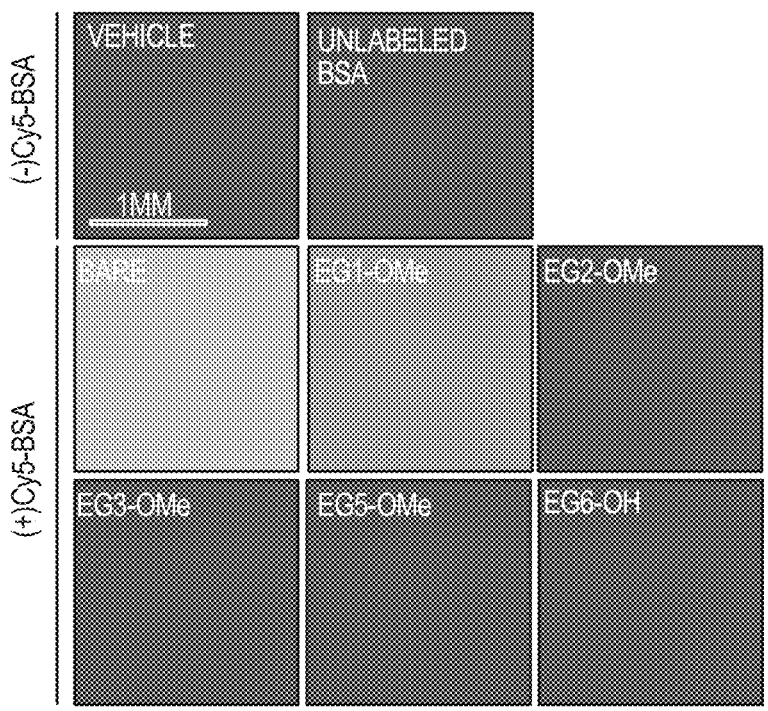
Figure 22C:
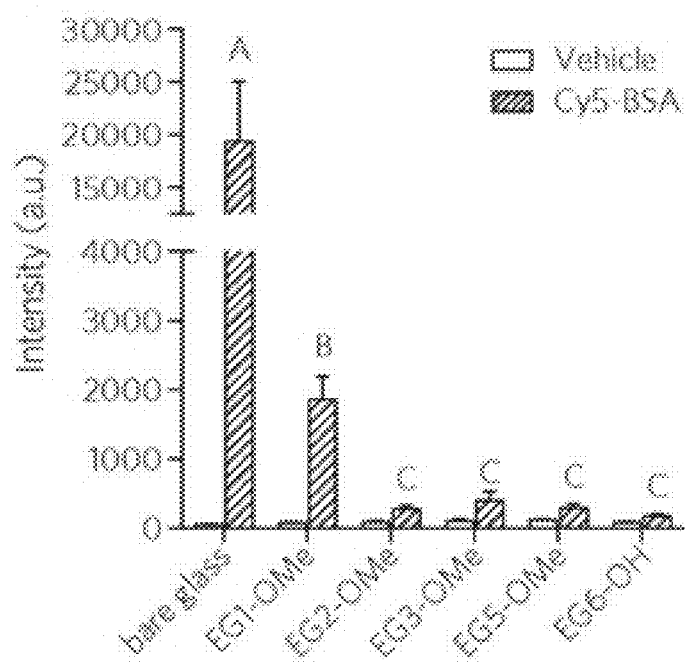
Figure 22D:
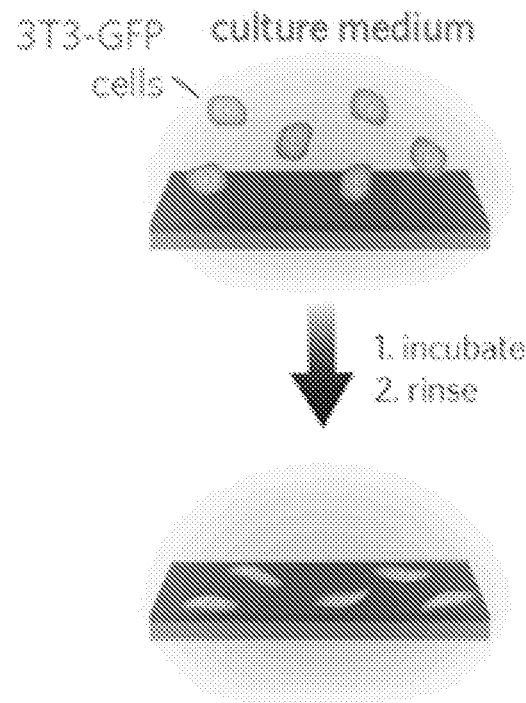
Figure 22E:
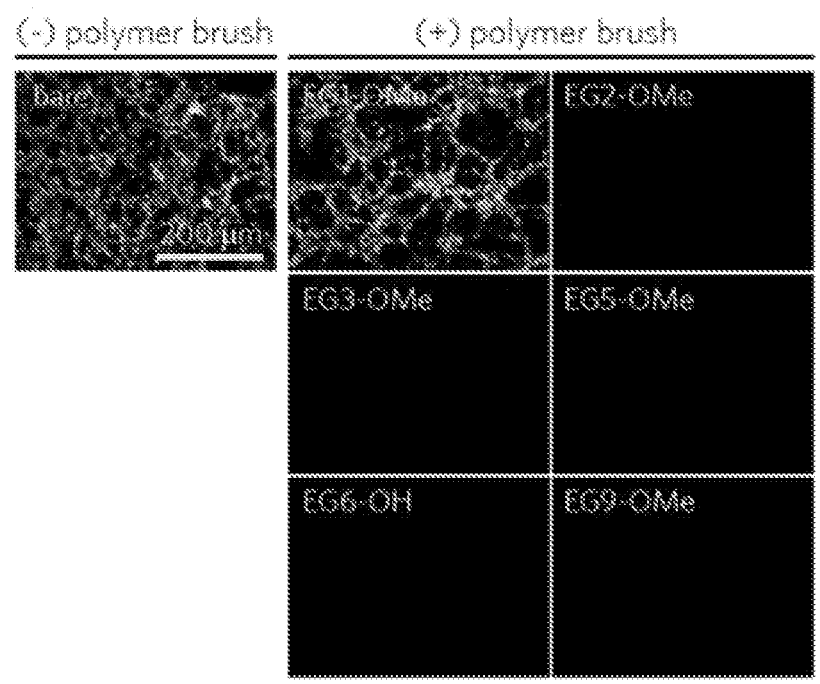
Figure 22F:
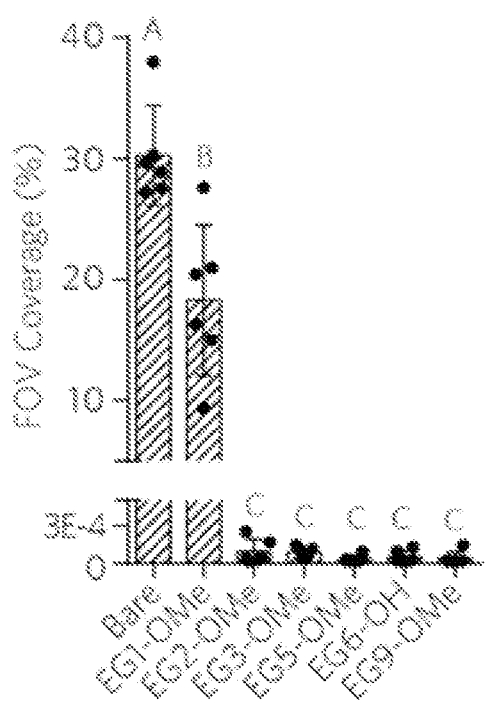

A similar trend was observed when investigating the adhesion of cultured fibroblast cells to the surface (FIG. 22D). Here, each surface was incubated with a solution of complete growth medium containing immortalized fibroblast cells expressing GFP (3T3-GFP) for 24 h, followed by rinsing and medium exchange, and epifluorescent imaging of GFP was then carried out to identify adherent cells. The fluorescence intensity was quantified by calculating percentage of pixels in the field of view showing positive signal in the GFP channel to represent surface coverage by cells ('% FOV). Results are plotted as mean of the % FOV±95% CI for at least 6 images per group. There was a statistically significant difference between groups, as determined by one-way ANOVA $F(6, 36)=122.2$, $p<0.0001$). Bars marked with different letters indicate significantly different groups (Tukey post hoc test, $p \leq 0.05$). Consistent with our BSA adsorption experiments, considerable adhesion of 3T3-GFP cells was observed for both uncoated and EG1-OMe surfaces but was virtually eliminated on POEGMA brushes with EG2 or longer sidechains (FIG. 22E-F). Taken together, these initial downselection experiments indicated that EG2-OMe and EG3-OMe POEGMA surfaces were the most viable candidates for meeting the established constraints of minimizing APA reactivity, BSA adsorption, and cell adhesion.

Building upon these initial downselection experiments, we next sought to directly compare the binding of pAPA1 to POEGMA brushes versus that of linear PEG. Specifically, we used inkjet-printing to immobilize microspots of linear PEG-protein conjugates (PEG20K-BSA) known to be APA-reactive onto EG2-OMe, EG3-OMe and EG5-OMe POEGMA brushes (schema shown in FIG. 23A). The surfaces were exposed to a dilution series of rabbit-derived pAPA1 in serum and then labeled with Cy5-donkey-α-rabbit dAbs and subsequently imaged on a fluorescence scanner. On EG2-OMe surfaces, we observed highly asymmetric APA reactivity in areas functionalized by PEG20K-BSA. EG2-OMe POEGMA background shows minimal signal, while an intense and spatially well-defined fluorescence response is observed in the circular feature defined by the printed PEG20K-BSA microspot (FIG. 23A). In quantitating the Cy5 signal in the surrounding EG2-OMe polymer brush to assess APA binding, baseline values of fluorescence were observed across all pAPA1 concentrations up to 2 µg/mL (open circles, FIG. 23B). In contrast, the microspots of PEG20K-BSA showed a dose-dependent Cy5 signal that scaled with increasing concentrations of pAPA1 analyte (black squares, FIG. 23B). Using the concentration curve derived from the PEG20K-BSA Ag spots, we calculated an LOD ("LODAg") of 1.4 ng/mL for pAPA1 fabricated on EG2-OMe POEGMA surfaces. An LOD for the polymer brush background ("LODbkg") could not be calculated in this case given the lack of dose-dependent behavior for the EG2-OMe POEGMA background, consistent with the fact that pAPA1 lacks affinity for EG2-OMe POEGMA.

Figure 23C:
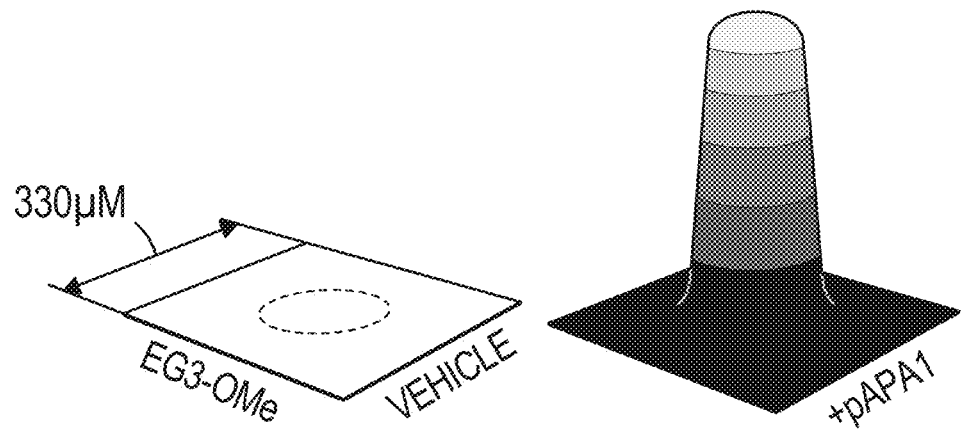
Figure 23D:
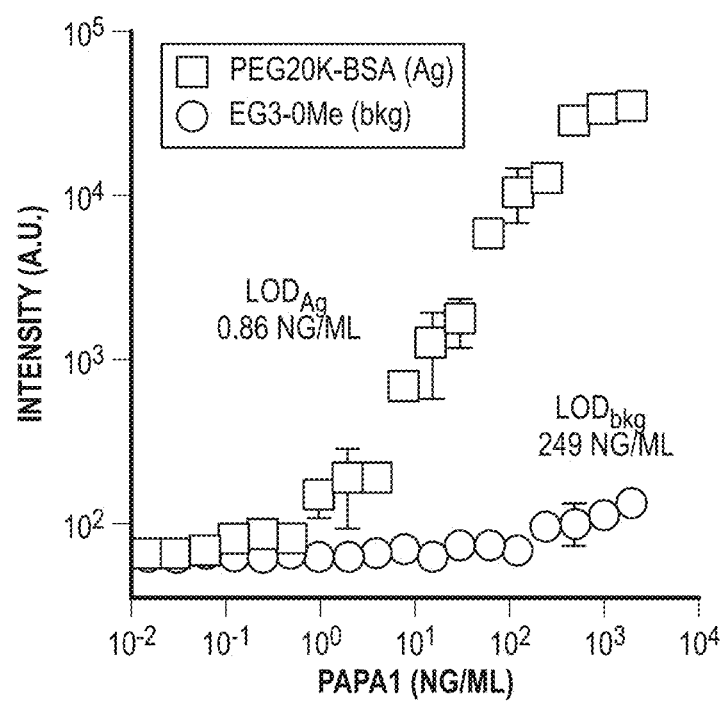
Figure 23E:
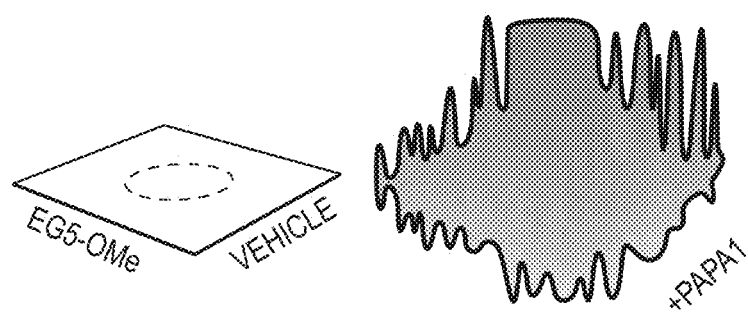
Figure 23F:
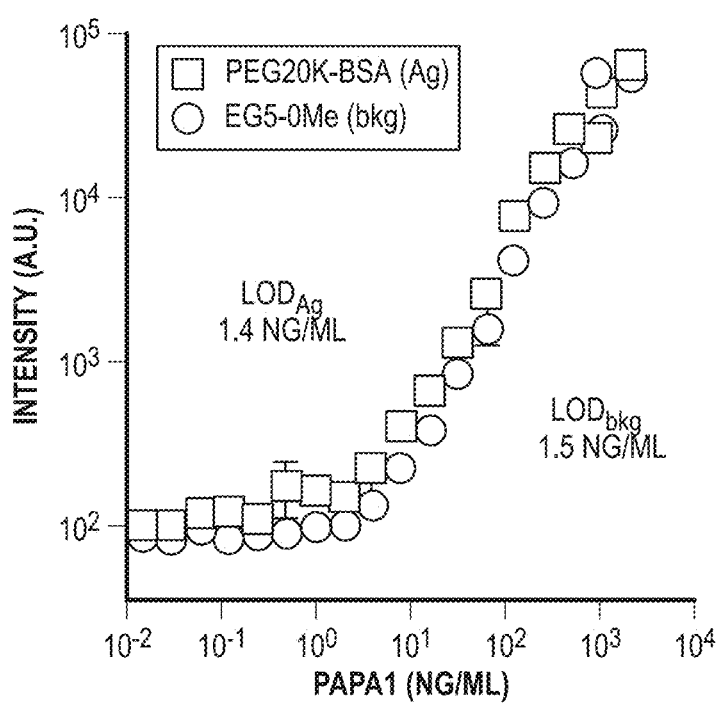

Similar behavior was observed for EG3-OMe surfaces (FIG. 23C-D), and a similar LODAg of 0.86 ng/mL was determined for pAPA1 binding to PEG20K-BSA. The Cy5 signal from the EG3-OMe POEGMA brush background remained at baseline values for the majority of pAPA1 concentrations (FIG. 23D). We did, however, note a gradual rise in background values at much higher pAPA1 concentrations; this behavior is consistent with the low level of binding of pAPA1 to EG3-OMe POEGMA observed in FIG. 20B. This allowed us to estimate a LODbkg of 249.5 ng/mL. In contrast, we observed that the sharply asymmetric reactivity to pAPA1 is lost for EG5-OMe POEGMA surfaces (FIG. 23E-F), as evidenced by the highly robust response to pAPA1 in both the Ag (BSA-PEG20K) spots and the POEGMA brush background. The calculated LODAg and LODbkg for these surfaces were similar at 1.4 and 1.5 ng/mL, respectively (FIG. 23F).

Example 13

Figure 26A:
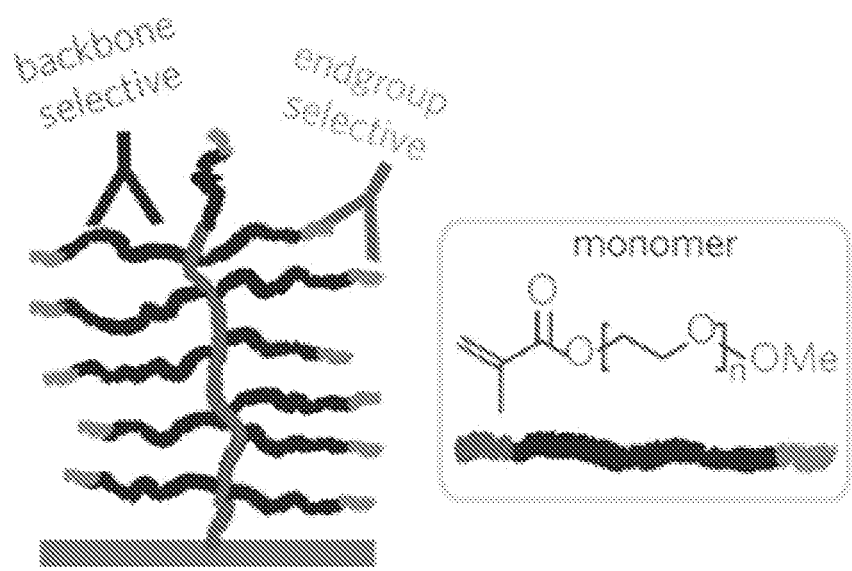
FIG. 26A-F. Reactivity of backbone-selective versus endgroup selective APAs toward EG2-OMe, EG3-OMe, and EG5-OMe POEGMA brushes.
Figure 26B:
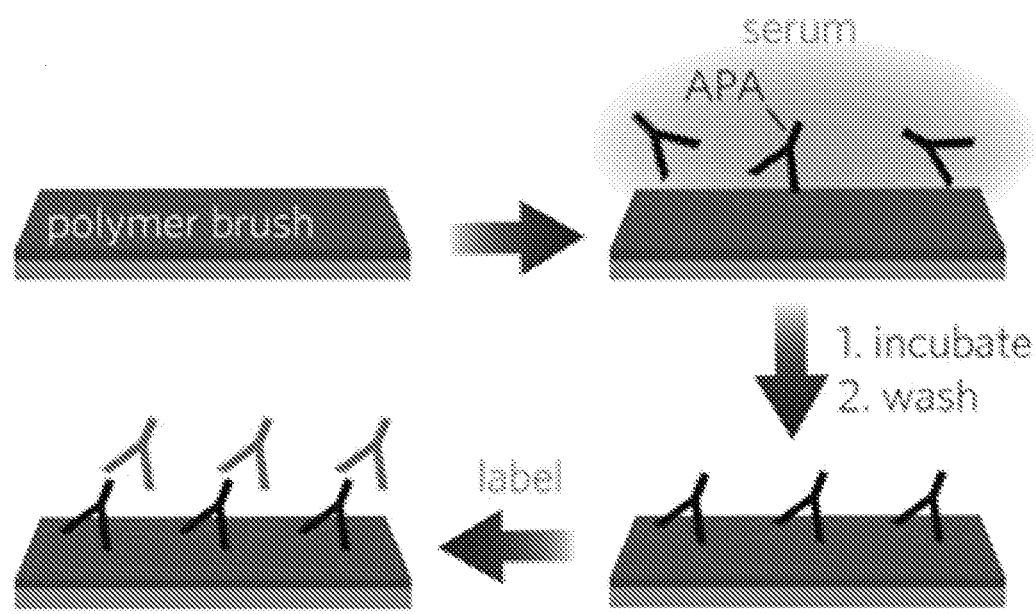

EG2-OMe and EG3-OMe Bottlebrush Reactivity Toward Endgroup-Selective Versus Backbone-Selective APAs We next sought to better understand how APAs targeting different structural features of PEG (methoxy endgroup vs. backbone) might uniquely interact—if at all—with EG2-OME and EG3-OMe POEGMA brush surfaces. We began our investigation by measuring the surface reactivity of EG2-OMe, EG3-OMe, and EG5-OMe surfaces with pAPA1 versus another rabbit-derived pAb—pAPA2—that is selective for the PEG backbone rather than the mPEG endgroup (as is the case for pAPA1) (FIG. 26A). Each surface was incubated with pAPA1- or pAPA2-spiked serum at 2 µg/mL and then labeled with a Cy5-dAb (FIG. 26B). This APA concentration was chosen based on previous results that individuals in the general population documented to have "high levels" of APA (500 ng/mL) have values reaching up to 2-6 µg/mL.

Figure 24A:
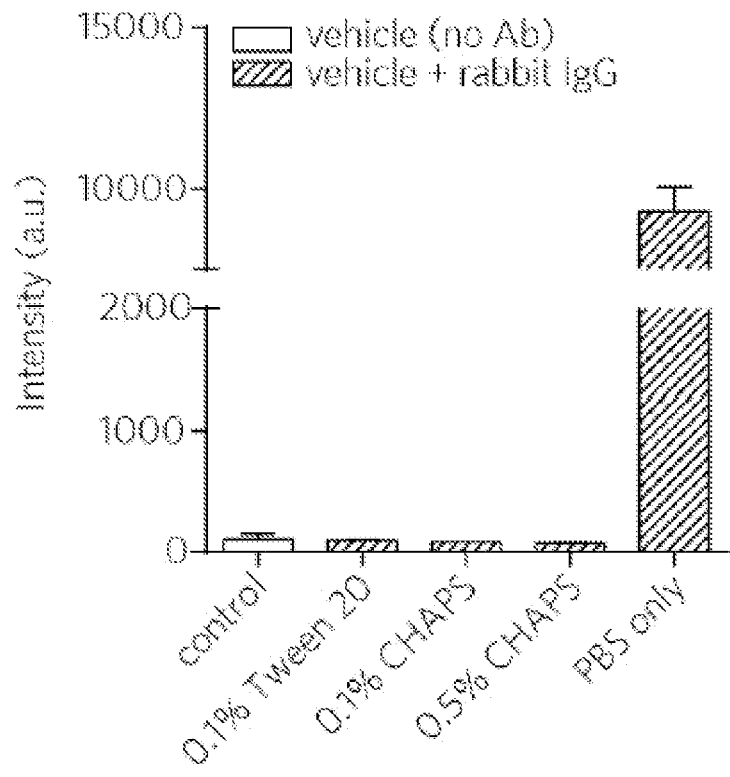
FIG. 24A shows residual binding of control rabbit IgG toward glass with various wash buffers. Bare glass surfaces were exposed to 0.01 mg/mL rabbit IgG in calf serum were incubated for 1 hour, and then washed with buffers comprised of 0.1% Tween20/PBS, 0.1% CHAPS/PBS, 0.5% CHAPS/PBS and PBS alone. Cy5-donkey-anti-rabbit dAbs (1 μg/mL in PBS) were used to label residual rabbit IgG bound to the surface for 30 minutes. After a final wash step, surfaces were imaged and quantified with a fluorescent scanner. Bar graphs represent mean±s.d. (n=3) fluorescence intensity values versus wash method. Representative intensity values for blanks without rabbit IgG is indicated by "control." Washing the surface with detergent-containing PBS effectively removes loosely-bound rabbit IgG from the surface, while washing with PBS alone does not.
Figure 24B:
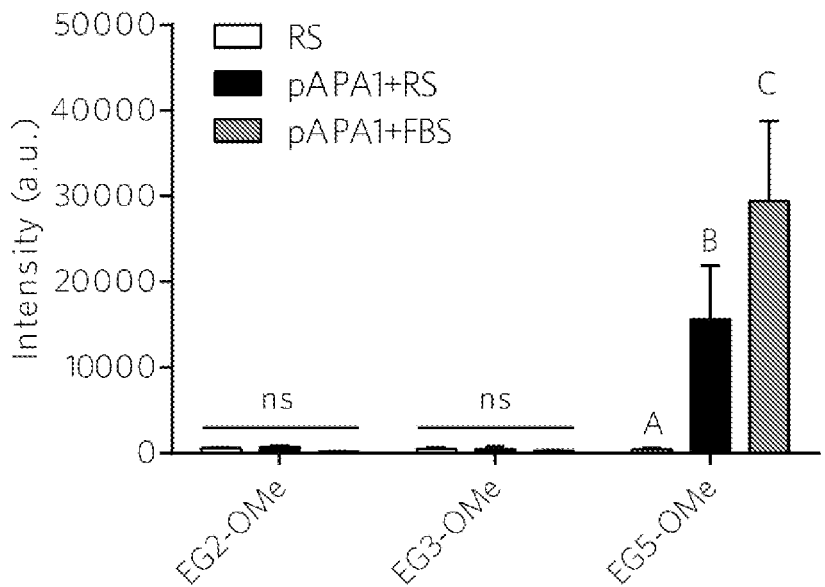
FIG. 24B shows surface binding of pAPA1 (rabbit-derived) against EG2-OMe, EG3-OMe, and EG5-OMe performed in rabbit plasma. Given the commercially obtained polyclonal APAs (e.g. pAPA1) were rabbit-derived, the surface APA binding assays were also performed in rabbit plasma (RP) to match the species of the APAs and assay vehicle. Results are plotted as mean fluorescence intensity±95% confidence interval for at least n=4. The overall binding patterns of pAPA1 against EG2-OMe, EG3-OMe, and EG5-OMe in RP versus fetal bovine serum (FBS) are similar. A statistically significant difference was observed, as determined by one-way ANOVA ($F(4, 43)=52.77$, $p<0.0001$). Bars marked with different letters indicate significant differences by multiple comparison testing for each surface (Tukey post hoc test, $p \leq 0.05$); "ns" indicates difference is not significant. We observed that the absolute intensity of pAPA1 binding signal was greater in FBS than in RP due to matrix effect.
Figure 25:
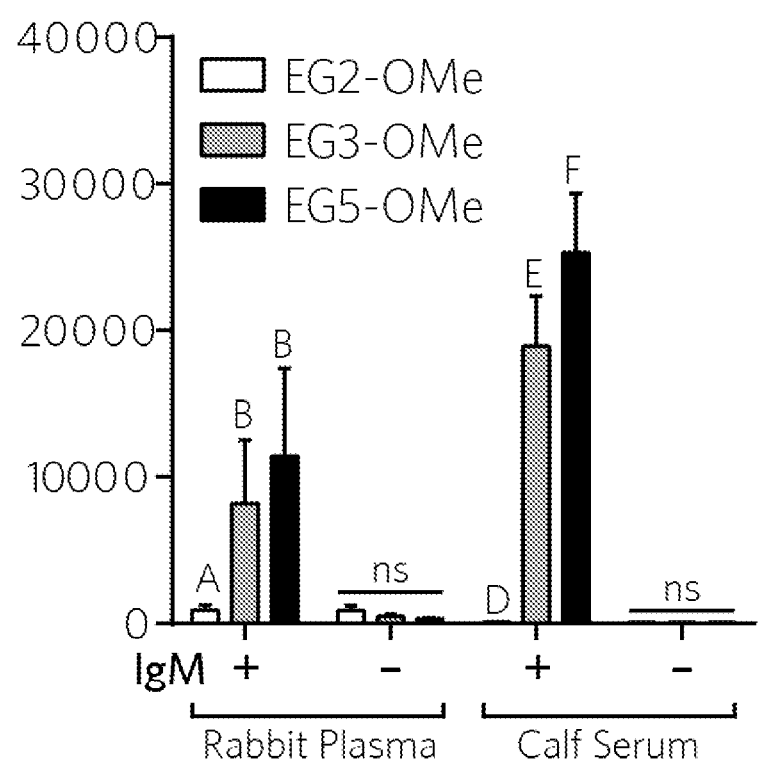
FIG. 25. Testing of IgM APA reactivity against EG2-OMe, EG3-OMe, and EG5-OMe surfaces. Rabbit-derived IgM APAs (backbone-selective) were tested against POEGMA surfaces following the standard procedure for surface fluoroimmunoassay for APA reactivity. Assays were performed in both rabbit plasma and calf serum. Results plotted as mean fluorescence intensity±s.d. (n=6). There was a statistically significant difference between groups, as determined by two-way ANOVA ($F (6, 60)=34.15$, $p<0.0001$). Bars marked with different letters indicate significant differences within each treatment condition by multiple comparison testing (Tukey post hoc test, $p \leq 0.05$).

The raw fluorescence images for binding of pAPA1 and pAPA2 are shown in FIG. 24A. The quantified data, shown in FIG. 26C for pAPA1 and FIG. 26D for pAPA2, indicate a statistically significant difference between groups for each polyclonal APA as determined by one-way ANOVA ($F(2, 24)=268.1$, $p<0.0001$ for pAPA1, and $F(2, 24)=62.3$, $p<0.0001$ for pAPA2). As observed previously, EG2-OMe and EG3-OMe were resistant to pAPA1 binding, compared to EG5-OMe (FIG. 27A (top row) and FIG. 26C). However, after exposure to 2 µg/mL pAPA2, we observed considerable pAPA2 binding to both EG3-OMe and EG5-OMe surfaces, whereas EG2-OMe surfaces remained resistant (FIG. 27A (bottom row) and FIG. 26D). These results suggest that EG3-OMe POEGMA brushes might be selectively resistant to endgroup-reactive APAs but not backbone-reactive APAs, whereas EG2-OMe may be resistant to both.

Figure 26C:
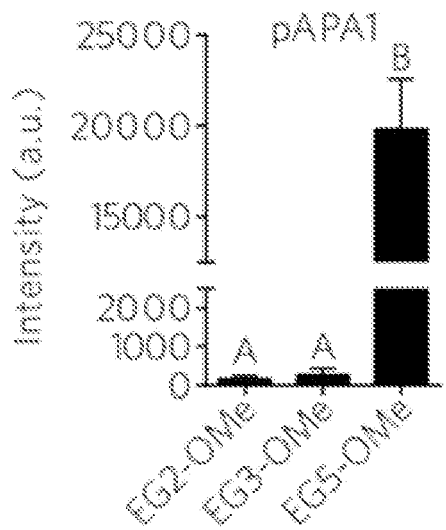
Figure 26D:
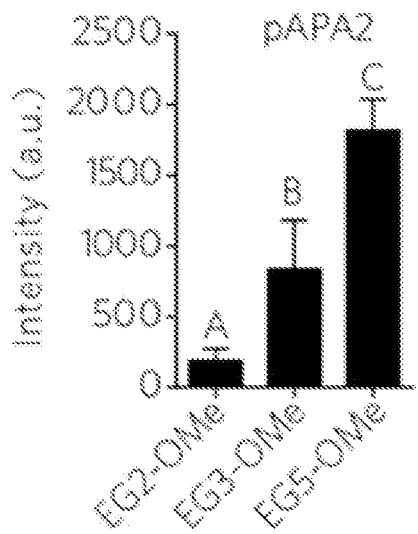
Figure 26E:
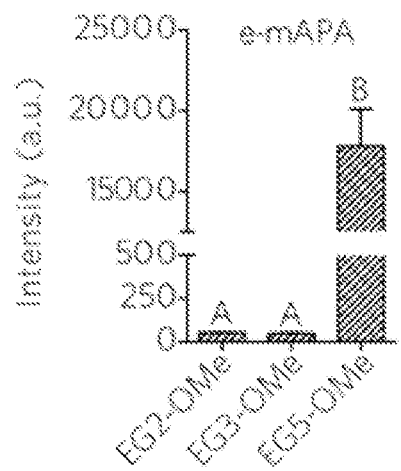
Figure 26F:
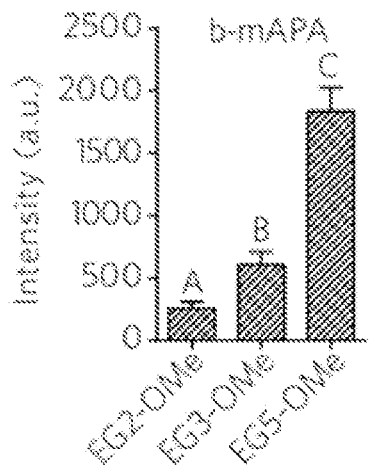
Figure 27A:
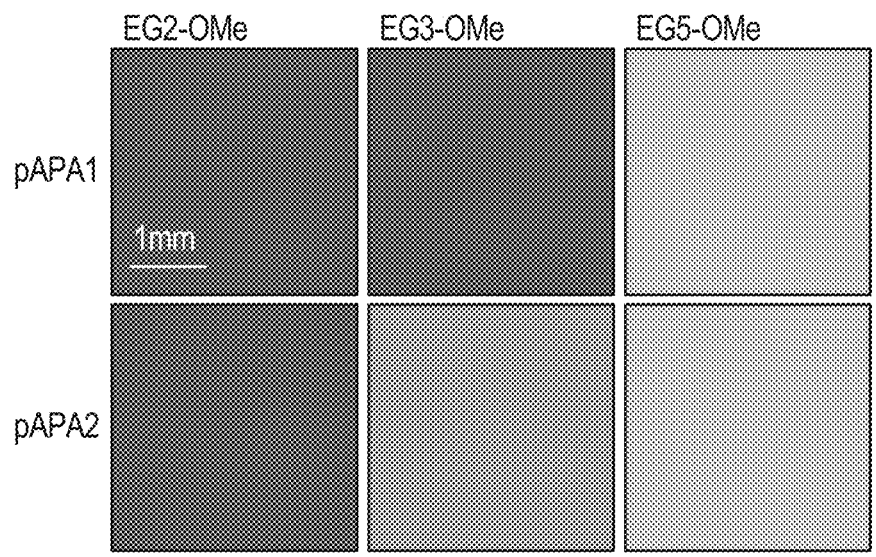
FIG. 27A-B. Representative image data of APA binding for FIG. 27. Shown are raw fluorescence images of pAPA1, pAPA2 (FIG. 27A), e-mAPA, and mAPA (FIG. 27B) binding to EG2, EG3, and EG5 POEGMA surfaces FIG. 28. Reactivity of EG2-OMe, EG3-OMe, EG5-OMe POEGMA brushes towards APAs in patient plasma. Four known APA-positive and one known APA-negative plasma samples were assessed by indirect ELISA against Adagen-coated plates for detecting bound IgG (right axis; solid black bars), and also by surface fluoroimmunoassay toward EG2-OMe, EG3-OMe, and EG5-OMe bottlebrush surfaces (left axis; empty, striped, and checkered bars, respectively). Results are shown as mean±s.d. (n=5 replicates for ELISA, n=4 replicates for EG2-OMe and EG5-OMe, and n=2 for EG3-OMe).
Figure 27B:
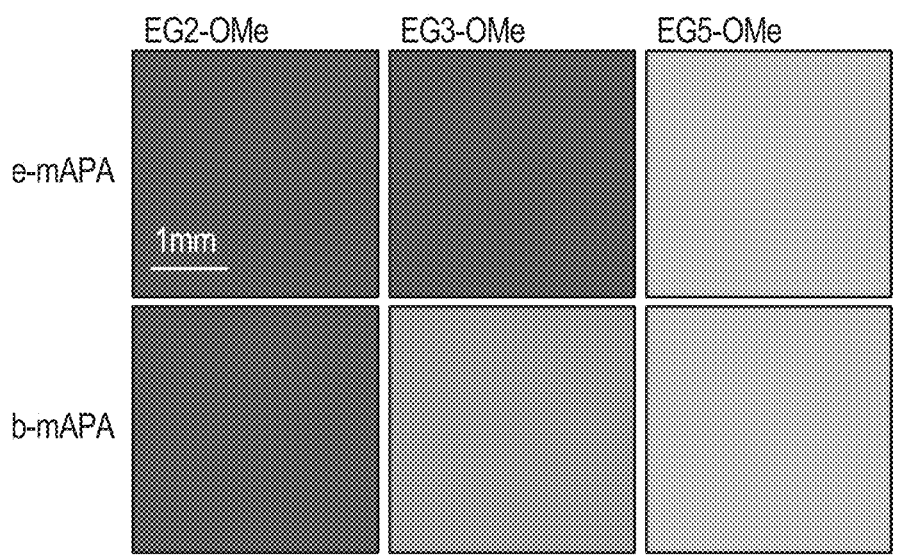

To explore this finding further, we then exposed the same surfaces to endgroup- vs. backbone-selective monoclonal APAs (e-mAPA vs. b-mAPA, respectively) under similar conditions as in the previous experiment. We observed robust binding of e-mAPA by the EG5-OMe POEGMA brush, but not by EG2-OMe or EG3-OMe brush at 2 μg/mL (similar to pAPA1) (FIG. 27B, top row). In contrast, b-mAPA was found to react with both EG3-OMe and EG5-OMe surfaces but not with EG2-OMe (FIG. 27B, bottom row). The quantified fluorescence intensity of the images and are shown in FIG. 26E for e-mAPA and in FIG. 26F for b-mAPA. The data show a statistically significant difference between groups for each APA, as determined by one-way ANOVA ($F_{(2,24)}=319.5$, $p<0.0001$ for e-mAPA, and $F_{(2,24)}=222.0$, $p<0.0001$ for b-mAPA). As shown in FIG. 26E-F, the binding behavior of these monoclonal APAs effectively recapitulated that of pAPA1 and pAPA2 (FIG. 26C-D). In addition to these studies using monoclonal APAs having IgG subtype, we also performed similar experiments using backbone-selective IgM subtype APAs (FIG. 25), and as expected their behavior overall paralleled that of b-mAPA and pAPA2 (FIG. 26F).

From these data, the following deductions can be made: (1) Sufficiently shortening the sidechains of POEGMA bottlebrushes to EG3 and shorter eliminates reactivity to endgroup-selective APA clones. Notably, this is achieved without needing to replace the more commonly-used (and stable) methoxy termini with a more reactive hydroxy endgroup. (2) Avoiding reactivity to backbone-specific APAs, however, requires a further reduction in sidechain length from EG3 to EG2; this effect is likely related to reducing the epitope length to shorter than the previously reported minimum of 3 EG units required for APA recognition.

Figure 28:
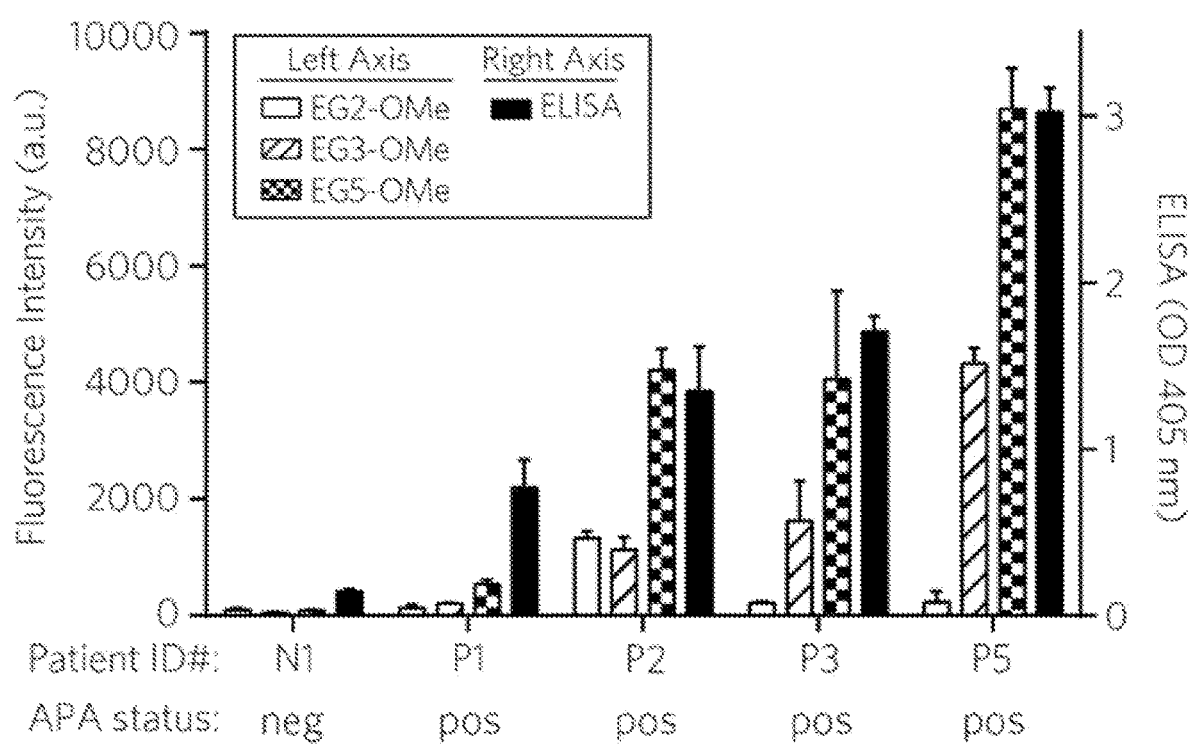

Assessing the Antigenicity of EG2-OMe, EG3-OMe, and EG5-OMe Bottlebrushes Toward APA-Positive Patient Plasma We next investigated the reactivity of EG2-OMe, EG3-OMe, and EG5-OMe POEGMA brush coatings against plasma samples of patients who were previously treated with a PEGylated drug, Krystexxa®. We tested plasma samples from 4 different patients from this cohort (samples P1-P4) and one patient known to be APA-negative (sample N1) using protocols described previously. We performed an indirect ELISA on these patient plasma samples to quantify the level of IgG binding to Adagen (PEGylated adenosine deaminase). Sample N1 exhibited baseline values compared to pooled APA-negative reference standards, while P1-P4 tested positive for reactivity toward Adagen (rank order P4>P3≈P2>P1), as expected (Table 8 and FIG. 28). Next, these samples were applied to EG2-OMe, EG3-OMe, and EG5-OMe and assessed for surface reactivity using a Cy5-goat-α-human IgG Ab, using a procedure similar to the approach shown in FIG. 20. The highest level of binding in this group is observed from EG5-OMe surfaces, as seen by the highest fluorescence intensities, which scaled according to the rank-ordering of Adagen reactivity by ELISA (FIG. 28). This was followed by EG3-OMe, which behaved in a similar manner but exhibited noticeably more resistance to APA binding than EG5-OMe. Finally, EG2-OMe surfaces showed the lowest levels of reactivity within the group toward APA-positive samples. Interestingly, sample P2 elicited a modest increase in fluorescence on EG2-OMe compared to other positive samples tested on this surface (reaching similar intensity levels as EG3-OMe, but much less than EG5-OMe). By and large, results from these experiments obtained from human plasma generally parallel our findings observed above in simulated specimens, wherein antigenicity of PEG-derived bottlebrushes is correlated with EG sidechain length.

TABLE 8

Indirect ELISA of Patient Specimens shown in FIG. 28.

| | | Internal | OD 405 nm | | | | | | |
|---|---|---|---|---|---|---|---|---|---|
| Pt# | APA | Sample# | Rep1 | Rep2 | Rep3 | Rep4 | Rep5 | Avg | s.d. |
| 1 | neg | 929-237-01 | 0.149 | 0.141 | 0.164 | 0.143 | 0.150 | 0.149 | 0.01 |
| 2 | pos | 929-219-07 | 0.905 | 0.636 | 0.712 | 0.647 | 0.671 | 0.714 | 0.11 |
| 3 | pos | 929-237-12 | 1.412 | 1.244 | 1.209 | 1.222 | 1.130 | 1.243 | 0.10 |
| 4 | pos | 929-241-07 | 1.685 | 1.762 | 1.673 | 1.691 | 1.583 | 1.679 | 0.06 |
| 5 | pos | 929-218-21 | 3.219 | 3.077 | 2.916 | 3.142 | 2.941 | 3.059 | 0.13 |

| Quality Control (QC) | |
|---|---|
| QC, blk | Avg OD405 |
| Blank | 0.102 |
| Neg | 0.205 |
| Low | 0.581 |
| High | 1.606 |

*Ag: ADAGEN; Secondary Ab: goat-anti-human IgG (Fab). Data for 5 replicate measurements (Rep#) for each patient specimen were used to calculate average (Avg) ± standard deviation (s.d.) values. Positive quality control (QC) were prepared from immune plasma of different individuals who had developed IgG antibodies with specificity toward PEG after receiving pegylated drug. Negative QC consisted of pooled nonimmune plasma from individuals in the same trial.

Application Toward Indirect Sandwich Immunoassay IVDs Fabricated on POEGMA

This study investigated settings other than drug delivery, under which the lack of PEG antigenicity of the EG2 and EG3 POEGMA coatings might have practical or translational relevance. The use of conformal POEGMA films as novel "zero-background" passivating surfaces to enhance the overall performance of next-generation immunoassays was tested. Immunoassays on POEGMA have several advantages over traditional formats, namely the enzyme linked immunosorbent assay (ELISA). Biological reagents can be directly printed onto the polymer brush surface without the need for covalent coupling, and the brush stabilizes printed reagents so that they remain active for prolonged periods without refrigeration. Further, POEGMA films minimize nonspecific binding of cells and proteins on the assay surface; this permits high signal-to-noise ratios in the assay, even in complex biological samples (e.g., whole blood) without needing to perform sample preprocessing or additional surface blocking steps.

The indirect sandwich immunoassay (ISIA), a popular serology assay format, in which host-derived anti-antigen (Ag) Abs in circulation first bind to pathogen Ags immobilized on a POEGMA-coated assay surface was investigated. These bound Ab-Ag complexes are subsequently labeled with dAbs that bind host-derived Abs. Recent reports estimating APA levels in the general population led to the hypothesis of whether so-called 'moderate' levels of APA (≥100 ng/mL) might be problematic for the performance of serology ISIAs fabricated on nonfouling POEGMA coatings. In this case, host APAs in circulation that recognize and bind to PEG epitopes across the polymer surface would subsequently get labeled (along with the desired pathogen-specific host Abs), thereby introducing background noise and impairing the sensitivity of the assay.

Figure 29A:
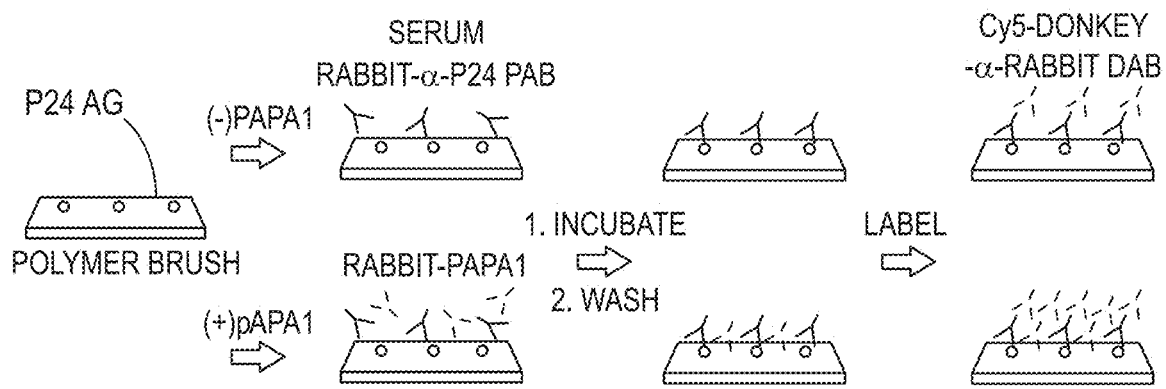
FIG. 29A-F. Evaluating interference from APA reactivity in indirect sandwich immunoassays (ISIAs) for antibody detection ("serology") fabricated on EG1-Ome, EG2-OMe, EG3-OMe, EG5-OMe, or EG6-OH POEGMA bottlebrushes.
Figure 29B:
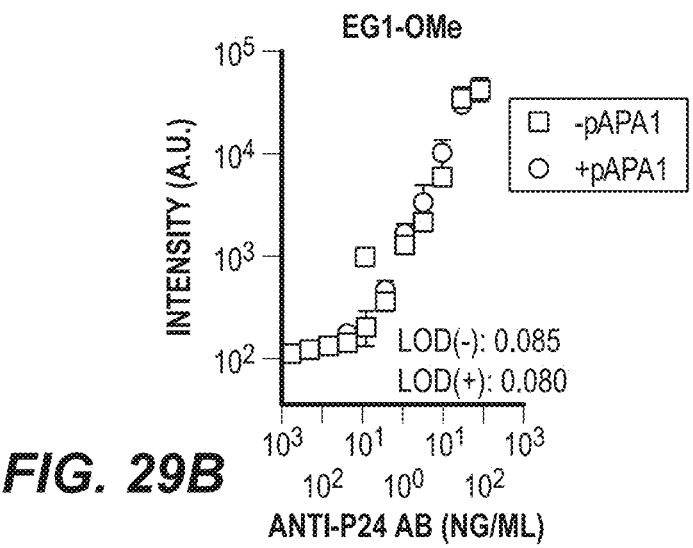
Figure 29C:
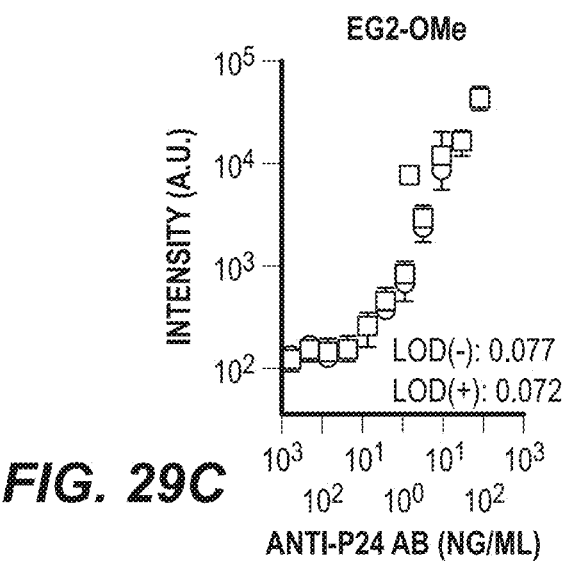
Figure 29D:
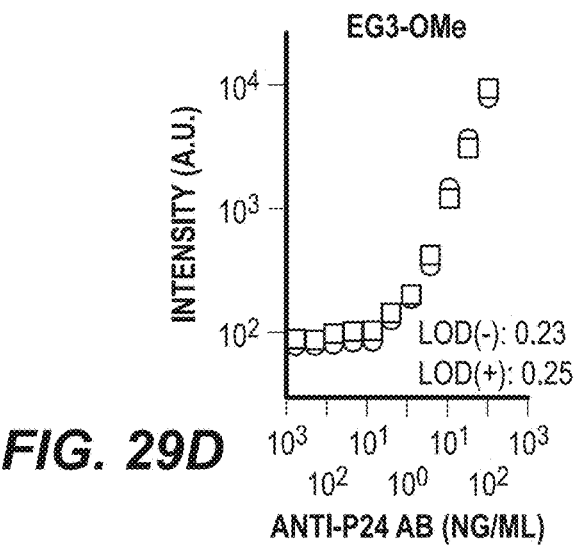
Figure 29E:
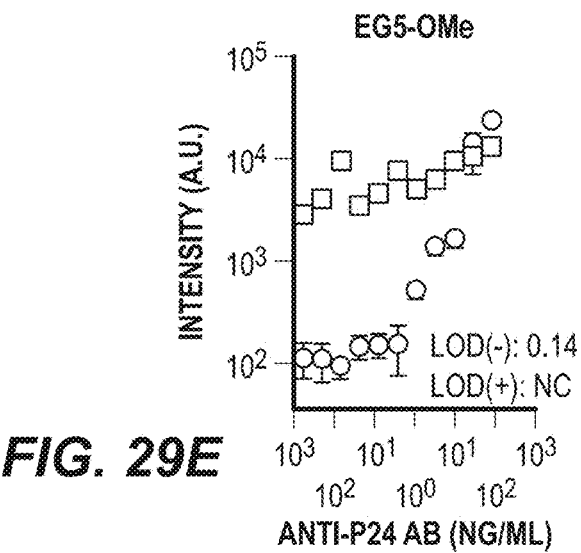
Figure 29F:
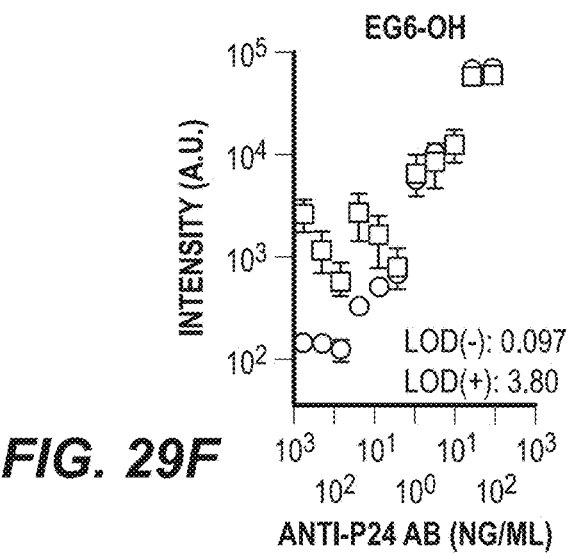
Figure 30:
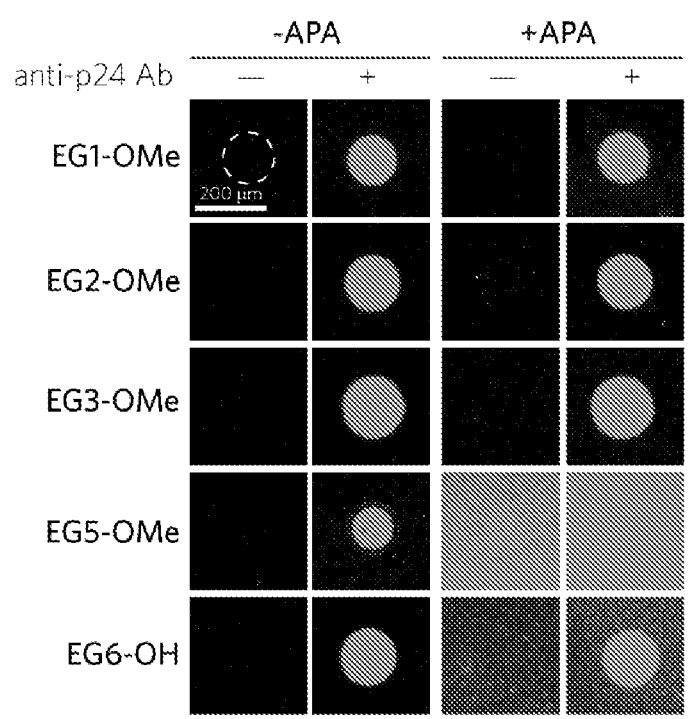
FIG. 30. Microarray images for indirect sandwich immunoassays (ISIAs) against anti-HIV p24 Abs on POEGMA shown in FIG. 29. Microspots of recombinant p24 Ag are printed on EG1-OMe, EG2-OMe, EG3-OMe, EG5-OMe, and EG6-OH surfaces (dashed white circle) and incubated with serum containing rabbit anti-HIV p24 polyclonal Ab, (±pAPA1 interferent), and then labeled with Cy5-donkey-anti-rabbit dAb. Shown here are microspots exposed to vehicle or 2 μg/mL of analyte with and without 100 ng/mL pAPA1 interference.

As proof-of-concept, ISIA conditions were simulated using POEGMA for the detection of circulating anti-HIV p24 Abs (FIG. 29A). ISIAs were fabricated by noncovalently printing HIV p24 Ag as microspots onto POEGMA-coated surfaces. The printed surfaces were then incubated with a dilution series of analyte-rabbit-α-p24 pAbs-spiked into undiluted serum, either with or without 100 ng/mL of rabbit-derived pAPA1 added as an interferent; hence, the Abs were species-matched to recapitulate host-derived APA interference. This was followed by rinsing and then labeling with Cy5-donkey-α-rabbit dAbs (the microspot images are shown in FIG. 30). The performance of ISIAs fabricated on EG1-OMe, EG2-OMe, and EG3-OMe surfaces were virtually unaffected by the presence of pAPA1 interference as seen by the overlap of concentration curves against anti-p24 pAb analyte and overall similarities in their calculated limits-of-detection (LODs) (FIG. 29B-D). However, for surfaces with longer EG sidechains (EG5-OMe and EG6-OH) that showed considerable APA reactivity in earlier screening experiments (FIG. 20). Significant interference by pAPA1 and loss of assay sensitivity were observed due to marked elevation in background noise from surface-bound APAs (FIG. 29E-F). The presence of pAPA1 led to a 40-fold increase in LOD for assays fabricated on EG6-OH polymer brush surfaces. Further, the introduction of pAPA1 to EG5-OMe based assays produced so much interference that an LOD was not calculated in this case.

Example 14

Conformal POEGMA brush coatings were synthesized by solution-based batch processing of glass substrates (via SI-ATRP), and the number EG repeats as a design parameter were systematically investigated to minimize: (1) APA antigenicity and (2) BSA adsorption and fibroblast adhesion. These studies identified EG2-OMe—and to a lesser extent, EG3-OMe-POEGMA brush surfaces as having the optimal architecture to minimize both attributes.

Drug-POEGMA conjugates with EG3-OMe sidechains virtually eliminated PEG antigenicity when tested against patient plasma samples and assayed in conventional ELISA experiments involving Adagen® and Krystexxa®. As with those studies, the present work on planar surface coatings revealed that EG3-OMe POEGMA brushes show minimal recognition by endgroup-selective APAs; however, two new surprising findings were made. First, EG3-OMe bottlebrush surfaces exhibit some, albeit low level of binding to backbone-selective APAs (FIG. 26). The tendency for EG3-OMe bottlebrushes to bind backbone-selective but not endgroup-selective APAs is somewhat counterintuitive, as methoxy endgroups in POEGMA sidechains are more 'exposed' than backbones. It is possible that bottlebrushes with longer EG repeats might have greater sidechain mobility to accommodate binding of endgroup-selective APAs to 3 terminal EG units (the minimum required for antigenicity) in a sterically favorable manner. Conversely, the reduced mobility of shorter sidechains in EG3-OMe bottlebrushes, combined with the requirement of binding to 3 EGs at sidechain termini in the appropriate orientation, might render binding of endgroup-selective APAs toward EG3-OMe brushes unfavorable, yet more studies are necessary to elucidate this phenomenon. Second, consistent with the first observation, surface-grown EG3-OMe exhibits some antigenicity toward APAs in human plasma, which was not observed in previous work. These differences are attributable, at least in part, to several factors. Patient plasma is expected to contain populations of both endgroup- and backbone-selective APAs, with larger titers of the former based on its greater immunogenicity. Hence, based on our current data, we speculate that the EG3-OMe drug conjugates in our earlier work avoided recognition by mostly endgroup-selective clones. However, measurement of the remaining backbone-selective clones that may have successfully bound to EG3-OMe drug conjugates likely fell below the detection limit of the ELISA used in that work. In contrast, using a more sensitive readout in the present work (the surface fluoroimmunoassay on the POEGMA brush) made it possible to detect low levels of backbone-selective APA binding on EG3-OMe surfaces. From a practical standpoint, most current PEGylated therapeutics (immunogens) are mPEG-modified, which are known to stimulate a fairly robust population of endgroup-directed clones when an immune response is elicited. This biological tendency, combined with (i) our prior observations with drug-POEGMA conjugates and (ii) the noticeable reduction in antigenicity in both simulated and human specimens by EG3-OMe shown herein, suggest that drugs conjugated to EG3-OMe brushes might be sufficiently evasive toward APAs in clinical practice.

In addition to studies on protein-polymer conjugates supporting the claim that the hyperbranched architecture of POEGMA leads to a reduction in antigenicity compared to long-chain linear PEG, similar comparisons were also made in a recent investigation on planar surface-grafted polymers by Zhang et al., *Anal. Chem.* 2017 89(16):8217-22. The authors fabricated surface plasmon resonance sensors (SPRSs) functionalized with linear PEG versus POEGMA overlayers and compared their response to APAs. Consistent with previous work, long-chain linear 5 KDa PEG ("PEG5K") grafted to gold surfaces on SPRSs were more reactive to APAs than EG9-OMe bottlebrushes grown by SI-ATRP. Next, although replacing linear PEG5K with linear EG4 self-assembled monolayers (SAMs) reduced APA binding below the detection limit of their measurements, the linear EG4 SAM surfaces noticeably suffered from nonspecific binding of serum proteins. While the extent of non-fouling behavior exhibited by EG3- to EG6-SAMs is debated in the literature, results from the present study show that assembling even shorter (EG2 to EG3) PEG moieties into a hyperbranched bottlebrush on a surface resists APA binding (EG2 more effectively than EG3) and also effectively minimizes adsorption by BSA and fibroblast cells. Additionally, PEG5K-coated SPRSs used in an ISIA format for APA sensing (chosen over EG9-OMe polymer brush SPRSs given greater APA reactivity) showed LODs of 10 to 50 ng/mL against APAs spiked into saline buffer. In contrast, the POEGMA-based anti-PEG assays described in the present work (FIG. 23)—whether measuring the local response of BSA-PEG20K microspots printed on EG2-OMe/EG3-OMe surfaces (FIG. 23B, D), or the total response of an entire EG5-OMe surface (FIG. 23F)—exhibited a far lower LOD of ~1-2 ng/mL in detecting APAs in undiluted serum. Hence, surface fluorescence measurements on PEG-derived bottlebrush coatings as described herein may offer a straightforward and highly sensitive assay for APAs in clinical samples compared to SPR based assays and ELISA.

Although the focus described herein is on surface-based screening of APAs and biofouling with application in immunodiagnostics, the importance of PEGylation in drug delivery is recognized and this study qualitatively assessed how results from surface screens might translate to drug-POEGMA conjugates. These results suggest that surface-based screening for APA binding agrees with results obtained for soluble drug-POEGMA conjugates, and that anti-biofouling behavior on POEGMA brush surfaces might be a good proxy for favorable-long circulation-pharmacokinetics of POEGMA conjugates in solution.

Concerns surrounding anti-PEG immunity, and that its relevance to human patients are still in the infant stage. There is still debate as to why some patients mount a robust immune response to PEG while others do not, and clarification is needed as to why administering PEG-modified products only sometimes generates clinically-observable outcomes. While thus far clinically-observable reaction to PEGylated drugs (e.g., accelerated clearance or hypersensitivity) have mostly been limited to patients with high titers of APAs, there is evidence that even low-to-medium titers of anti-drug Abs against other agents have been reported to alter their pharmacological behavior in vivo, justifying more thorough investigation of the APA response in patients. We also emphasize that results from the present study must be interpreted with caution since they focused on the antigenicity of POEGMA against APAs and did not investigate its immunogenicity. More studies are necessary to determine whether exposure to POEGMA conjugates can generate a robust, POEGMA-specific humoral response.

Nevertheless, given increasing reported cases of PEG-related complications in clinical settings, the prevalence of APAs in the general population, and the already considerable (and growing) investment into PEG-modified products, the results of our study, we believe, are broadly relevant to diagnostics and implants that might benefit from using POEGMA bottlebrushes as next-generation bioinert coatings and as a potential alternative to linear PEG for drug conjugation.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A surface having reduced antigenicity and non-specific binding comprising: a surface comprising a plurality of poly[oligo(ethylene glycol) methyl ether methacrylate (POEGMA) polymers comprising a poly(methyl methacrylate) backbone and a plurality of side chains covalently attached to the backbone, each side chain comprising 1 to 9 ethylene glycol monomers repeated in tandem and terminating with an alkoxy moeity.

Clause 2. The surface of clause 1, wherein the surface is not reactive with anti-PEG antibodies in a subject.

Clause 3. The surface of clause 1 or 2, wherein the surface does not bind proteins, lipids, or carbohydrates non-specifically.

Clause 4. The surface of any one of clauses 1-3, wherein the is non-antigenic and does not induce an immune response.

Clause 5. The surface of any one of clauses 1-4, wherein the side chain comprises 1 to 5 ethylene glycol monomers repeated in tandem.

Clause 6. The surface of any one of clauses 1-5, wherein the side chain comprises 1 to 3 ethylene glycol monomers repeated in tandem.

Clause 7. The surface of any one of clauses 1-6, wherein the side chain comprises 2 to 3 ethylene glycol monomers repeated in tandem.

Clause 8. The surface of any one of clauses 1-6, wherein the side chain comprises 2 ethylene glycol monomers repeated in tandem.

Clause 9. The surface of any one of clauses 1-6, wherein the side chain comprises 3 ethylene glycol monomers repeated in tandem.

Clause 10. The surface of any one of clauses 1-9, wherein the alkoxy is methoxy, ethoxy, or propoxy.

Clause 11. The surface of any one of clauses 1-10, wherein the alkoxy is methoxy.

Clause 12. The surface of any one of clauses 1-3, wherein the POEGMA comprises monomers of ethylene glycol methyl ether methacrylate (EG-1-OMe).

Clause 13. The surface of any one of clauses 1-3, wherein the POEGMA comprises monomers of di(ethylene glycol) methyl ether methacrylate (EG-3-OMe).

Clause 14. The surface of any one of clauses 1-3, wherein the POEGMA comprises monomers of tri(ethylene glycol) methyl ether methacrylate (EG-3-OMe).

Clause 15. The surface of any one of clauses 1-3, wherein the POEGMA comprises monomers of penta(ethylene glycol) methyl ether methacrylate (EG-5-OMe).

Clause 16. The surface of any one of clauses 1-3, wherein the POEGMA comprises monomers of nona(ethylene glycol) methyl ether methacrylate (EG-9-OMe).

Clause 17. The surface of any one of clauses 1-16, wherein the surface is a material or a biomolecule.

Clause 18. The surface of any one of clauses 1-17, wherein the surface is a protein or a protein complex.

Clause 19. The surface of any one of clauses 1-16, wherein the surface is a material comprising glass, plastic, metal, ceramic, textile, or paper.

Clause 20. A method for reducing antigenicity of and non-specific binding to a surface, the method comprising: affixing to a surface a plurality of poly[oligo(ethylene glycol) methyl ether methacrylate (POEGMA) polymers comprising a poly(methyl methacrylate) backbone and a plurality of side chains covalently attached to the backbone, each side chain comprising 1 to 9 ethylene glycol monomers repeated in tandem and terminating with an alkoxy moeity.

Clause 21. The method of clause 20, wherein the plurality of POEGMA polymers are affixed to the surface by contacting the surface with an initiator agent to form a macroinitiator; and incubating the macroinitiator with a monomer under conditions that permit free-radical polymerization and formation of a branched polymer to occur from the initiator agent to form the molecule-polymer conjugate.

Clause 22. The method of clause 20 or 21, wherein the side chain comprises 1 to 5 ethylene glycol monomers repeated in tandem.

Clause 23. The method of any one of clauses 20-22, wherein the side chain comprises 1 to 3 ethylene glycol monomers repeated in tandem.

Clause 24. The method of any one of clauses 20-24, wherein the side chain comprises 2 to 3 ethylene glycol monomers repeated in tandem.

Clause 25. The method of any one of clauses 20-24, wherein the side chain comprises 2 ethylene glycol monomers repeated in tandem.

Clause 26. The method of any one of clauses 20-24, wherein the side chain comprises 3 ethylene glycol monomers repeated in tandem.

Clause 27. The method of any one of clauses 20-26, wherein the alkoxy is methoxy, ethoxy, or propoxy.

Clause 28. The method of any one of clauses 20-27, wherein the alkoxy is methoxy.

Clause 29. The method of any one of clauses 20-21, wherein the POEGMA comprises monomers of ethylene glycol methyl ether methacrylate (EG-1-OMe).

Clause 30. The method of any one of clauses 20-21, wherein the POEGMA comprises monomers of di(ethylene glycol) methyl ether methacrylate (EG-3-OMe).

Clause 31. The method of any one of clauses 20-21, wherein the POEGMA comprises monomers of tri(ethylene glycol) methyl ether methacrylate (EG-3-OMe).

Clause 32. The method of any one of clauses 20-21, wherein the POEGMA comprises monomers of penta(ethylene glycol) methyl ether methacrylate (EG-5-OMe).

Clause 33. The method of any one of clauses 20-21, wherein the POEGMA comprises monomers of nona(ethylene glycol) methyl ether methacrylate (EG-9-OMe).

Clause 34. The method of any one of clauses 20-33, wherein the surface is a material or a biomolecule.

Clause 35. The method of any one of clauses 20-34, wherein the surface is a protein or a protein complex.

Clause 36. The method of any one of clauses 20-35, wherein the surface is a protein and one or more POEGMA polymers is affixed to the polypeptide at the C-terminus, the N-terminus, or an internal amino acid of the polypeptide.

Clause 37. The method of any one of clauses 20-33, wherein the surface is a material comprising glass, plastic, metal, ceramic, textile, or paper.

Clause 38. A surface coated with a plurality of POEGMA polymers by the method of any one of clauses 20-37.

Clause 39. The surface of claim 38, wherein the surface is a biomolecule or a material.

Clause 40. The surface of claim 38, wherein the surface does not non-specifically bind proteins, carbohydrates, or lipids; does not induce an immune response, and is not reactive with anti-PEG antibodies.

Clause 41. A method of reducing the antigenicity of a molecule, the method comprising conjugating at least one branched polymer to a molecule to form a molecule-polymer conjugate, wherein the molecule comprises a polypeptide, a polynucleotide, a small molecule, or a combination thereof, wherein the branched polymer comprises a backbone and a plurality of side chains, each side chain is covalently attached to the backbone, wherein the backbone comprises at least one of an acrylate, methacrylate, acrylamide, methacrylamide, carbonate, phosphoester, oxazoline, or a combination thereof, and wherein the molecule-polymer conjugate has reduced or eliminated antigenicity compared to a control.

Clause 42. The method of clause 41, wherein the molecule is conjugated to the backbone of the branched polymer.

Clause 43. The method of clause 41, wherein the molecule is conjugated to the backbone of the branched polymer via a linker.

Clause 44. The method of clause 41, wherein each side chain has a first terminal end and a second terminal end, wherein the first terminal end is covalently attached to the backbone, and wherein the second terminal end independently comprises an alkyl, ester, amine, amide, or carboxyl group.

Clause 45. The method of clause 41, wherein each side chain has a first terminal end and a second terminal end, wherein the first terminal end is covalently attached to the backbone, and wherein the second terminal end does not include a hydroxyl group.

Clause 46. The method of clause 41, wherein each side chain is a linear polymer.

Clause 47. The method of any one of the previous clauses, wherein at least one side chain comprises 1 monomer.

Clause 48. The method of any one of clauses 41-46, wherein each side chain comprises at least 2 monomers repeated in tandem.

Clause 49. The method of any one of clauses 41-46, wherein each side chain comprises less than 25 monomers repeated in tandem.

Clause 50. The method of any one of clauses 41-46, wherein each side chain comprises 3 to 9 monomers repeated in tandem.

Clause 51. The method of any one of clauses 41-46, wherein each side chain comprises 3 monomers repeated in tandem.

Clause 52. The method of any one of the previous clauses, wherein the monomer of each side chain is independently selected from betaine, phosphorylcholine, phosphorylethanolamine, sarcosine, ethylene glycol, or a combination thereof.

Clause 53. The method of clause 52, wherein the betaine comprises carboxybetaine, sulfobetaine, or a combination thereof.

Clause 54. The method of any one of the previous clauses, wherein the monomer of at least one side chain comprises ethylene glycol.

Clause 55. The method of any one of the previous clauses, wherein the monomer of each side chain comprises ethylene glycol.

Clause 56. The method of any one of the above clauses, wherein more than one branched polymer is conjugated to the molecule, each branched polymer conjugated to a different site of the molecule.

Clause 57. The method of any of one the above clauses, wherein the molecule comprises a polypeptide, and wherein one branched polymer is conjugated to the polypeptide at a site selected from the C-terminus, the N-terminus, and an internal amino acid of the polypeptide.

Clause 58. The method of any of one the above clauses, wherein the molecule comprises a polypeptide, and wherein more than one branched polymer is conjugated to the polypeptide, each branched polymer conjugated to a different site of the polypeptide selected from the C-terminus, the N-terminus, an internal amino acid, or a combination thereof.

Clause 59. The method of any one of clauses 41-58, wherein the molecule comprises a polypeptide comprising a sortase A recognition site, and wherein the branched polymer and the polypeptide are incubated with sortase A under conditions to conjugate the branched polymer to the sortase recognition site of the polypeptide.

Clause 60. The method of any one of clauses 41-58, wherein the molecule comprises a polypeptide comprising a sortase A recognition site, and wherein the conjugating comprises: a) contacting the molecule with a sortase A and an initiator agent under conditions that permit attachment of the initiator agent to the sortase A recognition site to form a macroinitiator; and b) incubating the macroinitiator with a monomer under conditions that permit free-radical polymerization and formation of a branched polymer to occur from the initiator agent to form the molecule-polymer conjugate.

Clause 61. The method of clause 59 or 60, wherein the sortase A recognition site comprises LPXTG (SEQ ID NO: 1), wherein X is any amino acid.

Clause 62. The method of clause 60 or 61, wherein the macroinitiator and monomer are incubated with a catalyst in step (b).

Clause 63. The method of any one of clauses 60 to 62, wherein the monomer in step (b) comprises at least one of an acrylate, methacrylate, acrylamide, and methacrylamide.

Clause 64. The method of any one of clauses 59 to 63, further comprising separating the molecule-polymer conjugate formed in step (b) from the unreacted macroinitiator.

Clause 65. The method of any one of clauses 41-58, wherein the branched polymer is synthesized and subsequently grafted to the moleculetoformthemolecule-polymer conjugate.

Clause 66. The method of any one of clauses 41-58, wherein the conjugating comprises attaching an initiator agent to the molecule to form a macroinitiator; and incubating the macroinitiator with a monomer under conditions that permit free-radical polymerization and formation of a branched polymer to occur from the initiator agent to form the molecule-polymer conjugate.

Clause 67. The method of clause 65 or 66, wherein the branched polymer is synthesized using free-radical polymerization.

Clause 68. The method of clause 65 or 66, wherein the branched polymer is synthesized using at least one method selected from ionic ring-opening polymerization (ionic ROP), ring opening metathesis polymerization, ionic polymerization, condensation polymerization, and coordination polymerization.

Clause 69. A method of making a molecule-polymer conjugate having reduced or eliminated antigenicity compared to a control, from a molecule comprising a polypeptide having a sortase A recognition site, the method comprising: a) contacting the molecule with a sortase A and an initiator agent under conditions that permit attachment of the initiator agent to the sortase A recognition site to form a macroinitiator; and b) incubating the macroinitiator with a monomer under conditions that permit free-radical polymerization and formation of a branched polymer to occur from the initiator agent to form the molecule-polymer conjugate, wherein the branched polymer comprises a backbone and a plurality of side chains, each side chain covalently attached to the backbone.

Clause 70. The method of clause 69, wherein the sortase A recognition site comprises LPXTG (SEQ ID NO: 1), wherein X is any amino acid.

Clause 71. The method of clause 69 or 70, wherein the macroinitiator and monomer are incubated with a catalyst in step (b).

Clause 72. The method of any one of clauses 69 to 71, wherein the monomer in step (b) comprises at least one of an acrylate, methacrylate, acrylamide, and methacrylamide.

Clause 73. The method of any one of clauses 69 to 72, further comprising separating the molecule-polymer conjugate formed in step (b) from the unreacted macroinitiator, wherein the yield of molecule-polymer conjugate is at least about 50% of the total conjugates and macroinitiators which are separated.

Clause 74. The method of clause 73 or 64, wherein the molecule-polymer conjugate is separated by chromatography.

Clause 75. The method of clause 74, wherein the chromatography comprises size-exclusion chromatography, ion exchange chromatography, affinity chromatography, or hydrophobic interaction chromatography, or a combination thereof.

Clause 76. The method of clause 75, wherein the chromatography comprises size-exclusion chromatography.

Clause 77. The method of any one of clauses 60-64, 67, and 69-76, wherein the free-radical polymerization comprises at least one of atom transfer radical polymerization (ATRP), reversible addition-fragmentation chain transfer (RAFT), radical ring-opening polymerization (radical ROP), nitroxide-mediated radical polymerization (NMP), iniferter polymerization, free radical polymerization, cobalt-mediated radical polymerization, telluride-mediated polymerization, and stibine-mediated polymerization.

Clause 78. The method of any one of clauses 69 to 77, wherein the molecule comprises a polypeptide, a polynucleotide, a small molecule, or a combination thereof.

Clause 79. A molecule-polymer conjugate having reduced or eliminated antigenicity compared to a control, the molecule-polymer conjugate comprising: a branched polymer comprising a backbone and a plurality of side chains, each side chain covalently attached to the backbone; and a molecule conjugated to the backbone of the branched polymer, wherein the molecule comprises a polypeptide, a polynucleotide, a small molecule, or a combination thereof, wherein each side chain is a linear polymer, wherein the backbone comprises at least one of an acrylate, methacrylate, acrylamide, methacrylamide, carbonate, phosphoester, oxazoline, or a combination thereof.

Clause 80. The conjugate of clause 79, wherein the molecule is conjugated to the backbone of the branched polymer via a linker.

Clause 81. The conjugate of any one of clauses 79-40, wherein each side chain has a first terminal end and a second terminal end, wherein the first terminal end is covalently attached to the backbone, and wherein the second terminal end independently comprises an alkyl, ester, amine, amide, or carboxyl group.

Clause 82. The conjugate of any one of clauses 79-81, wherein each side chain has a first terminal end and a second terminal end, wherein the first terminal end is covalently attached to the backbone, and wherein the second terminal end does not include a hydroxyl group.

Clause 83. The conjugate of any one of clauses 79-82, wherein at least one side chain comprises 1 monomer.

Clause 84. The conjugate of any one of clauses 79-82, wherein each side chain comprises at least 2 monomers repeated in tandem.

Clause 85. The conjugate of any one of clauses 79-82, wherein each side chain comprises less than 25 monomers repeated in tandem.

Clause 86. The conjugate of any one of clauses 79-82, wherein each side chain comprises 3 to 9 monomers repeated in tandem.

Clause 87. The conjugate of any one of clauses 79-82, wherein each side chain comprises 3 monomers repeated in tandem.

Clause 88. The conjugate of any one of clauses 79-87, wherein the monomer of each side chain is independently selected from betaine, phosphorylcholine, phosphorylethanolamine, sarcosine, ethylene glycol, or a combination thereof.

Clause 89. The conjugate of clause 88, wherein the betaine comprises carboxybetaine, sulfobetaine, or a combination thereof.

Clause 90. The conjugate of any one of clauses 79-89, wherein the monomer of at least one side chain comprises ethylene glycol.

Clause 91. The conjugate of any one of clauses 79-89, wherein the monomer of each side chain comprises ethylene glycol.

Clause 92. The conjugate of any one of clauses 79-91, wherein more than one branched polymer is conjugated to the molecule, each branched polymer conjugated to a different site of the molecule.

Clause 93. The conjugate of any one of clauses 79-91, wherein the molecule comprises a polypeptide, and wherein one branched polymer is conjugated to the polypeptide at a site selected from the C-terminus, the N-terminus, and an internal amino acid of the polypeptide.

Clause 94. The conjugate of any one of clauses 79-91, wherein the molecule comprises a polypeptide, and wherein more than one branched polymer is conjugated to the polypeptide, each branched polymer conjugated to a different site of the polypeptide selected from the C-terminus, the N-terminus, an internal amino acid, or a combination thereof.

Clause 95. The method or conjugate of any one of clauses 41-94, wherein the branched polymer comprises poly [oligo(ethylene glycol) methyl ether methacrylate] (POEGMA), and wherein the POEGMA comprises: a backbone comprising poly(methyl methacrylate); and a plurality of side chains covalently attached to the backbone, each side chain comprising at least 1 monomer of ethylene glycol (EG) repeated in tandem.

Clause 96. The method or conjugate of clause 95, wherein at least one side chain comprises 1 monomer of ethylene glycol (EG).

Clause 97. The method or conjugate of clause 95, wherein each side chain comprises at least 2 monomers of ethylene glycol (EG) repeated in tandem.

Clause 98. The method or conjugate of clause 95, wherein each side chain comprises at least 10 monomers of ethylene glycol (EG) repeated in tandem.

Clause 99. The method or conjugate of clause 95, wherein each side chain comprises less than 25 monomers of ethylene glycol (EG) repeated in tandem.

Clause 100. The method or conjugate of clause 95, wherein each side chain comprises 3 monomers of ethylene glycol (EG) repeated in tandem.

Clause 101. The method or conjugate of clause 95, wherein each side chain comprises 3 to 9 monomers of ethylene glycol (EG) repeated in tandem.

Clause 102. The method or conjugate of any one of clauses 95-101, wherein the molecule-POEGMA conjugate is not reactive with pre-existing anti-PEG antibodies in a subject.

Clause 103. The method or conjugate of any one of the preceding clauses, wherein the molecule comprises one or more peptides or protein therapeutic agents selected from a monoclonal antibody, blood factor, betatrophin, exendin, enzyme, asparaginase, glutamase, arginase, arginine deaminase, adenosine deaminase (ADA), ADA-2, ribonuclease, cytosine deaminase, trypsin, chymotrypsin, papain, growth factor, epidermal growth factor (EGF), insulin, insulin-like growth factor (IGF), transforming growth factor (TGF), nerve growth factor (NGF), platelet-derived growth factor (PDGF), bone morphogenic protein (BMP), fibroblast growth factor (FGF), somatostatin, somatotropin, somatropin, somatrem, calcitonin, parathyroid hormone, colony stimulating factors (CSF), clotting factors, tumor necrosis factors (TNF), gastrointestinal peptides, vasoactive intestinal peptide (VIP), cholecystokinin (CCK), gastrin, secretin, erythropoietins, growth hormone, GRF, vasopressins, octreotide, pancreatic enzymes, superoxide dismutase, thyrotropin releasing hormone (TRH), thyroid stimulating hormone, luteinizing hormone, luteinizing hormone-releasing hormone (LHRH), growth hormone releasing hormone (GHRH), tissue plasminogen activators, interleukins, interleukin-1, interleukin-15, interleukin-2, interleukin-10, colony stimulating factor, granulocyte macrophage colony-stimulating factor (GM-CSF), interleukin-1 receptor antagonist (IL-1RA), glucagon-like peptide-1 (GLP-1), exenatide, GLP-1 R multi-agonist, GLP-1 R antagonist, GLP-2, TNF-related apoptosis-inducing ligand (TRAIL), leptin, ghrelin, granulocyte monocyte colony stimulating factor (GM-CSF), interferons, interferon-α, interferon-gamma, human growth hormone (hGH) and antagonist, macrophage activator, chorionic gonadotropin, heparin, atrial natriuretic peptide, hemoglobin, relaxin, cyclosporine, oxytocin, vaccines, monoclonal antibodies, single chain antibodies, ankyrin repeat proteins, affibodies, activin receptor 2A extracellular domain, alpha-2 macroglobulin, alpha-melanocyte, apelin, bradykinin B2 receptor antagonist, cytotoxic T-lymphocyte-associated protein (CTLA-4), elafin, Factor IX, Factor VIIa, Factor VIII, hepcidin, infestin-4, kallikrein inhibitor, L4F peptide, lacritin, parathyroid hormone (PTH), peptide YY (PYY), thioredoxin, thymosin B4, urate oxidase, urodilatin, aptamers, silencing RNA, microRNA, long non-coding RNA, ribozymes, analogs and derivatives thereof, and combinations thereof.

Clause 104. The method or conjugate of any of one the above clauses, wherein the molecule comprises a polypeptide, and wherein the polypeptide comprises a His-tag, a stimulus-responsive polypeptide, or a combination thereof.

Clause 105. The method or conjugate of clause 104, wherein the stimulus-responsive polypeptide is selected from an elastin-like polypeptide, a polypeptide comprising a repeated motif, and a resilin-like polypeptide.

Clause 106. The method or conjugate of any one of the preceding clauses, wherein the molecule-polymer conjugate has: an in vivo half-life that is at least 25% greater compared with the in vivo half-life of the molecule itself; or an in vivo biodistribution to a tissue, organ, or disease site that is at least 25% greater than the in vivo biodistribution of the molecule itself; or a reduced binding to anti-PEG antibodies compared to a control; or a reduced immune response compared to a control; or a combination thereof.

Clause 107. The method or conjugate of clause 106, wherein the molecule-polymer conjugates have an in vivo half-life that is at least 80% greater than the in vivo half-life of the molecule itself.

Clause 108. The method or conjugate of any one of clauses 41-107, wherein the control comprises the molecule conjugated to a polymer that is not branched.

Clause 109. The method or conjugate of any one of clauses 41-107, wherein the control comprises the molecule by itself.

Clause 110. The method or conjugate of any one of clauses 41-107, wherein the control comprises the molecule conjugated to a linear polymer.

Clause 111. The method or conjugate of any one of clauses 41-107, wherein the control comprises the molecule conjugated to unbranched PEG.

Clause 112. The method or conjugate of any one of the preceding clauses, wherein the molecule comprises a polypeptide, and wherein at least about 20% of the polypeptides have a conjugated branched polymer solely at the C-terminus.

Clause 113. The method or conjugate of clause 112, wherein at least about 75% of the polypeptides have a conjugated branched polymer solely at the C-terminus.

Clause 114. The method or conjugate of clause 112, wherein at least about 90% of the polypeptides have a conjugated branched polymer solely at the C-terminus.

Clause 115. The method or conjugate of any one of the preceding clauses, wherein the yield of molecule-polymer conjugate is at least about 75%.

Clause 116. The method or conjugate of any one of the preceding clauses, wherein the yield of molecule-polymer conjugate is at least about 85%.

What is claimed:

1. A surface having reduced antigenicity and non-specific binding comprising: a surface comprising a plurality of poly[oligo(ethylene glycol) methyl ether methacrylate] (POEGMA) polymers comprising a poly(methyl methacrylate) backbone and a plurality of side chains covalently attached to the backbone, each side chain comprising 1 to 9 ethylene glycol monomers repeated in tandem and terminating with an alkoxy-moiety.

2. The surface of claim 1, wherein the surface is not reactive with anti-PEG antibodies in a subject.

3. The surface of claim 1, wherein the surface does not bind proteins, lipids, or carbohydrates non-specifically.

4. The surface of claim 1, wherein the surface is non-antigenic and does not induce an immune response.

5. The surface of claim 1, wherein the side chain comprises 1 to 5 ethylene glycol monomers repeated in tandem.

6. The surface of claim 1, wherein the side chain comprises 1 to 3 ethylene glycol monomers repeated in tandem.

7. The surface of claim 1, wherein the side chain comprises 2 to 3 ethylene glycol monomers repeated in tandem.

8. The surface of claim 1, wherein the side chain comprises 2 ethylene glycol monomers repeated in tandem.

9. The surface of claim 1, wherein the side chain comprises 3 ethylene glycol monomers repeated in tandem.

10. The surface of claim 1, wherein the alkoxy is methoxy, ethoxy, or propoxy.

11. The surface of claim 1, wherein the alkoxy is methoxy.

12. The surface of claim 1, wherein the POEGMA comprises monomers of ethylene glycol methyl ether methacrylate (EG-1-OMe).

13. The surface of claim 1, wherein the POEGMA comprises monomers of di(ethylene glycol) methyl ether methacrylate (EG-2-OMe).

14. The surface of claim 1, wherein the POEGMA comprises monomers of tri(ethylene glycol) methyl ether methacrylate (EG-3-OMe).

15. The surface of claim 1, wherein the POEGMA comprises monomers of penta(ethylene glycol) methyl ether methacrylate (EG-5-OMe).

16. The surface of claim 1, wherein the POEGMA comprises monomers of nona(ethylene glycol) methyl ether methacrylate (EG-9-OMe).

17. The surface of claim 1, wherein the surface is a material or a biomolecule.

18. The surface of claim 1, wherein the surface is a protein or a protein complex.

19. The surface of claim 1, wherein the surface is a material comprising glass, plastic, metal, ceramic, textile, or paper.

20. A method for reducing antigenicity of and non-specific binding to a surface, the method comprising: affixing to a surface a plurality of poly[oligo(ethylene glycol) methyl ether methacrylate] (POEGMA) polymers comprising a poly(methyl methacrylate) backbone and a plurality of side chains covalently attached to the backbone, each side chain comprising 1 to 9 ethylene glycol monomers repeated in tandem and terminating with an alkoxy moiety.

21. The method of claim 20, wherein the plurality of POEGMA polymers are affixed to the surface by contacting the surface with an initiator agent to form a macroinitiator; and incubating the macroinitiator with a monomer under conditions that permit free-radical polymerization and formation of a branched polymer to occur from the initiator agent.

22. The method of claim 20, wherein the side chain comprises 1 to 5 ethylene glycol monomers repeated in tandem.

23. The method of claim 20, wherein the side chain comprises 1 to 3 ethylene glycol monomers repeated in tandem.

24. The method of claim 20, wherein the side chain comprises 2 to 3 ethylene glycol monomers repeated in tandem.

25. The method of claim 20, wherein the side chain comprises 2 ethylene glycol monomers repeated in tandem.

26. The method of claim 20, wherein the side chain comprises 3 ethylene glycol monomers repeated in tandem.

27. The method of claim 20, wherein the alkoxy is methoxy, ethoxy, or propoxy.

28. The method of claim 20, wherein the alkoxy is methoxy.

29. The method of claim 20, wherein the POEGMA comprises monomers of ethylene glycol methyl ether methacrylate (EG-1-OMe).

30. The method of claim 20, wherein the POEGMA comprises monomers of di(ethylene glycol) methyl ether methacrylate (EG-2-OMec).

31. The method of claim 20, wherein the POEGMA comprises monomers of tri(ethylene glycol) methyl ether methacrylate (EG-3-OMe).

32. The method of claim 20, wherein the POEGMA comprises monomers of penta(ethylene glycol) methyl ether methacrylate (EG-5-OMe).

33. The method of claim 20, wherein the POEGMA comprises monomers of nona(ethylene glycol) methyl ether methacrylate (EG-9-OMe).

34. The method of claim 20, wherein the surface is a material or a biomolecule.

35. The method of claim 20, wherein the surface is a protein or a protein complex.

36. The method of claim 20, wherein the surface is a protein and one or more POEGMA polymers is affixed to the polypeptide at the C-terminus, the N-terminus, or an internal amino acid of the polypeptide.

37. The method of claim 20, wherein the surface is a material comprising glass, plastic, metal, ceramic, textile, or paper.

38. A surface coated with a plurality of POEGMA polymers by the method of claim 20.

39. The surface of claim 38, wherein the surface is a biomolecule or a material.

40. The surface of claim 38, wherein the surface does not non-specifically bind proteins, carbohydrates, or lipids; does not induce an immune response, and is not reactive with anti-PEG antibodies.

\* \* \* \* \*